US007060275B2

(12) United States Patent
Mueller et al.

(10) Patent No.: US 7,060,275 B2
(45) Date of Patent: Jun. 13, 2006

(54) USE OF PROTEIN BIOMOLECULAR TARGETS IN THE TREATMENT AND VISUALIZATION OF BRAIN TUMORS

(75) Inventors: Sabine Mueller, San Francisco, CA (US); Thorsten Melcher, San Francisco, CA (US); Daniel Chin, Foster City, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 168 days.

(21) Appl. No.: 10/652,981

(22) Filed: Aug. 28, 2003

(65) Prior Publication Data

US 2005/0074400 A1 Apr. 7, 2005

Related U.S. Application Data

(63) Continuation of application No. 09/983,000, filed on Oct. 17, 2001, now abandoned.

(51) Int. Cl.
*A61K 39/395* (2006.01)
*A61K 39/40* (2006.01)
*C07H 21/02* (2006.01)

(52) U.S. Cl. ................. 424/178.1; 436/23.1; 436/23.2; 436/23.5

(58) Field of Classification Search ............... 536/22.1, 536/23.1, 23.2, 23.5; 530/350; 424/178.1
See application file for complete search history.

(56) References Cited

U.S. PATENT DOCUMENTS

| | | | |
|---|---|---|---|
| 4,565,789 A | 1/1986 | Liotta et al. ................ 436/504 |
| 4,861,710 A | 8/1989 | Sobel et al. .................... 435/6 |
| 5,648,273 A | 7/1997 | Bottaro et al. .............. 436/501 |
| 5,686,292 A | 11/1997 | Schwall et al. ........ 435/240.27 |
| 5,720,720 A | 2/1998 | Laske et al. .................. 604/49 |
| 5,855,866 A | 1/1999 | Thorpe et al. ............. 424/1.49 |
| 5,871,959 A | 2/1999 | Rong et al. ................ 435/69.1 |
| 5,945,098 A | 8/1999 | Sarno et al. ............... 424/85.5 |
| 6,020,179 A * | 2/2000 | Goli .......................... 435/196 |
| 6,034,218 A | 3/2000 | Reed et al. ................. 530/350 |
| 6,051,230 A | 4/2000 | Thorpe et al. ........... 424/178.1 |
| 6,063,905 A | 5/2000 | Capra et al. ............. 530/387.3 |
| 6,147,203 A | 11/2000 | Pastan et al. ............ 536/23.53 |
| 6,174,708 B1 | 1/2001 | Sodoyer et al. ............ 435/91.1 |
| 6,187,287 B1 | 2/2001 | Leung et al. ................ 424/9.1 |
| 6,312,686 B1 | 11/2001 | Staddon et al. |
| 6,455,026 B1 | 9/2002 | Mueller et al. |

FOREIGN PATENT DOCUMENTS

| | | |
|---|---|---|
| EP | 0 520 158 A1 | 12/1992 |
| EP | 0 890 361 A1 | 1/1999 |
| EP | 0 962 530 A2 | 12/1999 |
| EP | 1 074 264 A1 | 2/2001 |
| WO | WO 93/15754 | 8/1993 |
| WO | WO 98/19696 | 5/1998 |
| WO | WO 98/29138 | 7/1998 |
| WO | WO 98/53838 | 12/1998 |
| WO | WO 00/10506 | 3/2000 |
| WO | WO 00/20869 | 4/2000 |
| WO | WO 00/40264 | 7/2000 |
| WO | WO 00/59938 | 10/2000 |
| WO | WO 00/70076 | 11/2000 |
| WO | WO 00/72679 | 12/2000 |
| WO | WO 00/78361 | 12/2000 |
| WO | WO 01/09159 | 2/2001 |
| WO | WO 01/13105 | 2/2001 |

OTHER PUBLICATIONS

Krueger et al. (Proc. Natl. Acad. Sci. USA 1992; 89: 7417-7421).*
Streuli et al. (Proc. Natl. Acad. Sci. 1989; 86: 8698-8702).*
Abounader, R. et al., "Signaling pathways in the induction of c-met receptor expression by its ligand scatter factor/hepatocyte growth factor in human flioblastoma", *Journal of Neurochemistry*, vol. 76, pp. 1497-1508, 2001.
Asher, R. et al., "Hyaluronate Binding and CD44 Expression in Human Glioblastoma Cells and Astrocytes", *Experimental Cell Research*, vol. 203, pp. 80-90, 1992.
Aspberg, A. et al., "The C-type lectin domains of lecticans, a family of aggregating chondroitin sulfate proteoglycans, bind tenascin-R by protein-protein interactions independent of carbohydrate moiety", *Proc. Natl. Acad. Sci. USA*, vol. 94, pp. 1016-10121, Sep. 1997.
Bajorath, J., "Molecular Organization, Structural Features, and Ligand Binding Characteristics of CD44, a Highly Variable Cell Surface Glycoprotein With Multiple Functions", *Proteins: Structure, Function, and Genetics*, vol. 39, No. 2, May 2000.

(Continued)

*Primary Examiner*—Jeff Siew
*Assistant Examiner*—Brandon Fetterolf
(74) *Attorney, Agent, or Firm*—Pamela J. Sherwood; Bozicevic, Field & Francis LLP; Rebecca D. Taylor

(57) ABSTRACT

The present invention relates to the use of proteins which are differentially expressed in primary brain tumor tissues, as compared to normal brain tissues, as biomolecular targets for brain tumor treatment therapies. Specifically, the present invention relates to the use of immunotherapeutic and immunoimaging agents which specifically bind to one or more of human proteins angiopoietin related protein 2 (ARP-2,) secreted protein acidic, rich in cysteine (SPARC,) c-met proto-oncogene (C-MET,) brevican (BEHAB,) CD-44 antigen (CD-44,) tetraspanin 3 (TSPN3,) pleiotrophin (PTN,) osteopontin (OPN,) vasoactive intestinal peptide receptor-2 (VIPR-2,) and receptor protein tyrosine phosphatase zeta (PTPζ) for the treatment and visualization of brain tumors in patients. The present invention also provides compounds and pharmaceutically acceptable compositions for administration in the methods of the invention. The present invention also provides novel splice variants of protein PTPζ, PTPζ SM1 and PTPζ SM2. Nucleic acid probes specific for the spliced mRNA encoding these variants and affinity reagents specific for the novel proteins are also provided.

17 Claims, 3 Drawing Sheets

OTHER PUBLICATIONS

Bartus, R.T., et al., "Evidence that Cereport's Ability to Increase Permeability of Rat Gliomas is Dependent Upon Extent of Tumor Growth: Implications for Treating Newly Emerging Tumor Colonies", *Experimental Neurology*, vol. 161, No. 1, pp. 234-244, Jan. 2000.

Berditchevski, F. et al., "Characterization of integrin-Tetraspanin Adhesion Complexes: role of Tetraspanins in Integrin Signaling", *J. Cell Biology*, vol. 146, No. 2, pp. 477-492, Jul. 1999.

Bickel, U. et al., "Delivery of peptides and proteins through the blood-brain barrier", *Advanced Drug Delivery Reviews*, vol. 46, pp. 247-279, 2001.

Birling, M. et al., "A Novel Rat Tetraspan Protein in Cells of the Oligodendrocyte Lineage", *J. Neurochem.*, vol. 73, pp. 2600-2608, 1999.

Castronovo, V., "Laminin Receptors and Laminin-Binding Proteins during Tumor Invasion and Metastasis", *Invasion Metastasis*, vol. 13, pp. 1-30, 1993.

Castronovo, V., et al., "Laminin and fibronectin increase the steady state level of the 67 kD high affinity metastasis-associated laminin receptor mRNA in human cancer cells", *Biochemical and Biophysical Research Communications*, vol. 168, No. 3, pp. 1110-1117, May 16, 1990

Cawthern, K.M. et al., "Blood Coagulation in Hemophilia A and Hemophilia C", *Blood*, vol. 91, No. 12, pp. 4581-4592, 1998.

Charrin, S. et al., "The major CD9 and CD81 molecular partner: Identification and characterization of the complexes", *The American Society for Biochemistry and Molecular Biology, Inc.*, JEC Papers in Press, Published on Jan. 18, 2001 as Manuscript MO11297200.

Crepaldi, T. et al., "Generation of a Truncated Hepatocyte Growth Factor Receptor in the Endoplasmic Reticulum", *J. Biol. Chem.*, vol. 269, No. 3, pp. 1750-1755, 1994.

Czubayko, F., et al., "Ribozyme-targeting Elucidates a Direct Role of Pleiotrophin in Tumor Growth", *J. Biol. Chem.*, vol. 269, No. 33, pp. 21358-21363, Aug. 15, 1994.

Dean, M. et al., "Characterization of the Rearranged tpr-met Oncogene Breakpoint", *Molecular and Cellular Biology*, vol. 7, No. 2, pp. 921-924, 1987.

Domanico, S.Z. et al., "Integrin $\alpha 6A\beta 1$ Induces CD81-dependent Cell Motility without Engaging the Extracellular Matrix Migration Substrate", *Molecular Biology of the Cell*, vol. 8. pp. 2253-2265, Nov. 1997.

Engering, A. et al., "Association of distinct tetraspanins with MHC class II molecules at different subcellular locations in human immature dendritic cells", *International Immunology*, vol. 13, No. 2, pp. 127-134 2001.

Fang, W. et al., "Pleiotrophin Stimulátes Fibroblasts and Endothelial and Epithelial Cells and Is Expressed in Human Cancer", *J. Biol. Chem.*, vol. 267, No. 36, pp. 25889-25897, 1992.

Ferrer, M. et al., "Pattern of expression of tetraspanin antigen genes in Burkitt lymphoma cell lines", *Clin. Exp. Immunol.*, vol. 113, pp. 346-352, 1998.

Fischer, U. et al., "Amplification of the MET Gene in Glioma", *Genes, Chromosomes & Cancer*, vol. 12, No. 1, pp. 63-65 (1995).

Föger, N. et al., "CD44 supports T cell proliferation and apoptosis by apposition of protein kinases", *Eur. J. immunol.*, vol. 30, No. 10, pp. 2888-2899, 2000.

Galimi, F. et al., "The Hepatocyte Growth Factor and Its Receptor", *Stem Cells*, vol. 11 (Suppl. 2), pp. 22-30, 1993.

Gary S.C., et al., "BEHAB/brevican: An Extracellular Matrix Component-Associated with Invasive Glioma", *Clinical Neurosurgery*, vol. 47, pp. 72-82, 1999.

Gary, S.C. et al., "BEHAB/Brevican: a brain-specific lectican implicated in gliomas and glial cell motility", *Current Opinion in Neurobiology*, vol. 8, pp. 576-581, 1998.

Gary, S.C. et al., "cDNA cloning, chromosomal localization, and expression analysis of human BEHAB/brevican, a brain specific proteoglycan regulated during cortical development and in glioma", *Gene*, vol. 256, pp. 139-147, 2000.

Gladson, C.L., "The Extracellular Matrix of Gliomas: Modulation of Cell Function", *Journal of Neuropathology and Experimental Neurology*, vol. 58, No. 10, pp. 1029-1040, Oct., 1999.

Golembieski, W.A. et al., "Increased SPARC Expression Promotes U87 Glioblastoma invation In Vitro", *Int. J. Devl. Neuroscience*, vol. 17, Nos. 5, 6, pp. 463-472, 1999.

Harabin-Slowinska, M. et al., "Expression of Adhesion Molecule CD44 in Metastatic Brain Tumors", *Folia Neuropathologica*, vol. 36, pp. 179-184, 1998.

Hamar, T. et al., "Multiple receptors for PACAP and VIP", *Trends in Pharmacological Sciences*, vol. 15, Apr. 1994.

Heimberger, A.B., et al., "Biological Principles of Brain Tumor Immunotherapy", *Brain Tumor Immunotherapy*, Edited by L.M. Liau, et al. © Humana Press Inc., Totowa, NJ. pp. 101-130.

Huang, H. et al., "Gene Expression Profiling of Low-Grade Diffuse Astrocytomas by cDNA Arrays", *J. Cancer Research*, vol. 60, pp. 6868-6874, 2000.

Huang, Y-Q.I et al., "Identification of a family of alternatively spliced mRNA species of angioproietin-1", *Blood*, vol. 95, No. 6, pp. 1993-1999, 2000.

Ilangumaran, S. et al., "Signal Transduction Via CD44: Role of Plasma Membrane Microdomains", *Leukemia and Lymphoma*, vol. 35, pp. 455-469, 1999.

Jaworski, D.M. et al., "Intracranial Injury Acutely Induces the Expression of the Secreted Isoform of the CNS-Specific Hyaluronan-Binding Protein BEHAB/Brevican", *Experimental Neurology*, vol. 157, pp. 327-337, 1999.

Jin, K.L. et al., "Vascular endothelial growth factor: Direct neuroprotective effect in in vitro ischemia", *Proc. Natl. Acad. Sci. USA*, vol. 97, No. 18, pp. 10242-10247, 2000.

Kim, I., et al., "Molecular Cloning, Expression, and Characterization of Angiopoietin-related Protein", *J. Biol. Chem.*, vol. 274, No. 37, pp. 26523-26528, 1999.

Kobayashi, T. et al., "The Tetraspanin CD63/lamp3 cycles between Endocytic and Secretory Compartments in Human Endothelial Cells", *Molecular Biology of the Cell*, vol. 11, No. 5, pp. 1829-1843, May 2000.

Koochekpour, S. et al., "Hyaluronic Acid/CD44H Interaction induces Cell Detachment and Stimulates Migration and Invation of Human Glioma Cells In Vitro", *Int. J. Cancer*, vol. 63, pp. 450-454, 1995.

Lal, A., et al., "A Public Database for Gene Expression in Human Cancers", *Cancer Research*, vol. 59, pp. 5403-5407, Nov. 1, 1999.

Lamszus, K. et al., "Scatter Factor/Hepatocyte Growth Factor (SF/HGF) Content and Function in Human Gliomas", *Int. J. Devl. Neuroscience*, vol. 17, Nos. 5-6, pp. 517-530, 1999.

Lee, C.C. et al., "Identification of a Novel Type of Alternative Splicing of a Tyrosine Kinase Receptor", *J. Biol. Chem.*, vol. 269, No. 30, pp. 19457-19461, 1994.

Lokker, N.A. et al., "Mutational analysis and molecular modeling of the N-terminal kringle-containing domain of hepatocyte growth factor identifies amino acid side chains important for interaction with the C-Met receptor", *Protein Engineering*, vol. 7, No. 7, pp. 895-903, 1994.

Lutz, E.M. et al., "Domains determining agonist selectivity in chimaeric $VIP_2(VPAC_2)/PACAP\ (PAC_1)$ receptors", *Brit J. Pharm.*, vol. 128, pp. 934-940, 1999.

Maecker, H.T., et al., "The tetraspanin superfamily: molecular facilitators", *FASEB J.*, vol. 11, No. 6, pp. 428-442, May 1997.

Mark, M.R. et al., "Expression and Characterization of Hepatocyte Growth Factor Receptor-IgG Fusion Proteins", *J. Biol. Chem.*, vol. 267, No. 36, pp. 26166-26171, 1992.

Matthews, R.T. et al., "Brain-enriched Hyaluronan Binding (BEHAB)/Brevican Cleavage in a Glioma Cell Line is Mediated by a Disintegrin and Metalloproteinase with Thrombospondin Motifs (ADAMTS) Family Member", *J. Biol. Chem.*, vol. 275, No. 30, pp. 22695-22703, 2000.

Monaghan, M. et al., "Epidermal growth factor up-regulates CD44-dependent astrocyloma invation in vitro", *J Pathol.*, vol. 192, pp. 519-525, 2000.

Moriyama, T. et al., "Simultaneous up-regulation of urokinase-type plasminogen activator (uPA) and uPA receptor by hepatocyte growth factor/scatter factor in uman glioma cells", *Clinical and Experimental Metastasis*. vol. 17. No. 10. pp. 873-879. 1999.

Nagasaka, S. et al., "Alternative RNA splicing of the hyaiuronic acid receptor CD44 in the normal human brain and in brain tumors", *J. Neurosurg.*, vol. 82, 858-863, 1995.

Nakagawara A., et al., "Differential Expression of Pleiotrophin and Midkine in Advanced Neuroblastomas", *Cancer Research*. vol. 55. pp. 1792-1797, Apr. 15, 1995.

Naldini, L. et al., "The Tyrosine Kinase Encoded by the MET Proto-Oncogene is Activated by Autophosphorylation". *Molecular and Cellular Biology*. vol. 11, No. 4, pp. 1793-1803, Apr. 1991.

Papapetropoulos, A. et al., "Angiopoietin-1 Inhibits Endothelial Cell Apoptosis via the Akt/Survivin Patway", *J. Biol. Chem.*, vol. 275, No. 13, pp. 9102-9105, 2000.

Park, M. et al., "Sequence of MET protooncogene cDNA has features characteristic of the tyrosine kinase family of growth-factor receptors", *Proc. Natl. Acad. Sci, USA*, vol. 84, pp. 6379-6383, Sep. 1987.

Prat, M. et al., "C-Terminal Truncated Forms of MET, the Hepatocyte Growth Factor Receptor", *Molecular and Cellular Biology*, vol. 11, No. 12, pp. 5954-5962, 1991.

Rempel, S.A. et al., "SPARC: A Potential Diagnostic Marker of Invasive Meningiomas", *Clinical Cancer Research*, vol. 5, pp. 237-241, Feb. 1999.

Rempel, S.A. et al., "SPARC: A Signal of Astrocytic Neoplastic Transformation and Reactive Response in Human Primary and Xenograft Gliomas", *Journal of Neuropathology and Experimental Neurology*, vol. 57, No. 12, pp. 1112-1121, Dec. 1998.

Rempel, S.A., "Molecular biology of central nervous system tumors", *Current Opinion in Oncology*, vol. 10, No. 3, pp. 179-185, May 1998.

Rodrigues, G.A. et al., "Alternative Splicing Generates Isoforms of the met Receptor Tyrosine Kinase Which Undergo Differential Processing", *Molecular and Cellular Biology*, vol. 11, No. 6, p. 2962-2970, Jun. 1991.

Sasaki, T. et al., "Crystal structure and mapping by site-directed mutagenesis of the collagen-binding epitope of an activated form of BM-40/SPARC/osteonectin", *The EMBO Journal*, vol. 17, No. 6, pp. 1625-1634, 1998.

Sasaki, T. et al., "Limited Cleavage of Extracellular Matrix Protein BM-40 by Matrix Metalloproteinases Increases Its Affinity for Collagens" *J. Biol. Chem.*, vol. 272, No. 14, pp. 9237-9243, 1997.

Shen, S. et al., "Overexpression of the human $VPAC_2$ receptor in the suprachiasmatic nucleus alters the circadian phenotype of mice", *PNAS*, vol. 97, No. 21, pp. 11575-11580, 2000.

Sherman, L. et al., "Schwann cell tumors express characteristic patterns of CD44 splice variants", *Journal of Neuro-Oncology*, vol. 26, pp. 171-184, 1995.

Sobel, M.E., "Differential expression of the 67 kDa laminin receptor in cancer", *Seminars in Cancer Biology*, vol. 4, pp. 311-317, 1993.

Sugiura, T. et al., "Function of $\alpha 3\beta 1$-Tetraspanin Protein Complexes in Tumor Cell Invasion. Evidence for the Role of the Complexes in Production of Matrix Metalloproteinase 2 (MMP-2)", *J. Cell Biol.*, vol. 146, No. 6, pp. 1375-1389, Sep. 1999.

Tachibana, I. et al., "NAG-2, a Novel Transmembrane-4 Superfamily (TM4SF) Protein That Complexes with Integrins and Other TM4SF Proteins", *J. Biol. Chem.*, vol. 272, No. 46, pp. 29181-29189, 1997.

Testa, J.E. et al., "Eukaryotic Expression Cloning with an Antimetastatic Monoclonal Antibody Identifies a Tetraspanin (PETA-3/CD151) as an Effector of Human Tumor Cell Migration and Metastasis", *Cancer Research*, vol. 59, No. 15, pp. 3812-3820, Aug. 1999.

Todd, S.C., et al., "Sequences and expression of six new members of the tetraspanin/M4SF family", *Biochimica et Biophysica Acta*, vol. 1399, pp. 101-104, 1998.

Thurston, G. et al., "Leakage-Resistance Blood Vessels in Mice Transgenically Overexperssing Angiopoietin-1", *Science*, vol. 286, pp. 2511-2514, Dec. 1999.

Uhm, J. H. et al., "The Role of Intergins in the Malignant Phenotype of GLI", *Frontiers in Bioscience*, vol. 4, pp. 188-199, 1999.

Vajkoczy, P. et al., "Targeting Angiogenesis Inhibits Tumor Infiltration and Expression of the Pro-Invasive Protein SPARC", *Int. J. Cancer*, vol. 87, pp. 261-268, 2000.

Wallenius, V. et al., "Overexpression of the Hepatocyte Growth Factor (HGF) Receptor (Met) and Presence of a Truncated and Activated Intracellular HGF Receptor Fragment in Locally Aggressive/Malignant Human Musculoskeletal Tumors", *Am. J. Pathology*, vol. 156, No. 3, pp. 821-829, Mar. 2000.

Wallenius, V.R. et al., "Chromosomal localization of rat hepatocyte growth factor (Hgf) and HGF receptor (Met and characterization of HGF receptor cDNA", *Mammalian Genome*, vol. 8, No. 9, pp. 661-667, Sep. 1997.

Wewer, U.M. et al., "Altered levels of laminin receptor mRNA in various human carcinoma cells that have different abilities to bind laminin", *Proc. Natl. Acad. Sci. USA*, vol. 83, pp. 7137-7141, Oct. 1986.

Wewetzer, K. et al., "Cell Blotting and Isoelectric Focusing of Neuroblastoma-Derived Heparin-Binding Neurotrophic Activities: Detection of Basic Fibroblast Growth Factor Protein and mRNA", *Journal of Neuroscience Research*, vol. 36, pp. 209-215, 1993.

Wikstrand, C.J., et al., "Radiolabeled Antibodies for Therapy of Brain Tumors", *Brain Tumor Immunotherapy*, Edited by L.M. Liau, et al. © Humana Press Inc., Totowa, NJ, pp. 205-229.

Wordinger, R.J. et al., "Expression of Alternatively Spliced Growth Factor Receptor Isoforms in the Human Trabecular Meshwork", *Investigative Ophthalmology & Visual Science*, vol. 40, No. 1, pp. 242-247, 1999.

Xie, R-L. et al., "Elements within the First 17 Amino Acids of Human Osteonectin Are Responsible for Binding to Type V Collagen", *J. Biol. Chem.*, vol. 271, No. 14, pp. 8121-8125, 1996.

Xie, R-L. et al., "Role of N-Linked Glycosylation in Human Osteonectin", *J. Biol. Chem.*, pp. 23212-23217, May 26, 1995.

Yamada, H. et al., "Molecular Cloning of Brevican, a Novel Brain Proteoglycan of the Aggrecan/Versican Family", *J. Biol. Chem.*, vol. 269, No. 13, pp. 10119-10126, 1994.

Yamaguchi, Y., "Brevican: A Major Proteoglycan in Adult Brain", *Perspectives on Development Neurobiology*, vol. 03, pp. 307-317, 1995.

Yanez-Mo, M., et al., "Tetraspanins in intercellular adhesion of polarized epithelial cells: spatial and functional relationship to integrins and cadherins", *Journal of Cell Science*, vol. 114, No. 3, pp. 577-587, Feb. 2001.

Yauch, R.L. et al., "Direct Extracellular Contact between integrin $\alpha_3\beta_1$ and TM4SF Protein CD151", *J. Biol. Chem.*, vol. 275, No. 13, pp. 9230-9238, 2000.

Yauch, R.L., et al., "Specific interactions among transmembrane 4 superfamily (TM4SF) proteins and phosphoinositide 4-kinase", *Biochem. J.*, vol. 351, pp. 629-637, 2000.

Zarnegar, R., "Regulation of HGF and HGFR gene expression", *Epithelial-Mesenchymal Interactions in Cancer*, , pp. 33-49, 1995.

Huang H. et al., Gene expression profiling of low-grade diffuse astrocytomas by cDNA arrays., Cancer Res., 2000, vol. 60, No. 24, pp. 6868-6874.

Huang Yo,et al., identification of a family of alternatively spliced mRNA species of angiopoietin-1., Blood, 2000, vol. 95, No. 6, pp. 1993-1999.

Ilangumaran S. et. al., Signal transduction via CD44: role of plasma membrane microdomains., Leuk Lymphoma., 1999, vol. 35, No. 5-6, pp. 455-489.

Jaworski DM, et al., Intracranial injury acutely induces the expression of the secreted isoform of the CNS-specific hyaluronan-binding protein BEHAB/brevican., Exp Neurol. 1999, vol. 157, pp. 327-337.

Jin KL, et. al., Vascular endothelial growth factor: direct neuroprotective effect in in vitro ischemia., Proc Natl Acad Sci U S A., 2000, vol. 97, No. 18, pp. 10242-10247.

Kim I. et al., Molecular cloning, expression, and characterization of angiopoietin-related protein, angiopoietin-related protein induces endothelial cell sprouting., J Biol Chem., 1999 ,vol. 274, No. 37, pp. 26523-26528.

Kobayashi T. et al., The tetraspanin CD63/tamp3 cycles between endocytic and secretory compartments in human endotheial cells., Mol-Biol Cell. 2000. vol. 11, No. 5, pp. 1829-1843.

Koochekpour S. et. al. Hyaluronic acid/CD44H interaction induces cell detachment and stimulates migration and invasion of human glioma cells in vitro., Int J Cancer. 1995, vol. 63, No. 3, pp. 450-454.

Lal A, et. al., A public database for gene expression in human cancers., Cancer Res. 1999, vol. 59, No. 21, pp. 5403-5407.

Lamszus K, et. al. Scattere factor/hepatocyte growth factor (SF/HGF) content and function in human gliomas., Int J Dev Neurosci. 1999, vol. 17, No. 5-6, pp. 517-530.

Lee CC, Yamada KM., Identification of a novel type of alternative splicing of a tyrosine kinase receptor. Juxtamembrane detetion of the c-met protein kinase C serine phosphorylation regulatory site., J Biol Chem. 1994, vol. 269, No. 30, pp. 19457-19458.

Lokker NA, et. al., Mutational analysis and molecular modeling of the N-terminal kringle-containing domain of hepatocyte growth factor identifies amino acid side chains important for interaction with the c-Met receptor., Protein Eng., 1994, vol. 7, No. 7, pp. 895-903.

Lutz EM,et. a. Domains determining agonist selectivity in chimaeric VIP2 (VPAC2)PACAP (PAC1) receptors.Br J Pharmacol., 1999, vol. 128 No. 4, pp. 934-940.

Maecker HT, et al., The tetraspanin superfamily: molecular facilitators., FASEB J., 1997, vol. 11, No. 6, pp. 428-442.

Mark MR, et. al. Expression and characterization of hepatocyte growth factor receptor-IgG fusion proteins. Effects of mutations in the potential proteolytic cleavage site on processing and ligand binding., J Biol Chem., 1992, vol. 267, No. 36, pp. 26166-26171.

Matthews RT. et. al. Brian-enriched hyaluronan binding (BEHAB)/brevican cleavage in a glioma cell line is mediated by a disintegrin and metalloproteinase with thrombospondin motifs (ADAMTS) family member.J Biol Chem. 2000, vol. 275, No. 30, pp. 22695-22703.

Monaghan M, et. al.. Epidermal growth factor up-regulates CD44-dependent astrocytoma invasion in vitro., J Pathol., 2000, vol. 192, No. 4, pp. 519-525.

Moriyama T, et. al. Simultaneous up-regulation of urokinase-type plasminogen activator (uPA) and uPA receptor by hepatocyte growth factor/scatter factor in human glioma cells., Clin Exp Metatasis., 1999, vol. 17, No. 10, pp. 873-879.

Nagasaka S. et al., Alternative RNA splicing of the hyaluronic acid receptor CD44 in the normal human brain and in brain tumors., J Neurosurg., 1995, vol. 82, No. 5, pp. 858-863.

Naldini L. et. al., The tyrosine kinase encoded by the MET proto-oncogene is activated by autophosphorylation., Mol Cell Biol., 1991, vol. 11, No. 4. pp. 1793-803.

Maeda et al. (1999) "A receptor-like protein-tyrosine phosphatase PTPζ/RPTPβ binds a heparin-binding growth factor midkine" *J. Biol. Chem.* 274(18):12474-12479.

* cited by examiner

USE OF PROTEIN BIOMOLECULAR TARGETS IN THE TREATMENT AND VISUALIZATION OF BRAIN TUMORS

FIELD OF USE

The present invention relates to the use of proteins which are differentially expressed in primary brain tumor tissues, as compared to normal brain tissues, as biomolecular targets for brain tumor treatment therapies. Specifically, the present invention relates to the use of immunotherapeutic and immunoimaging agents which specifically bind to one or more of angiopoietin related protein 2 (ARP-2,) secreted protein acidic, rich in cysteine (SPARC,) c-met proto-oncogene (C-MET,) brevican (BEHAB,) CD-44 antigen (CD-44,) tetraspanin 3 (TSPN3,) pleiotrophin (PTN,) osteopontin (OPN,) vasoactive intestinal peptide receptor-2 (VIPR-2,) and receptor protein tyrosine phosphatase zeta (PTPζ) for the treatment and visualization of brain tumors in patients. The present invention also provides compounds and pharmaceutically acceptable compositions for administration.

BACKGROUND OF THE INVENTION

Brain Tumor Biology and Etiology

Brain tumors are considered to have one of the least favorable prognoses for long term survival: the average life expectancy of an individual diagnosed with a central nervous system (CNS) tumor is just eight to twelve months. Several unique characteristics of both the brain and its particular types of neoplastic cells create daunting challenges for the complete treatment and management of brain tumors. Among these are 1) the physical characteristics of the intracranial space, 2) the relative biological isolation of the brain from the rest of the body, 3) the relatively essential and irreplaceable nature of the organ mass, and 4) the unique nature of brain tumor cells.

First and foremost, the intracranial space and physical layout of the brain create significant obstacles to treatment and recovery. The brain is made of, primarily, astrocytes (which make up the majority of the brain mass, and serve as a scaffold and support for the neurons), neurons (which carry the actual electrical impulses of the nervous system), and a minor contingent of other cells such as insulating oligodendrocytes (which produce myelin). These cell types give rise to primary brain tumors (e.g., astrocytomas, neuroblastomas, glioblastomas, oligodendrogliomas, etc.) Although the World Health Organization has recently established standard guidelines, the nomenclature for brain tumors is somewhat imprecise, and the terms astrocytoma and glioblastoma are often used broadly. The brain is encased in the relatively rigid shell of the skull, and is cushioned by the cerebrospinal fluid, much like a fetus in the womb. Because of the relatively small volume of the skull cavity, minor changes in the volume of tissue in the brain can dramatically increase intracranial pressure, causing damage to the entire organ (i.e., "water on the brain"). Thus, even small tumors can have a profound and adverse affect on the brain's function. In contrast, tumors in the relatively distensible abdomen may reach several pounds in size before the patient experiences adverse symptoms. The cramped physical location of the cranium also makes surgery and treatment of the brain a difficult and delicate procedure. However, because of the dangers of increased intracranial pressure from the tumor, surgery is often the first strategy of attack in treating brain tumors.

In addition to its physical isolation, the brain is chemically and biologically isolated from the rest of the body by the so-called "Blood-Brain-Barrier" (or BBB). This physiological phenomenon arises because of the "tightness" of the epithelial cell junctions in the lining of the blood vessels in the brain. Although nutrients, which are actively transported across the cell lining, may reach the brain, other molecules from the bloodstream are excluded. This prevents toxins, viruses, and other potentially dangerous molecules from entering the brain cavity. However, it also prevents therapeutic molecules, including many chemotherapeutic agents that are useful in other types of tumors, from crossing into the brain. Thus, many therapies directed at the brain must be delivered directly into the brain cavity (e.g., by an Ommaya reservoir), or administered in elevated dosages to ensure the diffusion of an effective amount across the BBB.

With the difficulties of administering chemotherapies to the brain, radiotherapy approaches have also been attempted. However, the amount of radiation necessary to completely destroy potential tumor-producing cells also produce unacceptable losses of healthy brain tissue. The retention of patient cognitive function while eliminating the tumor mass is another challenge to brain tumor treatment. Neoplastic brain cells are often pervasive, and travel throughout the entire brain mass. Thus, it is impossible to define a true "tumor margin," unlike, for example, in lung or bladder cancers. Unlike reproductive (ovarian, uterine, testicular, prostate, etc.), breast, kidney, or lung cancers, the entire organ, or even significant portions, cannot be removed to prevent the growth of new tumors. In addition, brain tumors are very heterogeneous, with different cell doubling times, treatment resistances, and other biochemical idiosyncrasies between the various cell populations that make up the tumor. This pervasive and variable nature greatly adds to the difficulty of treating brain tumors while preserving the health and function of normal brain tissue.

Although current surgical methods offer considerably better post-operative life for patients, the current combination therapy methods (surgery, low-dosage radiation, and chemotherapy) have only improved the life expectancy of patients by one month, as compared to the methods of 30 years ago. Without effective agents to prevent the growth of brain tumor cells that are present outside the main tumor mass, the prognosis for these patients cannot be significantly improved. Although some immuno-affinity agents have been proposed and tested for the treatment of brain tumors, see, e.g., the tenascin-targeting agents described in U.S. Pat. No. 5,624,659, these agents have not proven sufficient for the treatment of brain tumors. Thus, therapeutic agents which are directed towards new molecular targets, and are capable of specifically targeting and killing brain tumor cells, are urgently needed for the treatment of brain tumors.

ARP-2 (Angiopoeitin Related Protein-2, Angiopoeitin Like-2 [ANGPTL-2])

Angiopoeitin related protein-2 (ARP-2), is related to the angiopoeitin family of proteins, that includes Ang-1 and Ang-2. Like members of the angiopoeitin family, ARP-2 contains a coiled-coil domain in the amino terminal portion and a fibrinogen-like domain in the carboxyl terminal portion. However, ARP-2 has a low homology with Ang-1 and Ang-2 and unlike Ang-1 and Ang-2, ARP-2 does not bind to the Tie-2 receptor, nor does ARP-2 bind to the closely related Tie-1 receptor. Hence, ARP-2 is believed to be part of a newly identified family of proteins termed angiopoeitin related proteins. Like the angiopoeitins, ARP-2 is a member of the fibrinogen superfamily, which also includes the fibrinogens and lectins.

ARP-2 is a glycosylated, secretory protein that induces sprouting in endothelial cells, most likely through autocrine or paracrine signaling, and it is preferentially expressed in the blood vessels and muscle cells. Hence, ARP-2 mediates the differentiated state of endothelial cells or for vascular remodeling and development. ARP-2 has not heretofore been associated with brain tumors.

SPARC (Secreted Protein, Acidic, Cysteine-rich; Osteonectin, Basement Membrane Protein (bm) 40)

Secreted protein acidic and rich in cysteine, SPARC or BM-40, is a member of the counter-adhesive family of proteins. It is a developmentally regulated, secreted glycoprotein expressed in fetal astrocytes, particularity during tissue remodeling, vessel morphogenesis, and in response to stress. It has been hypothesized that SPARC may affect cell migration and vascular morphogenesis either by directly interacting with extracellular matrix (ECM) proteins (such as collagens I, III, IV and V) or by initiating a receptor mediated signaling event that induces changes in cytoplasmic components associated with focal adhesions. SPARC has been found to bind directly to vitronectin, a multifunctional adhesive protein that is a component of the brain vascular basement membranes.

SPARC may indirectly affect cell migration and motility by regulating the expression of matrix metallo-proteases and by modulating the expression of other proteolytic enzymes (such as collagenase) that degrade the ECM. Increased SPARC expression has also been observed in two forms of low-grade malignant gliomas, in all grades of human astrocytic tumors, and in tumor cells invading adjacent brain at the tumor/brain interface. Hence, SPARC may be an astrocytoma invasion related gene that functions in connection with vitronectin to balance the modulation of cellular adhesion to the ECM and it may promote diffuse tumor cell infiltration into adjacent brain by affecting both tumor and endothelial cell-ECM interactions.

Because SPARC is also found in bone, dentine, and many normal and neoplastic human soft tissues it may also play a regulatory function in the control of such diverse processes as bone mineralization, cell shape, tissue remodeling or repair, cell migration, proliferation, and differentiation. SPARC is also synthesized, stored, and secreted by human blood platelets, binds to plasminogen, and enhances tissue plasminogen activator conversion of plasminogen to plasmin.

c-MET (Met Proto-oncogene Tyrosine Kinase, Hepatocyte Growth Factor Receptor [HGFR])

c-MET is a member of the Hepatocyte Growth Factor Receptor (HGFR) family and a heterodimeric cellular receptor for Hepatocyte Growth Factor (HGF). c-MET contains a disulfide-linked α-chain of 50-kDa (which is located in the extracellular domain,) a 145-kDa β-chain (which includes an extracellular region,) a transmembrane spanning domain, and an intracellular tyrosine kinase domain that can be activated by autophosphorylation. Hence, HGFR is a subset of the protein tyrosine-kinase family of membrane-spanning, cell surface receptors.

The receptor-ligand pair, c-MET and HGF, function as a growth factor, regulating cell growth, migration, and morphogenesis, and hence, may play a role in neoplastic formation and metastasis. Upon HGF or macrophage stimulating protein (MSP) binding, the c-MET protein receptor goes through a conformational change wherein the intracellular tyrosine residues of the β subunit become phosphorylated at residue 1235, and a second messenger signal cascade is induced. This change activates c-MET's intracellular receptor kinase activity, which is important to the growth and differentiation of epithelial cells in normal and malignant tissues. c-MET has been identified in both normal brain and on glial tumors, and is thought to be determinant in the pathological processes of various malignancies. For instance, detailed studies have shown that glioblastoma multiforme (GBM), a highly malignant brain tumor of astrocytic origin, expresses c-MET, and this research suggests a role in tumor progression.

BEHAB (Brain-enriched Hyaluronan Binding Protein, Brevican)

BEHAB is a brain-specific, extracellular matrix protein, that is a member of the chondroitin sulfate proteoglycan (CSPG) family. BEHAB is expressed only in the CNS. Although its function is unclear, BEHAB is reported to bind to HA at the N-terminus, lectins at the C-terminus, and may mediate binding of other ECM components like tenascin. This suggests that BEHAB may play a role in cell-cell and cell-matrix interactions thereby maintaining the extracellular environment of the brain. It has been reported that the highest levels of expression of BEHAB is during brain development and at times and places where glial cells are highly motile, as in cases of brain injury or trauma. BEHAB expression is also unregulated in primary gliomas of the central nervous system, but not in tumors of non-glial origin. In surgical samples of human gliomas (including astrocytoma, oligodendroglioma, and glioblastoma tumors), BEHAB expression is consistently and dramatically increased over the level of expression in the normal brain. Hence, BEHAB expression correlates with an invasive phenotype that promotes gliogenesis by contributing to cell movement through the ECM.

CD-44 Antigen

CD-44 is a single-path, type I transmembrane protein with extracellular domains that are flexibly linked to the transmembrane segment. CD-44 is a member of the cartilage link protein family and belongs to the hyaloadherin or link protein superfamily (LPSF). As other members of the LPS family, CD-44 can be extensively glycosylated and is typically decorated with glycosaminoglycans (e.g., chondroitin, heparin, and keratin sulfate). The genomic structure of CD-44 consists of 21 exons, at least 11 of which can be variably spliced (v1–v10), that are located in the membrane-proximal extracellular region. Alternative splicing of these exons give rise to a variety of CD-44 isoforms (at least 30 different isoforms have been characterized to date) that are widely distributed and expressed in a cell-specific manner. Among the most frequently occurring isoforms are CD-44H, expressed on hematopoietic cells, and CD-44E, expressed in epithelial cells. CD-44(H) has also been found to be expressed in lymphocytes, macrophages, erythrocytes, fibroblasts, epithelial and endothelial cells, and neurons. It is the predominant isoform in normal brain and neuroectoderm-derived tumors and is expressed on both normal astrocytes and oligodendrocytes as well on neoplastic astrocytes and glioblastomas.

The family of CD-44 proteins has been implicated in lymphocyte activation and homing, endothelial migration, and tumor cell metastasis. CD-44 is believed to be the major receptor for Hyaluronic acid (HA). CD-44/HA interactions underlie a wide spectrum of functions in embryonic morphogenesis and organogenesis, hematopoeisis, lymphocyte homing. CD-44 also mediates the attachment of glioma cells to chondroitin sulfate, types I and IV collagen, fibronectin laminin, vitronectin and Martrigel. This suggest that CD-44 may play a role in cell-cell and cell-matrix interactions, affecting the extracellular environment of the brain. Because HA is a major component of the brain ECM, and CD-44 is one of the principal cellular receptors of HA, CD-44 expression coincides with brain tumor growth and invasiveness.

PTN (Pleiotrophin, Heparin Binding Growth Factor 8, Neurite Growth-promoting Factor 1)

Pleiotrophin or PTN, is a platelet-derived, growth factor inducible, member of the pleiotrophin family of proteins that includes midkine and retinoic acid-induced heparin-binding protein. It is a developmentally regulated, secreted cytokine that stimulates mitogenesis, angiogenesis, and neurite and glial process outgrowth guidance activities. During development PTN is expressed in the brain, intestine, muscle, skin, heart, lung and kidney. In the adult, PTN is found primarily in the brain in association with axonal tracts during active mitogenesis and may therefore play an important role in the development and maintenance of the nervous system. It has been found to bind heparin, heparin sulfate proteoglycans, the extracellular matrix, and is also a natural ligand for receptor protein tyrosine phosphatase (RPTP), signaling through ligand dependant receptor inactivation of RPTP. Receptor mediated endocytosis occurs following PTN binding and may be disrupted by heparin.

PTN has also been found to have oncogenic properties, inducing malignant transformation and tumor growth and progression. It has been described as a proto-oncogene that is expressed in many human tumors and cell lines derived from human tumors. PTN is a mitogen for fibroblasts, epithelial and endothelial cells, stimulates plasminogen-activator production, can induce tube formation, and therefore can serve as a tumor angiogenesis factor.

OPN (Osteopontin, Secreted Phosphoprotein 1, Bone Sialoprotein-1)

Osteopontin or OPN, is a member of the osteopontin family. It is a glycosylated sialoprotein that is heavily phosphorylated and expressed in a variety of cells including bone, kidney, placenta, nerve cells and macrophages, as well as T lymphocytes, epidermal and bone cells. OPN is a part of the mineralized bone matrix and may play a role in bone resorption, by facilitating the attachment of osteoclasts to the bone surface, and may be functionally important as an adhesive and chemotactic molecule for vascular cells. OPN is a secreted protein that binds tightly to hydroxyapatite, and hence, is important to cell matrix interactions. It has been observed to interact with the CD-44 homing receptor to physiologically induce macrophage chemotaxis, which may be a mechanism utilized by metastatic brain tumors in the process of dissemination.

OPN has been observed in the microvasculature of glioblastomas associated with VEGF expression and OPN mRNA has been found to be overexpressed in high grade and metastatic brain tumors. Hence, OPN expression correlates with the malignancy grade of gliomas.

VIPR-2 (Vasoactive Intestinal Peptide Receptor-2)

Vasoactive intestinal polypeptide receptor II (VIPR-2), VPAC-2, is a member of the G-protein receptor family, which includes such members as the calcitonin, parathyroid hormone, secretin, glucagon and VIP-1 receptors. VIPR-2 is a seven-transmembrane spanning G protein-coupled receptor that responds to VIP by stimulating cAMP production. VIPR-2 is found in the brain as well as peripheral tissues such as the pancreas, skeletal muscle, heart, lung, kidneys, stomach, adipocytes and the liver, and in various cells of the immune system. In the brain, VIPR-2 functions as a neuroendocrine hormone and neurotransmitter receptor, and is found in the thalamus, hippocampus, suprachiasmatic nucleus and hypothalamus.

VIPR-2 is encoded by a nucleotide sequence of approximately 2.8 kb, which codes for a 438 amino acid sequence of approximately 48–64 kDa. The receptor-ligand pair, VIPR-2 and VIP, have various functions dependent upon the tissue where in they are located. VIP is a late-developing, 28 amino acid peptide that, along with its receptor, is widely distributed throughout the peripheral body, and plays a role in cardiovascular, reproductive, pulmonary, immune and gastrointestinal systems, to effect vasodilatation, bronchodilation, immunosuppression, hormonal secretion, and increased gastric motility. However, the cerebral cortex has one of the highest reported concentrations of VIP, localized to intrinsic neurons throughout all neocortical regions. In the brain, VIP and its receptor, have behavioral, electrophysiological, secretory, metabolic, vascular, and mitogenic effects. For instance, the receptor-ligand pair play a role in cortical differentiation, the relaying of sensory information to the cortex, and the regulation of morphogenic events by the release of diffusible signals from glial cells. VIPR-2 and VIP also play a role in the growth and differentiation of neuroblastomas.

TSPAN3 (Tetraspanin 3, Tetraspanin TM-4A)

The Tetraspanin superfamily, is a family of approximately 20 integral membrane proteins that are broadly expressed in most human tissues including neural and bone marrow derived tissues. The family shares a common motif that includes four putative transmembrane domains (TM1–4), a small extracellular domain (EC1) of 20–27 amino acids, and a larger extracellular domain (EC2) between TMS3 and TMS4 of 70–130 amino acids. Two conserved features of tetraspanins are critical to their structure and function. First, charged residues are present in or near the TM domains, second, a cluster of cysteine residues is in the putative EC2 domain. Most of the tetraspanins are modified by N-glycosylation.

Many Tetraspanin proteins affect the regulation of cellular proliferation, motility, differentiation, development. In some cells, Tetraspanins may act as adapters in ultimeric complexes that link plasma membrane proteins, like integrins, into signaling complexes with other signaling molecules (e.g., phosphatidylinositol 4-kinase) at the plasma membrane and play a role in integrin-mediated cell migration, metastasis and tumor cell invasion. A number of tetraspanins have also been discovered as tumor-associated proteins, including C-029, PETA-3/SFA-1, and SAS, which is amplified in a subset of sarcomas. Of the various TM4SF proteins, CD9, CD63, CD81, CD82, and CD151 are the most widely distributed. CD9 is expressed on 90% of non-T cell acute lymphoblastic leukemia cells and on 50% of chronic lymphocytic and acute myeloblastic leukemias. CD63 is also expressed in early stage melanomas.

Protein Tyrosine Phosphatase Receptor Zeta (PTPζ)

Vital cellular functions, such as cell proliferation and signal transduction, are regulated in part by the balance between the activities of protein kinases and protein phosphatases. These protein-modifying enzymes add or remove a phosphate group from serine, threonine, or tyrosine residues in specific proteins. Some tyrosine kinases (PTK's) and phosphatases (PTPase's) have been theorized to have a role in some types of oncogenesis, which is thought to result from an imbalance in their activities. There are two classes of PTPase molecules: low molecular weight proteins with a single conserved phosphatase domain such as T-cell protein-tyrosine phosphatase (PTPT; MIM 176887), and high molecular weight receptor-linked PTPases with two tandemly repeated and conserved phosphatase domains separated by 56 to 57 amino acids. Examples of this latter group of receptor proteins include: leukocyte-common antigen (PTPRC; MIM 151460) and leukocyte antigen related tyrosine phosphatase (PTPRF; MIM 179590).

Protein tyrosine phosphatase zeta (PTPζ) [also known as PTPRZ, HPTP-ZETA, HPTPZ, RPTP-BETA(β), or RPTPB] was isolated as a cDNA sequence by two groups in the early nineties. The complete cDNA sequence of the protein is provided in SEQ ID NO. 1, and the complete deduced amino acid sequence is provided in SEQ ID NO. 2. Splicing variants and features are indicated in the sequences. Levy et al. ("The cloning of a receptor-type protein tyrosine phosphatase expressed in the central nervous system" *J. Biol. Chem.* 268: 10573–10581, (1993)) isolated cDNA clones from a human infant brain step mRNA expression library, and deduced the complete amino acid sequence of a large receptor-type protein tyrosine phosphatase containing 2,307 amino acids.

Levy found that the protein, which they designated PTP-β (PTPζ), is a transmembrane protein with 2 cytoplasmic PTPase domains and a 1,616-amino acid extracellular domain. As in PTP-γ (MIM 176886), the 266 N-terminal residues of the extracellular domain are have a high degree of similarity to carbonic anhydrases (see MIM 114880). The human gene encoding PTPζ has been mapped to chromosome 7q31.3–q32 by chromosomal in situ hybridization (Ariyama et al., "Assignment of the human protein tyrosine phosphatase, receptor-type, zeta (PTPRZ) gene to chromosome band 7q31.3" *Cytogenet. Cell Genet.* 70:52–54 (1995)). Northern blot analysis has shown that showed that PTP-zeta is expressed only in the human central nervous system. By in situ hybridization, Levy et al. (1993) localized the expression to different regions of the adult human brain, including the Purkinje cell layer of the cerebellum, the dentate gyrus, and the subependymal layer of the anterior horn of the lateral ventricle. Levy stated that this was the first mammalian tyrosine phosphatase whose expression is restricted to the nervous system. In addition, high levels of expression in the murine embryonic brain suggest an important role in CNS development.

Northern analysis has shown three splice variants: the extracellular proteoglycan phosphacan, which contains the full extracellular region of the protein, and the long (α) and short (β) forms of the transmembrane phosphatase. The β form lacks the extracellular 860 aa long insert domain of the protein, therefore it is not glycosylated. PCR studies of the gene in rat genomic DNA indicated that there are no introns at the putative 5' and 3' splice sites or in the 2.6 kb segment which is deleted in the short transmembrane protein. The phosphatases and the extracellular proteoglycan have different 3'-untranslated regions. Additional alternative mRNA splicing is likely to result in the deletion of a 7 amino acid insert from the intracellular juxtamembrane region of both long and short phosphatase isoforms. Simultaneous quantitation of the three major isoforms indicated that the mRNA encoding phosphacan had the highest relative abundance in the CNS while that encoding the short phosphatase isoform was most abundant relative to the other PTPζ variants in the PNS.

PTPζ has only been found to be expressed in the nervous system. By in situ hybridization, it has been localized to different regions of the adult brain, including the Purkinje cell layer of the cerebellum, the dentate gyrus, and the subependymal layer of the anterior horn of the lateral ventricle. High levels of PTPζ have been seen in regions of the brain where there is continued neurogenesis and neurite outgrowth, and it seems to play a role in morphogenesis and plasticity of the nervous system. Phosphacan immunoreactivity has been associated with perineuronal nets around parvalbumin-expressing neurons in adult rat cerebral cortex. Neurons as well as astrocytes have been shown to express phosphacan.

The transmembrane forms of PTPζ are expressed on the migrating neurons especially at the lamellipodia along the leading processes. PTPζ is postulated to be involved in the neuronal migration as a neuronal receptor of pleiotrophin distributed along radial glial fibers. PTPζ has been shown to be highly expressed in radial glia and other forms of glial cells that play an important role during development. The anti-PTPζ staining localizes to the radial processes of these cells, which act as guides during neuronal migration and axonal elongation. The pattern of RPTP-zeta expression has also been shown to change with the progression of glial cell differentiation.

The three splicing variants of RPTP-zeta have been shown to have different spatial and temporal patterns of expression in the developing brain. The 9.5-kb and 6.4-kb transcripts, which encode the α and β transmembrane protein tyrosine phosphatases, were predominantly expressed in glial progenitors located in the subventricular zone. The 8.4-kb transcript, which encodes the secreted chondroitin sulfate proteoglycan phosphacan, was expressed at high levels by more mature glia that have migrated out of the subventricular zone. The three transcripts have also been shown to be differentially expressed in glial cell cultures.

In knockout studies, PTPζ-deficient mice were viable, fertile, and showed no gross anatomical alterations in the nervous system or other organs. Therefore, it was deduced that PTPζ is not essential for neurite outgrowth and node formation in mice. The ultrastructure of nerves of the central nervous system in PTPζ-deficient mice suggests a fragility of myelin. However, conduction velocity was not altered. The normal development of neurons and glia in was thought to indicate that PTPζ function is not necessary for these processes in vivo, or that a loss of PTPζ can be compensated for by other protein tyrosine phosphatases expressed in the nervous system.

Following CNS injury, robust induction of phosphatase forms of PTPζ mRNA has been observed in areas of axonal sprouting, and of both phosphatases and phosphacan mRNAs in areas of glial scarring. This is thought to imply that the encoded proteins and the cell adhesion molecules and extracellular matrix proteins to which they bind may contribute to recovery from injury and perhaps also to the regulation of axonal regrowth in the nervous system. Following peripheral nerve crush, all PTPζ mRNAs, including phosphacan and the phosphatase variants with and without the 21 base insert, were observed to be significantly induced in the distal segments of the sciatic nerve with a time course that correlated well with the response of Schwann cells to this injury.

The extracellular domains of PTP, have been shown to be capable of binding to several cell adhesion molecules. Phosphacan, which is the shortest, secreted form of PTPζ, containing the full extracellular region, previously was designated 3F8 and 6B4 chondroitin sulfate proteoglycan or 3H1 keratin sulfate proteoglycan depending on the glycosylation status. It is synthesized mainly by glia and binds to neurons and to the neural cell adhesion molecules Ng-CAM/

L1, NCAM, TAG-1/axonin-1, to tenascin-C and R, to amphoterin and pleiotrophin/heparin-binding growth-associated molecule (HB-GAM) (amphoterin and pleiotrophin are heparin-binding proteins that are developmentally regulated in brain and functionally involved in neurite outgrowth). Binding of phosphacan to Ng-CAM/L1, NCAM, and tenascin-C (FNIII domain) is mediated by complex-type N-linked oligosaccharides on the proteoglycan. Phosphacan, shows saturable, reversible, high-affinity binding to fibroblast growth factor-2 (FGF-2). The interaction is mediated primarily through the core protein. Immunocytochemical studies have also shown an overlapping localization of FGF-2 and phosphacan in the developing central nervous system. The core protein of phosphacan may also regulate the access of FGF-2 to cell surface signaling receptors in nervous tissue.

The carbonic anhydrase (CAH) domain of PTPζ has been shown to bind specifically to contactin. Contactin is a 140 kDa GPI membrane-anchored neuronal cell recognition protein expressed on the surface of neuronal cells. The CAH domain of RPTP zeta was shown to induce cell adhesion and neurite growth of primary tectal neurons, and differentiation of neuroblastoma cells. These responses were blocked by antibodies against contactin, demonstrating that contactin is a neuronal receptor for RPTP zeta. Caspr ((p190/Caspr, a contactin-associated transmembrane receptor) and contactin exist as a complex in rat brain and are bound to each other by means of lateral (cis) interactions in the plasma membrane. The extracellular domain of Caspr contains a neurophilin/coagulation factor homology domain, a region related to fibrinogen beta/gamma, epidermal growth factor-like repeats, neurexin motifs as well as unique PGY repeats found in a molluscan adhesive protein. The cytoplasmic domain of Caspr contains a proline-rich sequence capable of binding to a subclass of SH3 domains of signaling molecules. Caspr may function as a signaling component of contactin, enabling recruitment and activation of intracellular signaling pathways in neurons. The role of the extracellular domains in neural adhesion and neurite growth induction was investigated by the use of fusion protein constructs. The results suggested that binding of glial PTPζ to the contactin/Nr-CAM complex is important for neurite growth and neuronal differentiation.

PTPζ was shown to bind to a heparin-binding growth factor midkine through the chondroitin sulfate portion of the receptor. The interactions of pleiotrophin (PTN) with the receptor in U373-MG cells was also studied. Pleiotrophin was shown to bind to the spacer domain. Results suggested that PTN signals through "ligand-dependent receptor inactivation" of PTPζ and disrupts its normal roles in the regulation of steady-state tyrosine phosphorylation of downstream signaling molecules. PTN was shown to bind to and functionally inactivate the catalytic activity of PTPζ. An active site-containing domain of PTPζ both binds β-catenin and functionally reduces its levels of tyrosine phosphorylation when added to lysates of pervanadate-treated cells. In unstimulated cells, PTPζ was shown to be intrinsically active, and thought to function as an important regulator in the reciprocal control of the steady-state tyrosine phosphorylation levels of β-catenin by tyrosine kinases and phosphatases.

Using the yeast substrate-trapping system, several substrate candidates for PTPζ were isolated. The results indicated that GIT1/Cat-1 is a substrate molecule of PTPζ. In addition, PTPζ was shown to bind to the PSD-95/SAP90 family through the second phosphatase domain. Immunohistochemical analysis revealed that PTPζ and PSD-95/SAP90 are similarly distributed in the dendrites of pyramidal neurons of the hippocampus and neocortex. Subcellular fractionation experiments indicated that PTPζ is concentrated in the postsynaptic density fraction. These results suggested that PTPζ is involved in the regulation of synaptic function as postsynaptic macromolecular complexes with PSD-95/SAP90.

Voltage-gated sodium channels in brain neurons were also found to associate with the membrane bound forms of PTPζ and phosphacan. Both the extracellular domain and the intracellular catalytic domain of PTPζ interacted with sodium channels. Sodium channels were tyrosine phosphorylated and were modulated by the associated catalytic domains of PTPζ.

SUMMARY OF THE INVENTION

The present invention provides novel methods and reagents for specifically targeting brain tumor neoplastic cells for both therapeutic and imaging purposes, by targeting brain tumor protein targets ($T_{BT}$). These targets have been identified by the applicants as being overexpressed in brain tumors, and thus allow for the selective inhibition of cell function or selective marking for visualization with therapeutic or visualizing compositions which have a specific affinity for these protein targets. Each of angiopoietin related protein 2 (ARP-2,) secreted protein acidic, rich in cysteine (SPARC,) c-met proto-oncogene (C-MET,) brevican (BEHAB,) CD-44 antigen (CD-44,) tetraspanin 3 (TSPN3,) pleiotrophin (PTN,) osteopontin (OPN,) vasoactive intestinal peptide receptor-2 (VIPR-2,) and receptor protein tyrosine phosphatase zeta (PTPζ) [including the two novel isoforms PTPζ SM1 and SM2], as the proteins are described below, have been identified as an independantly useful protein target $T_{BT}$. In some preferred embodiments of the invention, either novel isofom PTPζ SM1 or PTPζ SM2 is the protein target $T_{BT}$. Thus, the aspects of the invention with relation to each of these $T_{BT}$ are described generally as follows:

In a first aspect, the present invention provides $T_{BT}$ affinity-based compounds and compositions useful in treating a brain tumor in a patient. The compositions and compounds of this aspect of the invention generally fall into two groups: $T_{BT}$-binding conjugate compounds, which comprise a cytotoxic moiety (C), which inhibits the growth of tumor cells; and $T_{BT}$-binding compound compositions in which the $T_{BT}$ binding moiety alters the normal function of the $T_{BT}$ in or around the tumor cell, thus inhibiting cell growth and/or function.

In a first group of embodiments of this aspect of the invention, $T_{BT}$-binding therapeutic conjugate compounds are provided. These compounds have the general formula $\alpha(T_{BT})C$, wherein $\alpha(T_{BT})$ is one or more moieties which specifically binds to a $T_{BT}$, and C is one or more cytotoxic moieties. In preferred embodiments, $\alpha(T_{BT})$ is an antibody or an antibody fragment. In particularly preferred embodiments, $\alpha(T_{BT})$ is an antibody or an antibody fragment which elicits a reduced immune response when administered to a human patient. Preferred cytotoxic moieties for use in these embodiments of the invention include radioactive moieties, chemotoxic moieties, and toxin proteins. The invention also provides compositions comprising these $T_{BT}$-binding therapeutic conjugate compounds in a pharmaceutically acceptable carrier.

In a second group of embodiments of this first aspect of the invention, $T_{BT}$-binding therapeutic compounds are provided which alter the normal function of the $T_{BT}$ in or around brain tumor cells and inhibit brain tumor cell growth. These $T_{BT}$-binding therapeutic compounds have the general formula $\alpha(T_{BT})$, wherein $\alpha(T_{BT})$ is one or more moieties which specifically binds to a $T_{BT}$, and wherein the binding of $\alpha(T_{BT})$ alters the function of the $T_{BT}$. In preferred embodiments, $\alpha(T_{BT})$ is an antibody or an antibody fragment. In particularly preferred embodiments, $\alpha(T_{BT})$ is an antibody or an antibody fragment which elicits a reduced immune response when administered to a human patient. It is preferred that the therapeutic compounds of this second group of embodiments of the first aspect of the invention be formulated into therapeutic compositions comprising the $T_{BT}$-binding compound in a pharmaceutically acceptable carrier.

In a second aspect, the present invention provides methods for using these compounds and compositions to treat a brain tumor in a patient. The methods comprise administering an effective amount of a composition, comprising a $T_{BT}$-binding compound from the first or second group of embodiments of the first aspect and a pharmaceutically acceptable carrier, to a patient in need thereof. Brain tumors treated in this fashion may be glioblastomas, astrocytomas, neuroblastomas, or any type of brain tumor. Administration of the therapeutic composition may be by any acceptable means. One preferred method for administration is by intrathecal administration, although intravascular administration is also preferred.

In a third aspect, the present invention provides $T_{BT}$ affinity-based compounds and compositions for the visualization of brain tumors in patients. These compounds have the general formula $\alpha(T_{BT})I$, wherein $\alpha(T_{BT})$ is one or more moieties which specifically binds to a $T_{BT}$, and I is one or more imaging moieties. In preferred embodiments, $\alpha(T_{BT})$ is an antibody or an antibody fragment. In particularly preferred embodiments, $\alpha(T_{BT})$ is an antibody or an antibody fragment which elicits a reduced immune response when administered to a human patient. Preferred I moieties include radiographic moieties (useful in, e.g., x-ray, scintillation, or other radiation imaging methods,) positron-emitting moieties, magnetic spin contrast moieties, and optically visible moieties (such as visible particles, fluorescent dyes, and visible-spectrum dyes.) It is preferred that the imaging compounds of these embodiments of the third aspect of the invention be formulated into therapeutic compositions comprising the $T_{BT}$-binding compound in a pharmaceutically acceptable carrier.

In a fourth aspect, the present invention provides methods of using the compounds and compositions of the third aspect of the invention to visualize a brain tumor in a patient. These methods generally comprise administering an effective amount of an imaging compound of the general formula $\alpha(T_{BT})I$ in a pharmaceutically acceptable carrier to the patient, and then visualizing the imaging moieties of the compound. Administration of the imaging composition may be by any acceptable means. Intravascular administration of the imaging composition is preferred in these methods, although intrathecal administration is also preferred. Preferred methods of visualizing the imaging moieties of the compounds include radiographic imaging techniques (e.g., x-ray imaging and scintillation imaging techniques), positron-emission tomography, magnetic resonance imaging techniques, and direct or indirect (e.g., endoscopic) visual inspection.

Various particular embodiments of these aspects of the invention include:

A method to treat a brain tumor by administering a therapeutic amount of a composition comprising a compound of the general formula $\alpha(ARP2)C$, wherein $\alpha(ARP2)$ is one or more moieties which specifically binds to a human angiopoietin related protein-2, and C is one or more cytotoxic moieties, and a pharmaceutically acceptable carrier.

A compound for the treatment of a brain tumor of the general formula $\alpha(ARP2)C$, wherein $\alpha(ARP2)$ is one or more moieties which specifically binds to a human angiopoietin related protein-2, and C is one or more cytotoxic moieties.

A method to treat a brain tumor by administering a therapeutic amount of a composition comprising a compound of the general formula $\alpha(ARP2)$, wherein $\alpha(ARP2)$ is one or more moieties which specifically binds to a human angiopoietin related protein-2, wherein the binding of $\alpha(ARP2)$ alters the function of the angiopoietin related protein-2, and a pharmaceutically acceptable carrier.

A method for visualizing a brain tumor in a patient by first administering to a patient an effective amount of a composition comprising: a compound of the general formula $\alpha(ARP2)I$, wherein $\alpha(ARP2)$ is one or more moieties which specifically binds to a human angiopoietin related protein-2, and I is one or more imaging moieties and a pharmaceutically acceptable carrier, and then visualizing the imaging moieties of the compound.

A composition for the visualization of a brain tumor comprising a compound of the general formula $\alpha(ARP2)I$, wherein $\alpha(ARP2)$ is one or more moieties which specifically binds to a human angiopoietin related protein-2, and I is one or more imaging moieties, and a pharmaceutically acceptable carrier.

A method to treat a brain tumor by administering a therapeutic amount of a composition comprising a compound of the general formula $\alpha(TSPAN3)C$, wherein $\alpha(TSPAN3)$ is one or more moieties which specifically binds to a human tetraspanin 3, and C is one or more cytotoxic moieties, and a pharmaceutically acceptable carrier.

A compound for the treatment of a brain tumor of the general formula $\alpha(TSPAN3)C$, wherein $\alpha(TSPAN3)$ is one or more moieties which specifically binds to a human tetraspanin 3, and C is one or more cytotoxic moieties.

A method to treat a brain tumor by administering a therapeutic amount of a composition comprising a compound of the general formula $\alpha(TSPAN3)$, wherein $\alpha(TSPAN3)$ is one or more moieties which specifically binds to a human tetraspanin 3, wherein the binding of $\alpha(TSPAN3)$ alters the function of the tetraspanin 3, and a pharmaceutically acceptable carrier.

A composition for the treatment of a brain tumor comprising: a compound of the general formula $\alpha(TSPAN3)$, wherein $\alpha(TSPAN3)$ is one or more moieties which specifically binds to a human tetraspanin 3, wherein the binding of $\alpha(TSPAN3)$ alters the function of the tetraspanin 3, and a pharmaceutically acceptable carrier.

A method for visualizing a brain tumor in a patient by first administering to a patient an effective amount of a composition comprising: a compound of the general formula $\alpha(TSPAN3)I$, wherein $\alpha(TSPAN3)$ is one or more moieties which specifically binds to a human tetraspanin 3, and I is one or more imaging moieties, and a pharmaceutically acceptable carrier, and then visualizing the imaging moieties of the compound.

A composition for the visualization of a brain tumor comprising a compound of the general formula $\alpha(TSPAN3)I$, wherein $\alpha(TSPAN3)$ is one or more moieties which specifically binds to a human tetraspanin 3, and I is one or more imaging moieties, and a pharmaceutically acceptable carrier.

A method to treat a brain tumor by administering a therapeutic amount of a composition comprising a compound of the general formula α(PTPζ)C, wherein α(PTPζ) is one or more moieties which specifically binds to a human PTPζ selected from the group consisting of PTPζ SM1 and PTPζ SM2, further wherein α(PTPζ) does not specifically bind to human PTPζ α, human PTPζ β, or phosphacan, and C is one or more cytotoxic moieties, and a pharmaceutically acceptable carrier.

A compound for the treatment of a brain tumor of the general formula α(PTPζ)C, wherein α(PTPζ) is one or more moieties which specifically binds to a human PTPζ selected from the group consisting of PTPζ SM1 And PTPζ SM2, further wherein α(PTPζ) does not specifically bind to human PTPζ α, human PTPζ β, or human phosphacan, and C is one or more cytotoxic moieties.

A method to treat a brain tumor by administering a therapeutic amount of a composition comprising a compound of the general formula α(PTPζ), wherein α(PTPζ) is one or more moieties which specifically binds to a human PTPζ selected from the group consisting of PTPζ SM1 And PTPζ SM2, further wherein α(PTPζ) does not specifically bind to human PTPζ α, human PTPζ β, or phosphacan, wherein the binding of α(PTPζ) alters the function of the human PTPζ , and a pharmaceutically acceptable carrier.

A composition for the treatment of a brain tumor comprising a compound of the general formula α(PTPζ), wherein α(PTPζ) is one or more moieties which specifically binds to PTPζ selected from the group consisting of PTPζ SM1 And PTPζ SM2, further wherein α(PTPζ) does not specifically bind to human PTPζ α, human PTPζ β, or phosphacan, wherein the binding of α(PTPζ) alters the function of the PTPζ, and a pharmaceutically acceptable carrier.

A method for visualizing a brain tumor in a patient by first administering to a patient an effective amount of a composition comprising: a compound of the general formula α(PTPζ)I, wherein α(PTPζ) is one or more moieties which specifically binds to a human PTPζ selected from the group consisting of PTPζ SM1 And PTPζ SM2, further wherein α(PTPζ) does not specifically bind to human PTPζ α, human PTPζ β, or phosphacan, and I is one or more imaging moieties and a pharmaceutically acceptable carrier, and then visualizing the imaging moieties of the compound.

A composition for the visualization of a brain tumor comprising a compound of the general formula α(PTPζ)I, wherein α(PTPζ) is one or more moieties which specifically binds to a human PTPζ selected from the group consisting of PTPζ SM1 And PTPζ SM2, further wherein α(PTPζ) does not specifically bind to human PTPζ α, human PTPζ β, or phosphacan, and I is one or more imaging moieties, and a pharmaceutically acceptable carrier.

A method to treat a brain tumor by administering a therapeutic amount of a composition comprising a compound of the general formula α(SPARC)C, wherein α(SPARC) is one or more moieties which specifically binds to a human secreted protein, rich in cysteine, and C is one or more cytoloxic moieties, and a pharmaceutically acceptable carrier.

A compound for the treatment of a brain tumor of the general formula α(SPARC)C, wherein α(SPARC) is one or more moieties which specifically binds to a human secreted protein, rich in cysteine, and C is one or more cytotoxic moieties.

A method to treat a brain tumor by administering a therapeutic amount of a composition comprising a compound of the general formula α(SPARC), wherein α(SPARC) is one or more moieties which specifically binds to a human secreted protein, rich in cysteine, wherein the binding of α(SPARC) alters the function of the secreted protein, rich in cysteine, and a pharmaceutically acceptable carrier.

A method for visualizing a brain tumor in a patient by first administering to a patient an effective amount of a composition comprising: a compound of the general formula α(SPARC)I, wherein α(SPARC) is one or more moieties which specifically binds to a human secreted protein, rich in cysteine, and I is one or more imaging moieties, and a pharmaceutically acceptable carrier, and then visualizing the imaging moieties of the compound.

A composition for the visualization of a brain tumor comprising a compound of the general formula α(SPARC)I, wherein α(SPARC) is one or more moieties which specifically binds to a human secreted protein, rich in cysteine, and I is one or more imaging moieties, and a pharmaceutically acceptable carrier.

A method to treat a brain tumor by administering a therapeutic amount of a composition comprising a compound of the general formula α(c-MET)C, wherein α(c-MET) is one or more moieties which specifically binds to a human c-MET oncogene product, and C is one or more cytotoxic moieties and a pharmaceutically acceptable carrier.

A method to treat a brain tumor by administering a therapeutic amount of a composition comprising a compound of the general formula α(c-MET), wherein α(c-MET) is one or more moieties which specifically binds to a human c-MET oncogene product, wherein the binding of α(TSPAN3) alters the function of the c-MET oncogene product, and a pharmaceutically acceptable carrier.

A method for visualizing a brain tumor in a patient by first administering to a patient an effective amount of a composition comprising: a compound of the general formula α(c-MET)I, wherein α(c-MET) is one or more moieties which specifically binds to a human c-MET oncogene product, and I is one or more imaging moieties and a pharmaceutically acceptable carrier, and then visualizing the imaging moieties of the compound.

A method to treat a brain tumor by administering a therapeutic amount of a composition comprising a compound of the general formula α(CD44)C, wherein α(CD44) is one or more moieties which specifically binds to a human CD44 antigen, and C is one or more cytotoxic moieties, and a pharmaceutically acceptable carrier.

A method to treat a brain tumor by administering a therapeutic amount of a composition comprising a compound of the general formula α(CD44), wherein α(CD44) is one or more moieties which specifically binds to a human CD44 antigen, wherein the binding of α(CD44) alters the function of the CD44 antigen, and a pharmaceutically acceptable carrier.

A method for visualizing a brain tumor in a patient by first administering to a patient an effective amount of a composition comprising: a compound of the general formula α(CD44)I, wherein α(CD44) is one or more moieties which specifically binds to a human CD44 antigen, and I is one or more imaging moieties, and a pharmaceutically acceptable carrier, and then visualizing the imaging moieties of the compound.

A method to treat a brain tumor by administering a therapeutic amount of a composition comprising a compound of the general formula α(VIPR2)C, wherein α(VIPR2) is one or more moieties which specifically binds to a human vasoactive intestinal peptide receptor-2, and C is one or more cytotoxic moieties and a pharmaceutically acceptable carrier.

A method to treat a brain tumor by administering a therapeutic amount of a composition comprising a compound of the general formula α(VIPR2), wherein α(VIPR2) is one or more moieties which specifically binds to a human vasoactive intestinal peptide receptor-2, wherein the binding of α(VIPR2) alters the function of the vasoactive intestinal peptide receptor-2, and a pharmaceutically acceptable carrier.

A method for visualizing a brain tumor in a patient by first administering to a patient an effective amount of a composition comprising: a compound of the general formula α(VIPR2)I, wherein α(VIPR2) is one or more moieties which specifically binds to a human tetraspanin 3, and I is one or more imaging moieties, and a pharmaceutically acceptable carrier, and then visualizing the imaging moieties of the compound.

A method to treat a brain tumor by administering a therapeutic amount of a composition comprising a compound of the general formula α(OPN)C, wherein α(OPN) is one or more moieties which specifically binds to a human osteopontin, and C is one or more cytotoxic moieties and a pharmaceutically acceptable carrier.

A compound for the treatment of a brain tumor of the general formula α(OPN)C, wherein α(OPN) is one or more moieties which specifically binds to a human tetraspanin 3, and C is one or more cytotoxic moieties.

A method to treat a brain tumor by administering a therapeutic amount of a composition comprising a compound of the general formula α(OPN), wherein α(OPN) is one or more moieties which specifically binds to a human osteopontin, wherein the binding of α(OPN) alters the function of the osteopontin, and a pharmaceutically acceptable carrier.

A method for visualizing a brain tumor in a patient by first administering to a patient an effective amount of a composition comprising: a compound of the general formula α(OPN)I, wherein α(OPN) is one or more moieties which specifically binds to a human osteopontin, and I is one or more imaging moieties, and a pharmaceutically acceptable carrier, and then visualizing the imaging moieties of the compound.

A composition for the visualization of a brain tumor comprising a compound of the general formula α(OPN)I, wherein α(OPN) is one or more moieties which specifically binds to a human osteopontin, and I is one or more imaging moieties, and a pharmaceutically acceptable carrier.

A method to treat a brain tumor by administering a therapeutic amount of a composition comprising a compound of the general formula α(PTN)C, wherein α(PTN) is one or more moieties which specifically binds to a human pleiotrophin, and C is one or more cytotoxic moieties, and a pharmaceutically acceptable carrier.

A compound for the treatment of a brain tumor of the general formula α(PTN)C, wherein α(PTN) is one or more moieties which specifically binds to a human pleiotrophin, and C is one or more cytotoxic moieties.

A method to treat a brain tumor by administering a therapeutic amount of a composition comprising a compound of the general formula α(PTN), wherein α(PTN) is one or more moieties which specifically binds to a human pleiotrophin, wherein the binding of α(PTN) alters the function of the pleiotrophin, and a pharmaceutically acceptable carrier.

A method for visualizing a brain tumor in a patient by first administering to a patient an effective amount of a composition comprising: a compound of the general formula α(PTN)I, wherein α(PTN) is one or more moieties which specifically binds to a human pleiotrophin, and I is one or more imaging moieties, and a pharmaceutically acceptable carrier, and then visualizing the imaging moieties of the compound.

A composition for the visualization of a brain tumor comprising a compound of the general formula α(PTN)I, wherein α(PTN) is one or more moieties which specifically binds to a human pleiotrophin, and I is one or more imaging moieties, and a pharmaceutically acceptable carrier.

Brain tumors are known to be relatively heterogeneous, and thus all patients may not respond the same to a particular protein target treatment. Thus, in addition to the independent uses of each of the $T_{BT}$ protein targets as described above, the invention also provides, in yet another aspect, combination therapeutic and/or visualization agents, compositions, and methods. These combination embodiments of the invention may utilize as brain tumor protein targets any two or more of the identified targets angiopoietin related protein 2 (ARP-2,) secreted protein acidic, rich in cysteine (SPARC,) c-met proto-oncogene (c-MET,) brevican (BEHAB,) CD-44 antigen (CD-44,) tetraspanin 3 (TSPN3,) pleiotrophin (PTN,) osteopontin (OPN,) vasoactive intestinal peptide receptor-2 (VIPR-2,) and receptor protein tyrosine phosphatase zeta (PTPζ) [including the two novel isoforms PTPζ SM1 and SM2]. In some preferred embodiments, the brain tumor protein targets are selected from the group consisting of angiopoietin related protein 2 (ARP-2,) c-met proto-oncogene (c-MET,) CD-44 antigen (CD-44,) tetraspanin 3 (TSPN3,) osteopontin (OPN,) and receptor protein tyrosine phosphatase zeta (PTPζ). Embodiments of the combination aspect of the invention may target a group of proteins from the identified targets with similar compartmentalization characteristics. Thus, the combination aspects may target two or more secreted proteins from the group angiopoietin related protein 2 (ARP-2,) secreted protein acidic, rich in cysteine (SPARC,) brevican (BEHAB,) pleiotrophin (PTN,) secreted forms of receptor protein tyrosine phosphatase zeta (PTPζ) [including the novel isoform PTPζ SM 1]. Or, the combination aspects may target one or more of the extracellular matrix binding proteins secreted protein acidic, rich in cysteine (SPARC,) and/or brevican (BEHAB,) with one or more of the other identified protein targets. Or, the combination aspects may target one or more of the membrane-bound proteins from the group c-met proto-oncogene (c-MET,) CD-44 antigen (CD-44,) tetraspanin 3 (TSPN3,) osteopontin (OPN,) vasoactive intestinal peptide receptor-2 (VIPR-2,) and membrane bound forms of receptor protein tyrosine phosphatase zeta (PTPζ) [including the novel isoform PTPζ SM2].

In preferred embodiments, at least one of the protein targets is selected from the proteins angiopoietin related protein 2 (ARP-2,) tetraspanin 3 (TSPN3,), and receptor protein tyrosine phosphatase zeta (PTPζ) [including the two novel isoforms PTPζ SM1 and SM2]. In other preferred embodiments, one of these proteins and another protein selected from the secreted group, the extracellular matrix group, or the membrane-bound group. In another group of preferred embodiments are combination aspects targeting two or more of angiopoietin related protein 2 (ARP-2,) tetraspanin 3 (TSPN3,), and receptor protein tyrosine phosphatase zeta (PTPζ) [including the two novel isoforms PTPζ SM1 and SM2]. Another group of preferred embodiments are combination aspects which target angiopoietin related protein 2 (ARP-2), and one or more proteins selected from the group secreted protein acidic, rich in cysteine (SPARC,) c-met proto-oncogene (C-MET,) brevican (BEHAB,) CD-44 antigen (CD-44,) tetraspanin 3 (TSPN3,) pleiotrophin (PTN,) osteopontin (OPN,) vasoactive intestinal peptide receptor-2 (VIPR-2,) and receptor protein tyrosine phosphatase zeta (PTPζ) [including the two novel isoforms PTPζ SM1 and SM2]. Another group of preferred embodiments are combination aspects which target tetraspanin 3 (TSPN3), and one or more proteins selected from the group secreted protein acidic, rich in cysteine (SPARC,) c-met proto-oncogene (C-MET,) brevican (BEHAB,) CD-44 antigen (CD-44,) angiopoietin related protein 2 (ARP-2,) pleiotrophin (PTN,) osteopontin (OPN,) vasoactive intestinal peptide receptor-2 (VIPR-2,) and receptor protein tyrosine phosphatase zeta (PTPζ) [including the two novel isoforms PTPζ SM1 and SM2]. Another group of preferred embodiments are combination aspects which target receptor protein tyrosine phosphatase zeta (PTPζ) [including the two novel isoforms PTPζ SM1 and SM2] and one or more proteins selected from the group angiopoietin related protein 2 (ARP-2,) secreted protein acidic, rich in cysteine (SPARC,) c-met proto-oncogene (C-MET,) brevican (BEHAB,) CD-44 antigen (CD-44,) tetraspanin 3 (TSPN3,) pleiotrophin (PTN,) osteopontin (OPN,) and vasoactive intestinal peptide receptor-2 (VIPR-2.) As pleiotrophin (PTN) is a known ligand of PTPζ, another preferred embodiment of the combination aspects of the invention utilizes these proteins as targets, either alone or in combination with one or more of the other identified targets.

In yet another aspect, the present invention provides two novel splicing isoforms of PTPζ, shown to be expressed in brain tissue. These novel isoforms, PTPζ SM1 and PTPζ SM2, described in more detail below, differ in structure from the three known isoforms heretofore disclosed. PTPζ SM1 comprises the amino acids encoded by the first nine exons of PTPζ-.alpha., with three unique additional carboxy terminal amino acids encoded by additional 3' mRNA sequence from the intron of the gene between exons nine and ten. The mRNA for PTPζ SM2 comprises all exons of PTPζ-.alpha., with a 116 nucleotide insertion, in the correct reading frame, in the mRNA sequence between exons 23 and 24, from the intron of the gene between exons 23 and 24. Thus, embodiments of this aspect of the invention include the mature proteins of PTPζ splice variants SM1 or SM2, and nucleic acids encoding these novel spice variants, as well proteins with significant homology to the splice variants.

Thus, in one group of embodiments of this aspect, the invention provides nucleic acid polymers comprising the sequence of nucleotides 148 to 1272 of SEQ ID NO. 1, the complement of nucleotides 148 to 1272 of SEQ ID NO. 1, nucleotides 148 to 7209 of SEQ ID NO. 3, or the complement of nucleotides 148 to 7209 of SEQ ID NO. 3. In another group of embodiments of this aspect, the invention provides polypeptides comprising the amino acid sequence of SEQ ID NO. 2 or the amino acid sequence of SEQ ID NO. 4.

In an additional related aspect, the invention provides polypeptides comprising a distinctive portion of the amino acid sequence of SEQ ID NO. 2 or SEQ ID NO. 4. Such peptides are useful for the production of antibodies against the PTPζ SM1 or SM2 splicing variants. Preferably, these polypeptides comprise a portion of the amino acid sequence of SEQ ID NO. 2 or SEQ ID NO. 4 which is at least 6, more preferably at least 8, more preferably at least 10, more preferably at least 15, and most preferably at lest 20 amino acids in length. In some preferred embodiments of this aspect of the invention, the polypeptides comprise the three unique terminal amino acids of PTPζ SM1 after exon 9. In other preferred embodiments, the polypeptides comprise a portion of the unique exon 23a of PTPζ SM2, wherein the portion is preferably at least 3 amino acids in length, more preferably at least 6 amino acids in length, more preferably at least 9 amino acids in length, and most preferably at least 15 amino acids in length.

In an additional related aspect, the invention also provides affinity reagents which specifically bind to PTPζ splice variants SM1 or SM2, but do not bind to the other known splice variants of PTPζ (e.g., α, β, or phosphacan forms). In preferred embodiments these affinity reagents are antibodies or antibody fragments.

In an additional related aspect, the invention also provides nucleic acid sequences encoding the PTPζ splice variants SM1 or SM2. The invention also encompasses nucleic acid probes which hybridize to the mRNA encoding PTPζ splice variants SM1 or SM2, but not mRNA encoding other known splice variants of PTPζ.

DETAILED DESCRIPTION OF THE INVENTION

Figure 1:
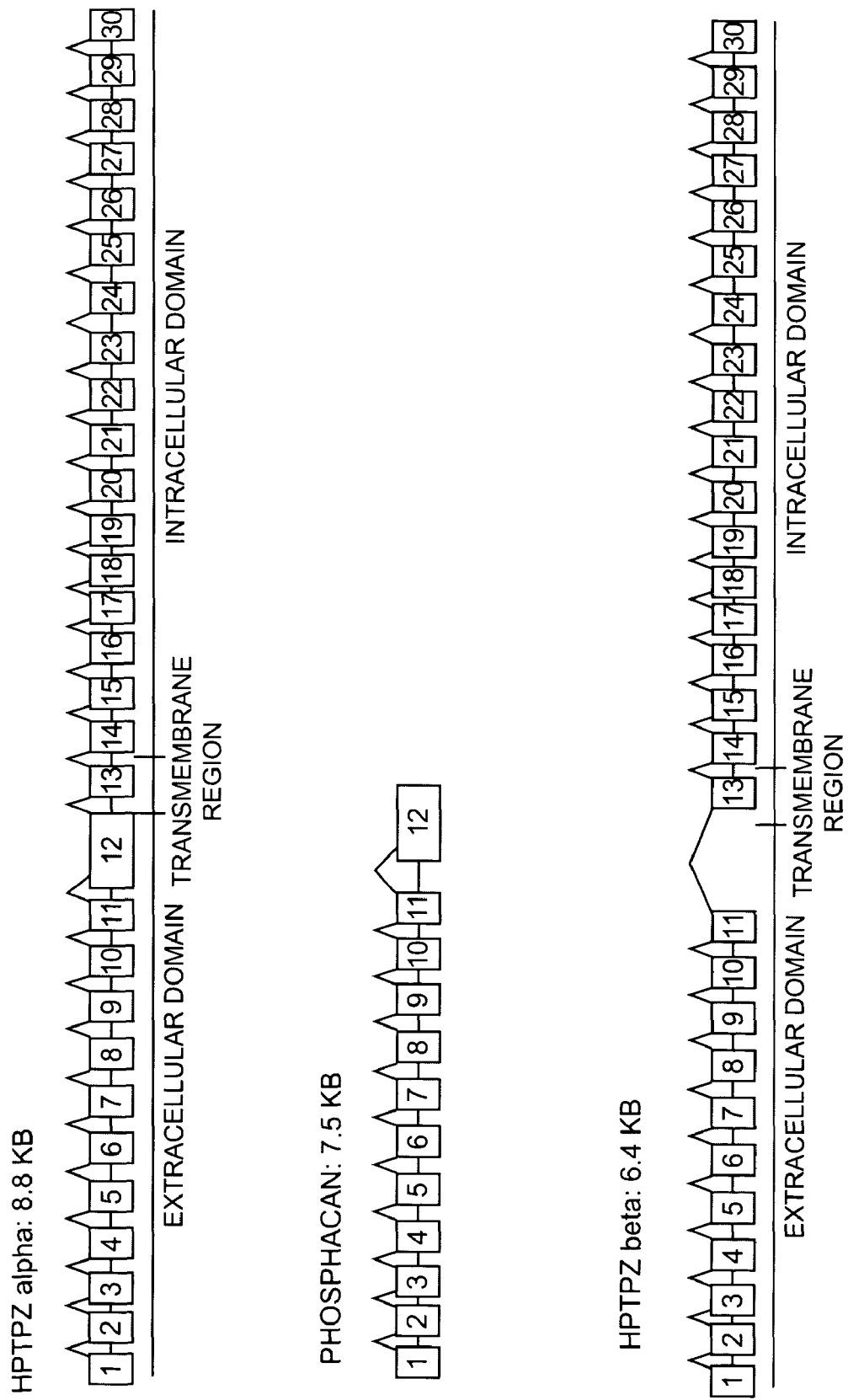
FIG. 1: A diagram of the three known splicing variant isoforms of PTPζ. The approximate position of the domains of the isoforms is indicated underneath the isoforms, as well as the approximate exon size (for size reference, exon 12 is 3.6 kilobases.) Isoform PTPζ-α is the full length isoform, which contains the primary amino acid sequence aa 25-2314 of SEQ ID NO. 2 (aa 1–24 are a signal polypeptide). In Isoform PTPζ-β, aa 755–1614 are missing. Isoform PTPζ-S (phosphacan), is a secreted isoform which comprise the extracellular domains of PTPζ-α, in which the transmembrane and cytosol domains are missing.

Applicants have identified several brain tumor protein targets and genes which are differentially regulated between brain cancer tissue (glioblastoma) and normal brain tissue. Applicants have performed differential cloning between cancerous and normal brains and have identified the brain tumor protein target genes by DNA sequence analysis. Based on the observation in other diseases, particularly other cancers, in which overexpressed genes can contribute to the pathology of the disease, these overexpressed genes and their protein products mediate the initiation and progression of brain tumors. Thus, the overexpressed brain tumor protein targets, which are presented on the cell surface, provide excellent targets for immunotherapeutic agents which either deliver cytotoxic agents to directly promote tumor cell death, or which alter the function of the brain tumor protein targets to inhibit the normal physiology of the tumor cell. In addition, immunoimaging agents targeted to the brain tumor protein targets may be utilized to visualize the tumor mass either in diagnostic methods (e.g., magnetic resonance imaging (MRI) or radiography), or in surgery (e.g., by the use of optically visual dye moieties in the immunoimaging agent).

Applicants have identified the brain tumor protein targets by a direct examination of the expression level of genes in actual tumor cells. These samples provide a more accurate and realistic picture of tumor cell biology, especially on the detailed transcriptome level, than animal models or established cell tissue culture cell lines. Several groups have found that cell lines established from astrocytomas and other cell lines do not exhibit expression patterns which reflect the actual expression of the original tumor. For instance, Schreiber, et. al., "Primary brain tumors differ in their expression of octamer deoxyribonucleic acid-binding transcription factors from long-term cultured glioma cell lines." *Neurosurgery* 34: 129–35 (1994), showed that nervous system-specific transcription factors known as N-Oct proteins are differentially expressed in human neuroblastoma and glioblastoma cell lines in vitro. However, when these results were compared to freshly isolated human primary and metastatic brain tumors, of the five astrocytomas and three glioblastomas analyzed, all but two tumors displayed the complete N-Oct protein profile, irrespective of histopathological tumor grade. Similarly, Eberle , et al., "The expression of angiogenin in tissue samples of different brain tumors and cultured glioma cells." *Anticancer Res* 20: 1679–84 (2000), could show that angiogenin is detectable in different kinds of intracranial tumor tissue samples. Although angiogenin could be detected in primary cultivated glioma cells, it was not detected in the permanent cell lines. Finally, Hartmann, et al., "The rate of homozygous CDKN2A/p16 deletions in glioma cell lines and in primary tumors." *Int J Oncol* 15: 975–82 (1999), showed that the rate of homozygous deletions of CDKN2A/p16 is variable between different tumor entities, but the rate of deletions is higher in established cell lines in comparison with primary tumors. Hartmann hypothesized that such incongruity may reflect statistical sampling errors, true differences depending on tissue derivatization and CDKN2A/p16 loss under selective pressure in tissue culture. After comparing established cell lines derived from human glioblastomas and their corresponding primary tumors by multiplex PCR methodology, they found that in 2 of 11 cases (18%) the primary tumor had no p16 alteration whereas the corresponding cell lines had a homozygous p16 deletion, and that CDKN2A/p16 was lost already in the earliest passages of the cell lines. Thus, Hartmann concluded that the deletion was the result of selective cell-culture pressures in many cases.

These inconsistent results arise because the tumor tissue samples are obtained from their native milieu, without allowing them the opportunity to alter their gene expression levels in response to artificial environmental stimuli. As recently reported by the Brain Tumor Progress Review group of the National Cancer Institute in November, 2000, conventionally used glioblastoma cell lines contain genetic and gene expression alterations that are well defined and do not necessarily reflect the primary tumors from which they were derived. In addition, these cell lines are highly homogenous, unlike a primary brain tumor. Therefore, data derived soley from a cell line cannot reliably reflect the biology, heterogeneity, or therapeutic response of a primary brain tumor.

Applicants obtained tumor tissue, snap frozen in the operation hall from unknown patients, which was confirmed as glioblastoma grade IV by neuropathology. These tissues served as the experimental sample. Human whole brain tissue (Clontech Laboratories, Palo Alto, USA) served as control sample. Poly-A$^+$ RNA prepared from the cells was converted into double-stranded cDNA (dscDNA).

Briefly, the ds-cDNA's from control and disease states were subjected to kinetic re-annealing hybridization during which normalization of transcript abundances and enrichment for differentially expressed transcripts (i.e., subtraction) occurs. Normalized-subtracted ds-cDNAs were cloned into a plasmid vector, a large number of recombinant bacterial clones were picked, and their recombinant inserts were isolated by PCR. High-density cDNA arrays of those PCR products were screened with cDNA probes derived from the original control and disease states. Thus, only clones displaying a significant transcriptional induction and/or repression were sequenced and carried forward for massive expression profiling using a variety of temporal, spatial and disease-related probe sets.

The selected PCR products (fragments of 200–2000 bp in size) from clones showing a significant transcriptional induction and/or repression were sequenced and functionally annotated in AGY's proprietary database structure (See WO01/13105). Because large sequence fragments were utilized in the sequencing step, the data generated has a much higher fidelity and specificity than other approaches, such as SAGE. The resulting sequence information was compared to public databases using the BLAST (blastn) and tblastx algorithm. The results are listed in Table 1, below:

TABLE 1

| PROTEIN | RELATIVE EXPRESSION LEVEL | NUMBER OF CLONES ISOLATED (out of 20,000) |
| --- | --- | --- |
| ARP2 | ~2 times | 13 |
| SPARC | ~2–5.6 times | 100 |
| CMET | ~1.2–2.5 times | 30 |
| CD 44 | ~2.3–3.0 times | 6 |
| BEHAB | ~2–6 times | 180 |
| TSPAN3 | ~2.0–3.0 times | 7 |
| VIPR2 | ~3.0 times | 3 |
| OPN | ~2.0–3.0 times | 19 |
| PTN | ~~1.8–2.6 times | 26 |
| PTPζ | ~2.0–4.0 times | 20 |

As one of skill in the art will appreciate from this data, each of these proteins is individually useful as a target for the treatment and/or imaging of brain tumors.

Characteristics of Protein Targets Utilized in the Invention

ARP2

Given the experiments described above, and the results of Table 1, ARP-2 was selected as a target for selective immuno-therapeutic agents in targeting and/or imaging brain tumors. The mature protein consists of 493 amino acids and contains two potential consensus glycosylation sites. The complete cDNA sequence encoding ARP-2 is provided in SEQ ID NO. 7, and the complete amino acid sequence of ARP-2 is provided in SEQ ID NO. 8. ARP-2 is a 64 kDa, single chain, acidic, angiopoeitin-like protein that includes multiple functional domains, such as a hydrophobic signal sequence from amino acids 1–21 (which is typical of secreted proteins), a coiled-coil domain at the amino terminal end from approximately-amino acid sequences 22–274, and a fibrinogen-like domain, from approximately about residues 275 through 493. Two major isoforms have been observed, one 2.4 Kb in size and the other about 4 Kb. Both forms are abundant in heart, small intestine, spleen and stomach.

As used herein, a compound that specifically binds to ARP-2 is any compound (such as an antibody) that has a binding affinity for any naturally occurring isoform, splice variant, or polymorphism of ARP-2, explicitly including the isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater than 99% identity) with the amino acid sequence of ARP-2. Such proteins include truncated forms or domains of ARP-2, and recombinantly engineered alterations of ARP-2. For example, a portion of SEQ ID NO. 8 may be engineered to include a non-naturally occurring cysteine for cross linking to an immunoconjugate protein, as described.

In general, it is preferred that the antibodies utilized in the compositions and methods of the invention bind to the fibrinogen domain but need not be restricted to this domain. The antibody may bind to the extracellular region of ARP-2. It is to be noted that antibodies which bind to this secreted protein are useful in the invention as cytotoxic delivery agents, as well as functional inhibition agents, as one of ordinary skill would expect that the concentration of ARP-2 would be increased adjacent the tumor cells which, due to the need for vascularization, over-express the protein.

When raising antibodies to ARP-2, the entire protein (either the unsecreted precursor or the secreted protein), or a portion thereof, may be utilized. For instance, the carboxyl-terminal fibrinogen like domain, or any portion of the amino-terminal coiled-coil domain may be utilized. For instance, amino acids 22–274, which make up the fibrinogen like domain, may be used. Larger ARP-2 proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the ARP-2 protein (or a portion thereof) can serve as the ARP-2 antigen. When a smaller peptide is utilized, it is advantageous to conjugate the peptide with a larger molecule to make an immunostimulatory conjugate for use as the ARP-2 antigen. Commonly utilized conjugate proteins that are commercially available for such use include bovine serum albumin (BSA) and keyhole limpet hemocyanin (KLH). In order to raise antibodies to particular epitopes, peptides derived from the full ARP-2 sequence may be utilized. Preferably, one or more 8–30 aa peptide portions of the EC domain of ARP-2 are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to ARP-2 may be deduced by those of skill in the art by homology analysis of SEQ ID NO. 8.

The fibrinogen domain of human ARP-2 is hypothesized to interact with one or more an unknown receptor for the purposes of angiogenesis. The interaction of ARP-2 to these molecules may be through either of the aforementioned structural motifs. Thus, in alternative embodiments of the compositions and methods of the invention, antibody moieties are utilized which bind to ARP-2 at a site on the protein that alters the binding of an extracellular molecule to ARP-2. Such ARP-2 activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ARP-2 to a receptor may be accomplished by a straightforward binding inhibition/enhancement assay. According to standard techniques, the binding of a labeled (e.g., fluorescently or enzyme-labeled) antibody to ARP-2, which has been immobilized in a microtiter well, is assayed in both the presence and absence of the appropriate ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as ARP-2 ligand-binding inhibitors or enhancers.

In addition, antibodies which are useful for altering the function of ARP-2 may be assayed in functional formats, such as endothelial sprouting assays and cell migration assays described in the examples. Thus, antibodies that exhibit the appropriate anti-tumor effect may be selected without direct knowledge of a binding ligand.

SPARC

Given the experiments described above, and the results of Table 1, SPARC was selected as a target for selective immuno-therapeutic agents in targeting and/or imaging brain tumors. The mature protein consists of 286 amino acids (after cleavage of the signal peptide) and contains two potential Asn-X-Thr/Ser N-glycosylation sites, located at positions 71 and 99 of the mature protein. The complete cDNA sequence encoding SPARC is provided in SEQ ID NO. 9, and the complete amino acid sequence of SPARC is provided in SEQ ID NO. 10. SPARC is an abundant 33 kDa, single chain, acidic, extracellular calcium binding protein that contains a flexible N-terminal acidic domain I (~50 amino acids), a follistatin-like (FS) domain (~75 residues), and a C-terminal extracellular calcium-binding (EC) domain with a pair of EF-hand loops (~150 residues). The N-terminal domain shows a low affinity Ca2+ binding site, a transglutaminase cross linking site, and inhibits cell spreading in cell culture assays. Calcium-dependent binding of SPARC to the triple helix of several fibrillar collagen types and basement membrane collagen type IV has been mapped to the EC domain. Two isoforms have been described, bone SPARC with a molecular weight of 31,000 kDa and platelet SPARC with a molecular weight of 33,000 kDa.

As used herein, a compound that specifically binds to SPARC is any compound (such as an antibody) that has a binding affinity for any naturally occurring isoform, splice variant, or polymorphism of SPARC, explicitly including the isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater than 99% identity) with the amino acid sequence of SPARC. Such proteins include truncated forms or domains of SPARC, and recombinantly engineered alterations of SPARC. For example, a portion of SEQ ID NO. 10 may be engineered to include a non-naturally occurring cysteine for cross linking to an immunoconjugate protein, as described.

In general, it is preferred that the antibodies utilized in the compositions and methods of the invention bind to the extracellular domain (amino acids 130–280). It is preferable that this binding inhibit the activity of SPARC. The antibody may bind to the EF hand which is known to bind Ca2+ with high affinity, but need not be restricted to this domain. It is to be noted that antibodies which bind to SPARC are useful in both cytotoxic and imaging embodiments of the invention, as one of ordinary skill would expect that the concentration of SPARC in the extracellular matrix would be increased around tumor cells which over-express the protein.

When raising antibodies to SPARC the entire protein (either the unsecreted precursor or the secreted protein), or a portion thereof, may be utilized. For instance, the C terminal extracellular (EC) domain, or any portion of the flexible N-terminal domain I, or FS domain may be utilized. For instance, amino acids 125–275, which make up the EC domain, may be used. Larger SPARC proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the SPARC protein (or a portion thereof) can serve as the SPARC antigen. When a smaller peptide is utilized, it is advantageous to conjugate the peptide with a larger molecule to make an immunostimulatory conjugate for use as the SPARC antigen. Commonly utilized conjugate proteins that are commercially available for such use include bovine serum albumin (BSA) and keyhole limpet hemocyanin (KLH). In order to raise antibodies to particular epitopes, peptides derived from the full SPARC sequence may be utilized. Preferably, one or more 8–30 aa peptide portions of the EC domain of SPARC are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to SPARC, including glycosylation sites, is provided in SEQ ID NO. 10.

The EC domain of human SPARC is known to interact with the collagens I, III, IV and V, and to bind to vitronectin, all of which are components of the extracellular matrix surrounding gliomas. The binding of SPARC to these molecules may play a significant role in the oncogenesis and growth of neoplastic cells in the brain. Thus, in alternative embodiments of the compositions and methods of the invention, antibody moieties are utilized which bind to SPARC at a site on the protein that alters the binding of an extracellular molecule, such as an ECM molecule, to SPARC. Such SPARC activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ligand to SPARC may be accomplished by a straightforward binding inhibition/enhancement assay. According to standard techniques, the binding of a labeled (e.g., fluorescently or enzyme-labeled) antibody to SPARC, which has been immobilized in a microtiter well, is assayed in both the presence and absence of the appropriate ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as SPARC ligand-binding inhibitors or enhancers.

In addition, antibodies which are useful for altering the function of SPARC may be assayed in functional formats, such as the HUVEC tube assay and cell migration assay. Thus, antibodies that exhibit the appropriate anti-tumor effect may be selected without direct knowledge of a binding ligand or molecular function.

c-MET

Given the experiments described above, and the results of Table 1, c-MET was selected as a target for selective immuno-therapeutic agents in targeting and/or imaging brain tumors. The complete cDNA sequence encoding c-MET is provided in SEQ ID NO. 11, and the complete amino acid sequence of c-MET is provided in SEQ ID NO. 12. c-MET is a type I membrane protein heterodimer. Generally, two different receptor variants originate by post-translational processing of a common singe-chain precursor of 170 kDa. Isoform p190MET is formed of a 50 kDa α-chain and a 145 kDa β-chain that are disulfide linked, and isoform p140Met is formed of a 50 kDa α-chain and an 85 kDa β-chain, lacking the cytoplasmic kinase domain. This 85 kDa β chain is likely a trans-membrane glycoprotein that is bound to the cell surface. Truncated forms of c-MET containing the 50 kDa α-chain and a carboxyl-terminally truncated 75 kDa β sub-unit have also been described. The 75 kDa form arises by post-translational proteolytic processing, lacks the trans-membrane domain, and is secreted from the cell.

As used herein, a compound that specifically binds to c-MET is any compound (such as an antibody) that has a binding affinity for any naturally occurring isoform, splice variant, or polymorphism of c-MET, explicitly including the three isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater then 99% identity) with the amino acid sequence of c-MET. Such proteins include truncated forms or domains of c-MET, and recombinantly engineered alterations of c-MET. For example, a portion of SEQ ID NO. 12 may be engineered to include a non-naturally occurring cysteine for cross-linking to an immunoconjugate protein, as described below.

In general, it is preferred that the antibodies utilized in the compositions and methods of the invention bind to the membrane-bound isoforms of the protein, as this will more specifically target the cytotoxic therapeutic agent, or the imaging agent, to the brain tumor cell. However, embodiments that utilize antibodies that bind to the secreted isoform of the protein are also useful in the invention, as one of ordinary skill would expect that the concentration of the secreted isoform would also be increased adjacent to brain tumor cells which over-express the protein.

The amino acid sequence of full length c-MET consists of 1408 amino acids, as the sequence was first deduced by Park et al., ("Sequence of MET proto-oncogene cDNA has features characteristic of the tyrosine kinase family of growth-factor receptors" *Proc. nat. Acad. Sci. U.S.A.* 84:6379–6383 (1987)) and 1390 amino acids, as later deduced by Prat et al. ("C-terminal truncated forms of Met, the Hepatocyte Growth Factor" *Mol. Cell. Biol.* 11:5954–5962 (1991)). According to Prat et al., the first N-terminal amino acids 1–24 of SEQ ID NO. B' [B'] are for the most part hydrophobic, and could serve as a signal sequence for transporting the protein into the lumen of the endoplasmic reticulum. The α chain makes up the extracellular domain of the mature c-MET protein and spans amino acids 24–306 of SEQ ID NO. 12. The β chain would consist of 1,084–5 amino acids with the predicted β chain extracellular domain being amino acids 306 to 932, the single transmembrane hydrophobic segment being amino acids 933 to 955, and the intracellular domain being amino acids 956 to 1390 of SEQ ID NO 12.

When raising antibodies to c-MET, the entire protein, a dimeric subunit, or a portion thereof may be utilized. For instance, the extracellular domain of the α or β sub-units or the secreted or extracellular portion of the truncated forms may be utilized. For instance, amino acids that constitute the α sub-unit, amino acids 24–306, may be used. Larger c-MET proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the c-MET protein (or a portion thereof) can serve as the c-MET antigen. When a smaller peptide is utilized, it is advantageous to conjugate the peptide with a larger molecule to make an immunostimulatory conjugate for use as the c-MET antigen. Commonly utilized conjugate proteins that are commercially available for such use include bovine serum albumin (BSA) and keyhole limpet hemocyanin (KLH). In order to raise antibodies to particular epitopes, peptides derived from the full c-MET sequence may be utilized. Preferably, one or more 8–30 amino acid peptide portions of an extracellular domain of c-MET are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to c-MET, including glycosylation sites, is provided in SEQ ID NO. 12.

The extracellular domain of human c-MET binds hepatocyte growth factor (HGF). Because HGF is largely expressed in mesenchymal and neuroectodermal tissues and released to the extracellular compartment, paracrine and/or autocrine signaling implicate tumor genesis in mesenchymal and neuroectodermal tumors and other tumor cells that over express the c-MET receptor. Recent studies have shown that the c-MET proto-oncogene is frequently overexpressed in many types of epithelial tumors, in spontaneously transformed NIH/3T3 fibroblasts, and in peripheral nerve sheath tumors. In alternative embodiments of the compositions and methods of the invention, antibody moieties are utilized which bind to c-MET at a site on the protein which alters the binding of an extracellular ligand molecule, such as HGF, to c-MET. Such c-MET activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies that alter (enhance or inhibit) the binding of a ligand to c-MET may be accomplished by a straightforward binding inhibition/enhancement assay. According to standard techniques, the binding of a labeled (e.g., fluorescently or enzyme-labeled) antibody to c-MET, which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as c-MET ligand-binding inhibitors or enhancers.

In addition, antibodies that are useful for altering the function of c-MET may be assayed in functional formats, such as the endothelial sprouting assay and cell migration assay. Thus, antibodies which exhibit the appropriate anti-tumor effect may be selected without direct knowledge of a molecular function.

BEHAB

Given the experiments described above, and the results of Table I, BEHAB was selected as a target for selective immuno-therapeutic agents in targeting and/or imaging brain tumors. The complete cDNA sequence encoding BEHAB GPI isoform is provided in SEQ ID NO. 13, and the complete amino acid sequence of this BEHAB isoform is provided in SEQ ID NO. 14. Two isoforms have been isolated to date: a full-length isoform that is secreted into the extracellular matrix and a shorter isoform that has a hydrophobic carboxy terminus instead of the typical lectican carboxyl terminus, which predicts a glycophosphatidylinositol (GPI) anchor. BEHAB contains an N-terminal hyaluronan (HA)-binding domain, which comprises an immunoglobulin-like loop and two proteoglycan tandem repeats, a C-terminal epidermal growth factor (EGF)-like repeat, a C-type lectin-like domain, and a complement regulatory protein (CRP)-like domain. The central region of the protein contains sites for glycosylation and proteolytic cleavage (between glu395-Ser396 of the mature protein, after signal peptide cleavage) by metallo-protease. The complete cDNA of the secreted isoform is 2878 bp encoding 912 amino acids of 99 kDa. The GPI isoform, for which sequences SEQ ID NO. 13 and SEQ ID NO. 14 are given, is 2558 bp encoding 672 amino acids of 72 kDa. The GPI-linked form is generated by a 'no splice' event, with the transcript reading through an exon/intron junction thereby extending the open reading frame to a stop codon 74 nucleotides further downstream.

As used herein, a compound that specifically binds to BEHAB is any compound (such as an antibody) that has a binding affinity for any naturally occurring isoform, splice variant, or polymorphism of BEHAB, explicitly including the two splice variants described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater then 99% identity) with the amino acid sequence of BEHAB. Such proteins include truncated forms or domains of BEHAB, and recombinantly engineered alterations of BEHAB. For example, a portion of SEQ ID NO. 14 may be engineered to include a non-naturally occurring cysteine for cross-linking to an immunoconjugate protein, as described below.

In general, it is preferred that the antibodies utilized in the compositions and methods of the invention bind to the membrane-bound isoform of the protein, as this will more specifically target the cytotoxic therapeutic agent, or the imaging agent, to the brain tumor cell. However, embodiments that utilize antibodies that bind to the secreted isoform of the protein are also useful in the invention, as one of ordinary skill would expect that the concentration of the secreted isoform would also be increased adjacent to brain tumor cells which over-express the protein.

When raising antibodies to BEHAB, the entire protein, or a portion thereof, may be utilized. For instance, any one of the aforementioned domains of the secreted protein or an extracellular portion of the truncated, membrane bound GPI form may be utilized. For instance, amino acids that constitute the hyaluronic acid binding domain, amino acids 44–247, which includes the Ig like domain at amino acids 44–140, may be used. Larger BEHAB proteins and domains may be produced utilizing any suitable recombinant vector/protein production system, such as the baculovirus transfection system outlined below, after being amplified from a fetal brain cDNA library (as available from, e.g., Clontech, Palo alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the Brevican protein (or a portion thereof) can serve as the BEHAB antigen. When a smaller peptide is utilized, it is advantageous to conjugate the peptide with a larger molecule to make an immunostimulatory conjugate for use as the BEHAB antigen. Commonly utilized conjugate proteins that are commercially available for such use include bovine serum albumin (BSA) and keyhole limpet hemocyanin (KLH). In order to raise antibodies to particular epitopes, peptides derived from the full Brevican sequence may be utilized. Preferably, one or more 8–30 amino acid peptide portions of an extracellular domain of BEHAB are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred.

The hyaluronic acid binding domain of human BEHAB binds to hyaluronic acid (HA). Because HA is largely expressed in the ECM surrounding gliomas and because recent studies have shown that the BEHAB protein is frequently overexpressed in primary brain tumors, it is suggested that the up-regulation of BEHAB may be a crucial step in returning the unmalleable mature extracellular matrix to a more immature matrix, permissive for cell growth, thereby promoting the progression of primary brain tumors. Thus, in alternative embodiments of the compositions and methods of the invention, antibody moieties are utilized which bind to BEHAB at a site on the protein which alters the binding of an extracellular ligand molecule (e.g., HA) to BEHAB. Such BEHAB activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies that alter (enhance or inhibit) the binding of a ligand to BEHAB may be accomplished by a straightforward binding inhibition/enhancement assay. According to standard techniques, the binding of a labeled (e.g., fluorescently or enzyme-labeled) antibody to BEHAB, which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as BEHAB ligand-binding inhibitors or enhancers.

In addition, antibodies that are useful for altering the function of BEHAB may be assayed in functional formats, such as the HUVEC tube assay and the cell migration assay described below. Thus, antibodies which exhibit the appropriate anti-tumor effect may be selected without direct knowledge of molecular function.

CD-44

Given the experiments described above, and the results of Table 1, CD-44 was selected as a target for selective immuno-therapeutic agents in targeting and/or imaging brain tumors. The complete cDNA sequence encoding CD-44 E is provided in SEQ ID NO. 15, and the complete amino acid sequence of CD-44, indicating various splicing variation locations, is provided in SEQ ID NO. 16. CD-44 is a proteoglycan that is expressed as two major splice variants. CD-44E is a 150 kDa protein isolated from epithelial cells. CD-44E has a C-terminal cytoplasmic tail, a hydrophobic transmembrane domain of 23 amino acids, and an N-terminal extracellular region of 248 amino acids. The extracellular domain is O-glycosylated and also binds chondroitin sulfate. In addition, CD-44E it has two of the three immunodominant epitope clusters of native gp90Hermes. CD-44E contains an additional 132 amino acids in the extracellular region. and CD-44H is a 90 kDa protein isolated from hematopoietic cells. In addition, CD-44R1 and CD-44R2 are 2 isoforms expressed by hematopoietic cells. The complete cDNA sequence of the 90 kDa CD-44H isoform consist of 1795 bps, encoding a 341 amino acid protein.

As used herein, a compound that specifically binds to CD-44 is any compound (such as an antibody) that has a binding affinity for any naturally occurring isoform, splice variant, or polymorphism of CD-44, explicitly including the isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater then 99% identity) with the amino acid sequence of CD-44. Such proteins include truncated forms or domains of CD-44, and recombinantly engineered alterations of CD-44. For example, a portion of SEQ ID NO. 16 may be engineered to include a non-naturally occurring cysteine for cross-linking to an immunoconjugate protein, as described below.

According to the human full length, CD-44H protein has an overall primary structure of 90 kDa, which consist of 341 amino acids. The N-terminus is located outside of the cell and the extracellular domain consist of 248 amino acids. The C-terminus is located inside of the cell and the intracellular domain consist of 72 amino acids, while the transmembrane region consist of 21 amino acids. The CD-44 gene contains 20 exons, of which exons 1–5, 15–17 and 19 encode the CD44H isoform. The intervening exons 6, 6a, 7–14 (also designated v1-v10) are alternatively spliced to generate the variant isoforms with an insertion at the membrane proximal region of the extracellular domain between amino acids 202 and 203. See Bajorath (2000). *Proteins: structure, function, and genetic,* 39:103–111; and Ilangumaram et al. *Leukemia and Lymphoma,* 35:455–469.

When raising antibodies to CD-44, the entire protein, or a portion thereof, may be utilized. For instance, any portion of the extracellular domain may be utilized. For instance, the amino acids between the signal sequence and amino acid 202 may be used. Larger CD-44 proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the CD-44 protein (or a portion thereof) can serve as the CD-44 antigen. When a smaller peptide is utilized, it is advantageous to conjugate the peptide with a larger molecule to make an immunostimulatory conjugate for use as the CD-44 antigen. Commonly utilized conjugate proteins that are commercially available for such use include bovine serum albumin (BSA) and keyhole limpet hemocyanin (KLH). In order to raise antibodies to particular epitopes, peptides derived from the full CD-44 sequence may be utilized. Preferably, one or more 8–30 amino acid peptide portions of an extracellular domain of CD-44 are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to CD-44, including glycosylation sites, is provided in SEQ ID NO. D'.

Hyaluronan (HA) is a polymeric glycosaminoglycan and a major component of the extracellular matrix. CD-44 is one of the principal receptors for HA. Within the normal CNS, the CD-44 protein has been localized to astrocytes in the white matter. CD-44H has been shown to be the predominant isoform in normal brain and neuroectoderm-derived tumors. Hence, the up-regulation of CD-44 may be a crucial step in brain tumor invasiveness and migration. Thus, in alternative embodiments of the compositions and methods of the invention, antibody moieties are utilized which bind to CD-44 at a site on the protein which alters the binding of an extracellular ligand molecule (e.g., HA) to CD-44. Such CD-44 activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies that alter (enhance or inhibit) the binding of a ligand to CD-44 may be accomplished by a straightforward binding inhibition/enhancement assay. According to standard techniques, the binding of a labeled (e.g., fluorescently or enzyme-labeled) antibody to CD-44, which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as CD-44 ligand-binding inhibitors or enhancers.

In addition, antibodies that are useful for altering the function of CD-44 may be assayed in functional formats, such as endothelial sprouting assay and cell migration assay. Thus, antibodies which exhibit the appropriate anti-tumor effect may be selected without direct knowledge of molecular function.

TSPAN3

Given the experiments described above, and the results of Table 1, TSPAN3 was selected as a target for selective immuno-therapeutic agents in targeting and/or imaging brain tumors. The complete cDNA sequence encoding TSPAN3 is provided in SEQ ID NO. 17, and the complete amino acid sequence of TSPAN3 is provided in SEQ ID NO. 18. Tetraspanin is a 253 amino acid membrane bound protein. No isoforms have been isolated to date. TSPAN3, as is characteristic of the tetraspanin family, contains four transmembrane domains, putatively comprising amino acids 12–32, 51–71, 86–106, and 213–233. The protein has two putative extracellular domains, amino acids 33–50 and 107–212, and three putative cytoplasmic domains, amino acids 1–11, 72–85, and 234–235. Putative N-linked glycosylation sites are listed in SEQ ID NO. 18.

As used herein, a compound that specifically binds to TSPAN3 is any compound (such as an antibody) that has a binding affinity for any naturally occurring isoform, splice variant, or polymorphism of TSPAN3. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater then 99% identity) with the amino acid sequence of TSPAN3. Such proteins include truncated forms or domains of TSPAN3, and recombinantly engineered alterations of TSPAN3. For example, a portion of SEQ ID NO. 18 may be engineered to include a non-naturally occurring cysteine for cross-linking to an immunoconjugate protein, as described below.

In general, it is preferred that the antibodies utilized in the compositions and methods of the invention bind to the membrane-bound isoform of the protein, as this will more specifically target the cytotoxic therapeutic agent, or the imaging agent, to the brain tumor cell. The only currently known form of TSPAN3 is membrane-bound. However, embodiments that utilize antibodies that bind to any secreted isoform of the protein are also useful in the invention, as one of ordinary skill would expect that the concentration of the secreted isoform would also be increased adjacent to brain tumor cells which over-express the protein. Likewise, it is preferred that the antibodies utilized in the invention bind to an extracellular domain of the protein, as are described in the SEQ ID NO. 18. The cysteine residues at positions 147, 148, and 197 of SEQ ID NO. 18 in the second extracellular domain are highly conserved among the tetraspanin family and are thought to be essential for proper tetraspanin function. Thus, in some preferred embodiments of the invention, the antibodies utilized in the invention bind to an epitope comprising, or alternatively very near to, one of these cysteine residues.

When raising antibodies to TSPAN3, the entire protein, or a portion thereof, may be utilized. For instance, any one of the aforementioned domains of the secreted protein or an extracellular portion of the truncated, membrane bound GPI form may be utilized. For instance, amino acids that constitute one of the extracellular domains, amino acids 33–50 or 107–212, may be used. Larger TSPAN3 proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the tetraspanin 3 protein (or a portion thereof) can serve as the TSPAN3 antigen. When a smaller peptide is utilized, it is advantageous to conjugate the peptide with a larger molecule to make an immunostimulatory conjugate for use as the TSPAN3 antigen. Commonly utilized conjugate proteins that are commercially available for such use include bovine serum albumin (BSA) and keyhole limpet hemocyanin (KLH). In order to raise antibodies to particular epitopes, peptides derived from the full Brevican sequence may be utilized. Preferably, one or more 8–30 amino acid peptide portions of an extracellular domain of TSPAN3 are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to TSPAN3, including glycosylation sites, is provided in SEQ ID NO. 18.

In alternative embodiments of the compositions and methods of the invention, antibody moieties are utilized which bind to TSPAN3 at a site on the protein which alters the binding of an extracellular ligand molecule to TSPAN3. Such TSPAN3 activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies that alter (enhance or inhibit) the binding of a ligand to TSPAN3 may be accomplished by a straightforward binding inhibition/enhancement assay. According to standard techniques, the binding of a labeled (e.g., fluorescently or enzyme-labeled) antibody to TSPAN3, which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as TSPAN3 ligand-binding inhibitors or enhancers.

In addition, antibodies that are useful for altering the function of TSPAN3 may be assayed in functional formats, such as the HUVEC tube assay and the cell migration assay described below. Thus, antibodies which exhibit the appropriate anti-tumor effect may be selected without direct knowledge of molecular function.

VIPR-2

Given the experiments described above, and the results of Table 1, VIPR-2 was selected as a prime target for selective immuno-therapeutic agents in targeting and/or imaging brain tumors. The complete cDNA sequence encoding VIPR-2 is provided in SEQ ID NO. 19, and the complete amino acid sequence of VIPR-2 is provided in SEQ ID NO. 20. VIPR-2 is a seven transmembrane spanning G-protein receptor. The complete VIPR-2 protein is encoded by 13 exons. The initiator codon of the approximated 438 amino acid-encoding open reading frame is located in exon 1 and the termination signal is located in exon 13. The 5' untranslated region extends 187 bp upstream of the initiator codon and is extremely GC-rich (80%). The polyadenylation signal is located 2416 bp downstream of the stop codon. Intron sizes range from 68 bp (intron 11) to 45 bp (intron 4), the entire human gene spans 117 kb, while the cDNA sequence spans 1317 bp. Recent studies have also isolated two VIP-2 receptor mRNAs of 4.6 kb and 2.3 kb in size.

As used herein, a compound that specifically binds to VIPR-2 is any compound (such as an antibody) that has a binding affinity for any naturally occurring isoform, splice variant, or polymorphism of VIPR-2, explicitly including any isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater then 99% identity) with the amino acid sequence of VIPR-2. Such proteins include truncated forms or domains of VIPR-2, and recombinantly engineered alterations of VIPR-2. For example, a portion of SEQ ID NO. 20 may be engineered to include a non-naturally occurring cysteine for cross-linking to an immunoconjugate protein, as described below.

In general, it is preferred that the antibodies utilized in the compositions and methods of the invention bind to the membrane-bound isoforms of the protein, as this will more specifically target the cytotoxic therapeutic agent, or the imaging agent, to the brain tumor cell. However, embodiments that utilize antibodies that bind to the secreted isoform of the protein are also useful in the invention, as one of ordinary skill would expect that the concentration of the secreted isoform would also be increased adjacent to brain tumor cells which over-express the protein.

The amino acid sequence of full length VIPR-2 consists of 437 amino acids with a predicted molecular mass is 49 kDa, as the sequence was first deduced by Lutz et al. *FEBS.* 334:3–8, 1993. Lutz et al. predicted that the receptor is a seven membrane spanning protein where in the first 22 amino acids constitute a typical hydrophobic signal sequence, and the remaining amino acids constitute two membrane spanning regions between amino acids 127 to 148 and 158 to 178, two more membrane spanning domains between amino acids 202 to 227 and 238 to 261, another between 278 to 303, and two final membrane spanning regions between 327 to 347 and 359 to 380, with three potential N-linked glycosylation sites found in the amino terminal extracellular domain at residues 57, 87 and 91. Sreedharan et al. describes the VIPR-2 receptor as being a 457 amino-acid protein encoded by a 2.8 kb cDNA of 52 kDa. Sreedharan et al. *Biochem. Biophys. Res. Commun.* 203:141–148, 1994.

When raising antibodies to VIPR-2, the entire protein or a portion thereof may be utilized. For instance, the extracellular domains of any of the seven transmembrane spanning portions of the protein may be utilized. For instance, amino acids 179 to 201 may be used. Larger VIPR-2 proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the VIPR-2 protein (or a portion thereof) can serve as the VIPR-2 antigen. When a smaller peptide is utilized, it is advantageous to conjugate the peptide with a larger molecule to make an immunostimulatory conjugate for use as the VIPR-2 antigen. Commonly utilized conjugate proteins that are commercially available for such use include bovine serum albumin (BSA) and keyhole limpet hemocyanin (KLH). In order to raise antibodies to particular epitopes, peptides derived from the full VIPR-2 sequence may be utilized. Preferably, one or more 8–30 amino acid peptide portions of an extracellular domain of VIPR-2 are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to VIPR-2, including glycosylation sites, is provided in SEQ ID NO. 20.

The extracellular domain of human VIPR-2 binds PACAP-27, PACAP-38, VIP and secretin. Because these factors have been found to affect tumor cell growth, and due to the recent discovery that the VIPR-2 receptor is overexpressed in glioblastomas (Astrocytoma grade IV), the binding of these factors to the VIPR-2 receptor may play a significant role in the oncogenesis and growth of astrocytoma cells in the brain. Thus, in alternative embodiments of the of the invention, antibody moieties are utilized which bind to VIPR-2 at a site on the protein which alters the binding of extracellular ligand molecules, such as VIP, to VIPR-2. Such VIPR-2 activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies that alter (enhance or inhibit) the binding of a ligand to VIPR-2 may be accomplished by a straightforward binding inhibition/enhancement assay. According to standard techniques, the binding of a labeled (e.g., fluorescently or enzyme-labeled) antibody to VIPR-2, which has been immobilized in a microtiter well, is assayed in both the presence and absence of the ligand (e.g., vasoactive intestinal peptide.) The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as VIPR-2 ligand-binding inhibitors or enhancers.

In addition, antibodies that are useful for altering the function of VIPR-2 may be assayed in functional formats, such as the HUVEC tube assay and cell migration assay. Thus, antibodies which exhibit the appropriate anti-tumor effect may be selected without direct knowledge of a binding ligand.

PTN

Given the experiments described above, and the results of Table 1, PTN was selected as a target for selective immunotherapeutic agents in targeting and/or imaging brain tumors. The entire PTN gene spans 65 kb and 7 exons, while the mature protein is approximately 136 amino acids (after cleavage of a 32 amino acid signal peptide) with distinctive lysine and arginine-rich clusters within both N- and C-terminal domains. The complete cDNA sequence encoding PTN is provided in SEQ ID NO. 21, and the complete amino acid sequence of PTN is provided in SEQ ID NO. 22. PTN is a 18 kDa, single chain, secreted protein with 10 conserved disulfide linked cysteine residues.

As used herein, a compound that specifically binds to PTN is any compound (such as an antibody) that has a binding affinity for any naturally occurring isoform, splice variant, or polymorphism of PTN, explicitly including the isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater than 99% identity) with the amino acid sequence of PTN. Such proteins include truncated forms or domains of PTN, and recombinantly engineered alterations of PTN. For example, a portion of SEQ ID NO. 22 may be engineered to include a non-naturally occurring cysteine for cross linking to an immunoconjugate protein, as described.

According to Milner et al. the gene sequence of PTN isolated from human genomic DNA consists of five exons and four introns. While exon 1 does not encode an amino acid sequence, exon 2 encodes the hydrophobic signal sequence of 32 amino acids, exons 3 and 4 code for the amino terminal and the ten cysteine residues, and exon 5 codes for the highly basic C-terminal domains. Interestingly, the human cDNA starts toward the end of exon 1, while the coded for protein begins at exon 2. Thus, the mature protein consist of 136 amino acids encoded by exons 2 to 5. As reported by Kretschmer et al. the minimum size of the gene is 42 kb, with a mRNA of 1650 nucleotides, spanning five exons, the majority of the protein being coded for by exon 3 (174 base pairs in length) and exon 4 (162 base pairs in length). See Kretschmer et al. (1993). *Biochem. Biophys. Res. Commun.* 192:420–429.

When raising antibodies to PTN, the entire protein or a portion thereof may be utilized. For instance, amino acid domains encoded for by exons 3 and 4 (i.e. amino acids 7 to 64 or 65 to 118, respectfully). Specifically, residues 41 to 64 may be used to abolish the transformation potential of PTN. Larger PTN proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source. It is to be noted that antibodies which bind to this secreted protein are useful in cytotoxic and imaging embodiments of the invention, as one of ordinary skill would expect that the concentration of the PTN would be increased adjacent to tumor cells which over-express the protein.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the PTN protein (or a portion thereof) can serve as the PTN antigen. When a smaller peptide is utilized, it is advantageous to conjugate the peptide with a larger molecule to make an immunostimulatory conjugate for use as the PTN antigen. Commonly utilized conjugate proteins that are commercially available for such use include bovine serum albumin (BSA) and keyhole limpet hemocyanin (KLH). In order to raise antibodies to particular epitopes, peptides derived from the full PTN sequence may be utilized. Preferably, one or more 8–30 aa peptide portions of the protein are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to PTN, including glycosylation sites, is provided in SEQ ID NO. 22.

PTN has been shown to bind to extracellular domain of RPTP beta and zeta. This binding inactivates the catalytic activity of RPTP, and PTN binds all the three major isoforms pf RPTP beta and zeta. PTN has also been shown to interact with syndecan-3. Thus, in alternative embodiments of the compositions and methods of the invention, antibody moieties are utilized which bind to PTN at a site on the protein that alters the binding of a cell surface molecule, such as the ones listed above, to PTN. Such PTN activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ligand to PTN may be accomplished by a straightforward binding inhibition/enhancement assay. According to standard techniques, the binding of a labeled (e.g., fluorescently or enzyme-labeled) antibody to PTN, which has been immobilized in a microtiter well, is assayed in both the presence and absence of the appropriate ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as PTN ligand-binding inhibitors or enhancers.

In addition, antibodies which are useful for altering the function of PTN may be assayed in functional formats, such as the HUVEC tube assay and the cell migration assay described below. Thus, antibodies that exhibit the appropriate anti-PTN activity may be selected without direct knowledge of a binding ligand or the particular biomolecular interactions of PTN.

OPN

Given the experiments described above, and the results of Table 1, OPN was selected as a target for selective immunotherapeutic agents in targeting and/or imaging brain tumors. The mature protein consists of approximately 298 amino acids (after cleavage of a 16 amino acid signal peptide) and contains two potential Asn-Xaa-Ser N-glycosylation site, located at positions 65 and 92 of the mature protein. The complete cDNA sequence encoding OPN is provided in SEQ ID NO. 23, and the complete amino acid sequence of OPN is provided in SEQ ID NO. 24. OPN is an abundant 34 kDa, single chain, phosphorylated glycoprotein, with a presumed site for cell attachment at residues 144–148. Three isoforms have been identified to be generated by post transcriptional modification, such as alternative splicing, OPN-A, OPN-B, and OPN-C. OPN-A and OPN-B differ by the addition of 14 amino acids at residue 58 of the protein. Amino acids 58–71 are absent in OPN-B, and amino acids 31–57 are absent in OPN-C. OPN is a negatively charged, highly hydrophilic secreted protein.

As used herein, a compound that specifically binds to OPN is any compound (such as an antibody) that has a binding affinity for any naturally occurring isoform, splice variant, or polymorphism of OPN, explicitly including the three isoforms described herein. As one of ordinary skill in the art will appreciate, such "specific" binding compounds (e.g., antibodies) may also bind to other closely related proteins that exhibit significant homology (such as greater than 90% identity, more preferably greater than 95% identity, and most preferably greater than 99% identity) with the amino acid sequence of OPN. Such proteins include truncated forms or domains of OPN, and recombinantly engineered alterations of OPN. For example, a portion of SEQ ID NO. 24 may be engineered to include a non-naturally occurring cysteine for cross linking to an immunoconjugate protein, as described.

According to Young et al. the cDNA sequence of OPN isolated from human bone cells (OPN-A) has an overall structure of approximately 34 kDA that consist of 298 amino acids, which is 14 amino acids less than the cDNA sequence of OPN isolated from human osteosarcoma by Keifer et al.

(OPN-B). The cDNA transcript for OPN-A is 1.5 kb with an open reading frame of 900 nucleotides, of which the first 16 amino acids are hydrophobic in nature and probably constitute a signal sequence for the secreted protein. The OPN gene contains 7 exons that are alternatively spliced to generate the variant isoforms, the most common variant being the addition of a 42 bp (14 amino acid) sequence located at base 280 of OPN-A. See Young et al. (1990). *Genomics,* 7:491–502 and Keifer et al. *Nucleic Acids Res.* 17:3306.

When raising antibodies to OPN, the entire protein or a portion thereof may be utilized. For instance, amino acid domains 4 to 12 (from the N-terminus) or 29 to 37 (from the N-terminus) may be utilized. Larger OPN proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source. It is to be noted that antibodies which bind to this secreted protein are useful in cytotoxic and imaging embodiments of the invention, as one of ordinary skill would expect that the concentration of OPN would be increased adjacent to tumor cells which over-express the protein.

When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the OPN protein (or a portion thereof) can serve as the OPN antigen. When a smaller peptide is utilized, it is advantageous to conjugate the peptide with a larger molecule to make an immunostimulatory conjugate for use as the OPN antigen. Commonly utilized conjugate proteins that are commercially available for such use include bovine serum albumin (BSA) and keyhole limpet hemocyanin (KLH). In order to raise antibodies to particular epitopes, peptides derived from the full OPN sequence may be utilized. Preferably, one or more 8–30 aa peptide portions of the protein are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to OPN, including glycosylation sites, is provided in SEQ ID NO. 22.

The cell attachment sequence of human OPN (amino acids 144 to 148) is believed to interact with various cell surface proteins (such as CD-44) to affect cell adhesion, and a highly acidic stretch composed almost exclusively of aspartic acid residues (amino acids 72 to 81) is believed to be the mineral binding site within the protein. Because CD-44 is frequently over expressed on primary brain tumors and metastases the binding of OPN to these various cell-surface adhesion protein molecules may play a significant role in the senescence and growth of tumor cells in the brain. Thus, in alternative embodiments of the compositions and methods of the invention, antibody moieties are utilized which bind to OPN at a site on the protein that alters the binding of a cell surface molecule, e.g., CD-44, to OPN. Such OPN activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ligand to OPN may be accomplished by a straightforward binding inhibition/enhancement assay. According to standard techniques, the binding of a labeled (e.g., fluorescently or enzyme-labeled) antibody to OPN, which has been immobilized in-a microtiter well, is assayed in both the presence and absence of the appropriate ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as OPN ligand-binding inhibitors or enhancers.

In addition, antibodies which are useful for altering the function of OPN may be assayed in functional formats, such as the HUVEC tube assay and the cell migration assay described below. Thus, antibodies that exhibit the appropriate anti-OPN activity may be selected without direct knowledge of a the biomolecular role of OPN.

PTPζ

PTPζ was also selected as a prime target for selective immuno-therapeutic agents in treating or imaging brain tumors. The complete cDNA sequence encoding PTPζ is provided in SEQ ID NO. 5, and the complete amino acid sequence of PTPζ is provided in SEQ ID NO. 6. Three different splice variants have been described, which include two membrane bound variants (full length: PTPζ-α, and shorter version PTPζ-β) and one secreted form (Phosphacan). See FIG. 1. Isoform PTPζ-α is the full length isoform, which contains the primary amino acid sequence aa 25–2314 of SEQ ID NO. 6 (aa 1–24 are a signal polypeptide). This full length long form of PTPζ is a type I membrane protein. After the signal peptide it contains a carbonic anhydrase like (CAH) and a fibronectin type III like (FN3) domain, followed by a long cysteine free spacer (S) domain. This follows a 860 amino acid long insert domain, which can be glycosylated. After a single transmembrane segment, in the intracellular region it has 2 phosphatase domains, but only the membrane-proximal PTPase domain is catalytically active (Krueger 1992).

In Isoform PTPζ-β, aa 755–1614 are missing. Isoform PTPζ-S (phosphacan), is a secreted isoform, which is comprises the extracellular domains of PTPζ-α. Northern Blot analysis have shown that the PTP zeta is exclusively expressed in the human central nervous system. In mouse embryos, the PTPζ transcript was mainly detected in the ventricular and subventricular zone of the brain and the spinal cord. The same pattern was detected in adult mice. Detailed studies have shown that during rat embryogenesis the two transmembrane splice variants of PTPζ are mainly expressed in glial precursor cells and that the secretory version (Phosphacan) is more abundant in mature astrocytes which have already migrated in the ventricle zone. Applicants have characterized two additional novel slice variants, PTPζ SM1 and PTPζ SM2, which are described in detail below.

As used herein, a compound which specifically binds to human protein tyrosine phosphatase-zeta (PTPζ) is any compound (such as an antibody) which has a binding affinity for any naturally occurring isoform, spice variant, or polymorphism of PTPζ, explicitly including the three splice variants describe herein. For example, the compounds which specifically bind to novel isoforms PTPζ SM1 and PTPζ SM2, described below, are subsets of compounds which specifically bind to PTPζ. As one of ordinary skill in the art will appreciate, such "specific" binding compounds (e.g., antibodies) may also bind to other closely related proteins which exhibit significant homology (such as greater than 90% identity, more preferably greater than 95% identity, and most preferably greater than 99% identity) with the amino acid sequence of PTPζ. Such proteins include truncated forms or domains of PTPζ, and recombinantly engineered alterations of PTPζ. For example, an portion of SEQ ID NO. 6 may be engineered to include a non-naturally occurring cysteine for cross-linking to an immunoconjugate protein, as described below.

In general, it is preferred that the antibodies utilized in the compositions and methods of the invention bind to the membrane-bound isoforms of the protein, as this will more specifically target the cytotoxic therapeutic agent, or the imaging agent, to the brain tumor cell. However, embodiments which utilize antibodies which bind to the secreted isoform of the protein are also useful in the invention, as one of ordinary skill would expect that the concentration of the secreted isoform would also be increased adjacent to brain tumor cells which over-express the protein.

The amino acid sequence of full length PTPζ consists of 2307 amino acids, as the sequence was deduced by Levy (in which aa 1722–1728 of SEQ ID NO. 2 were missing) (See also U.S. Pat. Nos. 5,604,094, and 6,160,090, fully incorporated herein by reference), or 2314 amino acids as the sequence was deduced by Krueger, et al., ("A human transmembrane protein-tyrosine phosphatase, PTP zeta, is expressed in brain and has an N-terminal receptor domain homologous to carbonic anhydrases" *Proc. Nat. Acad. Sci. U.S.A.* 89:7417–7421 (1992)). Amino acids 1–24 of SEQ ID NO. 6 are a signal sequence which directs the proper placement of the transmembrane protein. The extracellular domain of the mature PTPζ protein spans amino acids 25–1635 of SEQ ID NO. 6 in the long and secreted forms (this forms the entire secreted form), and amino acids 25–754, 1615–1635 in the short isoform. The transmembrane region of the protein spans amino acids 1636–1661 of SEQ ID NO. 6, and the balance of the protein forms the cytoplasmic domain, amino acids 1662–2314.

When raising antibodies to PTPζ, the entire protein (any of the three isoforms) or a portion thereof may be utilized. For instance, the extracellular domain of the long or short form, the entire secreted form, or a portion of extracellular domain may be utilized. For instance, amino acids 25–754, which are common to both α and β isoforms, may be used. Such larger PTPζ proteins and domains may be produced utilizing any suitable recombinant vector/protein production system, such as the baculovirus transfection system outlined below, after being amplified from a fetal brain cDNA library (as available from, e.g., Clontech, Palo Alto, Calif.) or another suitable source. When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the PTPζ protein (or a portion thereof) can serve as the PTPζ antigen. When a smaller peptide is utilized, it is advantageous to conjugate the peptide with a larger molecule to make an immunostimulatory conjugate for use as the PTPζ antigen. Commonly utilized conjugate proteins which are commercially available for such use include bovine serum albumin (BSA) and keyhole limpet hemocyanin (KLH). In order to raise antibodies to particular epitopes, peptides derived from the full PTPζ sequence may be utilized. Preferably, one or more 8–30 aa peptide portions of an extracellular domain of PTPζ are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to PTPζ, including glycosylation sites, is provided in SEQ ID NO. 6.

The extracellular domain of human PTPζ is known to bind to tenascin-C, tenascin-R, pleiotrophin (NM_002825), midkine (NM_002391), FGF-2 (XM_00366), Nr-CAM (NM_005010), L1/Ng-CAM, contactin (NM_001843), N-CAM (XM_006332), and axonin-1NM_005076.) The first 5 of these molecules are either components of the extracellular matrix in gliomas or are soluble factors known to be present in gliomas, and the latter 4 are neuronal surface molecules. The binding of PTPζ to these molecules may play a significant role in the oncogenesis and growth of neoplastic cells in the brain. Thus, in alternative embodiments of the compositions and methods of the invention, antibody moieties are utilized which bind to PTPζ at a site on the protein which alters the binding of an extracellular ligand molecule to PTPζ. Such PTPζ activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ligand to PTPζ may be accomplished by a straightforward binding inhibition/enhancement assay. According to standard techniques, the binding of a labeled (e.g., fluorescently or enzyme-labeled) antibody to PTPζ, which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as PTPζ ligand-binding inhibitors or enhancers.

In addition, antibodies which are useful for altering the function of PTPζ may be assayed in functional formats, such as the HUVEC tube assay and the cell migration assay described below. Thus, antibodies that exhibit the appropriate anti-PTPζ activity may be selected without direct knowledge of a the biomolecular role of PTPζ.

Novel PTPζ Splice Variants PTPζ SM1 and PTPζ SM2

Figure 2:
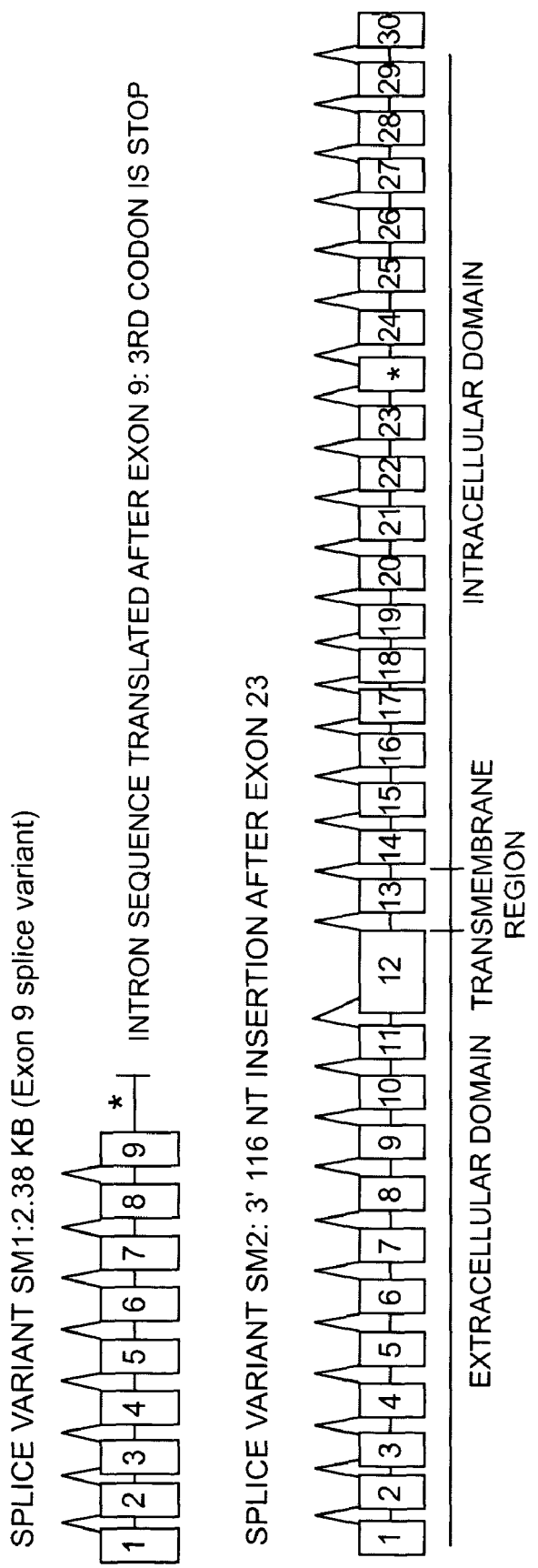
FIG. 2: A diagram of the two newly discovered splicing variant isoforms of PTPζ. The approximate position of the domains of the isoforms is indicated underneath the isoforms, as well as the approximate exon size (for size reference, exon 12 is 3.6 kilobases.) SM1 fails to splice correctly after the $9^{th}$ exon, yielding an mRNA with tow extra codons followed by a stop codon after the normal terminus of exon 9. SM 2 contains a 116 nucleotide insertion from between exons 23 &24.
Figure 3:
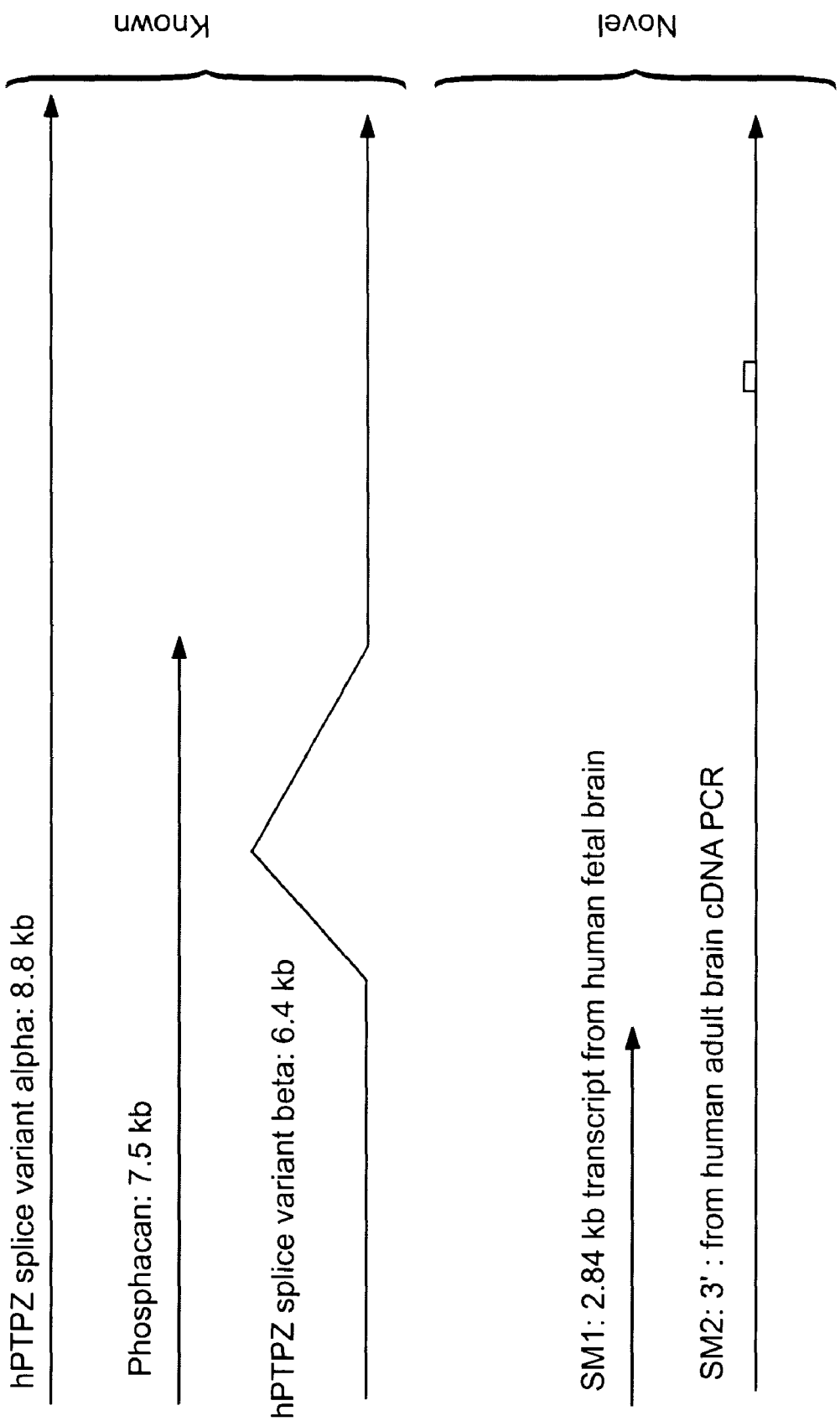
FIG. 3: A diagram comparing the three known PTPζ isoforms with the two novel isoforms.

In addition to the known variants of PTPζ for use in the invention, applicants have identified two novel splice variant isoforms of PTPζ, SM1 and SM2, from their clone libraries, see FIG. 2. These novel isoforms, PTPζ SM1 and PTPζ SM2, differ in structure from the three known isoforms heretofore disclosed, as is illustrated in FIG. 3. As only cDNA sequences for the known splice variants had been previously disclosed, rather than the full gene sequence, applicants verified the location of the novel sequences by comparison of the known splice variant sequences and the novel sequences with a publicly available genomic sequence database.

The protein PTPζ SM1 (amino acid sequence SEQ ID NO. 2, cDNA sequence SEQ ID NO. 1) comprises the amino acids encoded by the first nine exons of PTPζ-α, with three unique 5 additional carboxy terminal amino acids, see FIG. 2. These are encoded by additional 3' mRNA sequence (nucleotides 1262–1272 of SEQ ID NO. 1) from the intron of the gene between exons nine and ten. The PTPζ SM1 clone was isolated from a human fetal brain cDNA library, an has been shown to be expressed in several human glioblastoma cell lines. Expression of the SM1 splice variant has also been confirmed in primary brain tumor samples. The protein comprises only extracellular domains of PTPζ, and is expected to be secreted by the cell. Thus, PTPζ SM1 may serve a cell signaling or messenger function, and may have bind to a receptor on the surface of cells which are associated with or part of central nervous system tissues. Thus, antibodies specific for PTPζ SM1, and not specific for the other splicing isoforms of PTPζ, may be especially efficacious in the brain tumor therapeutic or imaging compositions of the invention. The PTPζ SM1 protein mainly comprises the carbonic anhydrase-like domain which has been identified in PTPζ α.

Applicants have explored the relationship between the putative carbonic anhydrase domain of PTPζ SM1 (SEQ ID NO. 2) and other human carbonic anhydrase domains from carbonic anhydrase III (SEQ ID NO. 25), carbonic anhydrase I (SEQ ID NO. 26), and carbonic anhydrase VIX [e] (SEQ ID NO. 27), shown below:

```
                                 1                                                      50
               cah3_human    ---------- ---------- ----------  ------AKEW GYASHNGPDH
               cah1_human    ---------- ---------- ----------  -----ASPDW GYDDKNGPEQ
               cahe_human    ---------- --------ML FSALLLEVIW  ILAADGGQHW TYEGPHGQDH
        rptpzetaexon9_frame1 MRILKRFLAC IQLLCVCRLD WANGYYRQQR  KLVEEIG..W SYTGALNQKN 51                                                    100
               cah3_human    WHELFPNAKG ENQSPIELHT KDIRHD...P  SLQPWSVSYD GGSAKTILNN
               cah1_human    WSKLYPIANG NNQSPVDIKT SETKHD...T  SLKPISVSYN PATAKEIINV
               cahe_human    WPASYPECGN NAQSPIDIQT DSVTFDPDLP  ALQPHGYDQP GTEPLDLHNN
        rptpzetaexon9_frame1 WGKKYPTCNS PKQSPINIDE DLTQVNVNLK  KLKFQGWDKT SLENTFIHNT 101                                                   150
               cah3_human    GKTCRVVFDD TYDRSMLRGG PLPGPYRLRQ  FHLHWGS.S. DDHGSEHTVD
               cah1_human    GHSFHVNFED NDNRSVLKGG PFSDSYRLFQ  FHFHWGS.T. NEHGSEHTVD
               cahe_human    GHTVQLSLP. ....STLYLG GLPRKYVAAQ  LHLHWGQ.KG SPGGSEHQIN
        rptpzetaexon9_frame1 GKTVEINLTN DYRVS...GG VSEMVFKASK  ITFHWGKCNM SSDGSEHSLE 151                                                   200
               cah3_human    GVKYAAELHL VHWN.PKYNT FKEALKQRDG  IAVIGIFLKI GH.ENGEFQI
               cah1_human    GVKYSAELHV AHWNSAKYSS LAEAASKADG  LAVIGVLMKV GE.ANPKLQK
               cahe_human    SEATFAELHI VHYDSDSYDS LSEAAERPQG  LAVLGILIEV GETKNIAYEH
        rptpzetaexon9_frame1 GQKFPLEMQI YCFDADRFSS FEEAVKGKGK  LRALSILFEV GTEENLDFKA 201                                                   250
               cah3_human    FLDALDKIKT KGKEAPFTKF DPSCLFPACR  .DYWTYQGSF TTPPCEECIV
               cah1_human    VLDALQAIKT KGKRAPFTNF DPSTLLPSSL  .DFWTYPGSL THPPLYESVT
               cahe_human    ILSHLHEVRH KDQKTSVPPF NLRELLPKQL  GQYFRYNGSL TTPPCYQSVL
        rptpzetaexon9_frame1 IIDGVESVSR FGKQAALDPF ILLNLLPNST  DKYYIYNGSL TSPPCTDTVD 251                                                   300
               cah3_human    WLLLKEPMTV SSDQMAKLRS LLSSAENEPP  VP...LVSNW RPPQPINNRV
               cah1_human    WIICKESISV SSEQLAQFRS LLSNVEGDNA  VP...MQHNN RPTQPLKGRT
               cahe_human    WTVFYRRSQI SMEQLEKLQG TLFSTEEEPS  KL...LVQNY RALQPLNQRM
        rptpzetaexon9_frame1 WIVFKDTVSI SESQLAVFCE VLTMQQSGYV  MLMDYLQNNF REQQYKFSRQ 301                                                   350
               cah3_human    VRASFK---- ---------- ----------  ---------- ----------
               cah1_human    VRASF----- ---------- ----------  ---------- ----------
               cahe_human    VFASFIQAGS SYTTGEMLSL GVGILVGCLC  LLLAVYFIAR KIRKKRLENR
        rptpzetaexon9_frame1 VFSSYTGKEE IHEAVCSSEP ENVQADPENY  TSLLVTWERP RVVYDTMIEK 351                          380
               cah3_human    ---------- ---------- ----------
               cah1_human    ---------- ---------- ----------
               cahe_human    KSVVFTSAQA TTEA------ ----------
        rptpzetaexon9_frame1 FAVLYQQLDG EDQTKHEFLT DGYQDLVTI*
```

Based on alignment with these catalytically active carbonic anhydrases, it seems unlikely that the CA domain could function as a carbonic anhydrase enzyme. Two of the three histidines implicated in binding of the catalytic zinc are missing from the CA domain of the receptor. In active enzymes there is a conserved HxHWG{18,20}ELH motif (the three histidines bind zinc), however, in the receptor this is modified to TFHWG{18,20}EMQ; i.e. two of the three critical zinc atoms would be missing. For comparison, it has been found that a carbonic anhydrase related protein (CAH 8) that lacks just one of these histidines also lacks catalytic activity.

The protein PTPζ SM2 (amino acid sequence SEQ ID NO. 4) comprises the amino acids encoded by all exons of PTPζ-α, plus a 116 nucleotide "extra" exon, in the correct reading frame, between exons 23 and 24 (nucleotides 6229–6345 of SEQ ID NO. 3). This extra exon, designated exon 23a, contains a portion of the intron sequence between exons 23 and 24 of the PTPζ gene. PTPζ SM2 expression has been verified in several human glioblastoma cell lines, and has also been confirmed in primary brain tumor samples. As PTPζ SM2 comprises all the domains of PTPζ α, the protein is expected to be membrane-bound. The extra exon lies within the cytoplasmic domain of the protein, and thus may alter the protein tyrosine phosphatase function of PTPζ SM2.

A novel splicing variant PTPζ protein having an amino acid sequence which includes the amino acid sequence of PTPζ SM1 (SEQ ID NO. 2) or PTPζ SM2 (SEQ. ID NO. 4) may be produced by recombinant techniques known in the art utilizing any suitable vector, in any suitable host cell. The term "vector" is intended to include any physical or biochemical vehicle containing nucleic acid polymers of interest, by which those nucleic acid polymers are transferred into a host cell, thereby transfecting that cell with the introduced nucleic acid polymers. The transfected nucleic acid sequence preferably contains a control sequence, such as a promoter sequence, suitable for transcription of the nucleic acid sequence in the host cell. Examples of vectors include DNA plasmids, viruses, liposomes, particle gun pellets, and transfection vectors known to those of skill in the molecular biology arts. The term "host cell" is intended to mean the target cell for vector transformation, in which the transferred nucleic acid polymer will be replicated and/or expressed. Although bacterial cells may be suitable for production of the proteins for antibody production or structural study purposes, eukaryotic cell hosts are preferred for production of the protein for functional assays or therapeutic purposes. Preferred eukaryotic cell hosts include insect cell lines (e.g, Sf9, Sf21, or High Five™ cell lines), and mammalian cell lines (e.g., HeLa, CHO-K1, COS-7, COS-1, HEK293, HEPG2, Jurkat, MDCK, PAE, PC-12, and other acceptable mammalian cell lines). Thus, the invention also provides vectors incorporating a nucleic acid sequence encoding PTPζ SM1 or PTPζ SM2, as well as host cells which express the proteins.

It is common in the molecular biology arts to utilize additional functional amino acid domains or proteins fused with a protein sequence of interest for purification or detection purposes. Such additional functionalities include, for example, polyhistidine domains, c-myc domains (specifically comprising amino acids 410–419 of the human c-myc oncogene product), β-galactosidase, β-glucuronidase, glutathione-S-transferase, maltose binding protein, human influenza virus hemagglutanin, green fluorescent protein, chloramphenicol acetyltransferase, luciferase, thioredoxin, and others. After purification (e.g., by antibody-affinity chromatography) or detection, these extra amino acid sequences may be cleaved (e.g., by thrombin, enterokinase, Factor Xa, or other protease) to yield a functional mature protein. Thus, the PTPζ SM1 and SM2 proteins of the invention also encompass proteins comprising the amino acid sequence of SEQ ID NO. 2 or SEQ ID NO. 4 and such additional amino acid functionalities.

The invention also provides polypeptides which have a unique activity of PTPζ SM1 or PTPζ SM2 which is not shared by the other PTPζ splice variant (e.g., an antigenic epitope) and which include a portion of the amino acid sequence of PTPζ SM1 or PTPζ SM2 which is at least about 8 to 12 amino acid residues in length, more preferably at least about 20 amino acids in length. These polypeptides preferably comprise an amino acid sequence which is not found in PTPζ α, PTPζ β, or phosphacan, wherein the included portion of the sequence confers the unique activity on the polypeptide. Such polypeptides may be utilized as described above to produce affinity reagents which specifically bind to PTPζ splice variants SM1 or SM2, but do not bind to the other known splice variants of PTPζ. The invention thus provides such specific affinity reagents, which may be produces from such polypeptides, or from an entire PTPζ SM1 or PTPζ SM2 protein. In preferred embodiments these affinity reagents are antibodies or antibody fragments.

In addition, although the understanding of the field of protein biochemistry is not as complete as that of molecular genetics, the person or ordinary skill in the art of biochemistry is capable of predicting, with reasonable certainty, when certain substitutions to the primary amino acid sequence structure of a protein will not result in any appreciable modification of a protein's structure or function. Such conservative substitutions are made by replacing an amino acid in the sequence with another containing a side chain with like charge, size, and other characteristics. Conservative substitutions in a protein sequence which would be expected to have minimal to no impact on protein structure or function can be readily devised by a person of ordinary skill in the biochemical arts. To the extent that such conservative substitutions can be made while retaining 90%, preferably 95%, and more preferably 99% or more identity to SEQ. ID NO. 2 or SEQ ID NO. 4, and maintain the activity of the native PTPζ SM1 or PTPζ SM2 protein, such altered proteins are within the scope of the present invention.

The invention also provides nucleic acid polymers encoding the PTPζ splice variants SM1 or SM2. These nucleic acid polymers most preferably comprises a nucleic acid sequence of SEQ. ID NO. 1 or SEQ ID NO. 3, or the predictable variants thereof which one of ordinary skill of the art could derive using the degeneracy of the genetic code. Such nucleic acid polymers are useful for the production of PTPζ SM1 or PTPζ SM2 by recombinant methods, as described above.

The invention also encompasses nucleic acid probes or primers which hybridize to the mRNA encoding PTPζ splice variants SM1 or SM2, but not mRNA encoding other known splice variants of PTPζ. Such probes or primers provided by the invention are preferably able to hybridize with SEQ. ID NO. 1 or SEQ. ID NO. 3 (or their complements) under stringent conditions (e.g., 0.5× to 2×SSC buffer, 0.1% SDS, and a temperature of 55–65° C.), but do not hybridize to SEQ ID NO. 5 (or its complement) under the same conditions. These PTPζ SM1 or PTPζ SM2 coding sequence specific probes are preferably from about 16 to about 40 nucleotides in length, more preferably from about 18 nucleotides to about 30 nucleotides in length. However, probes may be of a smaller size, preferably from about 8 to about 15 nucleotides in length, if two ore more probes are hybridized to adjacent sequences, so that terminal nucleic acid base-stacking interactions may stabilize their hybridization. In preferred embodiments of PTPζ SM1 specific nucleic acid probes, the probes hybridize at or near the novel splice site at the 3' end of exon 9, or its complement. In preferred embodiments of PTPζ SM2 specific probes, the probes hybridize at or adjacent to a location selected from: the novel splice site at the 3' end of exon 23, at least a portion of the novel exon 23a, the novel splice site at the 5' end of exon 24, or the complement of any one of these.

Because PTPζ SM1 and PTPζ SM2 have been shown to be expressed in glioblastoma cell lines and primary tumors, the level of the expression of these splice variants may be useful for staging or characterizing glioblastoma cells. Such cells may be extracted, for instance, from a primary tumor. Thus, the invention provides for the monitoring of the relative expression level of PTPζ SM1 or PTPζ SM2, or both, in relation to each other or to one or more of the known PTPζ splice variants. In one preferred embodiment, the level of expression of PTPζ SM1 is compare to at least one other splice variant selected from PTPζ SM2, PTPζ α, PTPζ β, and phosphacan. In another preferred embodiment, the level of expression of PTPζ SM2 is compare to at least one other splice variant selected from PTPζ SM1, PTPζ α, PTPζ β, and phosphacan. Such comparison may be made in either a qualitative or quantitative manner. One means for comparison is by hybridizing splice-variant specific nucleic acid probes to a sample of nucleic acids (which may be amplified) obtained from brain tumor cells. Alternatively, the expression level of the splice variants may be deduced by the amplification of splice variant nucleic acid sequences, and the analysis of the size of those amplified products using methods known in the art. In another alternative embodiment, protein levels may be studied utilizing splice-variant specific antibodies in either sandwich immunoassay or in-situ staining formats. Various expression level assay techniques are known to those of skill in the molecular biological arts, and thus the specific techniques mentioned above should be considered merely exemplary.

Antibodies for Use in the Antibody-Therapeutics Methods of the Invention

Generally, as the term is utilized in the specification, "antibody" or "antibody moiety" is intended to include any polypeptide chain-containing molecular structure that has a specific shape which fits to and recognizes an epitope, where one or more non-covalent binding interactions stabilize the complex between the molecular structure and the epitope. Antibodies which bind specifically to one of the brain tumor protein targets are referred to as anti-brain tumor protein target antibodies, or α($T_{BT}$), or more specifically α(ARP2), α(SPARC), α(CMET), α(CD44), α(BEHAB), α(TSPAN3), α(VIPR2), α(OPN), α(PTN), and α(PTPζ). The specific or selective fit of a given structure and its specific epitope is sometimes referred to as a "lock and key" fit. The archetypal antibody molecule is the immunoglobulin, and all types of immunoglobulins (IgG, IgM, IgA, IgE, IgD, etc.), from all sources (e.g., human, rodent, rabbit, cow, sheep, pig, dog, other mammal, chicken, turkey, emu, other avians, etc.) are considered to be "antibodies." Antibodies utilized in the present invention may be polyclonal antibodies, although monoclonal antibodies are preferred because they may be reproduced by cell culture or recombinantly, and may be modified to reduce their antigenicity.

Polyclonal antibodies may be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, an $T_{BT}$ antigen comprising an antigenic portion of the brain tumor protein targets' polypeptide is initially injected into any of a wide variety of mammals (e.g., mice, rats, rabbits, sheep or goats). Alternatively, in order to generate antibodies to relatively short peptide portions of the brain tumor protein target (see discussion above), a superior immune response may be elicited if the polypeptide is joined to a carrier protein, such as ovalbumin, BSA or KLH. The peptide-conjugate is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

Several monoclonal antibodies against various isoforms of the brain tumor protein targets are currently available from commercial sources. For instance, a non-exclusive list of available commercial antibodies includes: for SPARC/Osteonectin, from Zymed, mouse anti-bovine MAb (cross-reactivity with human), suitable for ELISA, WB, IH (paraffin), Cat# 33-5500; for c-MET, from Zymed, rabbit anti-human polyclonal, suitable for ELISA, WB, IH. Cat#

71-8000, and from RDI, rabbit anti-human MAb, suitable for WB, IP, IH. Cat# RDI-MET Cabr.; for CD44, from RDI, mouse anti-human MAb, only for IH and FACS, Cat# RDI-M1676clb., and from Lab vision, mouse anti-human MAb, known to block binding of hyaluronic acid to its receptor CD44, "CD44/H-CAM Ab-2"; for Brevican/BE-HAB, from *BD Transduction Lab.*, a mouse anti-human MAb, WB, IF, Cat# B68820; for VIP 2 receptor, from Exalpha, mouse anti-rat (possible human cross-specificity, which is easily assayed) MAb, WB, IH. Cat#2140M; for Laminin receptor 67 kDa, from Lab vision, mouse anti-human MAb, IH, ELISA, not for WB. "laminin receptor Ab-1"; for Osteopontin, from Chemicon, rat anti-human MAb, raised against rh-Osteopontin—recognizes native protein well, WB, IH, ELISA. "MAB3057"; for Pleiotrophin, from R&D goat anti-human polyclonal, WB, recognizes rh-Pleiotrophin. "BAF252", and from Oncogene goat anti-human polyclonal, WB, ELISA, detects rh-Pleiotrophin. "PC187L".; for PTPζ-α and PTPζ-β, from BD Transduction Labs, mouse anti-human MAb (WB, IH, IF), denominated "R20720" and from Chemicon, mouse anti-human MAb (WB, IH, IP), denominated "MAB5210", which recognizes both of the transmembrane isoforms, and also recognizes the soluble isoform (phosphacan, PTPζ-S). These antibodies are suitable for use in the compositions of the present invention, especially in Fab fragment form (which eliminates significant portions of the antigenic mouse constant heavy and light chain regions). However, it is preferred that such antibodies be humanized or chimerized according to one of the procedures outlined below.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Preferably, recombinant antibodies are produced in a recombinant protein production system which correctly glycosylates and processes the immunoglobulin chains, such as insect or mammalian cells. An advantage to using insect cells which utilize recombinant baculoviruses for the production of antibodies for use in the present invention is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50–75% of the total cellular protein late in viral infection, making this system an excellent means of producing milligram quantities of the recombinant antibodies.

The use of the baculovirus *Autographia californica* nuclear polyhedrosis virus (AcNPV) and recombinant viral stocks in *Spodoptera frugiperda* (Sf9) cells to prepare large quantities of protein has been described by Smith et al. (1985), Summers and Smith (1987). A preferred method of preparing recombinant antibodies is through the expression of DNA encoding recombinant antibody (produced by screening,. as above, or by protein engineering to include more human-like domains, as discussed below) via the baculoviral expression system in Sf9 insect cells. Production of recombinant proteins in Sf9 cells is well known in the art, and one of ordinary skill would be able to select from a number of acceptable protocols (e.g., that described in U.S. Pat. No. 6,603,905).

It should be noted that antibodies which have a reduced propensity to induce a violent or detrimental immune response in humans (such as anaphylactic shock), and which also exhibit a reduced propensity for priming an immune response which would prevent repeated dosage with the antibody therapeutic or imaging agent (e.g., the human-anti-murine-antibody "HAMA" response), are preferred for use in the invention. These antibodies are preferred for all administrative routes, including intrathecal administration. Even through the brain is relatively isolated in the cranial cavity, behind the blood brain barrier, an immune response still can occur in the form of increased leukocyte infiltration, and inflammation. Although some increased immune response against the tumor is desirable, the concurrent binding and inactivation of the therapeutic or imaging agent generally outweighs this benefit. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference). Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals which have been genetically altered to produce human immunoglobulins, such as the Abgenix XenoMouse or the Medarex HuMAb ® technology. The transgenic animal may be produced by initially producing a "knock-out" animal which does not produce the animal's natural antibodies, and stably transforming the animal with a human antibody locus (e.g., by the use of a human artificial chromosome). Only human antibodies are then made by the animal. Techniques for generating such animals, and deriving antibodies therefrom, are described in U.S. Pat. Nos. 6,162,963 and 6,150,584, incorporated fully herein by reference. Such fully human xenogenic antibodies are a preferred antibody for use in the methods and compositions of the present invention.

Alternatively, single chain antibodies (Fv, as described below) can be produced from phage libraries containing human variable regions. See U.S. Pat. No. 6,174,708, incorporated fully herein by reference. Also see Kuan, C. T., Reist, C. J., Foulon, C. F., Lorimer, I. A., Archer, G., Pegram, C. N., Pastan, I., Zalutsky, M. R., and Bigner, D. D. (1999). 1251-labeled anti-epidermal growth factor receptor-viii single-chain Fv exhibits specific and high-level targeting of glioma xenografts. *Clin Cancer Res.* 5, 1539–49;Lorimer, I. A., Keppler-Hafkemeyer, A., Beers, R. A., Pegram, C. N., Bigner, D. D., and Pastan, I. (1996). Recombinant immunotoxins specific for a mutant epidermal growth factor receptor: targeting with a single chain antibody variable domain isolated by phage display. *Proc. Nat. Acad. Sci. USA* 93, 14815–20; Pastan, I. H., Archer, G. E., McLendon, R. E., Friedman, H. S., Fuchs, H. E., Wang, Q. C., Pai, L. H., Herndon, J., and Bigner, D. D. (1995). Intrathecal administration of single-chain immunotoxin, LMB-7 [B3(Fv)-PE38], produces cures of carcinomatous meningitis in a rat model. *Proc Natl. Acad. Sci USA* 92, 2765–9, all of which are incorporated by reference fully herein.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879–5883 (1988) and Bird et al., Science 242:423–426 (1988), both fully incorporated herein, by reference. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties [fluorescent dyes, enzymes, substrates, chemiluminescent moieties], or specific binding moieties [such as streptavidin, avidin, or biotin] may be utilized in the methods and compositions of the present invention. For convenience, the term "antibody" or "antibody moiety" will be used throughout to generally refer to molecules which specifically bind to an epitope of the brain tumor protein targets, although the term will encompass all immunoglobulins, derivatives, fragments, recombinant or engineered immunoglobulins, and modified immunoglobulins, as described above.

Candidate anti-$T_{BT}$ antibodies can be tested for anti-$T_{BT}$ activity by any suitable standard means. As a first screen, the antibodies may be tested for binding against the brain tumor protein target antigen utilized to produce them, or against the entire brain tumor protein target extracellular domain or protein. As a second screen, anti-$T_{BT}$ candidates may be tested for binding to an appropriate glioblastoma cell line (i.e., one which approximates primary tumor brain tumor protein target expression), or to primary tumor tissue samples. For these screens, the anti-$T_{BT}$ candidate antibody may be labeled for detection (e.g., with fluorescein or another fluorescent moiety, or with an enzyme such as horseradish peroxidase). After selective binding to the brain tumor protein target is established, the candidate antibody, or an antibody conjugate produced as described below, may be tested for appropriate activity (i.e., the ability to decrease tumor cell growth and/or to aid in visualizing tumor cells) in an in vivo model, such as an appropriate glioblastoma cell line, or in a mouse or rat human brain tumor model, as described below.

General Functional Assay Methods for Antibodies for Use in the Invention

In addition to the specific binding assays and protein—specific functional assays described for individual proteins above, antibodies which are useful for altering the function of ARP-2, SPARC, c-MET, BEHAB, CD-44, TSPN3, PTN, OPN, VIPR-2, or PTPζ may be assayed in functional formats, such as glioblastoma cell culture or mouse/rat CNS tumor model studies. In glioblastoma cell models of activity, expression of the protein is first verified in the particular cell strain to be used. If necessary, the cell line may be stably transfected with a coding sequence of the protein under the control of an appropriate constituent promoter, in order to express the protein at a level comparable to that found in primary tumors. The ability of the glioblastoma cells to survive in the presence of the candidate function-altering anti-protein antibody is then determined. In addition to cell-survival assays, cell migration assays, as described below in Example 1, may be utilized to determine the effect of the candidate antibody therapeutic agent on the tumor-like behavior of the cells. Alternatively, if the brain tumor protein target is involved in angiogenesis, or endothelial cell sprouting assays such as described in Example 2 may be utilized to determine the ability of the candidate antibody therapeutic to inhibit vascular neogenesis, an important function in tumor biology.

Similarly, in vivo models for human brain tumors, particularly nude mice/SCID mice model or rat models, have been described [Antunes, L., Angioi-Duprez, K. S., Bracard, S. R., Klein-Monhoven, N. A., Le Faou, A. E., Duprez, A. M., and Plenat, F. M. (2000). Analysis of tissue chimerism in nude mouse brain and abdominal xenograft models of human glioblastoma multiforme: what does it tell us about the models and about glioblastoma biology and therapy? *J Histochem Cytochem* 48, 847–58; Price, A., Shi, Q., Morris, D., Wilcox, M. E., Brasher, P. M., Rewcastle, N. B., Shalinsky, D., Zou, H., Appelt, K., Johnston, R. N., Yong, V. W., Edwards, D., and Forsyth, P. (1999). Marked inhibition of tumor growth in a malignant glioma tumor model by a novel synthetic matrix metalloproteinase inhibitor AG3340. *Clin Cancer Res* 5, 845–54; and Senner, V., Sturm, A., Hoess, N., Wassmann, H., and Paulus, W. (2000). In vivo glioma model enabling regulated gene expression. *Acta Neuropathol* (Berl) 99, 603-8.] Once correct expression of the protein in the tumor model is verified, the effect of the candidate anti-protein antibodies on the tumor masses in these models can be evaluated, wherein the ability of the anti-protein antibody candidates to alter protein activity is indicated by a decrease in tumor growth or a reduction in the tumor mass. Thus, antibodies that exhibit the appropriate anti-tumor effect may be selected without direct knowledge of the particular biomolecular role of the protein in oncogenesis.

Therapeutic and Imaging Moieties, and Methods for Conjugating them with Anti-PTPζ Antibodies to Use in the Compositions and Methods of the Invention As described above, the anti-$T_{BT}$ antibodies for use in the present invention may have utility without conjugation when the native activity of the brain tumor protein target is altered in the tumor cell. Such antibodies, which may be selected as described above, may be utilized without further modification to include a cytotoxic or imaging moiety. These types of compositions have the advantage of reduced toxicity (in that only the toxicity of the antibody moieties themselves must be taken into account when dosing), and are simpler to manufacture. Thus, non-conjugated activity altering anti-$T_{BT}$ antibody therapeutics are a preferred embodiment of the invention. However, the conjugation of cytotoxic or imaging agents is yet another preferred embodiment when utilizing these antibodies because the added moieties add functionality to the therapeutic.

Thus, in many preferred embodiments of the invention, the anti-$T_{BT}$ antibodies may be coupled or conjugated to one or more therapeutic cytotoxic or imaging moieties. As used herein, "cytotoxic moiety" (C) simply means a moiety which inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. As utilized herein, "imaging moiety" (I) means a moiety which can be utilized to increase contrast between a tumor and the surrounding healthy tissue in a visualization technique (e.g., radiography, positron-emission tomography, magnetic resonance imaging, direct or indirect visual inspection). Thus, suitable imaging moieties include radiography moieties (e.g. heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between what is a therapeutic moiety and what is an imaging moiety. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the anti-PTPζ moiety by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the anti-$T_{BT}$ antibody moiety through a an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one cytotoxic and/or imaging moiety to an antibody. By poly-derivatizing the anti-$T_{BT}$ antibody, several cytotoxic strategies may be simultaneously implemented, an antibody may be made useful as a contrasting agent for several visualization techniques, or a therapeutic antibody may be labeled for tracking by a visualization technique. In one embodiment, multiple molecules of an imaging or cytotoxic moiety are coupled to one antibody molecule. In another embodiment, more than one type of moiety may be coupled to one antibody. Regardless of the particular embodiment, immunoconjugates with more than one moiety may be prepared in a variety of ways. For example, more than one moiety may be coupled directly to an antibody molecule, or linkers which provide multiple sites for attachment (e.g., dendrimers) can be used. Alternatively, a carrier with the capacity to hold more than one cytotoxic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to anti-$T_{BT}$ antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells.

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides which are suitable for pharmacological administration. Such radionuclides include $^{123}I$, $^{125}I$, $^{131}I$, $^{90}Y$, $^{211}At$, $^{67}Cu$, $^{186}Re$, $^{188}Re$, $^{212}Pb$, and $^{212}Bi$. Iodine and astatine isotopes are more preferred radionuclides for use in the therapeutic compositions of the present invention, as a large body of literature has been accumulated regarding their use. $^{131}I$ is particularly preferred, as are other β-radiation emitting nuclides, which have an effective range of several millimeters. $^{123}I$, $^{125}I$, $^{131}I$, or $^{211}At$ may be conjugated to antibody moieties for use in the compositions and methods utilizing any of several known conjugation reagents, including Iodogen, N-succinimidyl 3-[$^{211}At$]astatobenzoate, N-succinimidyl 3-[$^{131}I$]iodobenzoate (SIB), and, N-succinimidyl 5-[$^{131}I$]iodob-3-pyridinecarboxylate (SIPC). Any iodine isotope may be utilized in the recited iodo-reagents. For example, a suitable antibody for use in the present invention may be easily made by coupling an Fab fragment of the BD Transduction Labs R20720 anti-PTPζ MAb with $^{131}I$ Iodogen according to the manufacturer's instructions. Other radionuclides may be conjugated to anti-$T_{BT}$ antibody moieties by suitable chelation agents known to those of skill in the nuclear medicine arts.

Preferred chemotoxic agents include small-molecule drugs such as carboplatin, cisplatin, vincristine, taxanes such as paclitaxel and doceltaxel, hydroxyurea, gemcitabine, vinorelbine, irinotecan, tirapazamine, matrilysin, methotrexate, pyrimidine and purine analogs, and other suitable small toxins known in the art. Preferred chemotoxin differentiation inducers include phorbol esters and butyric acid. Chemotoxic moieties may be directly conjugated to the anti-$T_{BT}$ antibody moiety via a chemical linker, or may encapsulated in a carrier, which is in turn coupled to the anti-$T_{BT}$ antibody moiety.

Preferred toxin proteins for use as cytotoxic moieties include ricins A and B, abrin, diphtheria toxin, bryodin 1 and 2, momordin, trichokirin, cholera toxin, gelonin, *Pseudomonas exotoxin, Shigella* toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the anti-$T_{BT}$ antibody moiety.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions which may be utilized for x-ray radiography are described in U.S. Pat. No. 5,709,846, incorporated fully herein by reference. Such moieties may be conjugated to the anti-$T_{BT}$ antibody moiety through an acceptable chemical linker or chelation carrier. In addition, radionuclides which emit radiation capable of penetrating the scull may be useful for scintillation imaging techniques. Suitable radionuclides for conjugation include $^{99}Tc$, $^{111}In$, and $^{67}Ga$. Positron emitting moieties for use in the present invention include $^{18}F$, which can be easily conjugated by a fluorination reaction with the anti-$T_{BT}$ antibody moiety according to the method described in U.S. Pat. No. 6,187,284.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the anti-$T_{BT}$ antibody moieties through a suitable chemical linker.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. In preferred embodiments, such dyes are encapsulated in carrier moieties, which are in turn conjugated to the anti-$T_{BT}$ antibody. Alternatively, visible particles, such as colloidal gold particles or latex particles, may be coupled to the anti-$T_{BT}$ antibody moiety via a suitable chemical linker.

Delivery of Therapeutic and Imaging Agents to the Patient:

The Blood Brain Barrier (BBB) and Administration Strategies:

At one time, the BBB was not considered to present a problem in the diagnosis and treatment of brain tumors, because early scans of human brain tumors suggested that the BTB (blood tumor barrier) was "leaky." However, as the size of the molecule increases, the rate of movement across the barrier decreases. The BBB has been demonstrated to be heterogeneous in experimental human tumor xenograft animal models and in human patients. This lack of uniformity is because of the reduced integrity of tight junctions in the capillary endothelial cells of the tumor neovasculature, intratumoral variation in permeability, and altered intratumoral blood flow (Fuchs et al, 1990, Cancer research 50, 1954–59, Groothuis et al., 1984, Prog.Exp. Tumor Res.) Thus, although the BBB may not pose a delivery problem for some tumors in some patients, this cannot be said for all brain tumors. In addition, a preferred mode of administration of the therapeutics of the invention is after removal of the main tumor mass (resection of the tumor), which destroys much of the "leaky" neovasculature. Moreover, as brain carcinomas are usually pervasive throughout the organ, therapies which are directed towards eradicating all tumor-producing cells cannot rely exclusively on the localized tumor neovasculature.

A first strategy for drug delivery through the BBB entails disruption of the BBB, either by osmotic means such as mannitol or leukotrienes, or biochemically by the use of vasoactive substances such as bradykinin. The potential for using BBB opening to target specific agents to brain tumors is also an option. In preferred embodiments, a BBB disrupting agent is co-administered with the therapeutic or imaging compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. However, the best current strategy for drug delivery behind the BBB is by intrathecal delivery of therapeutics or imaging agents directly to the cranium, as through an Ommaya reservoir.

Delivery/Administration of Therapeutic Antibodies:

For administration, the antibody-therapeutic or antibody-imaging agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMPs), as approved by the FDA. The clinician of ordinary skill is familiar with appropriate ranges for pH, tonicity, and additives or preservatives when formulating pharmaceutical compositions for administration by intravascular injection, intrathecal injection, injection into the cerebro-spinal fluid, direct injection into the tumor, or by other routes. In addition to additives for adjusting pH or tonicity, the antibody-therapeutics and antibody-imaging agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11, 74, 76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

Intravascular injection may be by intravenous or intraarterial injection: carotid artery injection is thought to assist in administration to the brain, and is thus preferred. Antibody-agents injected into the blood stream have been shown to cross the blood-brain barrier and to infiltrate the cranial cavity to some extent, usually in the range of $10^{-4}$ to $10^{-3}$% [?UNITS?] injected dose per gram. This rate of uptake may be sufficient for imaging reagents, and also may be useful for tumor cell specific cytotoxic agents (e.g, those specifically directed to the inhibition of the function of tumor-cell overexpressed proteins). However, in order to achieve therapeutic concentrations of the antibody-therapeutic agents without unacceptable toxicity to the patient, it is preferred that the therapeutics compositions be administered by intrathecal injection, direct injection, or injection into the cerebro-spinal fluid.

Thus, a preferred method for administration of the therapeutic compositions of the invention is by depositing it into the inner cavity of a cystic tumor by any suitable technique, such as by direct injection (aided by stereotaxic positioning of an injection syringe, if necessary) or by placing the tip of an Ommaya reservoir into a cavity, or cyst, for administration. Where the tumor is a solid tumor, the antibody may be administered by first creating a resection cavity in the location of the tumor. This procedure differs from an ordinary craniotomy and tumor resection only in a few minor respects. As tumor resection is a common treatment procedure, and is often indicated to relieve pressure, administration of the therapeutic compositions of the invention following tumor resection is a preferred embodiment of the treatment methods of the invention. Following gross total resection in a standard neurosurgical fashion, the cavity is preferable rinsed with saline until all bleeding is stopped by cauterization. Next the pia-arachnoid membrane, surrounding the tumor cavity at the surface, is cauterized to enhance the formation of fibroblastic reaction and scarring in the pia-arachnoid area. The result is the formation of an enclosed, fluid-filled cavity within the brain tissue at the location from where the tumor was removed. After the cyst has been formed, either the tip of an Ommaya reservoir or a micro catheter, which is connected to a pump device and allows the continuos infusion of an antibody solution into the cavity, can be placed into the cavity. See, e.g., U.S. Pat. No. 5,558,852, incorporated fully herein by reference.

Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic or imaging composition to the brain and/or tumor mass. Such devices are described in U.S. Pat. No. 5,720,720, incorporated fully herein by reference.

The effective amount of the therapeutic antibody-conjugate composition or of the imaging antibody-conjugate compositions to be given to a particular patient will depend on a variety of factors, several of which will be different from patient to patient. A competent clinician will be able to determine an effective amount of a therapeutic antibody-conjugate composition to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per kilogram subject body weight. Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety. In a therapeutic example, where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The antibody conjugate can be administered to the subject in a series of more than one administration. For therapeutic compositions, regular periodic administration (e.g., every 2–3 days) will sometimes be required, or may be desirable to reduce toxicity. For therapeutic compositions which will be utilized in repeated-dose regimens, antibody moieties which do not provoke HAMA or other immune responses are preferred. The imaging antibody conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

In addition to the use of imaging antibody conjugates for simple visualization, these compositions may be utilized as a "dry run" for more toxic cytotoxic antibody conjugates. If the same antibody moiety is utilized for the imaging conjugate as for the therapeutic conjugate, the physician may first use a visualization technique to determine precisely where in the brain the cytotoxic conjugate will concentrate. If a sufficient degree of tissue selectivity is not achieved (e.g., if the tumor cells are too disperse in the normal tissue, or if the particular brain tumor protein target chosen is not sufficiently overexpressed in the particular patient's tumor cells), then the physician may choose another brain tumor protein target. The provision of numerous brain tumor protein targets by the present invention, along with both imaging and therapeutic agents, allows a high degree of flexibility in designing an effective treatment regimen for the individual patient.

Combination Therapies of the Invention

As mentioned previously, brain tumors tend to be heterogeneous in character, and pervasive throughout the brain tissue. This combination often makes them difficult to treat, as individual portions of the tumor cells in any particular patient may have differing biological characteristic. Thus, in some cases, it may be preferred to use various combinations of therapeutic or imaging agents, as described above in the Summary of Invention, in order to more fully target all of the cells exhibiting tumorigenic characteristics. Such combination treatments may be by administering blended antibody therapeutic or imaging compositions, individually prepared as described above, and administering the blended therapeutic to the patient as described. The skilled administering physician will be able to take such factors as combined toxicity, and individual antibody agent efficacy, into account when administering such combined agents. Additionally, those of skill in the art will be able to screen the antibodies to avoid potential cross-reaction with each other, in order to assure full efficacy of each antibody therapeutic or imaging agent.

Alternatively, several individual brain tumor protein target compositions may be administered simultaneously or in succession for a combined therapy. This may be desirable to avoid accumulated toxicity from several antibody conjugate reagents, or to more closely monitor potential adverse reactions to the individual antibody reagents. Thus, cycles such as where a first antibody therapeutic agent is administered on day one, followed by a second on day two, then a period with out administration, followed by re-administration of the antibody therapeutics on different successive days, is comprehended within the present invention.

EXAMPLES

Example 1

Identification of Two New Splicing Variant Isoforms of PTPζ: PTPζ SM1 and SM2

The mRNA nucleotide sequence for PTPζ SM1 was identified in a human fetal brain phage cDNA library by sequencing.

The mRNA nucleotide sequence for PTPζ SM2 was identified by PCR amplification of adult human brain cDNA, and sequencing of the resulting nucleic acids.

For the RT-PCR analyses performed below, total RNA was isolated from either cells (glioblastoma cultured lines) or tissue using Trizole (Gibco Life Technologies, Inc.), following the manufacture's protocol. cDNA was generated from total RNA using the 1$^{st}$ Strand synthesis kit from Gibco Life Technologies, Inc., and an oligo dT$_{30}$ anchored primer. For each RT-PCR reaction, 1 µl of cDNA was utilized. The PCR reaction was carried out using an Advantage 2 kit (Clontech) under standard conditions. The products of the PCR reactions were confirmed via sequencing.

Both clones were verified by RT-PCR analysis of glioblastoma cell lines and primary tumors. For PTPζ SM1, primers CAGCAGTTGGATGGAAGAGGAC [SEQ ID NO. 28] and CACTGAGATTCTGGCACTATTC [SEQ ID NO. 29] were used, producing an identifiable 1116 bp product. RT-PCR analysis was performed, confirming expression of the SM1 splice variant in 11 of 17 different glioblastoma cell lines tested, fetal brain, and adult brain, using the unique 3' end and portion of the 3' untranslated region as the hybridization target for the probe. In addition, RT-PCR analysis was performed on 28 primary brain tumor samples, confirming expression of the PTPζ SM1 variant in 16 of the 28 tumors.

For PTPζ SM2, primers AACAATTCCAGGGTCTCACTC [SEQ ID NO. 30] and TTGACTGGCTCAGGAGTATAG [SEQ ID NO. 31] were used, which produce a 130 bp product when the extra exon 23a is present, and a no product when the exon 23a is absent. RT-PCR analysis was performed, confirming expression in 6 of 17 different glioblastoma cell lines tested. In addition, RT-PCR analysis was performed on 28 primary brain tumor samples, confirming expression of the PTPζ SM1 variant in 19 of the 28 tumors.

For comparison, RT-PCR analysis was also done for the expression of PTPζ -α (primers CTGATAATGAGGGCTCCCAAC [SEQ ID NO. 32] and CTCTGCACTTCCTGGTAAAACTCT [SEQ ID NO. 33]) and PTPζ -β (primers CAGCAGTTGGATGGAAGAGGAC [SEQ ID NO. 34] and CTCTGCACTTCCTGGTAAAACTCT [SEQ ID NO. 35]) in the 28 brain tumor tissue samples. PTPζ -α was shown to be expressed in 16 of the 28 samples, and the short form PTPζ -β was shown to be expressed in 19 of the 28 samples.

The nucleotide sequence alignment of the two new splice variants with the reference sequence for PTPζ-α is shown in the following table:

TABLE 2

| PTP 5' | PTP 3' | | | Corresponding Exon Key: | |
|---|---|---|---|---|---|
| | | PAC 1 5' | PAC 1 3' | | |
| 1 | 48 | 87274 | 87321 | 5' UTR | PAC 1: RP5-1062J16 BAC: RP11-384A20 |
| 70 | 205 | 87343 | 87487 | 1 | PAC 2: RP5-1049N15 |
| 205 | 272 | 142076 | 142143 | 2 | |
| | | BAC 5' | BAC 3' | | |
| 291 | 451 | 24001 | 24161 | * 3 | * 88 nt deletion seen in 5' PCR clone from PTP 363–451 |
| 450 | 603 | 28570 | 28723 | 4 | |
| 602 | 701 | 32814 | 32888 | 5 | |
| 698 | 772 | 32814 | 32888 | 6 | |
| 766 | 924 | 39695 | 39853 | 7 | |
| 922 | 1075 | 39995 | 40148 | 8 | |
| 1074 | 1261 | 52411 | 52598 | * 9 | * not spliced at 1261 in phage library clones |
| 1260 | 1387 | 53910 | 54037 | 10 | |
| 1387 | 1435 | 60644 | 60692 | 11 | |
| 1432 | 2346 | 66362 | 67276 | 5' 12 (end of BAC) | |
| | | PAC 2 5' | PAC 2 3' | | |
| 2147 | 4409 | 1 | 2263 | mid 12 | |
| 4437 | 4987 | 2294 | 2844 | 3' 12 | |
| 4925 | 5133 | 8027 | 8224 | 13 | |
| 5131 | 5224 | 17505 | 17598 | 14 | |
| 5223 | 5310 | 20427 | 20514 | 15 | |
| 5309 | 5332 | 23048 | 23071 | 16 | |
| 5329 | 5428 | 23234 | 23333 | 17 | |
| 5429 | 5512 | 25555 | 25638 | 18 | |
| 5512 | 5646 | 27710 | 27844 | 19 | |
| 5572 | 5602 | 42925 | 42955 | * Duplicate of mid 19 | * duplicated regions of exons 19 |
| 5646 | 5768 | 28408 | 28530 | most of 20 (−12 bp 3') | and 26 vary by one aa/two nt |
| 5791 | 5945 | 29770 | 29934 | 21 (−10 bp 5') | |
| 5943 | 6082 | 31560 | 31699 | 22 | |

TABLE 2-continued

| PTP 5' | PTP 3' | | | Corresponding Exon Key: | | |
|---|---|---|---|---|---|---|
| 6080 | 6228 | 33375 | 33523 | ~ 23 | ~116 nt insert seen b/w exons 23 & 24 in 3' PCR clone: maps to PAC b/w 23 & 24 | |
| 6225 | 6322 | 40379 | 40476 | ~ 24 | PTP location   PAC 2 5'   PAC 2 3' | |
| 6322 | 6397 | 40820 | 40895 | 25 | 6228   36744 | 36629 |
| 6396 | 6526 | 42864 | 42994 | 26 | | |
| 6457 | 6487 | 27770 | 27800 | * Duplicate of mid 26 | | |
| 6525 | 6673 | 43895 | 44043 | 27 | | |
| 6671 | 6816 | 47753 | 47898 | 28 | | |
| 6816 | 6952 | 48708 | 48844 | 29 | | |

BOUNDARIES DETERMINED FROM HOMO SAPIENS CHROMOSOME 7 WORKING DRAFT (NT_007845.3)
Nucleotide location refers to position in full length RPTPZ (accession M93426)

Example 2

Cell Migration Assay For Determining Antibody Activity on Protein Targets

Tumor cells are known to migrate more rapidly towards chemoattractants. The cell migration assay measures the ability of a cell to migrate. The ability to migrate is taken as a measure of tumorigenicity. Chemoattractants generally used are fetal bovine serum, pleiotrophin, bFGF, and VEGF. Thus, this assay can be used to determine migration capability of a cell in which the gene has been knocked down or the gene of interest is being overexpressed.

The ChemoTx® disposable chemotaxis system (Neuroprobe, Inc., Gaithersburg, Md.) is used according to the manufacturer's instructions, with a few modifications. Briefly, glioblastoma cultured cells from cell line G55T2 are prepared by splitting the cells the day before the assay is performed. A ChemoTx® chamber with the following specifications is used: Pore size 8 μm, exposed filter area 8 mm$^2$, exposed filter area diameter 3.2 mm. The plate configuration is: 30 μper well, 96 well plate. The membrane type is: Track-etched polycarbonate.

In preparation for the assays, the filter membrane is coated in 100 ml PBS containing 0.1% acetic acid and 3.5 ml Vitrogen 100 (from Cohesion) at 37° C. overnight. About 30 minutes before starting the assay the coated membrane is washed and rinsed with PBS containing 0.1% BSA. Cells are harvested by using the standard technique (trypsin-EDTA). The cells are washed once with DMEM 10% FBS, and then spun at 1000 RPM, for 5 minutes at room temperature. The pellet is resuspended in DMEM without serum, containing 0.1% BSA (serum free medium). The cells are spun and resuspended again in serum free medium, and then spun and resuspended in the amount of serum free medium needed to provide a concentration of 1 mio. cells/ml, or 25,000 cells per 25 ul. Just prior to the assay, a suitable amount of the antibody to be tested for anti-target function activity is added to the cell suspension.

For the assay, a standard chemoattractant is used to measure the mobility of the cells. The chemoattractants are diluted in serum free medium. A suitable unspecific chemoattractant is DMEM with 5% FBS. The chemoattractant solutions and control solutions without chemoattractant are pipetted (29 μl) into the lower plate wells. After placing and securing the filter plate over the lower wells, ensuring contact with the solution in the bottom wells, serial dilutions of the cell suspension are pipetted onto each site on the filter top. The plates are them covered and incubated at 37° C., 5% $CO_2$, for 3–4 hours.

After incubation, the upper filter side is rinsed with PBS and exposed upper filter areas are cleaned with wet cotton swabs. The filter is stained using Diff-Quik™ (VWR) dye kit, according to the manufacturer's instructions. The migrated cells are counted on the lower filter side using a microscope (Magnification 200×), by counting of 5 high power field sections per well.

Example 2

HUVEC(Human Umbilical Vein Endothelial Cells) Endothelial Sprouting assay For Determining Antibody Activity on Protein Targets Cell-sprouting morphology can be utilized as an easily visualized assay to determine the inhibitory effect of a candidate antibody on the protein target function for protein targets which stimulate endothelial cell sprouting, such as ARP2. Such assays have been described extensively in the literature (Nehls, V., et al., Histochem. Cell Biol. 104: 459–466 (1995); Koblizek, T. I., et al., Curr. Biol. 8: 529–532 (1988); and Kwak, H. J., et al., FEBS Lett. 448: 249–253). Briefly, a endothelial cells from a suitable source, such as HUVECs or PPAECs (porcine pulmonary artery endothelial cells) are grown to confluence on microcarrier (MC) beads (diameter 175 μm, available from Sigma) and placed into a 2.5 mg/ml fibrinogen gel containing the protein target at an appropriate effective concentration (200 ng/ml is an suitable starting concentration, which the skilled practitioner may optimize) and the antibody in an appropriate range of concentrations (this will depend on antibody titer and affinity for the target), and 200 units/ml Trasylol (available from Bayer). Fibrin gels are incubated in M-199 with a daily supplement of the same amount of recombinant protein and antibody, 2.0% heat-inactivated fetal bovine serum, and 200 units/ml Trasylol. After three days, the extent of sprouting is determined using a phase-contrast microscope (such as those available from Zeiss). A decrease in cell sprouting as compared to controls without antibody indicates a reduction in protein target activity by the antibody.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

The invention claimed is:

1. An isolated nucleic acid molecule, comprising the sequence encoding the polypeptide set forth in SEQ ID NO: 4.

2. The isolated nucleic acid sequence according to claim 1, comprises comprising the sequence set forth in SEQ ID NO: 3.

3. A vector comprising the nucleic acid of claim 1.

4. The vector of claim 3, wherein the vector comprises a transcription cassette operably linked to said nucleic acid sequence.

5. The vector of claim 3, wherein said vector is a plasmid.

6. The vector of claim 3, wherein said vector is a retrovirus.

7. The vector of claim 3, wherein said vector is an adenovirus.

8. An isolated nucleic acid comprising the sequence set forth in SEQ ID NO:3, residues 148–7209.

9. An isolated nucleic acid comprising SEQ ID NO:3, nucleotides 6229–6345.

10. An isolated nucleic acid molecule comprising the sequence encoding a PTPζ splice variant polypeptide at least 99% identical to SEQ ID NO: 4.

11. An isolated nucleic acid molecule, comprising the sequence encoding a polypeptide set forth in SEQ ID NO: 2.

12. The isolated nucleic acid sequence according to claim 11 comprising the sequence set forth in SEQ ID NO:1.

13. A vector comprising the nucleic acid of claim 11.

14. The vector of claim 13, wherein said vector comprises a transcription cassette operably linked to said nucleic acid sequence.

15. The vector of claim 13, wherein said vector is selected from the group consisting of a plasmid, a retrovirus and an adenovirus.

16. The nucleic acid of claim 11, comprising the sequence set forth in SEQ ID NO:1, nucleotides 148–1272.

17. The nucleic acid of claim 11, consisting of SEQ ID NO: 1 nucleotides 1262–1272.

* * * * *

SEQUENCE LISTING

<160> NUMBER OF SEQ ID NOS: 35

<210> SEQ ID NO 1
<211> LENGTH: 3091
<212> TYPE: DNA
<213> ORGANISM: Homo sapiens
<220> FEATURE:
<221> NAME/KEY: gene
<222> LOCATION: (1)..(3091)
<223> OTHER INFORMATION: PTP-zeta SM1 exon 9 variant
<220> FEATURE:
<221> NAME/KEY: VARSPLIC
<222> LOCATION: (1262)..(1262)
<223> OTHER INFORMATION: Alternative splice site
<220> FEATURE:
<221> NAME/KEY: misc_feature
<222> LOCATION: (1273)..(3091)
<223> OTHER INFORMATION: 3' Untranslated Region
<220> FEATURE:
<221> NAME/KEY: CDS
<222> LOCATION: (148)..(1272)
<223> OTHER INFORMATION:

<400> SEQUENCE: 1

```
cacacatacg cacgcacgat ctcacttcga tctatacact ggaggattaa acaaacaaa      60 caaaaaaaac atttccttcg ctcccccctcc ctctccactc tgagaagcag aggagccgca    120
cggcgagggg ccgcagaccg tctggaa atg cga atc cta aag cgt ttc ctc gct    174
                              Met Arg Ile Leu Lys Arg Phe Leu Ala
                              1               5 tgc att cag ctc ctc tgt gtt tgc cgc ctg gat tgg gct aat gga tac       222
Cys Ile Gln Leu Leu Cys Val Cys Arg Leu Asp Trp Ala Asn Gly Tyr
10              15                  20                  25 tac aga caa cag aga aaa ctt gtt gaa gag att ggc tgg tcc tat aca       270
Tyr Arg Gln Gln Arg Lys Leu Val Glu Glu Ile Gly Trp Ser Tyr Thr
                30                  35                  40 gga gca ctg aat caa aaa aat tgg gga aag aaa tat cca aca tgt aat       318
Gly Ala Leu Asn Gln Lys Asn Trp Gly Lys Lys Tyr Pro Thr Cys Asn
            45                  50                  55 agc cca aaa caa tct cct atc aat att gat gaa gat ctt aca caa gta       366
Ser Pro Lys Gln Ser Pro Ile Asn Ile Asp Glu Asp Leu Thr Gln Val
        60                  65                  70 aat gtg aat ctt aag aaa ctt aaa ttt cag ggt tgg gat aaa aca tca       414
Asn Val Asn Leu Lys Lys Leu Lys Phe Gln Gly Trp Asp Lys Thr Ser
    75                  80                  85 ttg gaa aac aca ttc att cat aac act ggg aaa aca gtg gaa att aat       462
Leu Glu Asn Thr Phe Ile His Asn Thr Gly Lys Thr Val Glu Ile Asn
90                  95                  100                 105 ctc act aat gac tac cgt gtc agc gga gga gtt tca gaa atg gtg ttt       510
Leu Thr Asn Asp Tyr Arg Val Ser Gly Gly Val Ser Glu Met Val Phe
                110                 115                 120 aaa gca agc aag ata act ttt cac tgg gga aaa tgc aat atg tca tct       558
Lys Ala Ser Lys Ile Thr Phe His Trp Gly Lys Cys Asn Met Ser Ser
            125                 130                 135 gat gga tca gag cat agt tta gaa gga caa aaa ttt cca ctt gag atg       606
Asp Gly Ser Glu His Ser Leu Glu Gly Gln Lys Phe Pro Leu Glu Met
        140                 145                 150 caa atc tac tgc ttt gat gcg gac cga ttt tca agt ttt gag gaa gca       654
Gln Ile Tyr Cys Phe Asp Ala Asp Arg Phe Ser Ser Phe Glu Glu Ala
    155                 160                 165 gtc aaa gga aaa ggg aag tta aga gct tta tcc att ttg ttt gag gtt       702
Val Lys Gly Lys Gly Lys Leu Arg Ala Leu Ser Ile Leu Phe Glu Val
170                 175                 180                 185
```

```
ggg aca gaa gaa aat ttg gat ttc aaa gcg att att gat gga gtc gaa    750
Gly Thr Glu Glu Asn Leu Asp Phe Lys Ala Ile Ile Asp Gly Val Glu
                190                 195                 200 agt gtt agt cgt ttt ggg aag cag gct gct tta gat cca ttc ata ctg    798
Ser Val Ser Arg Phe Gly Lys Gln Ala Ala Leu Asp Pro Phe Ile Leu
                205                 210                 215 ttg aac ctt ctg cca aac tca act gac aag tat tac att tac aat ggc    846
Leu Asn Leu Leu Pro Asn Ser Thr Asp Lys Tyr Tyr Ile Tyr Asn Gly
                220                 225                 230 tca ttg aca tct cct ccc tgc aca gac aca gtt gac tgg att gtt ttt    894
Ser Leu Thr Ser Pro Pro Cys Thr Asp Thr Val Asp Trp Ile Val Phe
        235                 240                 245 aaa gat aca gtt agc atc tct gaa agc cag ttg gct gtt ttt tgt gaa    942
Lys Asp Thr Val Ser Ile Ser Glu Ser Gln Leu Ala Val Phe Cys Glu
250                 255                 260                 265 gtt ctt aca atg caa caa tct ggt tat gtc atg ctg atg gac tac tta    990
Val Leu Thr Met Gln Gln Ser Gly Tyr Val Met Leu Met Asp Tyr Leu
                270                 275                 280 caa aac aat ttt cga gag caa cag tac aag ttc tct aga cag gtg ttt   1038
Gln Asn Asn Phe Arg Glu Gln Gln Tyr Lys Phe Ser Arg Gln Val Phe
                285                 290                 295 tcc tca tac act gga aag gaa gag att cat gaa gca gtt tgt agt tca   1086
Ser Ser Tyr Thr Gly Lys Glu Glu Ile His Glu Ala Val Cys Ser Ser
                300                 305                 310 gaa cca gaa aat gtt cag gct gac cca gag aat tat acc agc ctt ctt   1134
Glu Pro Glu Asn Val Gln Ala Asp Pro Glu Asn Tyr Thr Ser Leu Leu
        315                 320                 325 gtt aca tgg gaa aga cct cga gtc gtt tat gat acc atg att gag aag   1182
Val Thr Trp Glu Arg Pro Arg Val Val Tyr Asp Thr Met Ile Glu Lys
330                 335                 340                 345 ttt gca gtt ttg tac cag cag ttg gat gga gag gac caa acc aag cat   1230
Phe Ala Val Leu Tyr Gln Gln Leu Asp Gly Glu Asp Gln Thr Lys His
                350                 355                 360 gaa ttt ttg aca gat ggc tat caa gac ttg gta act ata tga           1272
Glu Phe Leu Thr Asp Gly Tyr Gln Asp Leu Val Thr Ile
                365                 370 tcagttgttt tacatagggt aacattataa tttaatttcc aaggtaagaa cttacaaatg  1332
gttgtatatt attttcctcc attactttta gactttatgt gaaggtgggg taggctgagt  1392 attttttaaat ttaaaaaaaa attttaaatt agaagctata ctaaattatg tttaaagtta 1452 catttaatta aatggatatc ataactttgc caacaataac actatagagt agatacatat  1512
gacttatgaa ctggagatca tttagtgtgg cctttcttaa gatttcagtt gtagaatagt  1572
gccagaatct cagtgccctg atacatttta tattgtgtct tccattacgc tatatcagca  1632
caggaaaagt agagtagggg acatacaagt cctctttgtt gcaccaaaaa attttcagat  1692
aacagctggg aagtcatgat tgggtcagaa ctttggggat gtaagaaaac atttcttaca  1752
aaaagatcca cccctgcctc cctccaccag cgcatgcgaa taaagtacag attccctttg  1812
tggcctgagc atgtcagtat taaactttgc tctggtaggg aagtgttggc catagattag  1872
ggtgtagttg acaaaccttc atctggatgt aggtccagaa agtccccact gcaggttaaa  1932
ggacactgga ctctgcactc aggcacctag agtcctgcaa gtcctgggaa cctgcattta  1992
aataaaaatg cactattaat tatgtttcat atcatgtgga caaaatggat aaaattttag  2052
taacctttta attcagttgc ctggaatatg gagacacaat gacctgggaa aatcgtgaaa  2112
taaatagtaa taaaaatgtt tatttcataa ttacgtgaag aagataattc tattactgtt  2172
```

```
cttgcatata tattgtcaag aaaaagagat aacttagttg ttcacttttt cacattgctc      2232
cttgtttgca aatgccccccc atttatttgt ctaaaatatt aattttttagt ttgtagtact    2292 aatttatgaa tttgatgagt tctggctaaa aatgaaactt cctgaaacta aatctgattt      2352
ttaaaaagca aaaaaaaaa aaaagcctag ctttccagtt cttcataatt cacaaatacc       2412
acaagtttaa ctaagcaaca ttgcataaac ttttccttag gttaataaaa tagaagtatt      2472
ttccacggac cagggagaaa aagttttcta ggaaagatac ctagtgtgtt ggtagtccta      2532
tgagaataac atttgtataa ttactaacat cttttctttta gggtgctatt ctcaataatt     2592
tgctacccaa tatgagttat gttcttcaga tagtagccat atgcactaat ggcttatatg      2652
gaaaatacag cgaccaactg attgtcgaca tgcctactga taatcctggt aagtgccacc      2712
agatacatct atatattaac tcaataaatg aggttagttt aattactgta tgcattgatg      2772 cttctctct atattctttt ggccaaaagg caaagtgatt ttctcttaag tctggattgc       2832
cgggtaattt tttggggcat gggacccatt tctcattcag caggtctggt gccagacaat      2892
aagtaaactt atccttaata ttggagttta ccatttgtaa aataagagtg actaaacata      2952
tttataacat tgtaataatc attaaatgaa aattgctatg taaatgttga gactgttatt      3012
ttggataatt aagagttggt ttaatttgta tttatttcct cttttcagcc cccaaagcat      3072
tatgtagtaa gtgtataca                                                  3091

<210> SEQ ID NO 2
<211> LENGTH: 374
<212> TYPE: PRT
<213> ORGANISM: Homo sapiens
<220> FEATURE:
<221> NAME/KEY: gene
<222> LOCATION: (1)..(374)
<223> OTHER INFORMATION: PTP-zeta SM1 exon 9 variant

<400> SEQUENCE: 2

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
        115                 120                 125

His Trp Gly Lys Cys Asn Met Ser Ser Asp Gly Ser Glu His Ser Leu
    130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Glu Val Gly Thr Glu Glu Asn Leu Asp
            180                 185                 190
```

```
Phe Lys Ala Ile Ile Asp Gly Val Glu Ser Val Ser Arg Phe Gly Lys
        195                 200                 205
Gln Ala Ala Leu Asp Pro Phe Ile Leu Leu Asn Leu Leu Pro Asn Ser
    210                 215                 220
Thr Asp Lys Tyr Tyr Ile Tyr Asn Gly Ser Leu Thr Ser Pro Pro Cys
225                 230                 235                 240
Thr Asp Thr Val Asp Trp Ile Val Phe Lys Asp Thr Val Ser Ile Ser
                245                 250                 255
Glu Ser Gln Leu Ala Val Phe Cys Glu Val Leu Thr Met Gln Gln Ser
            260                 265                 270
Gly Tyr Val Met Leu Met Asp Tyr Leu Gln Asn Asn Phe Arg Glu Gln
        275                 280                 285
Gln Tyr Lys Phe Ser Arg Gln Val Phe Ser Ser Tyr Thr Gly Lys Glu
    290                 295                 300
Glu Ile His Glu Ala Val Cys Ser Ser Glu Pro Glu Asn Val Gln Ala
305                 310                 315                 320
Asp Pro Glu Asn Tyr Thr Ser Leu Leu Val Thr Trp Glu Arg Pro Arg
                325                 330                 335
Val Val Tyr Asp Thr Met Ile Glu Lys Phe Ala Val Leu Tyr Gln Gln
            340                 345                 350
Leu Asp Gly Glu Asp Gln Thr Lys His Glu Phe Leu Thr Asp Gly Tyr
        355                 360                 365
Gln Asp Leu Val Thr Ile
    370

<210> SEQ ID NO 3
<211> LENGTH: 8058
<212> TYPE: DNA
<213> ORGANISM: Homo sapiens
<220> FEATURE:
<221> NAME/KEY: gene
<222> LOCATION: (1)..(8058)
<223> OTHER INFORMATION: PTP-zeta SM2 exon 23a variant
<220> FEATURE:
<221> NAME/KEY: VARSPLIC
<222> LOCATION: (6229)..(6345)
<223> OTHER INFORMATION: Exon 23a
<220> FEATURE:
<221> NAME/KEY: misc_feature
<222> LOCATION: (7210)..(8058)
<223> OTHER INFORMATION: 3' Untranslated Region

<400> SEQUENCE: 3
cacacatacg cacgcacgat ctcacttcga tctatacact ggaggattaa acaaacaaa    60 caaaaaaaac atttccttcg ctcccccctcc ctctccactc tgagaagcag aggagccgca   120
cggcgagggg ccgcagaccg tctggaaatg cgaatcctaa agcgtttcct cgcttgcatt   180
cagctcctct gtgtttgccg cctggattgg gctaatggat actacagaca acagagaaaa   240
cttgttgaag agattggctg gtcctataca ggagcactga atcaaaaaaa ttggggaaag   300
aaatatccaa catgtaatag cccaaaaaca tctcctatca atattgatga agatcttaca   360
caagtaaatg tgaatcttaa gaaacttaaa tttcagggtt gggataaaac atcattggaa   420
aacacattca ttcataacac tgggaaaaca gtggaaatta atctcactaa tgactaccgt   480
gtcagcggag gagtttcaga aatggtgttt aaagcaagca agataacttt tcactgggga   540
aaatgcaata tgtcatctga tggatcagag catagtttag aaggacaaaa atttccactt   600
gagatgcaaa tctactgctt tgatgcggac cgattttcaa gttttgagga agcagtcaaa   660
```

```
ggaaaaggga agttaagagc tttatccatt ttgtttgagg ttgggacaga agaaaatttg    720
gatttcaaag cgattattga tggagtcgaa agtgttagtc gttttgggaa gcaggctgct    780
ttagatccat tcatactgtt gaaccttctg ccaaactcaa ctgacaagta ttacatttac    840
aatggctcat tgacatctcc tccctgcaca gacacagttg actggattgt ttttaaagat    900
acagttagca tctctgaaag ccagttggct gttttttgtg aagttcttac aatgcaacaa    960
tctggttatg tcatgctgat ggactactta caaaacaatt ttcgagagca acagtacaag   1020
ttctctagac aggtgttttc ctcatacact ggaaaggaag agattcatga agcagtttgt   1080
agttcagaac cagaaaatgt tcaggctgac ccagagaatt ataccagcct tcttgttaca   1140
tgggaaagac ctcgagtcgt ttatgatacc atgattgaga gtttgcagt  tttgtaccag   1200 cagttggatg gagaggacca aaccaagcat gaattttga  cagatggcta tcaagacttg   1260
ggtgctattc tcaataattt gctacccaat atgagttatg tcttcagat  agtagccata   1320 tgcactaatg gcttatatgg aaaatacagc gaccaactga ttgtcgacat gcctactgat   1380
aatcctgaac ttgatctttt ccctgaatta attggaactg aagaaataat caaggaggag   1440
gaagagggaa aagacattga agaaggcgct attgtgaatc ctggtagaga cagtgctaca   1500
aaccaaatca ggaaaaagga accccagatt ctaccacaa  cacactacaa tcgcataggg   1560
acgaaataca atgaagccaa gactaaccga tccccaacaa gaggaagtga attctctgga   1620
aagggtgatg ttcccaatac atctttaaat tccacttccc aaccagtcac taaattagcc   1680
acagaaaaag atatttcctt gacttctcag actgtgactg aactgccacc tcacactgtg   1740
gaaggtactt cagcctcttt aaatgatggc tctaaaactg ttcttagatc tccacatatg   1800
aacttgtcgg ggactgcaga atccttaaat acagtttcta taacagaata tgaggaggag   1860
agtttattga ccagtttcaa gcttgatact ggagctgaag attcttcagg ctccagtccc   1920
gcaacttctg ctatcccatt catctctgag aacatatccc aagggtatat attttcctcc   1980
gaaaacccag agacaataac atatgatgtc cttataccag aatctgctag aaatgcttcc   2040
gaagattcaa cttcatcagg ttcagaagaa tcactaaagg atccttctat ggagggaaat   2100
gtgtggtttc ctagctctac agacataaca gcacagcccg atgttggatc aggcagagag   2160
agctttctcc agactaatta cactgagata cgtgttgatg aatctgagaa gacaaccaag   2220
tccttttctg caggcccagt gatgtcacag ggtccctcag ttacagatct ggaaatgcca   2280
cattattcta cctttgccta cttcccaact gaggtaacac ctcatgcttt tacccccatcc   2340 tccagacaac aggatttggt ctccacggtc aacgtggtat actcgcagac aacccaaccg   2400
gtatacaatg gtgagacacc tcttcaacct cctacagta  gtgaagtctt tcctctagtc   2460
acccctttgt tgcttgacaa tcagatcctc aacactaccc ctgctgcttc aagtagtgat   2520
tcggccttgc atgctacgcc tgtatttccc agtgtcgatg tgtcatttga atccatcctg   2580
tcttcctatg atggtgcacc tttgcttcca ttttcctctg cttccttcag tagtgaattg   2640
tttcgccatc tgcatacagt ttctcaaatc cttccacaag ttacttcagc taccgagagt   2700
gataaggtgc ccttgcatgc ttctctgcca gtggctgggg gtgatttgct attagagccc   2760
agccttgctc agtattctga tgtgctgtcc actactcatg ctgcttcaga gacgctggaa   2820
tttggtagta atctggtgt  tctttataaa acgcttatgt tttctcaagt tgaaccaccc   2880
agcagtgatg ccatgatgca tgcacgttct tcagggcctg aaccttctta tgccttgtct   2940
gataatgagg gctcccaaca catcttcact gtttcttaca gttctgcaat acctgtgcat   3000
gattctgtgg gtgtaactta tcagggttcc ttatttagcg gccctagcca tataccaata   3060
```

```
cctaagtctt cgttaataac cccaactgca tcattactgc agcctactca tgccctctct    3120
ggtgatgggg aatggtctgg agcctcttct gatagtgaat ttcttttacc tgacacagat    3180
gggctgacag cccttaacat ttcttcacct gtttctgtag ctgaatttac atatacaaca    3240
tctgtgtttg gtgatgataa taaggcgctt tctaaaagtg aaataatata tggaaatgag    3300
actgaactgc aaattccttc tttcaatgag atggtttacc cttctgaaag cacagtcatg    3360
cccaacatgt atgataatgt aaataagttg aatgcgtctt tacaagaaac ctctgtttcc    3420
atttctagca ccaagggcat gtttccaggg tcccttgctc ataccaccac taaggttttt    3480
gatcatgaga ttagtcaagt tccagaaaat aacttttcag ttcaacctac acatactgtc    3540
tctcaagcat ctggtgacac ttcgcttaaa cctgtgctta gtgcaaactc agagccagca    3600
tcctctgacc ctgcttctag tgaaatgtta tctccttcaa ctcagctctt attttatgag    3660
acctcagctt cttttagtac tgaagtattg ctacaacctt cctttcaggc ttctgatgtt    3720
gacaccttgc ttaaaactgt tcttccagct gtgcccagtg atccaatatt ggttgaaacc    3780
cccaaagttg ataaaattag ttctacaagt ttgcatctca ttgtatcaaa ttctgcttca    3840
agtgaaaaca tgctgcactc tacatctgta ccagtttttg atgtgtcgcc tacttctcat    3900
atgcactctg cttcacttca aggtttgacc atttcctatg caagtgagaa atatgaacca    3960
gttttgttaa aaagtgaaag ttcccaccaa gtggtaccct ctttgtacag taatgatgag    4020
ttgttccaaa cggccaattt ggagattaac caggcccatc ccccaaaagg aaggcatgta    4080
tttgctacac ctgttttatc aattgatgaa ccattaaata cactaataaa taagcttata    4140
cattccgatg aaattttaac ctccaccaaa agttctgtta ctggtaaggt atttgctggt    4200
attccaacag ttgcttctga tacatttgta tctactgatc attctgttcc tataggaaat    4260
gggcatgttg ccattacagc tgtttctccc cacagagatg ttctgtaac ctcaacaaag    4320 ttgctgtttc cttctaaggc aacttctgag ctgagtcata gtgccaaatc tgatgccggt    4380
ttagtgggtg gtggtgaaga tggtgacact gatgatgatg gtgatgatga tgatgacaga    4440
gatagtgatg gcttatccat tcataagtgt atgtcatgct catcctatag agaatcacag    4500
gaaaaggtaa tgaatgattc agacacccac gaaaacagtc ttatggatca gaataatcca    4560
atctcatact cactatctga gaattctgaa gaagataata gagtcacaag tgtatcctca    4620
gacagtcaaa ctggtatgga cagaagtcct ggtaaatcac catcagcaaa tgggctatcc    4680
caaaagcaca atgatggaaa agaggaaaat gacattcaga ctggtagtgc tctgcttcct    4740
ctcagccctg aatctaaagc atgggcagtt ctgacaagtg atgaagaaag tggatcaggg    4800
caaggtacct cagatagcct taatgagaat gagacttcca cagatttcag ttttgcagac    4860
actaatgaaa aagatgctga tgggatcctg cagcaggtg actcagaaat aactcctgga    4920
ttcccacagt ccccaacatc atctgttact agcgagaact cagaagtgtt ccacgtttca    4980
gaggcagagg ccagtaatag tagccatgag tctcgtattg gtctagctga ggggttggaa    5040
tccgagaaga aggcagttat accccttgtg atcgtgtcag ccctgacttt tatctgtcta    5100
gtggttcttg tgggtattct catctactgg aggaaatgct tccagactgc acactttttac   5160 ttagaggaca gtacatcccc tagagttata tccacacctc caacacctat ctttccaatt    5220
tcagatgatg tcggagcaat tccaataaag cactttccaa agcatgttgc agatttacat    5280
gcaagtagtg ggtttactga agaatttgag acactgaaag agttttacca ggaagtgcag    5340
agctgtactg ttgacttagg tattacagca gacagctcca accacccaga caacaagcac    5400
```

```
aagaatcgat acataaatat cgttgcctat gatcatagca gggttaagct agcacagctt    5460
gctgaaaagg atggcaaact gactgattat atcaatgcca attatgttga tggctacaac    5520
agaccaaaag cttatattgc tgcccaaggc ccactgaaat ccacagctga agatttctgg    5580
agaatgatat gggaacataa tgtggaagtt attgtcatga taacaaacct cgtggagaaa    5640
ggaaggagaa aatgtgatca gtactggcct gccgatggga gtgaggagta cgggaacttt    5700
ctggtcactc agaagagtgt gcaagtgctt gcctattata ctgtgaggaa ttttactcta    5760
agaaacacaa aaataaaaaa gggctcccag aaaggaagac ccagtggacg tgtggtcaca    5820
cagtatcact acacgcagtg gcctgacatg ggagtaccag agtactccct gccagtgctg    5880
acctttgtga gaaaggcagc ctatgccaag cgccatgcag tggggcctgt tgtcgtccac    5940
tgcagtgctg gagttggaag aacaggcaca tatattgtgc tagacagtat gttgcagcag    6000
attcaacacg aaggaactgt caacatattt ggcttcttaa acacatccg ttcacaaaga    6060 aattatttgg tacaaactga ggagcaatat gtcttcattc atgatacact ggttgaggcc    6120
atacttagta aagaaactga ggtgctggac agtcatattc atgcctatgt taatgcactc    6180
ctcattcctg gaccagcagg caaaacaaag ctagagaaac aattccaggg tctcactctg    6240
tcacccaggc tggagtgcag aggcacaatc tcggctcact gcaaccttcc tctccctggc    6300
ttaactgatc ctcctacctc agcctcccga gtggctggga ctatactcct gagccagtca    6360
aatatacagc agagtgacta ttctgcagcc ctaaagcaat gcaacaggga aaagaatcga    6420
acttcttcta tcatccctgt ggaaagatca agggttggca tttcatccct gagtggagaa    6480
ggcacagact acatcaatgc ctcctatatc atgggctatt accagagcaa tgaattcatc    6540 attcccagc accctctcct tcataccatc aaggatttct ggaggatgat atgggaccat    6600
aatgcccaac tggtggttat gattcctgat ggccaaaaca tggcagaaga tgaatttgtt    6660
tactggccaa ataaagatga gcctataaat tgtgagagct ttaaggtcac tcttatggct    6720
gaagaacaca aatgtctatc taatgaggaa aaacttataa ttcaggactt tatcttagaa    6780
gctacacagg atgattatgt acttgaagtg aggcactttc agtgtcctaa atggccaaat    6840
ccagatagcc ccattagtaa aactttgaa cttataagtg ttataaaaga agaagctgcc    6900
aatagggatg ggcctatgat tgttcatgat gagcatggag gagtgacggc aggaactttc    6960
tgtgctctga caacccttat gcaccaacta gaaaaagaaa attccgtgga tgtttaccag    7020
gtagccaaga tgatcaatct gatgaggcca ggagtctttg ctgacattga gcagtatcag    7080
tttctctaca aagtgatcct cagccttgtg agcacaaggc aggaagagaa tccatccacc    7140
tctctggaca gtaatggtgc agcattgcct gatggaaata tagctgagag cttagagtct    7200
ttagtttaac acagaaaggg gtgggggac tcacatctga gcattgtttt cctcttccta    7260
aaattaggca ggaaaatcag tctagttctg ttatctgttg atttcccatc acctgacagt    7320
aactttcatg acataggatt ctgccgccaa atttatatca ttaacaatgt gtgccttttt    7380
gcaagacttg taatttactt attatgtttg aactaaaatg attgaatttt acagtatttc    7440
taagaatgga attgtggtat ttttttctgt attgattta acgaaaatt tcaatttata    7500 gaggttagga attccaaact acagaaaatg tttgttttta gtgtcaaatt tttagctgta    7560
tttgtagcaa ttatcaggtt tgctagaaat ataactttta atacagtagc ctgtaaataa    7620
aacactcttc catatgatat tcaacatttt acaactgcag tattcaccta agtagaaat    7680 aatctgttac ttattgtaaa tactgcccta gtgtctccat ggaccaaatt tatatttata    7740
attgtagatt tttatatttt actactgagt caagttttct agttctgtgt aattgtttag    7800
```

-continued

```
tttaatgacg tagttcatta gctggtctta ctctaccagt tttctgacat tgtattgtgt   7860
tacctaagtc attaactttg tttcagcatg taattttaac ttttgtggaa aatagaaata   7920
ccttcatttt gaaagaagtt tttatgagaa taacaccctta ccaaacattg ttcaaatggt   7980
ttttatccaa ggaattgcaa aaataaatat aaatattgcc attaaaaaaa aaaaaaaaa   8040 aaaaaaaaaa aaaaaaaa                                                 8058

<210> SEQ ID NO 4
<211> LENGTH: 2353
<212> TYPE: PRT
<213> ORGANISM: Homo sapiens
<220> FEATURE:
<221> NAME/KEY: gene
<222> LOCATION: (1)..(2353)
<223> OTHER INFORMATION: PTP-zeta SM2 23a exon variant

<400> SEQUENCE: 4

Met Arg Ile Leu Lys Arg Phe Leu Ala Cys Ile Gln Leu Leu Cys Val
 1               5                  10                  15

Cys Arg Leu Asp Trp Ala Asn Gly Tyr Tyr Arg Gln Arg Lys Leu
                20                  25                  30

Val Glu Glu Ile Gly Trp Ser Tyr Thr Gly Ala Leu Asn Gln Lys Asn
         35                  40                  45

Trp Gly Lys Lys Tyr Pro Thr Cys Asn Ser Pro Lys Gln Ser Pro Ile
     50                  55                  60

Asn Ile Asp Glu Asp Leu Thr Gln Val Asn Val Asn Leu Lys Lys Leu
 65                  70                  75                  80

Lys Phe Gln Gly Trp Asp Lys Thr Ser Leu Glu Asn Thr Phe Ile His
                 85                  90                  95

Asn Thr Gly Lys Thr Val Glu Ile Asn Leu Thr Asn Asp Tyr Arg Val
                100                 105                 110

Ser Gly Gly Val Ser Glu Met Val Phe Lys Ala Ser Lys Ile Thr Phe
            115                 120                 125

His Trp Gly Lys Cys Asn Met Ser Ser Asp Gly Ser Glu His Ser Leu
        130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Glu Val Gly Thr Glu Glu Asn Leu Asp
            180                 185                 190

Phe Lys Ala Ile Ile Asp Gly Val Glu Ser Val Ser Arg Phe Gly Lys
        195                 200                 205

Gln Ala Ala Leu Asp Pro Phe Ile Leu Leu Asn Leu Leu Pro Asn Ser
    210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
                245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
        275                 280                 285

Gln Tyr Lys Phe Ser Arg Gln Val Phe Ser Ser Tyr Thr Gly Lys Glu
    290                 295                 300
```

-continued

```
Glu Ile His Glu Ala Val Cys Ser Ser Glu Pro Glu Asn Val Gln Ala
305                 310                 315                 320

Asp Pro Glu Asn Tyr Thr Ser Leu Leu Val Thr Trp Glu Arg Pro Arg
                325                 330                 335

Val Val Tyr Asp Thr Met Ile Glu Lys Phe Ala Val Leu Tyr Gln Gln
                340                 345                 350

Leu Asp Gly Glu Asp Gln Thr Lys His Glu Phe Leu Thr Asp Gly Tyr
            355                 360                 365

Gln Asp Leu Gly Ala Ile Leu Asn Asn Leu Leu Pro Asn Met Ser Tyr
    370                 375                 380

Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
                405                 410                 415

Leu Phe Pro Glu Leu Ile Gly Thr Glu Glu Ile Ile Lys Glu Glu Glu
                420                 425                 430

Glu Gly Lys Asp Ile Glu Glu Gly Ala Ile Val Asn Pro Gly Arg Asp
            435                 440                 445

Ser Ala Thr Asn Gln Ile Arg Lys Lys Glu Pro Gln Ile Ser Thr Thr
    450                 455                 460

Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
                485                 490                 495

Asn Thr Ser Leu Asn Ser Thr Ser Gln Pro Val Thr Lys Leu Ala Thr
            500                 505                 510

Glu Lys Asp Ile Ser Leu Thr Ser Gln Thr Val Thr Glu Leu Pro Pro
    515                 520                 525

His Thr Val Glu Gly Thr Ser Ala Ser Leu Asn Asp Gly Ser Lys Thr
    530                 535                 540

Val Leu Arg Ser Pro His Met Asn Leu Ser Gly Thr Ala Glu Ser Leu
545                 550                 555                 560

Asn Thr Val Ser Ile Thr Glu Tyr Glu Glu Glu Ser Leu Leu Thr Ser
                565                 570                 575

Phe Lys Leu Asp Thr Gly Ala Glu Asp Ser Ser Gly Ser Ser Pro Ala
            580                 585                 590

Thr Ser Ala Ile Pro Phe Ile Ser Glu Asn Ile Ser Gln Gly Tyr Ile
    595                 600                 605

Phe Ser Ser Glu Asn Pro Glu Thr Ile Thr Tyr Asp Val Leu Ile Pro
610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
            660                 665                 670

Phe Leu Gln Thr Asn Tyr Thr Glu Ile Arg Val Asp Glu Ser Glu Lys
    675                 680                 685

Thr Thr Lys Ser Phe Ser Ala Gly Pro Val Met Ser Gln Gly Pro Ser
    690                 695                 700

Val Thr Asp Leu Glu Met Pro His Tyr Ser Thr Phe Ala Tyr Phe Pro
705                 710                 715                 720
```

-continued

```
Thr Glu Val Thr Pro His Ala Phe Thr Pro Ser Ser Arg Gln Gln Asp
                725                 730                 735

Leu Val Ser Thr Val Asn Val Val Tyr Ser Gln Thr Thr Gln Pro Val
            740                 745                 750

Tyr Asn Gly Glu Thr Pro Leu Gln Pro Ser Tyr Ser Ser Glu Val Phe
        755                 760                 765

Pro Leu Val Thr Pro Leu Leu Leu Asp Asn Gln Ile Leu Asn Thr Thr
770                 775                 780

Pro Ala Ala Ser Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ser Ala Ser Phe Ser Ser Glu Leu Phe
            820                 825                 830

Arg His Leu His Thr Val Ser Gln Ile Leu Pro Gln Val Thr Ser Ala
        835                 840                 845

Thr Glu Ser Asp Lys Val Pro Leu His Ala Ser Leu Pro Val Ala Gly
    850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
            900                 905                 910

Ser Asp Ala Met Met His Ala Arg Ser Ser Gly Pro Glu Pro Ser Tyr
        915                 920                 925

Ala Leu Ser Asp Asn Glu Gly Ser Gln His Ile Phe Thr Val Ser Tyr
    930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
            980                 985                 990

Asp Gly Glu Trp Ser Gly Ala Ser  Ser Asp Ser Glu Phe  Leu Leu Pro
        995                 1000                1005

Asp Thr  Asp Gly Leu Thr Ala  Leu Asn Ile Ser Ser  Pro Val Ser
    1010                1015                1020

Val Ala  Glu Phe Thr Tyr Thr  Thr Ser Val Phe Gly  Asp Asp Asn
    1025                1030                1035

Lys Ala  Leu Ser Lys Ser Glu  Ile Ile Tyr Gly Asn  Glu Thr Glu
    1040                1045                1050

Leu Gln  Ile Pro Ser Phe Asn  Glu Met Val Tyr Pro  Ser Glu Ser
    1055                1060                1065

Thr Val  Met Pro Asn Met Tyr  Asp Asn Val Asn Lys  Leu Asn Ala
    1070                1075                1080

Ser Leu  Gln Glu Thr Ser Val  Ser Ile Ser Ser Thr  Lys Gly Met
    1085                1090                1095

Phe Pro  Gly Ser Leu Ala His  Thr Thr Thr Lys Val  Phe Asp His
    1100                1105                1110

Glu Ile  Ser Gln Val Pro Glu  Asn Asn Phe Ser Val  Gln Pro Thr
    1115                1120                1125

His Thr  Val Ser Gln Ala Ser  Gly Asp Thr Ser Leu  Lys Pro Val
```

-continued

|     | 1130 |     |     | 1135 |     |     |     | 1140 |     |     |
|---|---|---|---|---|---|---|---|---|---|---|

Leu Ser Ala Asn Ser Glu Pro Ala Ser Asp Pro Ala Ser Ser
1145              1150              1155

Glu Met Leu Ser Pro Ser Thr Gln Leu Leu Phe Tyr Glu Thr Ser
1160              1165              1170

Ala Ser Phe Ser Thr Glu Val Leu Leu Gln Pro Ser Phe Gln Ala
1175              1180              1185

Ser Asp Val Asp Thr Leu Leu Lys Thr Val Leu Pro Ala Val Pro
1190              1195              1200

Ser Asp Pro Ile Leu Val Glu Thr Pro Lys Val Asp Lys Ile Ser
1205              1210              1215

Ser Thr Met Leu His Leu Ile Val Ser Asn Ser Ala Ser Ser Glu
1220              1225              1230

Asn Met Leu His Ser Thr Ser Val Pro Val Phe Asp Val Ser Pro
1235              1240              1245

Thr Ser His Met His Ser Ala Ser Leu Gln Gly Leu Thr Ile Ser
1250              1255              1260

Tyr Ala Ser Glu Lys Tyr Glu Pro Val Leu Leu Lys Ser Glu Ser
1265              1270              1275

Ser His Gln Val Val Pro Ser Leu Tyr Ser Asn Asp Glu Leu Phe
1280              1285              1290

Gln Thr Ala Asn Leu Glu Ile Asn Gln Ala His Pro Pro Lys Gly
1295              1300              1305

Arg His Val Phe Ala Thr Pro Val Leu Ser Ile Asp Glu Pro Leu
1310              1315              1320

Asn Thr Leu Ile Asn Lys Leu Ile His Ser Asp Glu Ile Leu Thr
1325              1330              1335

Ser Thr Lys Ser Ser Val Thr Gly Lys Val Phe Ala Gly Ile Pro
1340              1345              1350

Thr Val Ala Ser Asp Thr Phe Val Ser Thr Asp His Ser Val Pro
1355              1360              1365

Ile Gly Asn Gly His Val Ala Ile Thr Ala Val Ser Pro His Arg
1370              1375              1380

Asp Gly Ser Val Thr Ser Thr Lys Leu Leu Phe Pro Ser Lys Ala
1385              1390              1395

Thr Ser Glu Leu Ser His Ser Ala Lys Ser Asp Ala Gly Leu Val
1400              1405              1410

Gly Gly Gly Glu Asp Gly Asp Thr Asp Asp Gly Asp Asp Asp
1415              1420              1425

Asp Asp Arg Asp Ser Asp Gly Leu Ser Ile His Lys Cys Met Ser
1430              1435              1440

Cys Ser Ser Tyr Arg Glu Ser Gln Glu Lys Val Met Asn Asp Ser
1445              1450              1455

Asp Thr His Glu Asn Ser Leu Met Asp Gln Asn Asn Pro Ile Ser
1460              1465              1470

Tyr Ser Leu Ser Glu Asn Ser Glu Glu Asp Asn Arg Val Thr Ser
1475              1480              1485

Val Ser Ser Asp Ser Gln Thr Gly Met Asp Arg Ser Pro Gly Lys
1490              1495              1500

Ser Pro Ser Ala Asn Gly Leu Ser Gln Lys His Asn Asp Gly Lys
1505              1510              1515

Glu Glu Asn Asp Ile Gln Thr Gly Ser Ala Leu Leu Pro Leu Ser
1520              1525              1530

-continued

```
Pro Glu Ser Lys Ala Trp Ala Val Leu Thr Ser Asp Glu Glu Ser
1535                1540                1545

Gly Ser Gly Gln Gly Thr Ser Asp Ser Leu Asn Glu Asn Glu Thr
1550                1555                1560

Ser Thr Asp Phe Ser Phe Ala Asp Thr Asn Glu Lys Asp Ala Asp
1565                1570                1575

Gly Ile Leu Ala Ala Gly Asp Ser Glu Ile Thr Pro Gly Phe Pro
1580                1585                1590

Gln Ser Pro Thr Ser Ser Val Thr Ser Glu Asn Ser Glu Val Phe
1595                1600                1605

His Val Ser Glu Ala Glu Ala Ser Asn Ser Ser His Glu Ser Arg
1610                1615                1620

Ile Gly Leu Ala Glu Gly Leu Glu Ser Glu Lys Lys Ala Val Ile
1625                1630                1635

Pro Leu Val Ile Val Ser Ala Leu Thr Phe Ile Cys Leu Val Val
1640                1645                1650

Leu Val Gly Ile Leu Ile Tyr Trp Arg Lys Cys Phe Gln Thr Ala
1655                1660                1665

His Phe Tyr Leu Glu Asp Ser Thr Ser Pro Arg Val Ile Ser Thr
1670                1675                1680

Pro Pro Thr Pro Ile Phe Pro Ile Ser Asp Asp Val Gly Ala Ile
1685                1690                1695

Pro Ile Lys His Phe Pro Lys His Val Ala Asp Leu His Ala Ser
1700                1705                1710

Ser Gly Phe Thr Glu Glu Phe Glu Thr Leu Lys Glu Phe Tyr Gln
1715                1720                1725

Glu Val Gln Ser Cys Thr Val Asp Leu Gly Ile Thr Ala Asp Ser
1730                1735                1740

Ser Asn His Pro Asp Asn Lys His Lys Asn Arg Tyr Ile Asn Ile
1745                1750                1755

Val Ala Tyr Asp His Ser Arg Val Lys Leu Ala Gln Leu Ala Glu
1760                1765                1770

Lys Asp Gly Lys Leu Thr Asp Tyr Ile Asn Ala Asn Tyr Val Asp
1775                1780                1785

Gly Tyr Asn Arg Pro Lys Ala Tyr Ile Ala Ala Gln Gly Pro Leu
1790                1795                1800

Lys Ser Thr Ala Glu Asp Phe Trp Arg Met Ile Trp Glu His Asn
1805                1810                1815

Val Glu Val Ile Val Met Ile Thr Asn Leu Val Glu Lys Gly Arg
1820                1825                1830

Arg Lys Cys Asp Gln Tyr Trp Pro Ala Asp Gly Ser Glu Glu Tyr
1835                1840                1845

Gly Asn Phe Leu Val Thr Gln Lys Ser Val Gln Val Leu Ala Tyr
1850                1855                1860

Tyr Thr Val Arg Asn Phe Thr Leu Arg Asn Thr Lys Ile Lys Lys
1865                1870                1875

Gly Ser Gln Lys Gly Arg Pro Ser Gly Arg Val Thr Gln Tyr
1880                1885                1890

His Tyr Thr Gln Trp Pro Asp Met Gly Val Pro Glu Tyr Ser Leu
1895                1900                1905

Pro Val Leu Thr Phe Val Arg Lys Ala Ala Tyr Ala Lys Arg His
1910                1915                1920
```

-continued

| | | | | | | | | | | |
|---|---|---|---|---|---|---|---|---|---|---|
| Ala | Val | Gly | Pro | Val | Val | His | Cys | Ser | Ala | Gly | Val Gly Arg |
| | 1925 | | | | 1930 | | | | 1935 | | |
| Thr | Gly | Thr | Tyr | Ile | Val | Leu | Asp | Ser | Met | Leu | Gln Gln Ile Gln |
| | 1940 | | | | 1945 | | | | 1950 | | |
| His | Glu | Gly | Thr | Val | Asn | Ile | Phe | Gly | Phe | Leu | Lys His Ile Arg |
| | 1955 | | | | 1960 | | | | 1965 | | |
| Ser | Gln | Arg | Asn | Tyr | Leu | Val | Gln | Thr | Glu | Gln | Tyr Val Phe |
| | 1970 | | | | 1975 | | | | 1980 | | |
| Ile | His | Asp | Thr | Leu | Val | Glu | Ala | Ile | Leu | Ser | Lys Glu Thr Glu |
| | 1985 | | | | 1990 | | | | 1995 | | |
| Val | Leu | Asp | Ser | His | Ile | His | Ala | Tyr | Val | Asn | Ala Leu Leu Ile |
| | 2000 | | | | 2005 | | | | 2010 | | |
| Pro | Gly | Pro | Ala | Gly | Lys | Thr | Lys | Leu | Glu | Lys | Gln Phe Gln Gly |
| | 2015 | | | | 2020 | | | | 2025 | | |
| Leu | Thr | Leu | Ser | Pro | Arg | Leu | Glu | Cys | Arg | Gly | Thr Ile Ser Ala |
| | 2030 | | | | 2035 | | | | 2040 | | |
| His | Cys | Asn | Leu | Pro | Leu | Pro | Gly | Leu | Thr | Asp | Pro Pro Thr Ser |
| | 2045 | | | | 2050 | | | | 2055 | | |
| Ala | Ser | Arg | Val | Ala | Gly | Thr | Ile | Leu | Leu | Ser | Gln Ser Asn Ile |
| | 2060 | | | | 2065 | | | | 2070 | | |
| Gln | Gln | Ser | Asp | Tyr | Ser | Ala | Ala | Leu | Lys | Gln | Cys Asn Arg Glu |
| | 2075 | | | | 2080 | | | | 2085 | | |
| Lys | Asn | Arg | Thr | Ser | Ser | Ile | Ile | Pro | Val | Glu | Arg Ser Arg Val |
| | 2090 | | | | 2095 | | | | 2100 | | |
| Gly | Ile | Ser | Ser | Leu | Ser | Gly | Glu | Gly | Thr | Asp | Tyr Ile Asn Ala |
| | 2105 | | | | 2110 | | | | 2115 | | |
| Ser | Tyr | Ile | Met | Gly | Tyr | Tyr | Gln | Ser | Asn | Glu | Phe Ile Ile Thr |
| | 2120 | | | | 2125 | | | | 2130 | | |
| Gln | His | Pro | Leu | Leu | His | Thr | Ile | Lys | Asp | Phe | Trp Arg Met Ile |
| | 2135 | | | | 2140 | | | | 2145 | | |
| Trp | Asp | His | Asn | Ala | Gln | Leu | Val | Val | Met | Ile | Pro Asp Gly Gln |
| | 2150 | | | | 2155 | | | | 2160 | | |
| Asn | Met | Ala | Glu | Asp | Glu | Phe | Val | Tyr | Trp | Pro | Asn Lys Asp Glu |
| | 2165 | | | | 2170 | | | | 2175 | | |
| Pro | Ile | Asn | Cys | Glu | Ser | Phe | Lys | Val | Thr | Leu | Met Ala Glu Glu |
| | 2180 | | | | 2185 | | | | 2190 | | |
| His | Lys | Cys | Leu | Ser | Asn | Glu | Glu | Lys | Leu | Ile | Ile Gln Asp Phe |
| | 2195 | | | | 2200 | | | | 2205 | | |
| Ile | Leu | Glu | Ala | Thr | Gln | Asp | Asp | Tyr | Val | Leu | Glu Val Arg His |
| | 2210 | | | | 2215 | | | | 2220 | | |
| Phe | Gln | Cys | Pro | Lys | Trp | Pro | Asn | Pro | Asp | Ser | Pro Ile Ser Lys |
| | 2225 | | | | 2230 | | | | 2235 | | |
| Thr | Phe | Glu | Leu | Ile | Ser | Val | Ile | Lys | Glu | Glu | Ala Ala Asn Arg |
| | 2240 | | | | 2245 | | | | 2250 | | |
| Asp | Gly | Pro | Met | Ile | Val | His | Asp | Glu | His | Gly | Gly Val Thr Ala |
| | 2255 | | | | 2260 | | | | 2265 | | |
| Gly | Thr | Phe | Cys | Ala | Leu | Thr | Thr | Leu | Met | His | Gln Leu Glu Lys |
| | 2270 | | | | 2275 | | | | 2280 | | |
| Glu | Asn | Ser | Val | Asp | Val | Tyr | Gln | Val | Ala | Lys | Met Ile Asn Leu |
| | 2285 | | | | 2290 | | | | 2295 | | |
| Met | Arg | Pro | Gly | Val | Phe | Ala | Asp | Ile | Glu | Gln | Tyr Gln Phe Leu |
| | 2300 | | | | 2305 | | | | 2310 | | |
| Tyr | Lys | Val | Ile | Leu | Ser | Leu | Val | Ser | Thr | Arg | Gln Glu Glu Asn |

-continued

```
                2315                2320                2325
Pro Ser  Thr Ser Leu Asp Ser  Asn Gly Ala Ala Leu  Pro Asp Gly
    2330                2335                2340

Asn Ile  Ala Glu Ser Leu Glu  Ser Leu Val
    2345                2350
```

<210> SEQ ID NO 5
<211> LENGTH: 7941
<212> TYPE: DNA
<213> ORGANISM: Homo sapiens
<220> FEATURE:
<221> NAME/KEY: CDS
<222> LOCATION: (148)..(7092)
<223> OTHER INFORMATION:
<220> FEATURE:
<221> NAME/KEY: gene
<222> LOCATION: (1)..(7941)
<223> OTHER INFORMATION: PTP-zeta

<400> SEQUENCE: 5

| | |
|---|---|
| cacacatacg cacgcacgat ctcacttcga tctatacact ggaggattaa acaaacaaa | 60 |
| caaaaaaaac atttccttcg ctcccccctcc ctctccactc tgagaagcag aggagccgca | 120 |
| cggcgagggg ccgcagaccg tctggaa atg cga atc cta aag cgt ttc ctc gct | 174 |

```
                          Met Arg Ile Leu Lys Arg Phe Leu Ala
                            1               5
```

| | |
|---|---|
| tgc att cag ctc ctc tgt gtt tgc cgc ctg gat tgg gct aat gga tac | 222 |
| Cys Ile Gln Leu Leu Cys Val Cys Arg Leu Asp Trp Ala Asn Gly Tyr | |
| 10           15              20              25 | |
| tac aga caa cag aga aaa ctt gtt gaa gag att ggc tgg tcc tat aca | 270 |
| Tyr Arg Gln Gln Arg Lys Leu Val Glu Glu Ile Gly Trp Ser Tyr Thr | |
|              30              35              40 | |
| gga gca ctg aat caa aaa aat tgg gga aag aaa tat cca aca tgt aat | 318 |
| Gly Ala Leu Asn Gln Lys Asn Trp Gly Lys Lys Tyr Pro Thr Cys Asn | |
|          45              50              55 | |
| agc cca aaa caa tct cct atc aat att gat gaa gat ctt aca caa gta | 366 |
| Ser Pro Lys Gln Ser Pro Ile Asn Ile Asp Glu Asp Leu Thr Gln Val | |
|      60              65              70 | |
| aat gtg aat ctt aag aaa ctt aaa ttt cag ggt tgg gat aaa aca tca | 414 |
| Asn Val Asn Leu Lys Lys Leu Lys Phe Gln Gly Trp Asp Lys Thr Ser | |
| 75              80              85 | |
| ttg gaa aac aca ttc att cat aac act ggg aaa aca gtg gaa att aat | 462 |
| Leu Glu Asn Thr Phe Ile His Asn Thr Gly Lys Thr Val Glu Ile Asn | |
| 90              95              100             105 | |
| ctc act aat gac tac cgt gtc agc gga gga gtt tca gaa atg gtg ttt | 510 |
| Leu Thr Asn Asp Tyr Arg Val Ser Gly Gly Val Ser Glu Met Val Phe | |
|              110             115             120 | |
| aaa gca agc aag ata act ttt cac tgg gga aaa tgc aat atg tca tct | 558 |
| Lys Ala Ser Lys Ile Thr Phe His Trp Gly Lys Cys Asn Met Ser Ser | |
|          125             130             135 | |
| gat gga tca gag cat agt tta gaa gga caa aaa ttt cca ctt gag atg | 606 |
| Asp Gly Ser Glu His Ser Leu Glu Gly Gln Lys Phe Pro Leu Glu Met | |
|      140             145             150 | |
| caa atc tac tgc ttt gat gcg gac cga ttt tca agt ttt gag gaa gca | 654 |
| Gln Ile Tyr Cys Phe Asp Ala Asp Arg Phe Ser Ser Phe Glu Glu Ala | |
| 155             160             165 | |
| gtc aaa gga aaa ggg aag tta aga gct tta tcc att ttg ttt gag gtt | 702 |
| Val Lys Gly Lys Gly Lys Leu Arg Ala Leu Ser Ile Leu Phe Glu Val | |
| 170             175             180             185 | |
| ggg aca gaa gaa aat ttg gat ttc aaa gcg att att gat gga gtc gaa | 750 |
| Gly Thr Glu Glu Asn Leu Asp Phe Lys Ala Ile Ile Asp Gly Val Glu | |
|              190             195             200 | |

|   |   |
|---|---|
| agt gtt agt cgt ttt ggg aag cag gct gct tta gat cca ttc ata ctg<br>Ser Val Ser Arg Phe Gly Lys Gln Ala Ala Leu Asp Pro Phe Ile Leu<br>205                     210                   215 | 798 |
| ttg aac ctt ctg cca aac tca act gac aag tat tac att tac aat ggc<br>Leu Asn Leu Leu Pro Asn Ser Thr Asp Lys Tyr Tyr Ile Tyr Asn Gly<br>       220                   225                   230 | 846 |
| tca ttg aca tct cct ccc tgc aca gac aca gtt gac tgg att gtt ttt<br>Ser Leu Thr Ser Pro Pro Cys Thr Asp Thr Val Asp Trp Ile Val Phe<br>235                     240                   245 | 894 |
| aaa gat aca gtt agc atc tct gaa agc cag ttg gct gtt ttt tgt gaa<br>Lys Asp Thr Val Ser Ile Ser Glu Ser Gln Leu Ala Val Phe Cys Glu<br>250                     255                   260                   265 | 942 |
| gtt ctt aca atg caa caa tct ggt tat gtc atg ctg atg gac tac tta<br>Val Leu Thr Met Gln Gln Ser Gly Tyr Val Met Leu Met Asp Tyr Leu<br>               270                   275                   280 | 990 |
| caa aac aat ttt cga gag caa cag tac aag ttc tct aga cag gtg ttt<br>Gln Asn Asn Phe Arg Glu Gln Gln Tyr Lys Phe Ser Arg Gln Val Phe<br>               285                   290                   295 | 1038 |
| tcc tca tac act gga aag gaa gag att cat gaa gca gtt tgt agt tca<br>Ser Ser Tyr Thr Gly Lys Glu Glu Ile His Glu Ala Val Cys Ser Ser<br>       300                   305                   310 | 1086 |
| gaa cca gaa aat gtt cag gct gac cca gag aat tat acc agc ctt ctt<br>Glu Pro Glu Asn Val Gln Ala Asp Pro Glu Asn Tyr Thr Ser Leu Leu<br>315                     320                   325 | 1134 |
| gtt aca tgg gaa aga cct cga gtc gtt tat gat acc atg att gag aag<br>Val Thr Trp Glu Arg Pro Arg Val Val Tyr Asp Thr Met Ile Glu Lys<br>330                     335                   340                   345 | 1182 |
| ttt gca gtt ttg tac cag cag ttg gat gga gag gac caa acc aag cat<br>Phe Ala Val Leu Tyr Gln Gln Leu Asp Gly Glu Asp Gln Thr Lys His<br>               350                   355                   360 | 1230 |
| gaa ttt ttg aca gat ggc tat caa gac ttg ggt gct att ctc aat aat<br>Glu Phe Leu Thr Asp Gly Tyr Gln Asp Leu Gly Ala Ile Leu Asn Asn<br>               365                   370                   375 | 1278 |
| ttg cta ccc aat atg agt tat gtt ctt cag ata gta gcc ata tgc act<br>Leu Leu Pro Asn Met Ser Tyr Val Leu Gln Ile Val Ala Ile Cys Thr<br>380                     385                   390 | 1326 |
| aat ggc tta tat gga aaa tac agc gac caa ctg att gtc gac atg cct<br>Asn Gly Leu Tyr Gly Lys Tyr Ser Asp Gln Leu Ile Val Asp Met Pro<br>395                     400                   405 | 1374 |
| act gat aat cct gaa ctt gat ctt ttc cct gaa tta att gga act gaa<br>Thr Asp Asn Pro Glu Leu Asp Leu Phe Pro Glu Leu Ile Gly Thr Glu<br>410                     415                   420                   425 | 1422 |
| gaa ata atc aag gag gag gaa gag gga aaa gac att gaa gaa ggc gct<br>Glu Ile Ile Lys Glu Glu Glu Glu Gly Lys Asp Ile Glu Glu Gly Ala<br>               430                   435                   440 | 1470 |
| att gtg aat cct ggt aga gac agt gct aca aac caa atc agg aaa aag<br>Ile Val Asn Pro Gly Arg Asp Ser Ala Thr Asn Gln Ile Arg Lys Lys<br>               445                   450                   455 | 1518 |
| gaa ccc cag att tct acc aca aca cac tac aat cgc ata ggg acg aaa<br>Glu Pro Gln Ile Ser Thr Thr Thr His Tyr Asn Arg Ile Gly Thr Lys<br>460                     465                   470 | 1566 |
| tac aat gaa gcc aag act aac cga tcc cca aca aga gga agt gaa ttc<br>Tyr Asn Glu Ala Lys Thr Asn Arg Ser Pro Thr Arg Gly Ser Glu Phe<br>475                     480                   485 | 1614 |
| tct gga aag ggt gat gtt ccc aat aca tct tta aat tcc act tcc caa<br>Ser Gly Lys Gly Asp Val Pro Asn Thr Ser Leu Asn Ser Thr Ser Gln<br>490                     495                   500                   505 | 1662 |
| cca gtc act aaa tta gcc aca gaa aaa gat att tcc ttg act tct cag<br>Pro Val Thr Lys Leu Ala Thr Glu Lys Asp Ile Ser Leu Thr Ser Gln | 1710 |

```
                    510             515             520
act gtg act gaa ctg cca cct cac act gtg gaa ggt act tca gcc tct     1758
Thr Val Thr Glu Leu Pro Pro His Thr Val Glu Gly Thr Ser Ala Ser
            525                 530                 535 tta aat gat ggc tct aaa act gtt ctt aga tct cca cat atg aac ttg     1806
Leu Asn Asp Gly Ser Lys Thr Val Leu Arg Ser Pro His Met Asn Leu
            540                 545                 550 tcg ggg act gca gaa tcc tta aat aca gtt tct ata aca gaa tat gag     1854
Ser Gly Thr Ala Glu Ser Leu Asn Thr Val Ser Ile Thr Glu Tyr Glu
    555                 560                 565 gag gag agt tta ttg acc agt ttc aag ctt gat act gga gct gaa gat     1902
Glu Glu Ser Leu Leu Thr Ser Phe Lys Leu Asp Thr Gly Ala Glu Asp
570                 575                 580                 585 tct tca ggc tcc agt ccc gca act tct gct atc cca ttc atc tct gag     1950
Ser Ser Gly Ser Ser Pro Ala Thr Ser Ala Ile Pro Phe Ile Ser Glu
            590                 595                 600 aac ata tcc caa ggg tat ata ttt tcc tcc gaa aac cca gag aca ata     1998
Asn Ile Ser Gln Gly Tyr Ile Phe Ser Ser Glu Asn Pro Glu Thr Ile
            605                 610                 615 aca tat gat gtc ctt ata cca gaa tct gct aga aat gct tcc gaa gat     2046
Thr Tyr Asp Val Leu Ile Pro Glu Ser Ala Arg Asn Ala Ser Glu Asp
            620                 625                 630 tca act tca tca ggt tca gaa gaa tca cta aag gat cct tct atg gag     2094
Ser Thr Ser Ser Gly Ser Glu Glu Ser Leu Lys Asp Pro Ser Met Glu
    635                 640                 645 gga aat gtg tgg ttt cct agc tct aca gac ata aca gca cag ccc gat     2142
Gly Asn Val Trp Phe Pro Ser Ser Thr Asp Ile Thr Ala Gln Pro Asp
650                 655                 660                 665 gtt gga tca ggc aga gag agc ttt ctc cag act aat tac act gag ata     2190
Val Gly Ser Gly Arg Glu Ser Phe Leu Gln Thr Asn Tyr Thr Glu Ile
            670                 675                 680 cgt gtt gat gaa tct gag aag aca acc aag tcc ttt tct gca ggc cca     2238
Arg Val Asp Glu Ser Glu Lys Thr Thr Lys Ser Phe Ser Ala Gly Pro
            685                 690                 695 gtg atg tca cag ggt ccc tca gtt aca gat ctg gaa atg cca cat tat     2286
Val Met Ser Gln Gly Pro Ser Val Thr Asp Leu Glu Met Pro His Tyr
    700                 705                 710 tct acc ttt gcc tac ttc cca act gag gta aca cct cat gct ttt acc     2334
Ser Thr Phe Ala Tyr Phe Pro Thr Glu Val Thr Pro His Ala Phe Thr
    715                 720                 725 cca tcc tcc aga caa cag gat ttg gtc tcc acg gtc aac gtg gta tac     2382
Pro Ser Ser Arg Gln Gln Asp Leu Val Ser Thr Val Asn Val Val Tyr
730                 735                 740                 745 tcg cag aca acc caa ccg gta tac aat ggt gag aca cct ctt caa cct     2430
Ser Gln Thr Thr Gln Pro Val Tyr Asn Gly Glu Thr Pro Leu Gln Pro
            750                 755                 760 tcc tac agt agt gaa gtc ttt cct cta gtc acc cct ttg ttg ctt gac     2478
Ser Tyr Ser Ser Glu Val Phe Pro Leu Val Thr Pro Leu Leu Leu Asp
            765                 770                 775 aat cag atc ctc aac act acc cct gct gct tca agt agt gat tcg gcc     2526
Asn Gln Ile Leu Asn Thr Thr Pro Ala Ala Ser Ser Ser Asp Ser Ala
            780                 785                 790 ttg cat gct acg cct gta ttt ccc agt gtc gat gtg tca ttt gaa tcc     2574
Leu His Ala Thr Pro Val Phe Pro Ser Val Asp Val Ser Phe Glu Ser
    795                 800                 805 atc ctg tct tcc tat gat ggt gca cct ttg ctt cca ttt tcc tct gct     2622
Ile Leu Ser Ser Tyr Asp Gly Ala Pro Leu Leu Pro Phe Ser Ser Ala
810                 815                 820                 825 tcc ttc agt agt gaa ttg ttt cgc cat ctg cat aca gtt tct caa atc     2670
```

-continued

```
                Ser Phe Ser Ser Glu Leu Phe Arg His Leu His Thr Val Ser Gln Ile
                                830                 835                 840 ctt cca caa gtt act tca gct acc gag agt gat aag gtg ccc ttg cat              2718
Leu Pro Gln Val Thr Ser Ala Thr Glu Ser Asp Lys Val Pro Leu His
            845                 850                 855 gct tct ctg cca gtg gct ggg ggt gat ttg cta tta gag ccc agc ctt              2766
Ala Ser Leu Pro Val Ala Gly Gly Asp Leu Leu Leu Glu Pro Ser Leu
            860                 865                 870 gct cag tat tct gat gtg ctg tcc act act cat gct gct tca gag acg              2814
Ala Gln Tyr Ser Asp Val Leu Ser Thr Thr His Ala Ala Ser Glu Thr
            875                 880                 885 ctg gaa ttt ggt agt gaa tct ggt gtt ctt tat aaa acg ctt atg ttt              2862
Leu Glu Phe Gly Ser Glu Ser Gly Val Leu Tyr Lys Thr Leu Met Phe
890                 895                 900                 905 tct caa gtt gaa cca ccc agc agt gat gcc atg atg cat gca cgt tct              2910
Ser Gln Val Glu Pro Pro Ser Ser Asp Ala Met Met His Ala Arg Ser
            910                 915                 920 tca ggg cct gaa cct tct tat gcc ttg tct gat aat gag ggc tcc caa              2958
Ser Gly Pro Glu Pro Ser Tyr Ala Leu Ser Asp Asn Glu Gly Ser Gln
            925                 930                 935 cac atc ttc act gtt tct tac agt tct gca ata cct gtg cat gat tct              3006
His Ile Phe Thr Val Ser Tyr Ser Ser Ala Ile Pro Val His Asp Ser
            940                 945                 950 gtg ggt gta act tat cag ggt tcc tta ttt agc ggc cct agc cat ata              3054
Val Gly Val Thr Tyr Gln Gly Ser Leu Phe Ser Gly Pro Ser His Ile
955                 960                 965 cca ata cct aag tct tcg tta ata acc cca act gca tca tta ctg cag              3102
Pro Ile Pro Lys Ser Ser Leu Ile Thr Pro Thr Ala Ser Leu Leu Gln
970                 975                 980                 985 cct act cat gcc ctc tct ggt gat ggg gaa tgg tct gga gcc tct  tct             3150
Pro Thr His Ala Leu Ser Gly Asp Gly Glu Trp Ser Gly Ala Ser  Ser
            990                 995                 1000 gat agt gaa ttt  ctt tta cct gac aca  gat ggg ctg aca gcc  ctt               3195
Asp Ser Glu Phe  Leu Leu Pro Asp Thr  Asp Gly Leu Thr Ala  Leu
            1005                1010                1015 aac att tct tca  cct gtt tct gta gct  gaa ttt aca tat aca  aca               3240
Asn Ile Ser Ser  Pro Val Ser Val Ala  Glu Phe Thr Tyr Thr  Thr
            1020                1025                1030 tct gtg ttt ggt  gat gat aat aag gcg  ctt tct aaa agt gaa  ata               3285
Ser Val Phe Gly  Asp Asp Asn Lys Ala  Leu Ser Lys Ser Glu  Ile
            1035                1040                1045 ata tat gga aat  gag act gaa ctg caa  att cct tct ttc aat  gag               3330
Ile Tyr Gly Asn  Glu Thr Glu Leu Gln  Ile Pro Ser Phe Asn  Glu
            1050                1055                1060 atg gtt tac cct  tct gaa agc aca gtc  atg ccc aac atg tat  gat               3375
Met Val Tyr Pro  Ser Glu Ser Thr Val  Met Pro Asn Met Tyr  Asp
            1065                1070                1075 aat gta aat aag  ttg aat gcg tct tta  caa gaa acc tct gtt  tcc               3420
Asn Val Asn Lys  Leu Asn Ala Ser Leu  Gln Glu Thr Ser Val  Ser
            1080                1085                1090 att tct agc acc  aag ggc atg ttt cca  ggg tcc ctt gct cat  acc               3465
Ile Ser Ser Thr  Lys Gly Met Phe Pro  Gly Ser Leu Ala His  Thr
            1095                1100                1105 acc act aag gtt  ttt gat cat gag att  agt caa gtt cca gaa  aat               3510
Thr Thr Lys Val  Phe Asp His Glu Ile  Ser Gln Val Pro Glu  Asn
            1110                1115                1120 aac ttt tca gtt  caa cct aca cat act  gtc tct caa gca tct  ggt               3555
Asn Phe Ser Val  Gln Pro Thr His Thr  Val Ser Gln Ala Ser  Gly
            1125                1130                1135
```

```
                                                    -continued gac act tcg ctt aaa cct gtg ctt agt gca aac tca gag cca gca        3600
Asp Thr Ser Leu Lys Pro Val Leu Ser Ala Asn Ser Glu Pro Ala
            1140                1145                1150 tcc tct gac cct gct tct agt gaa atg tta tct cct tca act cag        3645
Ser Ser Asp Pro Ala Ser Ser Glu Met Leu Ser Pro Ser Thr Gln
            1155                1160                1165 ctc tta ttt tat gag acc tca gct tct ttt agt act gaa gta ttg        3690
Leu Leu Phe Tyr Glu Thr Ser Ala Ser Phe Ser Thr Glu Val Leu
            1170                1175                1180 cta caa cct tcc ttt cag gct tct gat gtt gac acc ttg ctt aaa        3735
Leu Gln Pro Ser Phe Gln Ala Ser Asp Val Asp Thr Leu Leu Lys
            1185                1190                1195 act gtt ctt cca gct gtg ccc agt gat cca ata ttg gtt gaa acc        3780
Thr Val Leu Pro Ala Val Pro Ser Asp Pro Ile Leu Val Glu Thr
            1200                1205                1210 ccc aaa gtt gat aaa att agt tct aca atg ttg cat ctc att gta        3825
Pro Lys Val Asp Lys Ile Ser Ser Thr Met Leu His Leu Ile Val
            1215                1220                1225 tca aat tct gct tca agt gaa aac atg ctg cac tct aca tct gta        3870
Ser Asn Ser Ala Ser Ser Glu Asn Met Leu His Ser Thr Ser Val
            1230                1235                1240 cca gtt ttt gat gtg tcg cct act tct cat atg cac tct gct tca        3915
Pro Val Phe Asp Val Ser Pro Thr Ser His Met His Ser Ala Ser
            1245                1250                1255 ctt caa ggt ttg acc att tcc tat gca agt gag aaa tat gaa cca        3960
Leu Gln Gly Leu Thr Ile Ser Tyr Ala Ser Glu Lys Tyr Glu Pro
            1260                1265                1270 gtt ttg tta aaa agt gaa agt tcc cac caa gtg gta cct tct ttg        4005
Val Leu Leu Lys Ser Glu Ser Ser His Gln Val Val Pro Ser Leu
            1275                1280                1285 tac agt aat gat gag ttg ttc caa acg gcc aat ttg gag att aac        4050
Tyr Ser Asn Asp Glu Leu Phe Gln Thr Ala Asn Leu Glu Ile Asn
            1290                1295                1300 cag gcc cat ccc cca aaa gga agg cat gta ttt gct aca cct gtt        4095
Gln Ala His Pro Pro Lys Gly Arg His Val Phe Ala Thr Pro Val
            1305                1310                1315 tta tca att gat gaa cca tta aat aca cta ata aat aag ctt ata        4140
Leu Ser Ile Asp Glu Pro Leu Asn Thr Leu Ile Asn Lys Leu Ile
            1320                1325                1330 cat tcc gat gaa att tta acc tcc acc aaa agt tct gtt act ggt        4185
His Ser Asp Glu Ile Leu Thr Ser Thr Lys Ser Ser Val Thr Gly
            1335                1340                1345 aag gta ttt gct ggt att cca aca gtt gct tct gat aca ttt gta        4230
Lys Val Phe Ala Gly Ile Pro Thr Val Ala Ser Asp Thr Phe Val
            1350                1355                1360 tct act gat cat tct gtt cct ata gga aat ggg cat gtt gcc att        4275
Ser Thr Asp His Ser Val Pro Ile Gly Asn Gly His Val Ala Ile
            1365                1370                1375 aca gct gtt tct ccc cac aga gat ggt tct gta acc tca aca aag        4320
Thr Ala Val Ser Pro His Arg Asp Gly Ser Val Thr Ser Thr Lys
            1380                1385                1390 ttg ctg ttt cct tct aag gca act tct gag ctg agt cat agt gcc        4365
Leu Leu Phe Pro Ser Lys Ala Thr Ser Glu Leu Ser His Ser Ala
            1395                1400                1405 aaa tct gat gcc ggt tta gtg ggt ggt gga gaa gat ggt gac act        4410
Lys Ser Asp Ala Gly Leu Val Gly Gly Gly Glu Asp Gly Asp Thr
            1410                1415                1420 gat gat gat ggt gat gat gat gat gac aga gat agt gat ggc tta        4455
Asp Asp Asp Gly Asp Asp Asp Asp Asp Arg Asp Ser Asp Gly Leu
            1425                1430                1435
```

```
                                                        -continued tcc att cat aag tgt atg tca tgc tca tcc tat aga gaa tca cag        4500
Ser Ile His Lys Cys Met Ser Cys Ser Ser Tyr Arg Glu Ser Gln
            1440                1445                1450 gaa aag gta atg aat gat tca gac acc cac gaa aac agt ctt atg        4545
Glu Lys Val Met Asn Asp Ser Asp Thr His Glu Asn Ser Leu Met
            1455                1460                1465 gat cag aat aat cca atc tca tac tca cta tct gag aat tct gaa        4590
Asp Gln Asn Asn Pro Ile Ser Tyr Ser Leu Ser Glu Asn Ser Glu
            1470                1475                1480 gaa gat aat aga gtc aca agt gta tcc tca gac agt caa act ggt        4635
Glu Asp Asn Arg Val Thr Ser Val Ser Ser Asp Ser Gln Thr Gly
            1485                1490                1495 atg gac aga agt cct ggt aaa tca cca tca gca aat ggg cta tcc        4680
Met Asp Arg Ser Pro Gly Lys Ser Pro Ser Ala Asn Gly Leu Ser
            1500                1505                1510 caa aag cac aat gat gga aaa gag gaa aat gac att cag act ggt        4725
Gln Lys His Asn Asp Gly Lys Glu Glu Asn Asp Ile Gln Thr Gly
            1515                1520                1525 agt gct ctg ctt cct ctc agc cct gaa tct aaa gca tgg gca gtt        4770
Ser Ala Leu Leu Pro Leu Ser Pro Glu Ser Lys Ala Trp Ala Val
            1530                1535                1540 ctg aca agt gat gaa gaa agt gga tca ggg caa ggt acc tca gat        4815
Leu Thr Ser Asp Glu Glu Ser Gly Ser Gly Gln Gly Thr Ser Asp
            1545                1550                1555 agc ctt aat gag aat gag act tcc aca gat ttc agt ttt gca gac        4860
Ser Leu Asn Glu Asn Glu Thr Ser Thr Asp Phe Ser Phe Ala Asp
            1560                1565                1570 act aat gaa aaa gat gct gat ggg atc ctg gca gca ggt gac tca        4905
Thr Asn Glu Lys Asp Ala Asp Gly Ile Leu Ala Ala Gly Asp Ser
            1575                1580                1585 gaa ata act cct gga ttc cca cag tcc cca aca tca tct gtt act        4950
Glu Ile Thr Pro Gly Phe Pro Gln Ser Pro Thr Ser Ser Val Thr
            1590                1595                1600 agc gag aac tca gaa gtg ttc cac gtt tca gag gca gag gcc agt        4995
Ser Glu Asn Ser Glu Val Phe His Val Ser Glu Ala Glu Ala Ser
            1605                1610                1615 aat agt agc cat gag tct cgt att ggt cta gct gag ggg ttg gaa        5040
Asn Ser Ser His Glu Ser Arg Ile Gly Leu Ala Glu Gly Leu Glu
            1620                1625                1630 tcc gag aag aag gca gtt ata ccc ctt gtg atc gtg tca gcc ctg        5085
Ser Glu Lys Lys Ala Val Ile Pro Leu Val Ile Val Ser Ala Leu
            1635                1640                1645 act ttt atc tgt cta gtg gtt ctt gtg ggt att ctc atc tac tgg        5130
Thr Phe Ile Cys Leu Val Val Leu Val Gly Ile Leu Ile Tyr Trp
            1650                1655                1660 agg aaa tgc ttc cag act gca cac ttt tac tta gag gac agt aca        5175
Arg Lys Cys Phe Gln Thr Ala His Phe Tyr Leu Glu Asp Ser Thr
            1665                1670                1675 tcc cct aga gtt ata tcc aca cct cca aca cct atc ttt cca att        5220
Ser Pro Arg Val Ile Ser Thr Pro Pro Thr Pro Ile Phe Pro Ile
            1680                1685                1690 tca gat gat gtc gga gca att cca ata aag cac ttt cca aag cat        5265
Ser Asp Asp Val Gly Ala Ile Pro Ile Lys His Phe Pro Lys His
            1695                1700                1705 gtt gca gat tta cat gca agt agt ggg ttt act gaa gaa ttt gag        5310
Val Ala Asp Leu His Ala Ser Ser Gly Phe Thr Glu Glu Phe Glu
            1710                1715                1720 aca ctg aaa gag ttt tac cag gaa gtg cag agc tgt act gtt gac        5355
Thr Leu Lys Glu Phe Tyr Gln Glu Val Gln Ser Cys Thr Val Asp
```

-continued

```
                  1725                1730                1735
tta ggt att aca  gca gac agc tcc  aac cac cca gac  aac aag cac      5400
Leu Gly Ile Thr  Ala Asp Ser Ser  Asn His Pro Asp  Asn Lys His
         1740                1745                1750 aag aat cga tac  ata aat atc gtt  gcc tat gat cat  agc agg gtt      5445
Lys Asn Arg Tyr  Ile Asn Ile Val  Ala Tyr Asp His  Ser Arg Val
         1755                1760                1765 aag cta gca cag  ctt gct gaa aag  gat ggc aaa ctg  act gat tat      5490
Lys Leu Ala Gln  Leu Ala Glu Lys  Asp Gly Lys Leu  Thr Asp Tyr
         1770                1775                1780 atc aat gcc aat  tat gtt gat ggc  tac aac aga cca  aaa gct tat      5535
Ile Asn Ala Asn  Tyr Val Asp Gly  Tyr Asn Arg Pro  Lys Ala Tyr
         1785                1790                1795 att gct gcc caa  ggc cca ctg aaa  tcc aca gct gaa  gat ttc tgg      5580
Ile Ala Ala Gln  Gly Pro Leu Lys  Ser Thr Ala Glu  Asp Phe Trp
         1800                1805                1810 aga atg ata tgg  gaa cat aat gtg  gaa gtt att gtc  atg ata aca      5625
Arg Met Ile Trp  Glu His Asn Val  Glu Val Ile Val  Met Ile Thr
         1815                1820                1825 aac ctc gtg gag  aaa gga agg aga  aaa tgt gat cag  tac tgg cct      5670
Asn Leu Val Glu  Lys Gly Arg Arg  Lys Cys Asp Gln  Tyr Trp Pro
         1830                1835                1840 gcc gat ggg agt  gag gag tac ggg  aac ttt ctg gtc  act cag aag      5715
Ala Asp Gly Ser  Glu Glu Tyr Gly  Asn Phe Leu Val  Thr Gln Lys
         1845                1850                1855 agt gtg caa gtg  ctt gcc tat tat  act gtg agg aat  ttt act cta      5760
Ser Val Gln Val  Leu Ala Tyr Tyr  Thr Val Arg Asn  Phe Thr Leu
         1860                1865                1870 aga aac aca aaa  ata aaa aag ggc  tcc cag aaa gga  aga ccc agt      5805
Arg Asn Thr Lys  Ile Lys Lys Gly  Ser Gln Lys Gly  Arg Pro Ser
         1875                1880                1885 gga cgt gtg gtc  aca cag tat cac  tac acg cag tgg  cct gac atg      5850
Gly Arg Val Val  Thr Gln Tyr His  Tyr Thr Gln Trp  Pro Asp Met
         1890                1895                1900 gga gta cca gag  tac tcc ctg cca  gtg ctg acc ttt  gtg aga aag      5895
Gly Val Pro Glu  Tyr Ser Leu Pro  Val Leu Thr Phe  Val Arg Lys
         1905                1910                1915 gca gcc tat gcc  aag cgc cat gca  gtg ggg cct gtt  gtc gtc cac      5940
Ala Ala Tyr Ala  Lys Arg His Ala  Val Gly Pro Val  Val Val His
         1920                1925                1930 tgc agt gct gga  gtt gga aga aca  ggc aca tat att  gtg cta gac      5985
Cys Ser Ala Gly  Val Gly Arg Thr  Gly Thr Tyr Ile  Val Leu Asp
         1935                1940                1945 agt atg ttg cag  cag att caa cac  gaa gga act gtc  aac ata ttt      6030
Ser Met Leu Gln  Gln Ile Gln His  Glu Gly Thr Val  Asn Ile Phe
         1950                1955                1960 ggc ttc tta aaa  cac atc cgt tca  caa aga aat tat  ttg gta caa      6075
Gly Phe Leu Lys  His Ile Arg Ser  Gln Arg Asn Tyr  Leu Val Gln
         1965                1970                1975 act gag gag caa  tat gtc ttc att  cat gat aca ctg  gtt gag gcc      6120
Thr Glu Glu Gln  Tyr Val Phe Ile  His Asp Thr Leu  Val Glu Ala
         1980                1985                1990 ata ctt agt aaa  gaa act gag gtg  ctg gac agt cat  att cat gcc      6165
Ile Leu Ser Lys  Glu Thr Glu Val  Leu Asp Ser His  Ile His Ala
         1995                2000                2005 tat gtt aat gca  ctc ctc att cct  gga cca gca ggc  aaa aca aag      6210
Tyr Val Asn Ala  Leu Leu Ile Pro  Gly Pro Ala Gly  Lys Thr Lys
         2010                2015                2020 cta gag aaa caa  ttc cag ctc ctg  agc cag tca aat  ata cag cag      6255
```

```
                Leu Glu Lys Gln  Phe Gln Leu Leu  Ser Gln Ser Asn  Ile Gln Gln
                        2025             2030             2035 agt gac tat tct  gca gcc cta aag  caa tgc aac agg  gaa aag aat                  6300
Ser Asp Tyr Ser  Ala Ala Leu Lys  Gln Cys Asn Arg  Glu Lys Asn
        2040             2045             2050 cga act tct tct  atc atc cct gtg  gaa aga tca agg  gtt ggc att                  6345
Arg Thr Ser Ser  Ile Ile Pro Val  Glu Arg Ser Arg  Val Gly Ile
        2055             2060             2065 tca tcc ctg agt  gga gaa ggc aca  gac tac atc aat  gcc tcc tat                  6390
Ser Ser Leu Ser  Gly Glu Gly Thr  Asp Tyr Ile Asn  Ala Ser Tyr
        2070             2075             2080 atc atg ggc tat  tac cag agc aat  gaa ttc atc att  acc cag cac                  6435
Ile Met Gly Tyr  Tyr Gln Ser Asn  Glu Phe Ile Ile  Thr Gln His
        2085             2090             2095 cct ctc ctt cat  acc atc aag gat  ttc tgg agg atg  ata tgg gac                  6480
Pro Leu Leu His  Thr Ile Lys Asp  Phe Trp Arg Met  Ile Trp Asp
        2100             2105             2110 cat aat gcc caa  ctg gtg gtt atg  att cct gat ggc  caa aac atg                  6525
His Asn Ala Gln  Leu Val Val Met  Ile Pro Asp Gly  Gln Asn Met
        2115             2120             2125 gca gaa gat gaa  ttt gtt tac tgg  cca aat aaa gat  gag cct ata                  6570
Ala Glu Asp Glu  Phe Val Tyr Trp  Pro Asn Lys Asp  Glu Pro Ile
        2130             2135             2140 aat tgt gag agc  ttt aag gtc act  ctt atg gct gaa  gaa cac aaa                  6615
Asn Cys Glu Ser  Phe Lys Val Thr  Leu Met Ala Glu  Glu His Lys
        2145             2150             2155 tgt cta tct aat  gag gaa aaa ctt  ata att cag gac  ttt atc tta                  6660
Cys Leu Ser Asn  Glu Glu Lys Leu  Ile Ile Gln Asp  Phe Ile Leu
        2160             2165             2170 gaa gct aca cag  gat gat tat gta  ctt gaa gtg agg  cac ttt cag                  6705
Glu Ala Thr Gln  Asp Asp Tyr Val  Leu Glu Val Arg  His Phe Gln
        2175             2180             2185 tgt cct aaa tgg  cca aat cca gat  agc ccc att agt  aaa act ttt                  6750
Cys Pro Lys Trp  Pro Asn Pro Asp  Ser Pro Ile Ser  Lys Thr Phe
        2190             2195             2200 gaa ctt ata agt  gtt ata aaa gaa  gaa gct gcc aat  agg gat ggg                  6795
Glu Leu Ile Ser  Val Ile Lys Glu  Glu Ala Ala Asn  Arg Asp Gly
        2205             2210             2215 cct atg att gtt  cat gat gag cat  gga gga gtg acg  gca gga act                  6840
Pro Met Ile Val  His Asp Glu His  Gly Gly Val Thr  Ala Gly Thr
        2220             2225             2230 ttc tgt gct ctg  aca acc ctt atg  cac caa cta gaa  aaa gaa aat                  6885
Phe Cys Ala Leu  Thr Thr Leu Met  His Gln Leu Glu  Lys Glu Asn
        2235             2240             2245 tcc gtg gat gtt  tac cag gta gcc  aag atg atc aat  ctg atg agg                  6930
Ser Val Asp Val  Tyr Gln Val Ala  Lys Met Ile Asn  Leu Met Arg
        2250             2255             2260 cca gga gtc ttt  gct gac att gag  cag tat cag ttt  ctc tac aaa                  6975
Pro Gly Val Phe  Ala Asp Ile Glu  Gln Tyr Gln Phe  Leu Tyr Lys
        2265             2270             2275 gtg atc ctc agc  ctt gtg agc aca  agg cag gaa gag  aat cca tcc                  7020
Val Ile Leu Ser  Leu Val Ser Thr  Arg Gln Glu Glu  Asn Pro Ser
        2280             2285             2290 acc tct ctg gac  agt aat ggt gca  gca ttg cct gat  gga aat ata                  7065
Thr Ser Leu Asp  Ser Asn Gly Ala  Ala Leu Pro Asp  Gly Asn Ile
        2295             2300             2305 gct gag agc tta  gag tct tta gtt  taa cacagaaagg ggtgggggga                     7112
Ala Glu Ser Leu  Glu Ser Leu Val
        2310
```

```
ctcacatctg agcattgttt tcctcttcct aaaattaggc aggaaaatca gtctagttct    7172
gttatctgtt gatttcccat cacctgacag taactttcat gacataggat tctgccgcca    7232
aatttatatc attaacaatg tgtgccttt tgcaagactt gtaatttact tattatgttt    7292
gaactaaaat gattgaattt tacagtattt ctaagaatgg aattgtggta ttttttttctg   7352 tattgatttt aacagaaaat ttcaattat agaggttagg aattccaaac tacagaaaat    7412
gtttgttttt agtgtcaaat ttttagctgt atttgtagca attatcaggt ttgctagaaa    7472 tataacttt aatacagtag cctgtaaata aaacactctt ccatatgata ttcaacattt     7532
tacaactgca gtattcacct aaagtagaaa taatctgtta cttattgtaa atactgcct    7592 agtgtctcca tggaccaaat ttatatttat aattgtagat ttttatattt tactactgag    7652 tcaagtttc tagttctgtg taattgttta gtttaatgac gtagttcatt agctggtctt    7712
actctaccag ttttctgaca ttgtattgtg ttacctaagt cattaacttt gtttcagcat    7772
gtaattttaa cttttgtgga aaatagaaat accttcattt tgaaagaagt ttttatgaga    7832
ataacacctt accaaacatt gttcaaatgg tttttatcca aggaattgca aaaataaata    7892
taaatattgc cattaaaaaa aaaaaaaaaa aaaaaaaaaa aaaaaaaa                 7941

<210> SEQ ID NO 6
<211> LENGTH: 2314
<212> TYPE: PRT
<213> ORGANISM: Homo sapiens
<220> FEATURE:
<221> NAME/KEY: gene
<222> LOCATION: (1)..(2314)
<223> OTHER INFORMATION: PTP-zeta
<220> FEATURE:
<221> NAME/KEY: SIGNAL
<222> LOCATION: (1)..(24)
<223> OTHER INFORMATION: By similarity
<220> FEATURE:
<221> NAME/KEY: DOMAIN
<222> LOCATION: (25)..(1635)
<223> OTHER INFORMATION: Extracellular (potential)
<220> FEATURE:
<221> NAME/KEY: MISC_FEATURE
<222> LOCATION: (25)..(2314)
<223> OTHER INFORMATION: Mature chain; protein-tyrosine phosphatase zeta
<220> FEATURE:
<221> NAME/KEY: DOMAIN
<222> LOCATION: (34)..(302)
<223> OTHER INFORMATION: Carbonic-anhydrase like
<220> FEATURE:
<221> NAME/KEY: SITE
<222> LOCATION: (105)..(105)
<223> OTHER INFORMATION: Glycosylation; N-linked (GLCNAC...) (potential)
<220> FEATURE:
<221> NAME/KEY: SITE
<222> LOCATION: (134)..(134)
<223> OTHER INFORMATION: Glycosylation; N-linked (GLCNAC...) (potential)
<220> FEATURE:
<221> NAME/KEY: SITE
<222> LOCATION: (223)..(223)
<223> OTHER INFORMATION: Glycosylation; N-linked (GLCNAC...) (potential)
<220> FEATURE:
<221> NAME/KEY: SITE
<222> LOCATION: (232)..(232)
<223> OTHER INFORMATION: Glycosylation; N-linked (GLCNAC...) (potential)
<220> FEATURE:
<221> NAME/KEY: SITE
<222> LOCATION: (324)..(324)
<223> OTHER INFORMATION: Glycosylation; N-linked (GLCNAC...) (potential)
<220> FEATURE:
<221> NAME/KEY: DOMAIN
<222> LOCATION: (312)..(406)
<223> OTHER INFORMATION: Fibronectin Type-III
<220> FEATURE:
<221> NAME/KEY: SITE
```

```
<222> LOCATION: (381)..(381)
<223> OTHER INFORMATION: Glycosylation; N-linked (GLCNAC...) (potential)
<220> FEATURE:
<221> NAME/KEY: SITE
<222> LOCATION: (497)..(497)
<223> OTHER INFORMATION: Glycosylation; N-linked (GLCNAC...) (potential)
<220> FEATURE:
<221> NAME/KEY: SITE
<222> LOCATION: (501)..(501)
<223> OTHER INFORMATION: Glycosylation; N-linked (GLCNAC...) (potential)
<220> FEATURE:
<221> NAME/KEY: SITE
<222> LOCATION: (552)..(552)
<223> OTHER INFORMATION: Glycosylation; N-linked (GLCNAC...) (potential)
<220> FEATURE:
<221> NAME/KEY: BINDING
<222> LOCATION: (587)..(587)
<223> OTHER INFORMATION: Chondrrroitin Sulfate (potential)
<220> FEATURE:
<221> NAME/KEY: SITE
<222> LOCATION: (602)..(602)
<223> OTHER INFORMATION: Glycosylation; N-linked (GLCNAC...) (potential)
<220> FEATURE:
<221> NAME/KEY: SITE
<222> LOCATION: (629)..(629)
<223> OTHER INFORMATION: Glycosylation; N-linked (GLCNAC...) (potential)
<220> FEATURE:
<221> NAME/KEY: BINDING
<222> LOCATION: (637)..(637)
<223> OTHER INFORMATION: Chondroitin sulfate (potential)
<220> FEATURE:
<221> NAME/KEY: SITE
<222> LOCATION: (677)..(677)
<223> OTHER INFORMATION: Glycosylation; N-linked (GLCNAC...) (potential)
<220> FEATURE:
<221> NAME/KEY: VARSPLIC
<222> LOCATION: (755)..(1614)
<223> OTHER INFORMATION: Splicing variant; missing (in short isoform)
<220> FEATURE:
<221> NAME/KEY: BINDING
<222> LOCATION: (997)..(997)
<223> OTHER INFORMATION: Chondroitin sulfate (potential)
<220> FEATURE:
<221> NAME/KEY: SITE
<222> LOCATION: (1017)..(1017)
<223> OTHER INFORMATION: Glycosylation; N-linked (GLCNAC...) (potential)
<220> FEATURE:
<221> NAME/KEY: SITE
<222> LOCATION: (1050)..(1050)
<223> OTHER INFORMATION: Glycosylation; N-linked (GLCNAC...) (potential)
<220> FEATURE:
<221> NAME/KEY: SITE
<222> LOCATION: (1082)..(1082)
<223> OTHER INFORMATION: Glycosylation; N-linked (GLCNAC...) (potential)
<220> FEATURE:
<221> NAME/KEY: SITE
<222> LOCATION: (1122)..(1122)
<223> OTHER INFORMATION: Glycosylation; N-linked (GLCNAC...) (potential)
<220> FEATURE:
<221> NAME/KEY: SITE
<222> LOCATION: (1456)..(1456)
<223> OTHER INFORMATION: Glycosylation; N-linked (GLCNAC...) (potential)
<220> FEATURE:
<221> NAME/KEY: BINDING
<222> LOCATION: (1548)..(1548)
<223> OTHER INFORMATION: Chondroitin sulfate (potential)
<220> FEATURE:
<221> NAME/KEY: BINDING
<222> LOCATION: (1550)..(1550)
<223> OTHER INFORMATION: Chondroitin sulfate (potential)
<220> FEATURE:
<221> NAME/KEY: SITE
<222> LOCATION: (1561)..(1561)
<223> OTHER INFORMATION: Glycosylation; N-linked (GLCNAC...) (potential)
<220> FEATURE:
<221> NAME/KEY: SITE
<222> LOCATION: (1617)..(1617)
<223> OTHER INFORMATION: Glycosylation; N-linked (GLCNAC...) (potential)
<220> FEATURE:
```

-continued

```
<221> NAME/KEY: TRANSMEM
<222> LOCATION: (1636)..(1661)
<223> OTHER INFORMATION: Transmembrane region; potential
<220> FEATURE:
<221> NAME/KEY: DOMAIN
<222> LOCATION: (1662)..(2314)
<223> OTHER INFORMATION: Cytoplasmic (potential)
<220> FEATURE:
<221> NAME/KEY: CONFLICT
<222> LOCATION: (1722)..(1728)
<223> OTHER INFORMATION: Missing (in ref. 2)
<220> FEATURE:
<221> NAME/KEY: DOMAIN
<222> LOCATION: (1744)..(1997)
<223> OTHER INFORMATION: Protein-tyrosine phosphates
<220> FEATURE:
<221> NAME/KEY: ACT_SITE
<222> LOCATION: (1932)..(1932)
<223> OTHER INFORMATION: Active site; by similarity
<220> FEATURE:
<221> NAME/KEY: DOMAIN
<222> LOCATION: (1998)..(2314)
<223> OTHER INFORMATION: Protein-tyrosine phosphatase
<220> FEATURE:
<221> NAME/KEY: MISC_FEATURE
<222> LOCATION: (2222)..(2222)
<223> OTHER INFORMATION: Ancestral active site
<300> PUBLICATION INFORMATION:
<301> AUTHORS: Krueger, N.X. and Saito, H.
<302> TITLE: A human transmembrane protein-tyrosine-phosphatase, PTP
      zeta, is expressed in brain and has an N-terminal receptor domain
      homologous to carbonic anhydrases
<303> JOURNAL: Proc. Natl. Acad. Sci. USA
<304> VOLUME: 89
<305> ISSUE: 16
<306> PAGES: 7417-7421
<307> DATE: 1992
<309> DATABASE ENTRY DATE:
<313> RELEVANT RESIDUES: (1)..(2314)
<300> PUBLICATION INFORMATION:
<301> AUTHORS: Levy, J.B., et al.
<302> TITLE: The cloning of a receptor-type protein tyrosine phosphatase
      expressed in the central nervous system
<303> JOURNAL: J. Biol. Chem.
<304> VOLUME: 268
<305> ISSUE: 14
<306> PAGES: 10573-10581
<307> DATE: 1993
<309> DATABASE ENTRY DATE:
<313> RELEVANT RESIDUES: (1)..(2314)

<400> SEQUENCE: 6

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
        115                 120                 125

His Trp Gly Lys Cys Asn Met Ser Ser Asp Gly Ser Glu His Ser Leu
    130                 135                 140
```

```
Glu Gly Gln Lys Phe Pro Leu Glu Met Gln Ile Tyr Cys Phe Asp Ala
145                 150                 155                 160

Asp Arg Phe Ser Ser Phe Glu Ala Val Lys Gly Lys Gly Lys Leu
            165                 170                 175

Arg Ala Leu Ser Ile Leu Phe Glu Val Gly Thr Glu Asn Leu Asp
            180                 185                 190

Phe Lys Ala Ile Ile Asp Gly Val Glu Ser Val Ser Arg Phe Gly Lys
            195                 200                 205

Gln Ala Ala Leu Asp Pro Phe Ile Leu Leu Asn Leu Leu Pro Asn Ser
    210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
            245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
    275                 280                 285

Gln Tyr Lys Phe Ser Arg Gln Val Phe Ser Ser Tyr Thr Gly Lys Glu
    290                 295                 300

Glu Ile His Glu Ala Val Cys Ser Ser Glu Pro Glu Asn Val Gln Ala
305                 310                 315                 320

Asp Pro Glu Asn Tyr Thr Ser Leu Leu Val Thr Trp Glu Arg Pro Arg
            325                 330                 335

Val Val Tyr Asp Thr Met Ile Glu Lys Phe Ala Val Leu Tyr Gln Gln
            340                 345                 350

Leu Asp Gly Glu Asp Gln Thr Lys His Glu Phe Leu Thr Asp Gly Tyr
            355                 360                 365

Gln Asp Leu Gly Ala Ile Leu Asn Asn Leu Leu Pro Asn Met Ser Tyr
    370                 375                 380

Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
            405                 410                 415

Leu Phe Pro Glu Leu Ile Gly Thr Glu Ile Ile Lys Glu Glu
            420                 425                 430

Glu Gly Lys Asp Ile Glu Glu Gly Ala Ile Val Asn Pro Gly Arg Asp
            435                 440                 445

Ser Ala Thr Asn Gln Ile Arg Lys Lys Glu Pro Gln Ile Ser Thr Thr
    450                 455                 460

Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
            485                 490                 495

Asn Thr Ser Leu Asn Ser Thr Ser Gln Pro Val Thr Lys Leu Ala Thr
            500                 505                 510

Glu Lys Asp Ile Ser Leu Thr Ser Gln Thr Val Thr Glu Leu Pro Pro
    515                 520                 525

His Thr Val Glu Gly Thr Ser Ala Ser Leu Asn Asp Gly Ser Lys Thr
    530                 535                 540

Val Leu Arg Ser Pro His Met Asn Leu Ser Gly Thr Ala Glu Ser Leu
545                 550                 555                 560
```

-continued

```
Asn Thr Val Ser Ile Thr Glu Tyr Glu Glu Ser Leu Leu Thr Ser
                565                 570                 575

Phe Lys Leu Asp Thr Gly Ala Glu Asp Ser Ser Gly Ser Ser Pro Ala
                580                 585                 590

Thr Ser Ala Ile Pro Phe Ile Ser Glu Asn Ile Ser Gln Gly Tyr Ile
                595                 600                 605

Phe Ser Ser Glu Asn Pro Glu Thr Ile Thr Tyr Asp Val Leu Ile Pro
            610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
                660                 665                 670

Phe Leu Gln Thr Asn Tyr Thr Glu Ile Arg Val Asp Glu Ser Glu Lys
                675                 680                 685

Thr Thr Lys Ser Phe Ser Ala Gly Pro Val Met Ser Gln Gly Pro Ser
            690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735

Leu Val Ser Thr Val Asn Val Val Tyr Ser Gln Thr Thr Gln Pro Val
                740                 745                 750

Tyr Asn Gly Glu Thr Pro Leu Gln Pro Ser Tyr Ser Ser Glu Val Phe
            755                 760                 765

Pro Leu Val Thr Pro Leu Leu Asp Asn Gln Ile Leu Asn Thr Thr
            770                 775                 780

Pro Ala Ala Ser Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ser Ala Ser Phe Ser Ser Glu Leu Phe
                820                 825                 830

Arg His Leu His Thr Val Ser Gln Ile Leu Pro Gln Val Thr Ser Ala
            835                 840                 845

Thr Glu Ser Asp Lys Val Pro Leu His Ala Ser Leu Pro Val Ala Gly
850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
            900                 905                 910

Ser Asp Ala Met Met His Ala Arg Ser Ser Gly Pro Glu Pro Ser Tyr
            915                 920                 925

Ala Leu Ser Asp Asn Glu Gly Ser Gln His Ile Phe Thr Val Ser Tyr
            930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
```

-continued

```
              980                 985                 990
Asp Gly Glu Trp Ser Gly Ala Ser  Ser Asp Ser Glu Phe  Leu Leu Pro
        995                 1000                1005
Asp Thr Asp Gly Leu Thr Ala  Leu Asn Ile Ser Ser  Pro Val Ser
        1010                1015                1020
Val Ala Glu Phe Thr Tyr Thr  Thr Ser Val Phe Gly  Asp Asp Asn
        1025                1030                1035
Lys Ala Leu Ser Lys Ser Glu  Ile Ile Tyr Gly Asn  Glu Thr Glu
        1040                1045                1050
Leu Gln Ile Pro Ser Phe Asn  Glu Met Val Tyr Pro  Ser Glu Ser
        1055                1060                1065
Thr Val Met Pro Asn Met Tyr  Asp Asn Val Asn Lys  Leu Asn Ala
        1070                1075                1080
Ser Leu Gln Glu Thr Ser Val  Ser Ile Ser Ser Thr  Lys Gly Met
        1085                1090                1095
Phe Pro Gly Ser Leu Ala His  Thr Thr Thr Lys Val  Phe Asp His
        1100                1105                1110
Glu Ile Ser Gln Val Pro Glu  Asn Asn Phe Ser Val  Gln Pro Thr
        1115                1120                1125
His Thr Val Ser Gln Ala Ser  Gly Asp Thr Ser Leu  Lys Pro Val
        1130                1135                1140
Leu Ser Ala Asn Ser Glu Pro  Ala Ser Ser Asp Pro  Ala Ser Ser
        1145                1150                1155
Glu Met Leu Ser Pro Ser Thr  Gln Leu Leu Phe Tyr  Glu Thr Ser
        1160                1165                1170
Ala Ser Phe Ser Thr Glu Val  Leu Leu Gln Pro Ser  Phe Gln Ala
        1175                1180                1185
Ser Asp Val Asp Thr Leu Leu  Lys Thr Val Leu Pro  Ala Val Pro
        1190                1195                1200
Ser Asp Pro Ile Leu Val Glu  Thr Pro Lys Val Asp  Lys Ile Ser
        1205                1210                1215
Ser Thr Met Leu His Leu Ile  Val Ser Asn Ser Ala  Ser Ser Glu
        1220                1225                1230
Asn Met Leu His Ser Thr Ser  Val Pro Val Phe Asp  Val Ser Pro
        1235                1240                1245
Thr Ser His Met His Ser Ala  Ser Leu Gln Gly Leu  Thr Ile Ser
        1250                1255                1260
Tyr Ala Ser Glu Lys Tyr Glu  Pro Val Leu Leu Lys  Ser Glu Ser
        1265                1270                1275
Ser His Gln Val Val Pro Ser  Leu Tyr Ser Asn Asp  Glu Leu Phe
        1280                1285                1290
Gln Thr Ala Asn Leu Glu Ile  Asn Gln Ala His Pro  Pro Lys Gly
        1295                1300                1305
Arg His Val Phe Ala Thr Pro  Val Leu Ser Ile Asp  Glu Pro Leu
        1310                1315                1320
Asn Thr Leu Ile Asn Lys Leu  Ile His Ser Asp Glu  Ile Leu Thr
        1325                1330                1335
Ser Thr Lys Ser Ser Val Thr  Gly Lys Val Phe Ala  Gly Ile Pro
        1340                1345                1350
Thr Val Ala Ser Asp Thr Phe  Val Ser Thr Asp His  Ser Val Pro
        1355                1360                1365
Ile Gly Asn Gly His Val Ala  Ile Thr Ala Val Ser  Pro His Arg
        1370                1375                1380
```

-continued

```
Asp Gly Ser Val Thr Ser Thr Lys Leu Leu Phe Pro Ser Lys Ala
    1385                1390                1395

Thr Ser Glu Leu Ser His Ser Ala Lys Ser Asp Ala Gly Leu Val
    1400                1405                1410

Gly Gly Gly Glu Asp Gly Asp Thr Asp Asp Gly Asp Asp Asp
    1415                1420                1425

Asp Asp Arg Asp Ser Asp Gly Leu Ser Ile His Lys Cys Met Ser
    1430                1435                1440

Cys Ser Ser Tyr Arg Glu Ser Gln Glu Lys Val Met Asn Asp Ser
    1445                1450                1455

Asp Thr His Glu Asn Ser Leu Met Asp Gln Asn Asn Pro Ile Ser
    1460                1465                1470

Tyr Ser Leu Ser Glu Asn Ser Glu Glu Asp Asn Arg Val Thr Ser
    1475                1480                1485

Val Ser Ser Asp Ser Gln Thr Gly Met Asp Arg Ser Pro Gly Lys
    1490                1495                1500

Ser Pro Ser Ala Asn Gly Leu Ser Gln Lys His Asn Asp Gly Lys
    1505                1510                1515

Glu Glu Asn Asp Ile Gln Thr Gly Ser Ala Leu Leu Pro Leu Ser
    1520                1525                1530

Pro Glu Ser Lys Ala Trp Ala Val Leu Thr Ser Asp Glu Glu Ser
    1535                1540                1545

Gly Ser Gly Gln Gly Thr Ser Asp Ser Leu Asn Glu Asn Glu Thr
    1550                1555                1560

Ser Thr Asp Phe Ser Phe Ala Asp Thr Asn Glu Lys Asp Ala Asp
    1565                1570                1575

Gly Ile Leu Ala Ala Gly Asp Ser Glu Ile Thr Pro Gly Phe Pro
    1580                1585                1590

Gln Ser Pro Thr Ser Ser Val Thr Ser Glu Asn Ser Glu Val Phe
    1595                1600                1605

His Val Ser Glu Ala Glu Ala Ser Asn Ser Ser His Glu Ser Arg
    1610                1615                1620

Ile Gly Leu Ala Glu Gly Leu Glu Ser Glu Lys Lys Ala Val Ile
    1625                1630                1635

Pro Leu Val Ile Val Ser Ala Leu Thr Phe Ile Cys Leu Val Val
    1640                1645                1650

Leu Val Gly Ile Leu Ile Tyr Trp Arg Lys Cys Phe Gln Thr Ala
    1655                1660                1665

His Phe Tyr Leu Glu Asp Ser Thr Ser Pro Arg Val Ile Ser Thr
    1670                1675                1680

Pro Pro Thr Pro Ile Phe Pro Ile Ser Asp Asp Val Gly Ala Ile
    1685                1690                1695

Pro Ile Lys His Phe Pro Lys His Val Ala Asp Leu His Ala Ser
    1700                1705                1710

Ser Gly Phe Thr Glu Glu Phe Glu Thr Leu Lys Glu Phe Tyr Gln
    1715                1720                1725

Glu Val Gln Ser Cys Thr Val Asp Leu Gly Ile Thr Ala Asp Ser
    1730                1735                1740

Ser Asn His Pro Asp Asn Lys His Lys Asn Arg Tyr Ile Asn Ile
    1745                1750                1755

Val Ala Tyr Asp His Ser Arg Val Lys Leu Ala Gln Leu Ala Glu
    1760                1765                1770
```

-continued

```
Lys Asp Gly Lys Leu Thr Asp Tyr Ile Asn Ala Asn Tyr Val Asp
1775                1780                1785

Gly Tyr Asn Arg Pro Lys Ala Tyr Ile Ala Ala Gln Gly Pro Leu
1790                1795                1800

Lys Ser Thr Ala Glu Asp Phe Trp Arg Met Ile Trp Glu His Asn
1805                1810                1815

Val Glu Val Ile Val Met Ile Thr Asn Leu Val Glu Lys Gly Arg
1820                1825                1830

Arg Lys Cys Asp Gln Tyr Trp Pro Ala Asp Gly Ser Glu Glu Tyr
1835                1840                1845

Gly Asn Phe Leu Val Thr Gln Lys Ser Val Gln Val Leu Ala Tyr
1850                1855                1860

Tyr Thr Val Arg Asn Phe Thr Leu Arg Asn Thr Lys Ile Lys Lys
1865                1870                1875

Gly Ser Gln Lys Gly Arg Pro Ser Gly Arg Val Val Thr Gln Tyr
1880                1885                1890

His Tyr Thr Gln Trp Pro Asp Met Gly Val Pro Glu Tyr Ser Leu
1895                1900                1905

Pro Val Leu Thr Phe Val Arg Lys Ala Ala Tyr Ala Lys Arg His
1910                1915                1920

Ala Val Gly Pro Val Val Val His Cys Ser Ala Gly Val Gly Arg
1925                1930                1935

Thr Gly Thr Tyr Ile Val Leu Asp Ser Met Leu Gln Gln Ile Gln
1940                1945                1950

His Glu Gly Thr Val Asn Ile Phe Gly Phe Leu Lys His Ile Arg
1955                1960                1965

Ser Gln Arg Asn Tyr Leu Val Gln Thr Glu Glu Gln Tyr Val Phe
1970                1975                1980

Ile His Asp Thr Leu Val Glu Ala Ile Leu Ser Lys Glu Thr Glu
1985                1990                1995

Val Leu Asp Ser His Ile His Ala Tyr Val Asn Ala Leu Leu Ile
2000                2005                2010

Pro Gly Pro Ala Gly Lys Thr Lys Leu Glu Lys Gln Phe Gln Leu
2015                2020                2025

Leu Ser Gln Ser Asn Ile Gln Gln Ser Asp Tyr Ser Ala Ala Leu
2030                2035                2040

Lys Gln Cys Asn Arg Glu Lys Asn Arg Thr Ser Ser Ile Ile Pro
2045                2050                2055

Val Glu Arg Ser Arg Val Gly Ile Ser Ser Leu Ser Gly Glu Gly
2060                2065                2070

Thr Asp Tyr Ile Asn Ala Ser Tyr Ile Met Gly Tyr Tyr Gln Ser
2075                2080                2085

Asn Glu Phe Ile Ile Thr Gln His Pro Leu Leu His Thr Ile Lys
2090                2095                2100

Asp Phe Trp Arg Met Ile Trp Asp His Asn Ala Gln Leu Val Val
2105                2110                2115

Met Ile Pro Asp Gly Gln Asn Met Ala Glu Asp Glu Phe Val Tyr
2120                2125                2130

Trp Pro Asn Lys Asp Glu Pro Ile Asn Cys Glu Ser Phe Lys Val
2135                2140                2145

Thr Leu Met Ala Glu Glu His Lys Cys Leu Ser Asn Glu Glu Lys
2150                2155                2160

Leu Ile Ile Gln Asp Phe Ile Leu Glu Ala Thr Gln Asp Asp Tyr
```

-continued

```
                    2165                2170                2175

Val  Leu  Glu  Val  Arg  His  Phe  Gln  Cys  Pro  Lys  Trp  Pro  Asn  Pro
     2180                2185                2190

Asp  Ser  Pro  Ile  Ser  Lys  Thr  Phe  Glu  Leu  Ile  Ser  Val  Ile  Lys
     2195                2200                2205

Glu  Glu  Ala  Ala  Asn  Arg  Asp  Gly  Pro  Met  Ile  Val  His  Asp  Glu
     2210                2215                2220

His  Gly  Gly  Val  Thr  Ala  Gly  Thr  Phe  Cys  Ala  Leu  Thr  Thr  Leu
     2225                2230                2235

Met  His  Gln  Leu  Glu  Lys  Glu  Asn  Ser  Val  Asp  Val  Tyr  Gln  Val
     2240                2245                2250

Ala  Lys  Met  Ile  Asn  Leu  Met  Arg  Pro  Gly  Val  Phe  Ala  Asp  Ile
     2255                2260                2265

Glu  Gln  Tyr  Gln  Phe  Leu  Tyr  Lys  Val  Ile  Leu  Ser  Leu  Val  Ser
     2270                2275                2280

Thr  Arg  Gln  Glu  Glu  Asn  Pro  Ser  Thr  Ser  Leu  Asp  Ser  Asn  Gly
     2285                2290                2295

Ala  Ala  Leu  Pro  Asp  Gly  Asn  Ile  Ala  Glu  Ser  Leu  Glu  Ser  Leu
     2300                2305                2310

Val
```

<210> SEQ ID NO 7
<211> LENGTH: 1518
<212> TYPE: DNA
<213> ORGANISM: Homo sapiens
<220> FEATURE:
<221> NAME/KEY: gene
<222> LOCATION: (1)..(1518)
<223> OTHER INFORMATION: Angiopoietin-like 2 (ANGPTL2), mRNA
<220> FEATURE:
<221> NAME/KEY: CDS
<222> LOCATION: (22)..(1503)
<223> OTHER INFORMATION:
<300> PUBLICATION INFORMATION:
<301> AUTHORS: Kim, I., Moon, S.O., Koh, K.N., Kim, H., Uhm, C.S., Kwak,
       H.J., Kim, N.G. and Koh, G.Y.
<302> TITLE: Molecular cloning, expression, and characterization of
       angiopoietin-related protein. angiopoietin-related protein induces
       endothelial cell sprouting
<303> JOURNAL: J. Biol. Chem.
<304> VOLUME: 274
<305> ISSUE: 37
<306> PAGES: 26523-26528
<307> DATE: 1999
<309> DATABASE ENTRY DATE:
<313> RELEVANT RESIDUES: (1)..(1518)

<400> SEQUENCE: 7

```
aaccaccatt ttgcaaggac c atg agg cca ctg tgc gtg aca tgc tgg tgg         51
                        Met Arg Pro Leu Cys Val Thr Cys Trp Trp
                         1               5                  10 ctc gga ctg ctg gct gcc atg gga gct gtt gca ggc cag gag gac ggt         99
Leu Gly Leu Leu Ala Ala Met Gly Ala Val Ala Gly Gln Glu Asp Gly
                15                  20                  25 ttt gag ggc act gag gag ggc tcg cca aga gag ttc att tac cta aac        147
Phe Glu Gly Thr Glu Glu Gly Ser Pro Arg Glu Phe Ile Tyr Leu Asn
         30                  35                  40 agg tac aag cgg gcg ggc gag tcc cag gac aag tgc acc tac acc ttc        195
Arg Tyr Lys Arg Ala Gly Glu Ser Gln Asp Lys Cys Thr Tyr Thr Phe
     45                  50                  55 att gtg ccc cag cag cgg gtc acg ggt gcc atc tgc gtc aac tcc aag        243
Ile Val Pro Gln Gln Arg Val Thr Gly Ala Ile Cys Val Asn Ser Lys
 60                  65                  70
```

-continued

| | |
|---|---|
| gag cct gag gtg ctt ctg gag aac cga gtg cat aag cag gag cta gag<br>Glu Pro Glu Val Leu Leu Glu Asn Arg Val His Lys Gln Glu Leu Glu<br>75                      80                      85                      90 | 291 |
| ctg ctc aac aat gag ctg ctc aag cag aag cgg cag atc gag aca ctg<br>Leu Leu Asn Asn Glu Leu Leu Lys Gln Lys Arg Gln Ile Glu Thr Leu<br>                      95                      100                      105 | 339 |
| cag cag ctg gtg gag gtg gac ggc ggc att gtg agc gag gtg aag ctg<br>Gln Gln Leu Val Glu Val Asp Gly Gly Ile Val Ser Glu Val Lys Leu<br>           110                      115                      120 | 387 |
| ctg cgc aag gag agc cgc aac atg aac tcg cgg gtc acg cag ctc tac<br>Leu Arg Lys Glu Ser Arg Asn Met Asn Ser Arg Val Thr Gln Leu Tyr<br>           125                      130                      135 | 435 |
| atg cag ctc ctg cac gag atc atc cgc aag cgg gac aac gcg ttg gag<br>Met Gln Leu Leu His Glu Ile Ile Arg Lys Arg Asp Asn Ala Leu Glu<br>140                      145                      150 | 483 |
| ctc tcc cag ctg gag aac agg atc ctg aac cag aca gcc gac atg ctg<br>Leu Ser Gln Leu Glu Asn Arg Ile Leu Asn Gln Thr Ala Asp Met Leu<br>155                      160                      165                      170 | 531 |
| cag ctg gcc agc aag tac aag gac ctg gag cac aag tac cag cac ctg<br>Gln Leu Ala Ser Lys Tyr Lys Asp Leu Glu His Lys Tyr Gln His Leu<br>           175                      180                      185 | 579 |
| gcc aca ctg gcc cac aac caa tca gag atc atc gcg cag ctt gag gag<br>Ala Thr Leu Ala His Asn Gln Ser Glu Ile Ile Ala Gln Leu Glu Glu<br>                190                      195                      200 | 627 |
| cac tgc cag agg gtg ccc tcg gcc agg ccc gtc ccc cag cca ccc ccc<br>His Cys Gln Arg Val Pro Ser Ala Arg Pro Val Pro Gln Pro Pro Pro<br>           205                      210                      215 | 675 |
| gct gcc ccg ccc cgg gtc tac caa cca ccc acc tac aac cgc atc atc<br>Ala Ala Pro Pro Arg Val Tyr Gln Pro Pro Thr Tyr Asn Arg Ile Ile<br>220                      225                      230 | 723 |
| aac cag atc tct acc aac gag atc cag agt gac cag aac ctg aag gtg<br>Asn Gln Ile Ser Thr Asn Glu Ile Gln Ser Asp Gln Asn Leu Lys Val<br>235                      240                      245                      250 | 771 |
| ctg cca ccc cct ctg ccc act atg ccc act ctc acc agc ctc cca tct<br>Leu Pro Pro Pro Leu Pro Thr Met Pro Thr Leu Thr Ser Leu Pro Ser<br>                255                      260                      265 | 819 |
| tcc acc gac aag ccg tcg ggc cca tgg aga gac tgc ctg cag gcc ctg<br>Ser Thr Asp Lys Pro Ser Gly Pro Trp Arg Asp Cys Leu Gln Ala Leu<br>           270                      275                      280 | 867 |
| gag gat ggc cac gac acc agc tcc atc tac ctg gtg aag ccg gag aac<br>Glu Asp Gly His Asp Thr Ser Ser Ile Tyr Leu Val Lys Pro Glu Asn<br>           285                      290                      295 | 915 |
| acc aac cgc ctc atg cag gtg tgg tgc gac cag aga cac gac ccc ggg<br>Thr Asn Arg Leu Met Gln Val Trp Cys Asp Gln Arg His Asp Pro Gly<br>300                      305                      310 | 963 |
| ggc tgg acc gtc atc cag aga cgc ctg gat ggc tct gtt aac ttc ttc<br>Gly Trp Thr Val Ile Gln Arg Arg Leu Asp Gly Ser Val Asn Phe Phe<br>315                      320                      325                      330 | 1011 |
| agg aac tgg gag acg tac aag caa ggg ttt ggg aac att gat ggc gaa<br>Arg Asn Trp Glu Thr Tyr Lys Gln Gly Phe Gly Asn Ile Asp Gly Glu<br>                335                      340                      345 | 1059 |
| tac tgg ctg ggc ctg gag aac att tac tgg ctg acg aac caa ggc aac<br>Tyr Trp Leu Gly Leu Glu Asn Ile Tyr Trp Leu Thr Asn Gln Gly Asn<br>           350                      355                      360 | 1107 |
| tac aaa ctc ctg gtg acc atg gag gac tgg tcc ggc cgc aaa gtc ttt<br>Tyr Lys Leu Leu Val Thr Met Glu Asp Trp Ser Gly Arg Lys Val Phe<br>           365                      370                      375 | 1155 |
| gca gaa tac gcc agt ttc cgc ctg gaa cct gag agc gag tat tat aag<br>Ala Glu Tyr Ala Ser Phe Arg Leu Glu Pro Glu Ser Glu Tyr Tyr Lys | 1203 |

-continued

```
           380               385               390
ctg cgg ctg ggg cgc tac cat ggc aat gcg ggt gac tcc ttt aca tgg    1251
Leu Arg Leu Gly Arg Tyr His Gly Asn Ala Gly Asp Ser Phe Thr Trp
395                 400               405               410 cac aac ggc aag cag ttc acc acc ctg gac aga gat cat gat gtc tac    1299
His Asn Gly Lys Gln Phe Thr Thr Leu Asp Arg Asp His Asp Val Tyr
                415               420               425 aca gga aac tgt gcc cac tac cag aag gga ggc tgg tgg tat aac gcc    1347
Thr Gly Asn Cys Ala His Tyr Gln Lys Gly Gly Trp Trp Tyr Asn Ala
            430               435               440 tgt gcc cac tcc aac ctc aac ggg gtc tgg tac cgc ggg ggc cat tac    1395
Cys Ala His Ser Asn Leu Asn Gly Val Trp Tyr Arg Gly Gly His Tyr
        445               450               455 cgg agc cgc tac cag gac gga gtc tac tgg gct gag ttc cga gga ggc    1443
Arg Ser Arg Tyr Gln Asp Gly Val Tyr Trp Ala Glu Phe Arg Gly Gly
    460               465               470 tct tac tca ctc aag aaa gtg gtg atg atg atc cga ccg aac ccc aac    1491
Ser Tyr Ser Leu Lys Lys Val Val Met Met Ile Arg Pro Asn Pro Asn
475               480               485               490 acc ttc cac taa gccagctccc cctcc                                    1518
Thr Phe His
```

<210> SEQ ID NO 8
<211> LENGTH: 493
<212> TYPE: PRT
<213> ORGANISM: Homo sapiens
<220> FEATURE:
<221> NAME/KEY: gene
<222> LOCATION: (1)..(493)
<223> OTHER INFORMATION: Angiopoietin-like 2 (ANGPTL2), protein
<220> FEATURE:
<221> NAME/KEY: SIGNAL
<222> LOCATION: (1)..(22)
<223> OTHER INFORMATION: Potential
<220> FEATURE:
<221> NAME/KEY: CHAIN
<222> LOCATION: (23)..(493)
<223> OTHER INFORMATION: Angiopoietin-related protein 2
<220> FEATURE:
<221> NAME/KEY: DOMAIN
<222> LOCATION: (76)..(115)
<223> OTHER INFORMATION: Coiled Coil (potential)
<220> FEATURE:
<221> NAME/KEY: DOMAIN
<222> LOCATION: (152)..(206)
<223> OTHER INFORMATION: Coiled Coil (potential)
<220> FEATURE:
<221> NAME/KEY: DOMAIN
<222> LOCATION: (438)..(450)
<223> OTHER INFORMATION: Fibrinogen C-terminal
<220> FEATURE:
<221> NAME/KEY: CARBOHYD
<222> LOCATION: (164)..(164)
<223> OTHER INFORMATION: N-linked (GLCNAC...) (potential)
<220> FEATURE:
<221> NAME/KEY: CARBOHYD
<222> LOCATION: (192)..(192)
<223> OTHER INFORMATION: N-linked (GLCNAC...) (potential)

<400> SEQUENCE: 8

```
Met Arg Pro Leu Cys Val Thr Cys Trp Trp Leu Gly Leu Leu Ala Ala
1               5                   10                  15

Met Gly Ala Val Ala Gly Gln Glu Asp Gly Phe Glu Gly Thr Glu Glu
                20                  25                  30

Gly Ser Pro Arg Glu Phe Ile Tyr Leu Asn Arg Tyr Lys Arg Ala Gly
            35                  40                  45

Glu Ser Gln Asp Lys Cys Thr Tyr Thr Phe Ile Val Pro Gln Gln Arg
```

-continued

```
             50                  55                  60
Val Thr Gly Ala Ile Cys Val Asn Ser Lys Glu Pro Glu Val Leu Leu
 65                  70                  75                  80

Glu Asn Arg Val His Lys Gln Glu Leu Glu Leu Leu Asn Asn Glu Leu
                     85                  90                  95

Leu Lys Gln Lys Arg Gln Ile Glu Thr Leu Gln Gln Leu Val Glu Val
                100                 105                 110

Asp Gly Gly Ile Val Ser Glu Val Lys Leu Leu Arg Lys Glu Ser Arg
                115                 120                 125

Asn Met Asn Ser Arg Val Thr Gln Leu Tyr Met Gln Leu Leu His Glu
130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
                165                 170                 175

Lys Asp Leu Glu His Lys Tyr Gln His Leu Ala Thr Leu Ala His Asn
                180                 185                 190

Gln Ser Glu Ile Ile Ala Gln Leu Glu Glu His Cys Gln Arg Val Pro
                195                 200                 205

Ser Ala Arg Pro Val Pro Gln Pro Pro Ala Ala Pro Pro Arg Val
210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Pro Leu Pro
                245                 250                 255

Thr Met Pro Thr Leu Thr Ser Leu Pro Ser Ser Thr Asp Lys Pro Ser
                260                 265                 270

Gly Pro Trp Arg Asp Cys Leu Gln Ala Leu Glu Asp Gly His Asp Thr
                275                 280                 285

Ser Ser Ile Tyr Leu Val Lys Pro Glu Asn Thr Asn Arg Leu Met Gln
                290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
                325                 330                 335

Lys Gln Gly Phe Gly Asn Ile Asp Gly Glu Tyr Trp Leu Gly Leu Glu
                340                 345                 350

Asn Ile Tyr Trp Leu Thr Asn Gln Gly Asn Tyr Lys Leu Leu Val Thr
                355                 360                 365

Met Glu Asp Trp Ser Gly Arg Lys Val Phe Ala Glu Tyr Ala Ser Phe
370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
                405                 410                 415

Thr Thr Leu Asp Arg Asp His Asp Val Tyr Thr Gly Asn Cys Ala His
                420                 425                 430

Tyr Gln Lys Gly Gly Trp Trp Tyr Asn Ala Cys Ala His Ser Asn Leu
                435                 440                 445

Asn Gly Val Trp Tyr Arg Gly Gly His Tyr Arg Ser Arg Tyr Gln Asp
                450                 455                 460

Gly Val Tyr Trp Ala Glu Phe Arg Gly Gly Ser Tyr Ser Leu Lys Lys
465                 470                 475                 480
```

```
Val Val Met Met Ile Arg Pro Asn Pro Asn Thr Phe His
            485                 490

<210> SEQ ID NO 9
<211> LENGTH: 2133
<212> TYPE: DNA
<213> ORGANISM: Homo sapiens
<220> FEATURE:
<221> NAME/KEY: gene
<222> LOCATION: (1)..(2133)
<223> OTHER INFORMATION: Human SPARC/osteonectin mRNA
<220> FEATURE:
<221> NAME/KEY: CDS
<222> LOCATION: (58)..(969)
<223> OTHER INFORMATION:

<400> SEQUENCE: 9
cgggagagcg cgctctgcct gccgcctgcc tgcctgccac tgagggttcc cagcacc          57 atg agg gcc tgg atc ttc ttt ctc ctt tgc ctg gcc ggg agg gcc ttg        105
Met Arg Ala Trp Ile Phe Phe Leu Leu Cys Leu Ala Gly Arg Ala Leu
 1               5                  10                  15 gca gcc cct cag caa gaa gcc ctg cct gat gag aca gag gtg gtg gaa        153
Ala Ala Pro Gln Gln Glu Ala Leu Pro Asp Glu Thr Glu Val Val Glu
                 20                  25                  30 gaa act gtg gca gag gtg act gag gta tct gtg gga gct aat cct gtc        201
Glu Thr Val Ala Glu Val Thr Glu Val Ser Val Gly Ala Asn Pro Val
             35                  40                  45 cag gtg gaa gta gga gaa ttt gat gat ggt gca gag gaa acc gaa gag        249
Gln Val Glu Val Gly Glu Phe Asp Asp Gly Ala Glu Glu Thr Glu Glu
         50                  55                  60 gag gtg gtg gcg gaa aat ccc tgc cag aac cac cac tgc aaa cac ggc        297
Glu Val Val Ala Glu Asn Pro Cys Gln Asn His His Cys Lys His Gly
 65                  70                  75                  80 aag gtg tgc gag ctg gat gag aac aac acc ccc atg tgc gtg tgc cag        345
Lys Val Cys Glu Leu Asp Glu Asn Asn Thr Pro Met Cys Val Cys Gln
                 85                  90                  95 gac ccc acc agc tgc cca gcc ccc att ggc gag ttt gag aag gtg tgc        393
Asp Pro Thr Ser Cys Pro Ala Pro Ile Gly Glu Phe Glu Lys Val Cys
                100                 105                 110 agc aat gac aac aag acc ttc gac tct tcc tgc cac ttc ttt gcc aca        441
Ser Asn Asp Asn Lys Thr Phe Asp Ser Ser Cys His Phe Phe Ala Thr
            115                 120                 125 aag tgc acc ctg gag ggc acc aag aag ggc cac aag ctc cac ctg gac        489
Lys Cys Thr Leu Glu Gly Thr Lys Lys Gly His Lys Leu His Leu Asp
        130                 135                 140 tac atc ggg cct tgc aaa tac atc ccc cct tgc ctg gac tct gag ctg        537
Tyr Ile Gly Pro Cys Lys Tyr Ile Pro Pro Cys Leu Asp Ser Glu Leu
145                 150                 155                 160 acc gaa ttc ccc ctg cgc atg cgg gac tgg ctc aag aac gtc ctg gtc        585
Thr Glu Phe Pro Leu Arg Met Arg Asp Trp Leu Lys Asn Val Leu Val
                165                 170                 175 acc ctg tat gag agg gat gag gac aac aac ctt ctg act gag aag cag        633
Thr Leu Tyr Glu Arg Asp Glu Asp Asn Asn Leu Leu Thr Glu Lys Gln
            180                 185                 190 aag ctg cgg gtg aag aag atc cat gag aat gag aag cgc ctg gag gca        681
Lys Leu Arg Val Lys Lys Ile His Glu Asn Glu Lys Arg Leu Glu Ala
        195                 200                 205 gga gac cac ccc gtg gag ctg ctg gcc cgg gac ttc gag aag aac tat        729
Gly Asp His Pro Val Glu Leu Leu Ala Arg Asp Phe Glu Lys Asn Tyr
    210                 215                 220 aac atg tac atc ttc cct gta cac tgg cag ttc ggc cag ctg gac cag        777
Asn Met Tyr Ile Phe Pro Val His Trp Gln Phe Gly Gln Leu Asp Gln
```

```
                                                                -continued

Asn Met Tyr Ile Phe Pro Val His Trp Gln Phe Gly Gln Leu Asp Gln
225                 230                 235                 240 cac ccc att gac ggg tac ctc tcc cac acc gag ctg gct cca ctg cgt      825
His Pro Ile Asp Gly Tyr Leu Ser His Thr Glu Leu Ala Pro Leu Arg
            245                 250                 255 gct ccc ctc atc ccc atg gag cat tgc acc acc cgc ttt ttc gag acc      873
Ala Pro Leu Ile Pro Met Glu His Cys Thr Thr Arg Phe Phe Glu Thr
                260                 265                 270 tgt gac ctg gac aat gac aag tac atc gcc ctg gat gag tgg gcc ggc      921
Cys Asp Leu Asp Asn Asp Lys Tyr Ile Ala Leu Asp Glu Trp Ala Gly
        275                 280                 285 tgc ttc ggc atc aag cag aag gat atc gac aag gat ctt gtg atc taa      969
Cys Phe Gly Ile Lys Gln Lys Asp Ile Asp Lys Asp Leu Val Ile
    290                 295                 300 atccactcct tccacagtac cggattctct ctttaaccct ccccttcgtg tttcccccaa   1029
tgtttaaaat gtttggatgg tttgttgttc tgcctggaga caaggtgcta acatagattt   1089
aagtgaatac attaacggtg ctaaaaatga aaattctaac ccaagacatg acattcttag   1149
ctgtaactta actattaagg ccttttccac acgcattaat agtcccattt ttctcttgcc   1209
atttgtagct ttgcccattg tcttattggc acatggtgg acacggatct gctgggctct    1269
gccttaaaca cacattgcag cttcaacttt tctctttagt gttctgtttg aaactaatac   1329
ttaccgagtc agactttgtg ttcatttcat ttcagggtct tggctgcctg tgggcttccc   1389
caggtggcct ggaggtgggc aaagggaagt aacagacaca cgatgttgtc aaggatggtt   1449
ttgggactag aggctcagtg gtgggagaga tccctgcaga atccaccaac cagaacgtgg   1509
tttgcctgag gctgtaactg agagaaagat tctgggctg tcttatgaaa atatagacat    1569
tctcacataa gcccagttca tcaccatttc ctccttacc tttcagtgca gtttcttttc    1629
acattaggct gttggttcaa acttttggga gcacggactg tcagttctct gggaagtggt   1689
cagcgcatcc tgcagggctt ctcctcctct gtcttttgga gaaccagggc tcttctcagg   1749
ggctctaggg actgccaggc tgtttcagcc aggaaggcca aaatcaagag tgagatgtag   1809
aaagttgtaa aatagaaaaa gtggagttgg tgaatcggtt gttctttcct cacatttgga   1869
tgattgtcat aaggtttta gcatgttcct ccttttcttc accctcccct ttgttcttct    1929
attaatcaag agaaacttca agttaatgg gatggtcgga tctcacaggc tgagaactcg    1989
ttcacctcca agcatttcat gaaaaagctg cttcttatta atcatacaaa ctctcaccat   2049
gatgtgaaga gtttcacaaa tctttcaaaa taaaaagtaa tgacttagaa actgaaaaaa   2109
aaaaaaaaaa aaaaaaaaaa aaaa                                         2133

<210> SEQ ID NO 10
<211> LENGTH: 303
<212> TYPE: PRT
<213> ORGANISM: Homo sapiens
<220> FEATURE:
<221> NAME/KEY: SIGNAL
<222> LOCATION: (1)..(17)
<223> OTHER INFORMATION:
<220> FEATURE:
<221> NAME/KEY: gene
<222> LOCATION: (1)..(303)
<223> OTHER INFORMATION: SPARC, osteonectin
<220> FEATURE:
<221> NAME/KEY: CHAIN
<222> LOCATION: (18)..(303)
<223> OTHER INFORMATION: SPARC
<220> FEATURE:
<221> NAME/KEY: DOMAIN
<222> LOCATION: (22)..(69)
```

```
<223> OTHER INFORMATION: ASP/GLU-RICH (ACIDIC, BINDS CALCIUM)
<220> FEATURE:
<221> NAME/KEY: DOMAIN
<222> LOCATION: (94)..(149)
<223> OTHER INFORMATION: KAZAL-LIKE
<220> FEATURE:
<221> NAME/KEY: DOMAIN
<222> LOCATION: (185)..(221)
<223> OTHER INFORMATION: ALPHA-HELIX CONFORMATION (PROBABLE)
<220> FEATURE:
<221> NAME/KEY: CA_BIND
<222> LOCATION: (274)..(285)
<223> OTHER INFORMATION: 12  EF-HAND
<220> FEATURE:
<221> NAME/KEY: CARBOHYD
<222> LOCATION: (116)..(116)
<223> OTHER INFORMATION: N-LINKED (GLCNAC ...) (PROBABLE)
<220> FEATURE:
<221> NAME/KEY: DISULFID
<222> LOCATION: (72)..(83)
<223> OTHER INFORMATION:
<220> FEATURE:
<221> NAME/KEY: DISULFID
<222> LOCATION: (77)..(93)
<223> OTHER INFORMATION:
<220> FEATURE:
<221> NAME/KEY: DISULFID
<222> LOCATION: (95)..(130)
<223> OTHER INFORMATION:
<220> FEATURE:
<221> NAME/KEY: DISULFID
<222> LOCATION: (101)..(123)
<223> OTHER INFORMATION:
<220> FEATURE:
<221> NAME/KEY: DISULFID
<222> LOCATION: (112)..(149)
<223> OTHER INFORMATION:
<220> FEATURE:
<221> NAME/KEY: DISULFID
<222> LOCATION: (155)..(265)
<223> OTHER INFORMATION:
<220> FEATURE:
<221> NAME/KEY: DISULFID
<222> LOCATION: (273)..(289)
<223> OTHER INFORMATION:

<400> SEQUENCE: 10

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
```

```
                            165                 170                 175
Thr Leu Tyr Glu Arg Asp Glu Asp Asn Leu Leu Thr Glu Lys Gln
                180                 185                 190

Lys Leu Arg Val Lys Lys Ile His Glu Asn Glu Lys Arg Leu Glu Ala
            195                 200                 205

Gly Asp His Pro Val Glu Leu Leu Ala Arg Asp Phe Glu Lys Asn Tyr
        210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270

Cys Asp Leu Asp Asn Asp Lys Tyr Ile Ala Leu Asp Glu Trp Ala Gly
        275                 280                 285

Cys Phe Gly Ile Lys Gln Lys Asp Ile Asp Lys Asp Leu Val Ile
    290                 295                 300

<210> SEQ ID NO 11
<211> LENGTH: 4586
<212> TYPE: DNA
<213> ORGANISM: Homo sapiens
<220> FEATURE:
<221> NAME/KEY: gene
<222> LOCATION: (1)..(4586)
<223> OTHER INFORMATION: mRNA for met proto-oncogene
<220> FEATURE:
<221> NAME/KEY: CDS
<222> LOCATION: (195)..(4367)
<223> OTHER INFORMATION:
<300> PUBLICATION INFORMATION:
<301> AUTHORS: Park,M., Dean,M., Kaul,K., Braun,M.J., Gonda,M.A. and
       Vande Woude,G.
<302> TITLE: Sequence of MET protooncogene cDNA has features
       characteristic of the tyrosine kinase family of growth-factor
       receptors
<303> JOURNAL: Proc. Natl. Acad. Sci. U.S.A.
<304> VOLUME: 84
<305> ISSUE: 18
<306> PAGES: 6379-6383
<307> DATE: 1987
<309> DATABASE ENTRY DATE:
<313> RELEVANT RESIDUES: (1)..(4586)

<400> SEQUENCE: 11
gaattccgcc ctcgccgccc gcggcgcccc gagcgctttg tgagcagatg cggagccgag      60
tggagggcgc gagccagatg cggggcgaca gctgacttgc tgagaggagg cggggaggcg     120
cggagcgcgc gtgtggtcct tgcgccgctg acttctccac tggttcctgg caccgaaag     180 ataaacctct cata atg aag gcc ccc gct gtg ctt gca cct ggc atc ctc      230
              Met Lys Ala Pro Ala Val Leu Ala Pro Gly Ile Leu
                1               5                   10 gtg ctc ctg ttt acc ttg gtg cag agg agc aat ggg gag tgt aaa gag      278
Val Leu Leu Phe Thr Leu Val Gln Arg Ser Asn Gly Glu Cys Lys Glu
         15                  20                  25 gca cta gca aag tcc gag atg aat gtg aat atg aag tat cag ctt ccc      326
Ala Leu Ala Lys Ser Glu Met Asn Val Asn Met Lys Tyr Gln Leu Pro
     30                  35                  40 aac ttc acc gcg gaa aca ccc atc cag aat gtc att cta cat gag cat      374
Asn Phe Thr Ala Glu Thr Pro Ile Gln Asn Val Ile Leu His Glu His
 45                  50                  55                  60 cac att ttc ctt ggt gcc act aac tac att tat gtt tta aat gag gaa      422
His Ile Phe Leu Gly Ala Thr Asn Tyr Ile Tyr Val Leu Asn Glu Glu
```

-continued

```
                    65                  70                  75
gac ctt cag aag gtt gct gag tac aag act ggg cct gtg ctg gaa cac      470
Asp Leu Gln Lys Val Ala Glu Tyr Lys Thr Gly Pro Val Leu Glu His
             80                  85                  90 cca gat tgt ttc cca tgt cag gac tgc agc agc aaa gcc aat tta tca      518
Pro Asp Cys Phe Pro Cys Gln Asp Cys Ser Ser Lys Ala Asn Leu Ser
         95                  100                 105 gga ggt gtt tgg aaa gat aac atc aac atg gct cta gtt gtc gac acc      566
Gly Gly Val Trp Lys Asp Asn Ile Asn Met Ala Leu Val Val Asp Thr
     110                 115                 120 tac tat gat gat caa ctc att agc tgt ggc agc gtc aac aga ggg acc      614
Tyr Tyr Asp Asp Gln Leu Ile Ser Cys Gly Ser Val Asn Arg Gly Thr
125                 130                 135                 140 tgc cag cga cat gtc ttt ccc cac aat cat act gct gac ata cag tcg      662
Cys Gln Arg His Val Phe Pro His Asn His Thr Ala Asp Ile Gln Ser
                 145                 150                 155 gag gtt cac tgc ata ttc tcc cca cag ata gaa gag ccc agc cag tgt      710
Glu Val His Cys Ile Phe Ser Pro Gln Ile Glu Glu Pro Ser Gln Cys
             160                 165                 170 cct gac tgt gtg gtg agc gcc ctg gga gcc aaa gtc ctt tca tct gta      758
Pro Asp Cys Val Val Ser Ala Leu Gly Ala Lys Val Leu Ser Ser Val
         175                 180                 185 aag gac cgg ttc atc aac ttc ttt gta ggc aat acc ata aat tct tct      806
Lys Asp Arg Phe Ile Asn Phe Phe Val Gly Asn Thr Ile Asn Ser Ser
     190                 195                 200 tat ttc cca gat cat cca ttg cat tcg ata tca gtg aga agg cta aag      854
Tyr Phe Pro Asp His Pro Leu His Ser Ile Ser Val Arg Arg Leu Lys
205                 210                 215                 220 gaa acg aaa gat ggt ttt atg ttt ttg acg gac cag tcc tac att gat      902
Glu Thr Lys Asp Gly Phe Met Phe Leu Thr Asp Gln Ser Tyr Ile Asp
                 225                 230                 235 gtt tta cct gag ttc aga gat tct tac ccc att aag tat gtc cat gcc      950
Val Leu Pro Glu Phe Arg Asp Ser Tyr Pro Ile Lys Tyr Val His Ala
             240                 245                 250 ttt gaa agc aac aat ttt att tac ttc ttg acg gtc caa agg gaa act      998
Phe Glu Ser Asn Asn Phe Ile Tyr Phe Leu Thr Val Gln Arg Glu Thr
         255                 260                 265 cta gat gct cag act ttt cac aca aga ata atc agg ttc tgt tcc ata     1046
Leu Asp Ala Gln Thr Phe His Thr Arg Ile Ile Arg Phe Cys Ser Ile
     270                 275                 280 aac tct gga ttg cat tcc tac atg gaa atg cct ctg gag tgt att ctc     1094
Asn Ser Gly Leu His Ser Tyr Met Glu Met Pro Leu Glu Cys Ile Leu
285                 290                 295                 300 aca gaa aag aga aaa aag aga tcc aca aag aag gaa gtg ttt aat ata     1142
Thr Glu Lys Arg Lys Lys Arg Ser Thr Lys Lys Glu Val Phe Asn Ile
                 305                 310                 315 ctt cag gct gcg tat gtc agc aag cct ggg gcc cag ctt gct aga caa     1190
Leu Gln Ala Ala Tyr Val Ser Lys Pro Gly Ala Gln Leu Ala Arg Gln
             320                 325                 330 ata gga gcc agc ctg aat gat gac att ctt ttc ggg gtg ttc gca caa     1238
Ile Gly Ala Ser Leu Asn Asp Asp Ile Leu Phe Gly Val Phe Ala Gln
         335                 340                 345 agc aag cca gat tct gcc gaa cca atg gat cga tct gcc atg tgt gca     1286
Ser Lys Pro Asp Ser Ala Glu Pro Met Asp Arg Ser Ala Met Cys Ala
     350                 355                 360 ttc cct atc aaa tat gtc aac gac ttc ttc aac aag atc gtc aac aaa     1334
Phe Pro Ile Lys Tyr Val Asn Asp Phe Phe Asn Lys Ile Val Asn Lys
365                 370                 375                 380 aac aat gtg aga tgt ctc cag cat ttt tac gga ccc aat cat gag cac     1382
```

```
                Asn Asn Val Arg Cys Leu Gln His Phe Tyr Gly Pro Asn His Glu His
                            385                 390                 395 tgc ttt aat agg aca ctt ctg aga aat tca tca ggc tgt gaa gcg cgc            1430
Cys Phe Asn Arg Thr Leu Leu Arg Asn Ser Ser Gly Cys Glu Ala Arg
            400                 405                 410 cgt gat gaa tat cga aca gag ttt acc aca gct ttg cag cgc gtt gac            1478
Arg Asp Glu Tyr Arg Thr Glu Phe Thr Thr Ala Leu Gln Arg Val Asp
            415                 420                 425 tta ttc atg ggt caa ttc agc gaa gtc ctc tta aca tct ata tcc acc            1526
Leu Phe Met Gly Gln Phe Ser Glu Val Leu Leu Thr Ser Ile Ser Thr
    430                 435                 440 ttc att aaa gga gac ctc acc ata gct aat ctt ggg aca tca gag ggt            1574
Phe Ile Lys Gly Asp Leu Thr Ile Ala Asn Leu Gly Thr Ser Glu Gly
445                 450                 455                 460 cgc ttc atg cag gtt gtg gtt tct cga tca gga cca tca acc cct cat            1622
Arg Phe Met Gln Val Val Val Ser Arg Ser Gly Pro Ser Thr Pro His
                465                 470                 475 gtg aat ttt ctc ctg gac tcc cat cca gtg tct cca gaa gtg att gtg            1670
Val Asn Phe Leu Leu Asp Ser His Pro Val Ser Pro Glu Val Ile Val
            480                 485                 490 gag cat aca tta aac caa aat ggc tac aca ctg gtt atc act ggg aag            1718
Glu His Thr Leu Asn Gln Asn Gly Tyr Thr Leu Val Ile Thr Gly Lys
            495                 500                 505 aag atc acg aag atc cca ttg aat ggc ttg ggc tgc aga cat ttc cag            1766
Lys Ile Thr Lys Ile Pro Leu Asn Gly Leu Gly Cys Arg His Phe Gln
            510                 515                 520 tcc tgc agt caa tgc ctc tct gcc cca ccc ttt gtt cag tgt ggc tgg            1814
Ser Cys Ser Gln Cys Leu Ser Ala Pro Pro Phe Val Gln Cys Gly Trp
525                 530                 535                 540 tgc cac gac aaa tgt gtg cga tcg gag gaa tgc ctg agc ggg aca tgg            1862
Cys His Asp Lys Cys Val Arg Ser Glu Glu Cys Leu Ser Gly Thr Trp
                545                 550                 555 act caa cag atc tgt ctg cct gca atc tac aag gtt ttc cca aat agt            1910
Thr Gln Gln Ile Cys Leu Pro Ala Ile Tyr Lys Val Phe Pro Asn Ser
            560                 565                 570 gca ccc ctt gaa gga ggg aca agg ctg acc ata tgt ggc tgg gac ttt            1958
Ala Pro Leu Glu Gly Gly Thr Arg Leu Thr Ile Cys Gly Trp Asp Phe
            575                 580                 585 gga ttt cgg agg aat aat aaa ttt gat tta aag aaa act aga gtt ctc            2006
Gly Phe Arg Arg Asn Asn Lys Phe Asp Leu Lys Lys Thr Arg Val Leu
            590                 595                 600 ctt gga aat gag agc tgc acc ttg act tta agt gag agc acg atg aat            2054
Leu Gly Asn Glu Ser Cys Thr Leu Thr Leu Ser Glu Ser Thr Met Asn
605                 610                 615                 620 aca ttg aaa tgc aca gtt ggt cct gcc atg aat aag cat ttc aat atg            2102
Thr Leu Lys Cys Thr Val Gly Pro Ala Met Asn Lys His Phe Asn Met
            625                 630                 635 tcc ata att att tca aat ggc cac ggg aca aca caa tac agt aca ttc            2150
Ser Ile Ile Ile Ser Asn Gly His Gly Thr Thr Gln Tyr Ser Thr Phe
            640                 645                 650 tcc tat gtg gat cct gta ata aca agt att tcg ccg aaa tac ggt cct            2198
Ser Tyr Val Asp Pro Val Ile Thr Ser Ile Ser Pro Lys Tyr Gly Pro
            655                 660                 665 atg gct ggt ggc act tta ctt act tta act gga aat tac cta aac agt            2246
Met Ala Gly Gly Thr Leu Leu Thr Leu Thr Gly Asn Tyr Leu Asn Ser
            670                 675                 680 ggg aat tct aga cac att tca att ggt gga aaa aca tgt act tta aaa            2294
Gly Asn Ser Arg His Ile Ser Ile Gly Gly Lys Thr Cys Thr Leu Lys
685                 690                 695                 700
```

```
                                                                -continued agt gtg tca aac agt att ctt gaa tgt tat acc cca gcc caa acc att        2342
Ser Val Ser Asn Ser Ile Leu Glu Cys Tyr Thr Pro Ala Gln Thr Ile
            705                 710                 715 tca act gag ttt gct gtt aaa ttg aaa att gac tta gcc aac cga gag        2390
Ser Thr Glu Phe Ala Val Lys Leu Lys Ile Asp Leu Ala Asn Arg Glu
        720                 725                 730 aca agc atc ttc agt tac cgt gaa gat ccc att gtc tat gaa att cat        2438
Thr Ser Ile Phe Ser Tyr Arg Glu Asp Pro Ile Val Tyr Glu Ile His
    735                 740                 745 cca acc aaa tct ttt att agt ggt ggg agc aca ata aca ggt gtt ggg        2486
Pro Thr Lys Ser Phe Ile Ser Gly Gly Ser Thr Ile Thr Gly Val Gly
750                 755                 760 aaa aac ctg aat tca gtt agt gtc ccg aga atg gtc ata aat gtg cat        2534
Lys Asn Leu Asn Ser Val Ser Val Pro Arg Met Val Ile Asn Val His
765                 770                 775                 780 gaa gca gga agg aac ttt aca gtg gca tgt caa cat cgc tct aat tca        2582
Glu Ala Gly Arg Asn Phe Thr Val Ala Cys Gln His Arg Ser Asn Ser
                785                 790                 795 gag ata atc tgt tgt acc act cct tcc ctg caa cag ctg aat ctg caa        2630
Glu Ile Ile Cys Cys Thr Thr Pro Ser Leu Gln Gln Leu Asn Leu Gln
            800                 805                 810 ctc ccc ctg aaa acc aaa gcc ttt ttc atg tta gat ggg atc ctt tcc        2678
Leu Pro Leu Lys Thr Lys Ala Phe Phe Met Leu Asp Gly Ile Leu Ser
        815                 820                 825 aaa tac ttt gat ctc att tat gta cat aat cct gtg ttt aag cct ttt        2726
Lys Tyr Phe Asp Leu Ile Tyr Val His Asn Pro Val Phe Lys Pro Phe
    830                 835                 840 gaa aag cca gtg atg atc tca atg ggc aat gaa aat gta ctg gaa att        2774
Glu Lys Pro Val Met Ile Ser Met Gly Asn Glu Asn Val Leu Glu Ile
845                 850                 855                 860 aag gga aat gat att gac cct gaa gca gtt aaa ggt gaa gtg tta aaa        2822
Lys Gly Asn Asp Ile Asp Pro Glu Ala Val Lys Gly Glu Val Leu Lys
                865                 870                 875 gtt gga aat aag agc tgt gag aat ata cac tta cat tct gaa gcc gtt        2870
Val Gly Asn Lys Ser Cys Glu Asn Ile His Leu His Ser Glu Ala Val
            880                 885                 890 tta tgc acg gtc ccc aat gac ctg ctg aaa ttg aac agc gag cta aat        2918
Leu Cys Thr Val Pro Asn Asp Leu Leu Lys Leu Asn Ser Glu Leu Asn
        895                 900                 905 ata gag tgg aag caa gca att tct tca acc gtc ctt gga aaa gta ata        2966
Ile Glu Trp Lys Gln Ala Ile Ser Ser Thr Val Leu Gly Lys Val Ile
    910                 915                 920 gtt caa cca gat cag aat ttc aca gga ttg att gct ggt gtt gtc tca        3014
Val Gln Pro Asp Gln Asn Phe Thr Gly Leu Ile Ala Gly Val Val Ser
925                 930                 935                 940 ata tca aca gca ctg tta tta cta ctt ggg ttt ttc ctg tgg ctg aaa        3062
Ile Ser Thr Ala Leu Leu Leu Leu Leu Gly Phe Phe Leu Trp Leu Lys
                945                 950                 955 aag aga aag caa att aaa gat ctg ggc agt gaa tta gtt cgc tac gat        3110
Lys Arg Lys Gln Ile Lys Asp Leu Gly Ser Glu Leu Val Arg Tyr Asp
            960                 965                 970 gca aga gta cac act cct cat ttg gat agg ctt gta agt gcc cga agt        3158
Ala Arg Val His Thr Pro His Leu Asp Arg Leu Val Ser Ala Arg Ser
        975                 980                 985 gta agc cca act aca gaa atg gtt tca aat gaa tct gta gac tac cga        3206
Val Ser Pro Thr Thr Glu Met Val Ser Asn Glu Ser Val Asp Tyr Arg
    990                 995                 1000 gct act ttt cca gaa gat cag ttt cct aat tca tct cag aac ggt             3251
Ala Thr Phe Pro Glu Asp Gln Phe Pro Asn Ser Ser Gln Asn Gly
1005                1010                1015
```

-continued

```
tca tgc cga caa gtg cag tat cct ctg aca gac atg tcc ccc atc      3296
Ser Cys Arg Gln Val Gln Tyr Pro Leu Thr Asp Met Ser Pro Ile
1020                1025                1030 cta act agt ggg gac tct gat ata tcc agt cca tta ctg caa aat      3341
Leu Thr Ser Gly Asp Ser Asp Ile Ser Ser Pro Leu Leu Gln Asn
1035                1040                1045 act gtc cac att gac ctc agt gct cta aat cca gag ctg gtc cag      3386
Thr Val His Ile Asp Leu Ser Ala Leu Asn Pro Glu Leu Val Gln
1050                1055                1060 gca gtg cag cat gta gtg att ggg ccc agt agc ctg att gtg cat      3431
Ala Val Gln His Val Val Ile Gly Pro Ser Ser Leu Ile Val His
1065                1070                1075 ttc aat gaa gtc ata gga aga ggg cat ttt ggt tgt gta tat cat      3476
Phe Asn Glu Val Ile Gly Arg Gly His Phe Gly Cys Val Tyr His
1080                1085                1090 ggg act ttg ttg gac aat gat ggc aag aaa att cac tgt gct gtg      3521
Gly Thr Leu Leu Asp Asn Asp Gly Lys Lys Ile His Cys Ala Val
1095                1100                1105 aaa tcc ttg aac aga atc act gac ata gga gaa gtt tcc caa ttt      3566
Lys Ser Leu Asn Arg Ile Thr Asp Ile Gly Glu Val Ser Gln Phe
1110                1115                1120 ctg acc gag gga atc atc atg aaa gat ttt agt cat ccc aat gtc      3611
Leu Thr Glu Gly Ile Ile Met Lys Asp Phe Ser His Pro Asn Val
1125                1130                1135 ctc tcg ctc ctg gga atc tgc ctg cga agt gaa ggg tct ccg ctg      3656
Leu Ser Leu Leu Gly Ile Cys Leu Arg Ser Glu Gly Ser Pro Leu
1140                1145                1150 gtg gtc cta cca tac atg aaa cat gga gat ctt cga aat ttc att      3701
Val Val Leu Pro Tyr Met Lys His Gly Asp Leu Arg Asn Phe Ile
1155                1160                1165 cga aat gag act cat aat cca act gta aaa gat ctt att ggc ttt      3746
Arg Asn Glu Thr His Asn Pro Thr Val Lys Asp Leu Ile Gly Phe
1170                1175                1180 ggt ctt caa gta gcc aaa ggc atg aaa tat ctt gca agc aaa aag      3791
Gly Leu Gln Val Ala Lys Gly Met Lys Tyr Leu Ala Ser Lys Lys
1185                1190                1195 ttt gtc cac aga gac ttg gct gca aga aac tgt atg ctg gat gaa      3836
Phe Val His Arg Asp Leu Ala Ala Arg Asn Cys Met Leu Asp Glu
1200                1205                1210 aaa ttc aca gtc aag gtt gct gat ttt ggt ctt gcc aga gac atg      3881
Lys Phe Thr Val Lys Val Ala Asp Phe Gly Leu Ala Arg Asp Met
1215                1220                1225 tat gat aaa gaa tac tat agt gta cac aac aaa aca ggt gca aag      3926
Tyr Asp Lys Glu Tyr Tyr Ser Val His Asn Lys Thr Gly Ala Lys
1230                1235                1240 ctg cca gtg aag tgg atg gct ttg gaa agt ctg caa act caa aag      3971
Leu Pro Val Lys Trp Met Ala Leu Glu Ser Leu Gln Thr Gln Lys
1245                1250                1255 ttt acc acc aag tca gat gtg tgg tcc ttt ggc gtc gtc ctc tgg      4016
Phe Thr Thr Lys Ser Asp Val Trp Ser Phe Gly Val Val Leu Trp
1260                1265                1270 gag ctg atg aca aga gga gcc cca cct tat cct gac gta aac acc      4061
Glu Leu Met Thr Arg Gly Ala Pro Pro Tyr Pro Asp Val Asn Thr
1275                1280                1285 ttt gat ata act gtt tac ttg ttg caa ggg aga aga ctc cta caa      4106
Phe Asp Ile Thr Val Tyr Leu Leu Gln Gly Arg Arg Leu Leu Gln
1290                1295                1300 ccc gaa tac tgc cca gac ccc tta tat gaa gta atg cta aaa tgc      4151
Pro Glu Tyr Cys Pro Asp Pro Leu Tyr Glu Val Met Leu Lys Cys
```

|  |  |  |  |  |  |  |  |  |  |  |
|---|---|---|---|---|---|---|---|---|---|---|
| tgg | cac | cct | aaa | gcc | gaa | atg | cgc | cca | tcc | ttt | tct | gaa | ctg | gtg | 4196 |
| Trp | His | Pro | Lys | Ala | Glu | Met | Arg | Pro | Ser | Phe | Ser | Glu | Leu | Val |  |
| 1320 |  |  |  | 1325 |  |  |  |  | 1330 |  |  |  |  |  |  |

```
tgg cac cct aaa gcc gaa atg cgc cca tcc ttt tct gaa ctg gtg    4196
Trp His Pro Lys Ala Glu Met Arg Pro Ser Phe Ser Glu Leu Val
1320            1325                1330 tcc cgg ata tca gcg atc ttc tct act ttc att ggg gag cac tat    4241
Ser Arg Ile Ser Ala Ile Phe Ser Thr Phe Ile Gly Glu His Tyr
1335            1340                1345 gtc cat gtg aac gct act tat gtg aac gta aaa tgt gtc gct ccg    4286
Val His Val Asn Ala Thr Tyr Val Asn Val Lys Cys Val Ala Pro
1350            1355                1360 tat cct tct ctg ttg tca tca gaa gat aac gct gat gat gag gtg    4331
Tyr Pro Ser Leu Leu Ser Ser Glu Asp Asn Ala Asp Asp Glu Val
1365            1370                1375 gac aca cga cca gcc tcc ttc tgg gag aca tca tag tgctagtact    4377
Asp Thr Arg Pro Ala Ser Phe Trp Glu Thr Ser
1380            1385                1390 atgtcaaagc aacagtccac actttgtcca atgttttttt cactgcctga cctttaaaag    4437
gccatcgata ttctttgctc cttgccaaat tgcactatta ataggacttg tattgttatt    4497
taaattactg gattctaagg aatttcttat ctgacagagc atcagaacca gaggcttggt    4557
cccacaggcc agggaccaat gcgctgcag                                      4586
```

<210> SEQ ID NO 12
<211> LENGTH: 1390
<212> TYPE: PRT
<213> ORGANISM: Homo sapiens
<220> FEATURE:
<221> NAME/KEY: SIGNAL
<222> LOCATION: (1)..(24)
<223> OTHER INFORMATION:
<220> FEATURE:
<221> NAME/KEY: gene
<222> LOCATION: (1)..(1390)
<223> OTHER INFORMATION: C-Met Proto Oncogene
<220> FEATURE:
<221> NAME/KEY: CHAIN
<222> LOCATION: (25)..(1390)
<223> OTHER INFORMATION: HEPATOCYTE GROWTH FACTOR RECEPTOR
<220> FEATURE:
<221> NAME/KEY: DOMAIN
<222> LOCATION: (25)..(932)
<223> OTHER INFORMATION: EXTRACELLULAR (POTENTIAL)
<220> FEATURE:
<221> NAME/KEY: TRANSMEM
<222> LOCATION: (933)..(955)
<223> OTHER INFORMATION: POTENTIAL
<220> FEATURE:
<221> NAME/KEY: DOMAIN
<222> LOCATION: (956)..(1390)
<223> OTHER INFORMATION: CYTOPLASMIC (POTENTIAL)
<220> FEATURE:
<221> NAME/KEY: DOMAIN
<222> LOCATION: (55)..(500)
<223> OTHER INFORMATION: SEMA.
<220> FEATURE:
<221> NAME/KEY: DOMAIN
<222> LOCATION: (1078)..(1345)
<223> OTHER INFORMATION: PROTEIN KINASE
<220> FEATURE:
<221> NAME/KEY: SITE
<222> LOCATION: (1009)..(1010)
<223> OTHER INFORMATION: Breakpoint for Translocation to Form TPR-Met
      Oncogene
<220> FEATURE:
<221> NAME/KEY: NP_BIND
<222> LOCATION: (1084)..(1092)
<223> OTHER INFORMATION: ATP (BY SIMILARITY)
<220> FEATURE:
<221> NAME/KEY: BINDING
<222> LOCATION: (1110)..(1110)

```
<223> OTHER INFORMATION: ATP (BY SIMILARITY)
<220> FEATURE:
<221> NAME/KEY: ACT_SITE
<222> LOCATION: (1204)..(1204)
<223> OTHER INFORMATION: BY SIMILARITY
<220> FEATURE:
<221> NAME/KEY: SITE
<222> LOCATION: (307)..(308)
<223> OTHER INFORMATION: CLEAVAGE (POTENTIAL)
<220> FEATURE:
<221> NAME/KEY: MOD_RES
<222> LOCATION: (1235)..(1235)
<223> OTHER INFORMATION: PHOSPHORYLATION (AUTO-)
<220> FEATURE:
<221> NAME/KEY: CARBOHYD
<222> LOCATION: (45)..(45)
<223> OTHER INFORMATION: N-LINKED (GLCNAC...) (POTENTIAL)
<220> FEATURE:
<221> NAME/KEY: CARBOHYD
<222> LOCATION: (106)..(106)
<223> OTHER INFORMATION: N-LINKED (GLCNAC...) (POTENTIAL)
<220> FEATURE:
<221> NAME/KEY: CARBOHYD
<222> LOCATION: (149)..(149)
<223> OTHER INFORMATION: N-LINKED (GLCNAC...) (POTENTIAL)
<220> FEATURE:
<221> NAME/KEY: CARBOHYD
<222> LOCATION: (202)..(202)
<223> OTHER INFORMATION: N-LINKED (GLCNAC...) (POTENTIAL)
<220> FEATURE:
<221> NAME/KEY: CARBOHYD
<222> LOCATION: (399)..(399)
<223> OTHER INFORMATION: N-LINKED (GLCNAC...) (POTENTIAL)
<220> FEATURE:
<221> NAME/KEY: CARBOHYD
<222> LOCATION: (405)..(405)
<223> OTHER INFORMATION: N-LINKED (GLCNAC...) (POTENTIAL)
<220> FEATURE:
<221> NAME/KEY: CARBOHYD
<222> LOCATION: (607)..(607)
<223> OTHER INFORMATION: N-LINKED (GLCNAC...) (POTENTIAL)
<220> FEATURE:
<221> NAME/KEY: CARBOHYD
<222> LOCATION: (635)..(635)
<223> OTHER INFORMATION: N-LINKED (GLCNAC...) (POTENTIAL)
<220> FEATURE:
<221> NAME/KEY: CARBOHYD
<222> LOCATION: (785)..(785)
<223> OTHER INFORMATION: N-LINKED (GLCNAC...) (POTENTIAL)
<220> FEATURE:
<221> NAME/KEY: CARBOHYD
<222> LOCATION: (879)..(879)
<223> OTHER INFORMATION: N-LINKED (GLCNAC...) (POTENTIAL)
<220> FEATURE:
<221> NAME/KEY: CARBOHYD
<222> LOCATION: (930)..(930)
<223> OTHER INFORMATION: N-LINKED (GLCNAC...) (POTENTIAL)
<220> FEATURE:
<221> NAME/KEY: VARSPLIC
<222> LOCATION: (755)..(755)
<223> OTHER INFORMATION: S -> STWWKEPLNIVSFLFCFAS (IN ISOFORM 2)
<220> FEATURE:
<221> NAME/KEY: VARIANT
<222> LOCATION: (320)..(320)
<223> OTHER INFORMATION: A -> V
<220> FEATURE:
<221> NAME/KEY: VARIANT
<222> LOCATION: (1131)..(1131)
<223> OTHER INFORMATION: M -> T (IN HPRC; GERMLINE MUTATION)
<220> FEATURE:
<221> NAME/KEY: VARIANT
<222> LOCATION: (1188)..(1188)
<223> OTHER INFORMATION: V -> L (IN HPRC; GERMLINE MUTATION)
<220> FEATURE:
<221> NAME/KEY: VARIANT
<222> LOCATION: (1195)..(1195)
<223> OTHER INFORMATION: L -> V (IN HPRC; GERMLINE MUTATION)
<220> FEATURE:
<221> NAME/KEY: VARIANT
```

-continued

```
<222> LOCATION: (1220)..(1220)
<223> OTHER INFORMATION: V -> I (IN HPRC; GERMLINE MUTATION)
<220> FEATURE:
<221> NAME/KEY: VARIANT
<222> LOCATION: (1228)..(1228)
<223> OTHER INFORMATION: D -> N (IN HPRC; GERMLINE MUTATION)
<220> FEATURE:
<221> NAME/KEY: VARIANT
<222> LOCATION: (1228)..(1228)
<223> OTHER INFORMATION: D -> H (IN HPRC; GERMLINE MUTATION)
<220> FEATURE:
<221> NAME/KEY: VARIANT
<222> LOCATION: (1230)..(1230)
<223> OTHER INFORMATION: Y -> C (IN HPRC; GERMLINE MUTATION)
<220> FEATURE:
<221> NAME/KEY: VARIANT
<222> LOCATION: (1230)..(1230)
<223> OTHER INFORMATION: Y -> H (IN HPRC; GERMLINE MUTATION)
<220> FEATURE:
<221> NAME/KEY: VARIANT
<222> LOCATION: (1250)..(1250)
<223> OTHER INFORMATION: M -> T (IN HPRC; GERMLINE MUTATION)

<400> SEQUENCE: 12

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
    275                 280                 285
```

```
His Ser Tyr Met Glu Met Pro Leu Glu Cys Ile Leu Thr Glu Lys Arg
    290                 295                 300
Lys Lys Arg Ser Thr Lys Lys Glu Val Phe Asn Ile Leu Gln Ala Ala
305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
            355                 360                 365
Tyr Val Asn Asp Phe Phe Asn Lys Ile Val Asn Lys Asn Asn Val Arg
    370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
        595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
```

-continued

```
            705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
            755                 760                 765
Ser Val Ser Val Pro Arg Met Val Ile Asn Val His Glu Ala Gly Arg
        770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
    850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
            900                 905                 910
Gln Ala Ile Ser Ser Thr Val Leu Gly Lys Val Ile Val Gln Pro Asp
        915                 920                 925
Gln Asn Phe Thr Gly Leu Ile Ala Gly Val Val Ser Ile Ser Thr Ala
    930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
            965                 970                 975
Thr Pro His Leu Asp Arg Leu Val Ser Ala Arg Ser Val Ser Pro Thr
        980                 985                 990
Thr Glu Met Val Ser Asn Glu Ser  Val Asp Tyr Arg Ala  Thr Phe Pro
        995                 1000                1005
Glu Asp  Gln Phe Pro Asn Ser  Ser Gln Asn Gly Ser  Cys Arg Gln
    1010                1015                1020
Val Gln  Tyr Pro Leu Thr Asp  Met Ser Pro Ile Leu  Thr Ser Gly
    1025                1030                1035
Asp Ser  Asp Ile Ser Ser Pro  Leu Leu Gln Asn Thr  Val His Ile
    1040                1045                1050
Asp Leu  Ser Ala Leu Asn Pro  Glu Leu Val Gln Ala  Val Gln His
    1055                1060                1065
Val Val  Ile Gly Pro Ser Ser  Leu Ile Val His Phe  Asn Glu Val
    1070                1075                1080
Ile Gly  Arg Gly His Phe Gly  Cys Val Tyr His Gly  Thr Leu Leu
    1085                1090                1095
Asp Asn  Asp Gly Lys Lys Ile  His Cys Ala Val Lys  Ser Leu Asn
    1100                1105                1110
Arg Ile  Thr Asp Ile Gly Glu  Val Ser Gln Phe Leu  Thr Glu Gly
    1115                1120                1125
```

-continued

```
Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Val Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 13
<211> LENGTH: 2558
<212> TYPE: DNA
<213> ORGANISM: Homo sapiens
<220> FEATURE:
<221> NAME/KEY: gene
<222> LOCATION: (1)..(2558)
<223> OTHER INFORMATION: Chondroitin sulfate proteoglycan BEHAB/brevican
      mRNA, GPI isoform, complete cds
<220> FEATURE:
<221> NAME/KEY: CDS
<222> LOCATION: (48)..(2063)
<223> OTHER INFORMATION:
<300> PUBLICATION INFORMATION:
<301> AUTHORS: Gary,S.C., Zerillo,C.A., Chiang,V.L., Gaw,J.U., Gray,G.
      and Hockfield,S.
<302> TITLE: cDNA cloning, chromosomal localization, and expression
      analysis of human BEHAB/brevican, a brain specific proteoglycan
      regulated during cortical development and in glioma
<303> JOURNAL: Gene
<304> VOLUME: 256
<305> ISSUE: 1
<306> PAGES: 139-147
```

```
<307> DATE: 2000
<309> DATABASE ENTRY DATE:
<313> RELEVANT RESIDUES: (1)..(2558)

<400> SEQUENCE: 13
```

| | | | | | | | | | | | | | | | | |
|---|---|---|---|---|---|---|---|---|---|---|---|---|---|---|---|---|
| tgtggcactg cctgcgtacc caaccccagc cctgggtagc ctgcagc | atg<br>Met<br>1 | gcc<br>Ala | cag<br>Gln | | | | | | | | | | | | | 56 |
| ctg<br>Leu | ttc<br>Phe<br>5 | ctg<br>Leu | ccc<br>Pro | ctg<br>Leu | ctg<br>Leu | gca<br>Ala<br>10 | gcc<br>Ala | ctg<br>Leu | gtc<br>Val | ctg<br>Leu | gcc<br>Ala<br>15 | cag<br>Gln | gct<br>Ala | cct<br>Pro | gca<br>Ala | 104 |
| gct<br>Ala<br>20 | tta<br>Leu | gca<br>Ala | gat<br>Asp | gtt<br>Val | ctg<br>Leu<br>25 | gaa<br>Glu | gga<br>Gly | gac<br>Asp | agc<br>Ser | tca<br>Ser<br>30 | gag<br>Glu | gac<br>Asp | cgc<br>Arg | gct<br>Ala | ttt<br>Phe<br>35 | 152 |
| cgc<br>Arg | gtg<br>Val | cgc<br>Arg | atc<br>Ile | gcg<br>Ala<br>40 | ggc<br>Gly | gac<br>Asp | gcg<br>Ala | cca<br>Pro | ctg<br>Leu<br>45 | cag<br>Gln | ggc<br>Gly | gtg<br>Val | ctc<br>Leu | ggc<br>Gly<br>50 | ggc<br>Gly | 200 |
| gcc<br>Ala | ctc<br>Leu | acc<br>Thr | atc<br>Ile<br>55 | cct<br>Pro | tgc<br>Cys | cac<br>His | gtc<br>Val | cac<br>His<br>60 | tac<br>Tyr | ctg<br>Leu | cgg<br>Arg | cca<br>Pro | ccg<br>Pro<br>65 | ccg<br>Pro | agc<br>Ser | 248 |
| cgc<br>Arg | cgg<br>Arg | gct<br>Ala<br>70 | gtg<br>Val | ctg<br>Leu | ggc<br>Gly | tct<br>Ser | ccg<br>Pro<br>75 | cgg<br>Arg | gtc<br>Val | aag<br>Lys | tgg<br>Trp | act<br>Thr<br>80 | ttc<br>Phe | ctg<br>Leu | tcc<br>Ser | 296 |
| cgg<br>Arg | ggc<br>Gly<br>85 | cgg<br>Arg | gag<br>Glu | gca<br>Ala | gag<br>Glu | gtg<br>Val<br>90 | ctg<br>Leu | gtg<br>Val | gcg<br>Ala | cgg<br>Arg | gga<br>Gly<br>95 | gtg<br>Val | cgc<br>Arg | gtc<br>Val | aag<br>Lys | 344 |
| gtg<br>Val<br>100 | aac<br>Asn | gag<br>Glu | gcc<br>Ala | tac<br>Tyr | cgg<br>Arg<br>105 | ttc<br>Phe | cgc<br>Arg | gtg<br>Val | gca<br>Ala | ctg<br>Leu<br>110 | cct<br>Pro | gcg<br>Ala | tac<br>Tyr | cca<br>Pro | gcg<br>Ala<br>115 | 392 |
| tcg<br>Ser | ctc<br>Leu | acc<br>Thr | gac<br>Asp | gtc<br>Val<br>120 | tcc<br>Ser | ctg<br>Leu | gcg<br>Ala | ctg<br>Leu | agc<br>Ser<br>125 | gag<br>Glu | ctg<br>Leu | cgc<br>Arg | ccc<br>Pro | aac<br>Asn<br>130 | gac<br>Asp | 440 |
| tca<br>Ser | ggt<br>Gly | atc<br>Ile | tat<br>Tyr<br>135 | cgc<br>Arg | tgt<br>Cys | gag<br>Glu | gtc<br>Val | cag<br>Gln<br>140 | cac<br>His | ggc<br>Gly | atc<br>Ile | gat<br>Asp | gac<br>Asp<br>145 | agc<br>Ser | agc<br>Ser | 488 |
| gac<br>Asp | gct<br>Ala | gtg<br>Val<br>150 | gag<br>Glu | gtc<br>Val | aag<br>Lys | gtc<br>Val | aaa<br>Lys<br>155 | ggg<br>Gly | gtc<br>Val | gtc<br>Val | ttt<br>Phe | ctc<br>Leu<br>160 | tac<br>Tyr | cga<br>Arg | gag<br>Glu | 536 |
| ggc<br>Gly | tct<br>Ser<br>165 | gcc<br>Ala | cgc<br>Arg | tat<br>Tyr | gct<br>Ala | ttc<br>Phe<br>170 | tcc<br>Ser | ttt<br>Phe | tct<br>Ser | ggg<br>Gly | gcc<br>Ala<br>175 | cag<br>Gln | gag<br>Glu | gcc<br>Ala | tgt<br>Cys | 584 |
| gcc<br>Ala<br>180 | cgc<br>Arg | att<br>Ile | gga<br>Gly | gcc<br>Ala | cac<br>His<br>185 | atc<br>Ile | gcc<br>Ala | acc<br>Thr | ccg<br>Pro | gag<br>Glu<br>190 | cag<br>Gln | ctc<br>Leu | tat<br>Tyr | gcc<br>Ala | gcc<br>Ala<br>195 | 632 |
| tac<br>Tyr | ctt<br>Leu | ggg<br>Gly | ggc<br>Gly | tat<br>Tyr<br>200 | gag<br>Glu | caa<br>Gln | tgt<br>Cys | gat<br>Asp | gct<br>Ala<br>205 | ggc<br>Gly | tgg<br>Trp | ctg<br>Leu | tcg<br>Ser | gat<br>Asp<br>210 | cag<br>Gln | 680 |
| acc<br>Thr | gtg<br>Val | agg<br>Arg<br>215 | tat<br>Tyr | ccc<br>Pro | atc<br>Ile | cag<br>Gln | acc<br>Thr<br>220 | cca<br>Pro | cga<br>Arg | gag<br>Glu | gcc<br>Ala | tgt<br>Cys<br>225 | tac<br>Tyr | gga<br>Gly | gac<br>Asp | 728 |
| atg<br>Met | gat<br>Asp | ggc<br>Gly<br>230 | ttc<br>Phe | ccc<br>Pro | ggg<br>Gly | gtc<br>Val | cgg<br>Arg<br>235 | aac<br>Asn | tat<br>Tyr | ggt<br>Gly | gtg<br>Val | gtg<br>Val<br>240 | gac<br>Asp | ccg<br>Pro | gat<br>Asp | 776 |
| gac<br>Asp | ctc<br>Leu<br>245 | tat<br>Tyr | gat<br>Asp | gtg<br>Val | tac<br>Tyr | tgt<br>Cys<br>250 | tat<br>Tyr | gct<br>Ala | gaa<br>Glu | gac<br>Asp | cta<br>Leu<br>255 | aat<br>Asn | gga<br>Gly | gaa<br>Glu | ttg<br>Leu | 824 |
| ttc<br>Phe<br>260 | ctg<br>Leu | ggt<br>Gly | gac<br>Asp | cct<br>Pro | cca<br>Pro<br>265 | gag<br>Glu | aag<br>Lys | ctg<br>Leu | aca<br>Thr | ttg<br>Leu<br>270 | gag<br>Glu | gaa<br>Glu | gca<br>Ala | cgg<br>Arg | gcg<br>Ala<br>275 | 872 |
| tac<br>Tyr | tgc<br>Cys | cag<br>Gln | gag<br>Glu | cgg<br>Arg | ggt<br>Gly | gca<br>Ala | gag<br>Glu | att<br>Ile | gcc<br>Ala | acc<br>Thr | acg<br>Thr | ggc<br>Gly | caa<br>Gln | ctg<br>Leu | tat<br>Tyr | 920 |

```
                Tyr Cys Gln Glu Arg Gly Ala Glu Ile Ala Thr Thr Gly Gln Leu Tyr
                                    280                 285                 290 gca gcc tgg gat ggt ggc ctg gac cac tgc agc cca ggg tgg cta gct        968
Ala Ala Trp Asp Gly Gly Leu Asp His Cys Ser Pro Gly Trp Leu Ala
            295                 300                 305 gat ggc agt gtg cgc tac ccc atc gtc aca ccc agc cag cgc tgt ggt        1016
Asp Gly Ser Val Arg Tyr Pro Ile Val Thr Pro Ser Gln Arg Cys Gly
        310                 315                 320 ggg ggc ttg cct ggt gtc aag act ctc ttc ctc ttc ccc aac cag act        1064
Gly Gly Leu Pro Gly Val Lys Thr Leu Phe Leu Phe Pro Asn Gln Thr
325                 330                 335 ggc ttc ccc aat aag cac agc cgc ttc aac gtc tac tgc ttc cga gac        1112
Gly Phe Pro Asn Lys His Ser Arg Phe Asn Val Tyr Cys Phe Arg Asp
340                 345                 350                 355 tcg gcc cag cct tct gcc atc cct gag gcc tcc aac cca gcc tcc aac        1160
Ser Ala Gln Pro Ser Ala Ile Pro Glu Ala Ser Asn Pro Ala Ser Asn
                360                 365                 370 cca gcc tct gat gga cta gag gct atc gtc aca gtg aca gag acc ctg        1208
Pro Ala Ser Asp Gly Leu Glu Ala Ile Val Thr Val Thr Glu Thr Leu
            375                 380                 385 gag gaa ctg cag ctg cct cag gaa gcc aca gag agt gaa tcc cgt ggg        1256
Glu Glu Leu Gln Leu Pro Gln Glu Ala Thr Glu Ser Glu Ser Arg Gly
        390                 395                 400 gcc atc tac tcc atc ccc atc atg gag gac gga gga ggt gga agc tcc        1304
Ala Ile Tyr Ser Ile Pro Ile Met Glu Asp Gly Gly Gly Gly Ser Ser
    405                 410                 415 act cca gaa gac cca gca gag gcc cct agg acg ctc cta gaa ttt gaa        1352
Thr Pro Glu Asp Pro Ala Glu Ala Pro Arg Thr Leu Leu Glu Phe Glu
420                 425                 430                 435 aca caa tcc atg gta ccg ccc acg ggg ttc tca gaa gag gaa ggt aag        1400
Thr Gln Ser Met Val Pro Pro Thr Gly Phe Ser Glu Glu Glu Gly Lys
                440                 445                 450 gca ttg gag gaa gaa gag aaa tat gaa gat gaa gaa gag aaa gag gag        1448
Ala Leu Glu Glu Glu Glu Lys Tyr Glu Asp Glu Glu Glu Lys Glu Glu
            455                 460                 465 gaa gaa gaa gag gag gag gtg gag gat gag gct ctg tgg gca tgg ccc        1496
Glu Glu Glu Glu Glu Glu Val Glu Asp Glu Ala Leu Trp Ala Trp Pro
        470                 475                 480 agc gag ctc agc agc ccg ggc cct gag gcc tct ctc ccc act gag cca        1544
Ser Glu Leu Ser Ser Pro Gly Pro Glu Ala Ser Leu Pro Thr Glu Pro
    485                 490                 495 gca gcc cag gag gag tca ctc tcc cag gcg cca gca agg gca gtc ctg        1592
Ala Ala Gln Glu Glu Ser Leu Ser Gln Ala Pro Ala Arg Ala Val Leu
500                 505                 510                 515 cag cct ggt gca tca cca ctt cct gat gga gag tca gaa gct tcc agg        1640
Gln Pro Gly Ala Ser Pro Leu Pro Asp Gly Glu Ser Glu Ala Ser Arg
                520                 525                 530 cct cca agg gtc cat gga cca cct act gag act ctg ccc act ccc agg        1688
Pro Pro Arg Val His Gly Pro Pro Thr Glu Thr Leu Pro Thr Pro Arg
            535                 540                 545 gag agg aac cta gca tcc cca tca cct tcc act ctg gtt gag gca aga        1736
Glu Arg Asn Leu Ala Ser Pro Ser Pro Ser Thr Leu Val Glu Ala Arg
        550                 555                 560 gag gtg ggg gag gca act ggt ggt cct gag cta tct ggg gtc cct cga        1784
Glu Val Gly Glu Ala Thr Gly Gly Pro Glu Leu Ser Gly Val Pro Arg
    565                 570                 575 gga gag agc gag gag aca gga agc tcc gag ggt gcc cct tcc ctg ctt        1832
Gly Glu Ser Glu Glu Thr Gly Ser Ser Glu Gly Ala Pro Ser Leu Leu
580                 585                 590                 595
```

-continued

```
cca gcc aca cgg gcc cct gag ggt acc agg gag ctg gag gcc ccc tct      1880
Pro Ala Thr Arg Ala Pro Glu Gly Thr Arg Glu Leu Glu Ala Pro Ser
            600                 605                 610 gaa gat aat tct gga aga act gcc cca gca ggg acc tca gtg cag gcc      1928
Glu Asp Asn Ser Gly Arg Thr Ala Pro Ala Gly Thr Ser Val Gln Ala
        615                 620                 625 cag cca gtg ctg ccc act gac agc gcc agc cga ggt gga gtg gcc gtg      1976
Gln Pro Val Leu Pro Thr Asp Ser Ala Ser Arg Gly Gly Val Ala Val
    630                 635                 640 gtc ccc gca tca ggt aat tct gcc caa ggc tca act gcc ctc tct atc      2024
Val Pro Ala Ser Gly Asn Ser Ala Gln Gly Ser Thr Ala Leu Ser Ile
645                 650                 655 cta ctc ctt ttc ttc ccc ctg cag ctc tgg gtc acc tga cctgtagtcc       2073
Leu Leu Leu Phe Phe Pro Leu Gln Leu Trp Val Thr
660                 665                 670 tttaacccac catcatccca aactctcctg tcctttgcct tcattctctt acccacctct    2133
acctatgggt ctccaatctc ggatatccac cttgtgggta tctcagctct ccgcgtcttt    2193
accctgtgat cccagccccg ccactgacca tctgtgaccc ttccctgcca ttgggccctc    2253
cacctgtggc tcacatctcg ccagccccac agagcatcct caggcctctc caagggtcct    2313
catcacctat tgcagccttc agggctcggc ctattttcca ctactcccctt catccgcctg   2373 tgtgccgtcc cctttagctg cctcctattg atctcaggga agcctgggag tcccttctca    2433 ccccctcaacc tccggagtcc aggagaaccc gtaccccccac agagccttaa gcaactactt  2493
ctgtgaagta tttttttgact gtttcatgga aaacaagcct tggaaataaa tctctattaa   2553
accgc                                                                2558
```

<210> SEQ ID NO 14
<211> LENGTH: 671
<212> TYPE: PRT
<213> ORGANISM: Homo sapiens
<220> FEATURE:
<221> NAME/KEY: gene
<222> LOCATION: (1)..(671)
<223> OTHER INFORMATION: Chondroitin sulfate proteoglycan BEHAB/brevican

<400> SEQUENCE: 14

```
Met Ala Gln Leu Phe Leu Pro Leu Leu Ala Ala Leu Val Leu Ala Gln
1               5                   10                  15

Ala Pro Ala Ala Leu Ala Asp Val Leu Glu Gly Asp Ser Ser Glu Asp
            20                  25                  30

Arg Ala Phe Arg Val Arg Ile Ala Gly Asp Ala Pro Leu Gln Gly Val
        35                  40                  45

Leu Gly Gly Ala Leu Thr Ile Pro Cys His Val His Tyr Leu Arg Pro
    50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
        115                 120                 125

Pro Asn Asp Ser Gly Ile Tyr Arg Cys Glu Val Gln His Gly Ile Asp
    130                 135                 140

Asp Ser Ser Asp Ala Val Glu Val Lys Val Lys Gly Val Val Phe Leu
145                 150                 155                 160
```

```
Tyr Arg Glu Gly Ser Ala Arg Tyr Ala Phe Ser Phe Ser Gly Ala Gln
            165                 170                 175

Glu Ala Cys Ala Arg Ile Gly Ala His Ile Ala Thr Pro Glu Gln Leu
        180                 185                 190

Tyr Ala Ala Tyr Leu Gly Gly Tyr Glu Gln Cys Asp Ala Gly Trp Leu
    195                 200                 205

Ser Asp Gln Thr Val Arg Tyr Pro Ile Gln Thr Pro Arg Glu Ala Cys
210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Glu Lys Leu Thr Leu Glu Glu
            260                 265                 270

Ala Arg Ala Tyr Cys Gln Glu Arg Gly Ala Glu Ile Ala Thr Thr Gly
        275                 280                 285

Gln Leu Tyr Ala Ala Trp Asp Gly Gly Leu Asp His Cys Ser Pro Gly
    290                 295                 300

Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
                325                 330                 335

Asn Gln Thr Gly Phe Pro Asn Lys His Ser Arg Phe Asn Val Tyr Cys
            340                 345                 350

Phe Arg Asp Ser Ala Gln Pro Ser Ala Ile Pro Glu Ala Ser Asn Pro
        355                 360                 365

Ala Ser Asn Pro Ala Ser Asp Gly Leu Glu Ala Ile Val Thr Val Thr
    370                 375                 380

Glu Thr Leu Glu Glu Leu Gln Leu Pro Gln Glu Ala Thr Glu Ser Glu
385                 390                 395                 400

Ser Arg Gly Ala Ile Tyr Ser Ile Pro Ile Met Glu Asp Gly Gly Gly
                405                 410                 415

Gly Ser Ser Thr Pro Glu Asp Pro Ala Glu Ala Pro Arg Thr Leu Leu
            420                 425                 430

Glu Phe Glu Thr Gln Ser Met Val Pro Pro Thr Gly Phe Ser Glu Glu
        435                 440                 445

Glu Gly Lys Ala Leu Glu Glu Glu Lys Tyr Glu Asp Glu Glu Glu
    450                 455                 460

Lys Glu Glu Glu Glu Glu Glu Glu Val Glu Asp Glu Ala Leu Trp
465                 470                 475                 480

Ala Trp Pro Ser Glu Leu Ser Ser Pro Gly Pro Glu Ala Ser Leu Pro
                485                 490                 495

Thr Glu Pro Ala Ala Gln Glu Glu Ser Leu Ser Gln Ala Pro Ala Arg
            500                 505                 510

Ala Val Leu Gln Pro Gly Ala Ser Pro Leu Pro Asp Gly Glu Ser Glu
        515                 520                 525

Ala Ser Arg Pro Pro Arg Val His Gly Pro Pro Thr Glu Thr Leu Pro
    530                 535                 540

Thr Pro Arg Glu Arg Asn Leu Ala Ser Pro Ser Thr Leu Val
545                 550                 555                 560

Glu Ala Arg Glu Val Gly Glu Ala Thr Gly Gly Pro Glu Leu Ser Gly
                565                 570                 575
```

```
                                                        -continued

Val Pro Arg Gly Glu Ser Glu Thr Gly Ser Ser Glu Gly Ala Pro
            580                 585                 590

Ser Leu Leu Pro Ala Thr Arg Ala Pro Glu Gly Thr Arg Glu Leu Glu
        595                 600                 605

Ala Pro Ser Glu Asp Asn Ser Gly Arg Thr Ala Pro Ala Gly Thr Ser
    610                 615                 620

Val Gln Ala Gln Pro Val Leu Pro Thr Asp Ser Ala Ser Arg Gly Gly
625                 630                 635                 640

Val Ala Val Val Pro Ala Ser Gly Asn Ser Ala Gln Gly Ser Thr Ala
                645                 650                 655

Leu Ser Ile Leu Leu Phe Phe Pro Leu Gln Leu Trp Val Thr
            660                 665                 670

<210> SEQ ID NO 15
<211> LENGTH: 2316
<212> TYPE: DNA
<213> ORGANISM: Homo sapiens
<220> FEATURE:
<221> NAME/KEY: gene
<222> LOCATION: (1)..(2316)
<223> OTHER INFORMATION: Human mRNA for CD44E (epithelial form)
<220> FEATURE:
<221> NAME/KEY: CDS
<222> LOCATION: (124)..(1605)
<223> OTHER INFORMATION:
<300> PUBLICATION INFORMATION:
<301> AUTHORS: Stamenkovic,I., Aruffo,A., Amiot,M. and Seed,B.
<302> TITLE: The hematopoietic and epithelial forms of CD44 are distinct
       polypeptides with different adhesion potentials for hyaluronate-
       bearing cells
<303> JOURNAL: EMBO J.
<304> VOLUME: 10
<305> ISSUE: 2
<306> PAGES: 343-348
<307> DATE: 1991
<309> DATABASE ENTRY DATE:
<313> RELEVANT RESIDUES: (1)..(2316)

<400> SEQUENCE: 15
agcggacccc agcctctgcc aggttcggtc cgccatcctc gtcccgtcct ccgccggccc      60
ctgccccgcg cccagggatc ctccagctcc tttcgcccgc gccctccgtt cgctccggac     120 acc atg gac aag ttt tgg tgg cac gca gcc tgg gga ctc tgc ctc gtg      168
    Met Asp Lys Phe Trp Trp His Ala Ala Trp Gly Leu Cys Leu Val
    1               5                   10                  15 ccg ctg agc ctg gcg cag atc gat ttg aat ata acc tgc cgc ttt gca      216
Pro Leu Ser Leu Ala Gln Ile Asp Leu Asn Ile Thr Cys Arg Phe Ala
                20                  25                  30 ggt gta ttc cac gtg gag aaa aat ggt cgc tac agc atc tct cgg acg      264
Gly Val Phe His Val Glu Lys Asn Gly Arg Tyr Ser Ile Ser Arg Thr
            35                  40                  45 gag gcc gct gac ctc tgc aag gct ttc aat agc acc ttg ccc aca atg      312
Glu Ala Ala Asp Leu Cys Lys Ala Phe Asn Ser Thr Leu Pro Thr Met
        50                  55                  60 gcc cag atg gag aaa gct ctg agc atc gga ttt gag acc tgc agg tat      360
Ala Gln Met Glu Lys Ala Leu Ser Ile Gly Phe Glu Thr Cys Arg Tyr
    65                  70                  75 ggg ttc ata gaa ggg cat gtg gtg att ccc cgg atc cac ccc aac tcc      408
Gly Phe Ile Glu Gly His Val Val Ile Pro Arg Ile His Pro Asn Ser
80                  85                  90                  95 atc tgt gca gca aac aac aca ggg gtg tac atc ctc aca tac aac acc      456
Ile Cys Ala Ala Asn Asn Thr Gly Val Tyr Ile Leu Thr Tyr Asn Thr
                100                 105                 110 tcc cag tat gac aca tat tgc ttc aat gct tca gct cca cct gaa gaa      504
```

```
                                                              -continued

Ser Gln Tyr Asp Thr Tyr Cys Phe Asn Ala Ser Ala Pro Pro Glu Glu
        115                 120                 125 gat tgt aca tca gtc aca gac ctg ccc aat gcc ttt gat gga cca att        552
Asp Cys Thr Ser Val Thr Asp Leu Pro Asn Ala Phe Asp Gly Pro Ile
        130                 135                 140 acc ata act att gtt aac cgt gat ggc acc cgc tat gtc cag aaa gga        600
Thr Ile Thr Ile Val Asn Arg Asp Gly Thr Arg Tyr Val Gln Lys Gly
        145                 150                 155 gaa tac aga acg aat cct gaa gac atc tac ccc agc aac cct act gat        648
Glu Tyr Arg Thr Asn Pro Glu Asp Ile Tyr Pro Ser Asn Pro Thr Asp
160                 165                 170                 175 gat gac gtg agc agc ggc tcc tcc agt gaa agg agc agc act tca gga        696
Asp Asp Val Ser Ser Gly Ser Ser Ser Glu Arg Ser Ser Thr Ser Gly
                180                 185                 190 ggt tac atc ttt tac acc ttt tct act gta cac ccc atc cca gac gaa        744
Gly Tyr Ile Phe Tyr Thr Phe Ser Thr Val His Pro Ile Pro Asp Glu
                195                 200                 205 gac agt ccc tgg atc acc gac agc aca gac aga atc cct cgt acc aat        792
Asp Ser Pro Trp Ile Thr Asp Ser Thr Asp Arg Ile Pro Arg Thr Asn
            210                 215                 220 atg gac tcc agt cat agt aca acg ctt cag cct act gca aat cca aac        840
Met Asp Ser Ser His Ser Thr Thr Leu Gln Pro Thr Ala Asn Pro Asn
225                 230                 235 aca ggt ttg gtg gaa gat ttg gac agg aca gga cct ctt tca atg aca        888
Thr Gly Leu Val Glu Asp Leu Asp Arg Thr Gly Pro Leu Ser Met Thr
240                 245                 250                 255 acg cag cag agt aat tct cag agc ttc tct aca tca cat gaa ggc ttg        936
Thr Gln Gln Ser Asn Ser Gln Ser Phe Ser Thr Ser His Glu Gly Leu
                260                 265                 270 gaa gaa gat aaa gac cat cca aca act tct act ctg aca tca agc aat        984
Glu Glu Asp Lys Asp His Pro Thr Thr Ser Thr Leu Thr Ser Ser Asn
                275                 280                 285 agg aat gat gtc aca ggt gga aga aga gac cca aat cat tct gaa ggc       1032
Arg Asn Asp Val Thr Gly Gly Arg Arg Asp Pro Asn His Ser Glu Gly
            290                 295                 300 tca act cat tta ctg gaa ggt tat acc tct cat tac cca cac acg aag       1080
Ser Thr His Leu Leu Glu Gly Tyr Thr Ser His Tyr Pro His Thr Lys
305                 310                 315 gaa agc agg acc ttc atc cca gtg acc tca gct aag act ggg tcc ttt       1128
Glu Ser Arg Thr Phe Ile Pro Val Thr Ser Ala Lys Thr Gly Ser Phe
320                 325                 330                 335 gga gtt act gca gtt act gtt gga gat tcc aac tct aat gtc aat cgt       1176
Gly Val Thr Ala Val Thr Val Gly Asp Ser Asn Ser Asn Val Asn Arg
                340                 345                 350 tcc tta tca gga gac caa gac aca ttc cac ccc agt ggg ggg tcc cat       1224
Ser Leu Ser Gly Asp Gln Asp Thr Phe His Pro Ser Gly Gly Ser His
                355                 360                 365 acc act cat gga tct gaa tca gat gga cac tca cat ggg agt caa gaa       1272
Thr Thr His Gly Ser Glu Ser Asp Gly His Ser His Gly Ser Gln Glu
            370                 375                 380 ggt gga gca aac aca acc tct ggt cct ata agg aca ccc caa att cca       1320
Gly Gly Ala Asn Thr Thr Ser Gly Pro Ile Arg Thr Pro Gln Ile Pro
385                 390                 395 gaa tgg ctg atc atc ttg gca tcc ctc ttg gcc ttg gct ttg att ctt       1368
Glu Trp Leu Ile Ile Leu Ala Ser Leu Leu Ala Leu Ala Leu Ile Leu
400                 405                 410                 415 gca gtt tgc att gca gtc aac agt cga aga agg tgt ggg cag aag aaa       1416
Ala Val Cys Ile Ala Val Asn Ser Arg Arg Arg Cys Gly Gln Lys Lys
                420                 425                 430
```

-continued

| | | | | | | | | | | | | | | | |
|---|---|---|---|---|---|---|---|---|---|---|---|---|---|---|---|
| aag | cta | gtg | atc | aac | agt | ggc | aat | gga | gct | gtg | gag | gac | aga | aag | cca | 1464 |
| Lys | Leu | Val | Ile | Asn | Ser | Gly | Asn | Gly | Ala | Val | Glu | Asp | Arg | Lys | Pro |
| | | | 435 | | | | 440 | | | | | 445 | | | | agt gga ctc aac gga gag gcc agc aag tct cag gaa atg gtg cat ttg    1512
Ser Gly Leu Asn Gly Glu Ala Ser Lys Ser Gln Glu Met Val His Leu
        450                 455                 460 gtg aac aag gag tcg tca gaa act cca gac cag ttt atg aca gct gat    1560
Val Asn Lys Glu Ser Ser Glu Thr Pro Asp Gln Phe Met Thr Ala Asp
465                 470                 475 gag aca agg aac ctg cag aat gtg gac atg aag att ggg gtg taa         1605
Glu Thr Arg Asn Leu Gln Asn Val Asp Met Lys Ile Gly Val
480                 485                 490 cacctacacc attatcttgg aaagaaacaa cgttggaaac ataaccatta caggggagct  1665
gggacactta acagatgcaa tgtgctactg attgtttcat ttcgaatcta taatagcata  1725
aaatttttcta ctcttttttgt tttttgtgtt ttgttcttta aagtcaggtc caatttgtaa 1785
aaacagcatt gctttctgaa attagggccc aattaataat cagcaagaat tttgatcgtt  1845
tcagttcccc acttggaggc ctttcatccc tcgggtgtgc tatggatggc ttctaacaaa  1905
aacctaccac atagttattc ctgatcgcca accttgcccc ccaccagcta aggacatttc  1965
cagggttaat agggcctggt cctgggagga aatttgaatg ggtcattttg cccttccatt  2025
agcctaatcc ctgggcattg ctttccactg aggttgggg ttggggtgta ctagttacac   2085
atcttcaaca gacccctct agaaattttt cagatgcttc tgggagacac ccaaagggta   2145
agtctattta tctgtagtaa actatttatc tgtgttttg aaatattaaa ccctggatca    2205
gtccttttat tcagtataat tttttaaagt tactttgtca gaggcacaaa aagggtttaa   2265
actgattcat aataaatatc tgtaccttct tcgaaaaaaa aaaaaaaaa a             2316

<210> SEQ ID NO 16
<211> LENGTH: 742
<212> TYPE: PRT
<213> ORGANISM: Homo sapiens
<220> FEATURE:
<221> NAME/KEY: SIGNAL
<222> LOCATION: (1)..(20)
<223> OTHER INFORMATION: BY SIMILARITY
<220> FEATURE:
<221> NAME/KEY: Gene
<222> LOCATION: (1)..(742)
<223> OTHER INFORMATION: CD-44 Antigen
<220> FEATURE:
<221> NAME/KEY: CHAIN
<222> LOCATION: (21)..(742)
<223> OTHER INFORMATION: CD44 ANTIGEN
<220> FEATURE:
<221> NAME/KEY: DOMAIN
<222> LOCATION: (21)..(649)
<223> OTHER INFORMATION: EXTRACELLULAR (POTENTIAL)
<220> FEATURE:
<221> NAME/KEY: TRANSMEM
<222> LOCATION: (650)..(670)
<223> OTHER INFORMATION: POTENTIAL
<220> FEATURE:
<221> NAME/KEY: DOMAIN
<222> LOCATION: (671)..(742)
<223> OTHER INFORMATION: CYTOPLASMIC (POTENTIAL)
<220> FEATURE:
<221> NAME/KEY: DOMAIN
<222> LOCATION: (48)..(119)
<223> OTHER INFORMATION: LINK
<220> FEATURE:
<221> NAME/KEY: MOD_RES
<222> LOCATION: (21)..(21)
<223> OTHER INFORMATION: PYRROLIDONE CARBOXYLIC ACID (PROBABLE)
<220> FEATURE:
<221> NAME/KEY: DISULFID

```
<222> LOCATION: (53)..(118)
<223> OTHER INFORMATION: BY SIMILARITY
<220> FEATURE:
<221> NAME/KEY: DISULFID
<222> LOCATION: (77)..(97)
<223> OTHER INFORMATION: BY SIMILARITY
<220> FEATURE:
<221> NAME/KEY: CARBOHYD
<222> LOCATION: (25)..(25)
<223> OTHER INFORMATION: N-LINKED (GLCNAC ...) (POTENTIAL)
<220> FEATURE:
<221> NAME/KEY: CARBOHYD
<222> LOCATION: (57)..(57)
<223> OTHER INFORMATION: N-LINKED (GLCNAC ...) (POTENTIAL)
<220> FEATURE:
<221> NAME/KEY: CARBOHYD
<222> LOCATION: (100)..(100)
<223> OTHER INFORMATION: N-LINKED (GLCNAC ...) (POTENTIAL)
<220> FEATURE:
<221> NAME/KEY: CARBOHYD
<222> LOCATION: (110)..(110)
<223> OTHER INFORMATION: N-LINKED (GLCNAC ...) (POTENTIAL)
<220> FEATURE:
<221> NAME/KEY: CARBOHYD
<222> LOCATION: (120)..(120)
<223> OTHER INFORMATION: N-LINKED (GLCNAC ...) (POTENTIAL)
<220> FEATURE:
<221> NAME/KEY: CARBOHYD
<222> LOCATION: (350)..(350)
<223> OTHER INFORMATION: N-LINKED (GLCNAC ...) (POTENTIAL)
<220> FEATURE:
<221> NAME/KEY: CARBOHYD
<222> LOCATION: (548)..(548)
<223> OTHER INFORMATION: N-LINKED (GLCNAC ...) (POTENTIAL)
<220> FEATURE:
<221> NAME/KEY: CARBOHYD
<222> LOCATION: (599)..(599)
<223> OTHER INFORMATION: N-LINKED (GLCNAC ...) (POTENTIAL)
<220> FEATURE:
<221> NAME/KEY: CARBOHYD
<222> LOCATION: (636)..(636)
<223> OTHER INFORMATION: N-LINKED (GLCNAC ...) (POTENTIAL)
<220> FEATURE:
<221> NAME/KEY: VARSPLIC
<222> LOCATION: (23)..(29)
<223> OTHER INFORMATION: DLNITCR -> GVGRRKS (IN ISOFORM CD44SP)
<220> FEATURE:
<221> NAME/KEY: VARSPLIC
<222> LOCATION: (30)..(742)
<223> OTHER INFORMATION: MISSING (IN ISOFORM CD44SP)
<220> FEATURE:
<221> NAME/KEY: VARSPLIC
<222> LOCATION: (192)..(192)
<223> OTHER INFORMATION: G -> A (IN ISOFORM WITH ALTERNATIVE SPLICE
     DONOR/ACCEPTOR ON EXON 5)
<220> FEATURE:
<221> NAME/KEY: VARSPLIC
<222> LOCATION: (193)..(223)
<223> OTHER INFORMATION: MISSING (IN ISOFORM WITH ALTERNATIVE SPLICE
     DONOR/ACCEPTOR ON EXON 5)
<220> FEATURE:
<221> NAME/KEY: VARSPLIC
<222> LOCATION: (223)..(223)
<223> OTHER INFORMATION: T -> S (IN ISOFORM WITHOUT EXON 6)
<220> FEATURE:
<221> NAME/KEY: VARSPLIC
<222> LOCATION: (224)..(266)
<223> OTHER INFORMATION: MISSING (IN ISOFORM WITHOUT EXON 6)
<220> FEATURE:
<221> NAME/KEY: VARSPLIC
<222> LOCATION: (223)..(223)
<223> OTHER INFORMATION: T -> N (IN ISOFORMS WITHOUT EXONS 6 TO 11)
<220> FEATURE:
<221> NAME/KEY: VARSPLIC
<222> LOCATION: (224)..(472)
<223> OTHER INFORMATION: MISSING (IN ISOFORMS WITHOUT EXONS 6 TO 11)
<220> FEATURE:
<221> NAME/KEY: VARSPLIC
<222> LOCATION: (223)..(223)
```

```
<223> OTHER INFORMATION: T -> R (IN ISOFORMS WITHOUT EXONS 6 TO 14)
<220> FEATURE:
<221> NAME/KEY: VARSPLIC
<222> LOCATION: (224)..(604)
<223> OTHER INFORMATION: MISSING (IN ISOFORMS WITHOUT EXONS 6 TO 14)
<220> FEATURE:
<221> NAME/KEY: VARSPLIC
<222> LOCATION: (266)..(273)
<223> OTHER INFORMATION: MISSING (IN ISOFORM WITH ALTERNATIVE SPLICE
      DONOR/ACCEPTOR ON EXON 7)
<220> FEATURE:
<221> NAME/KEY: VARSPLIC
<222> LOCATION: (385)..(385)
<223> OTHER INFORMATION: I -> T (IN ISOFORMS WITHOUT EXON 10)
<220> FEATURE:
<221> NAME/KEY: VARSPLIC
<222> LOCATION: (386)..(428)
<223> OTHER INFORMATION: MISSING (IN ISOFORMS WITHOUT EXON 10)
<220> FEATURE:
<221> NAME/KEY: VARSPLIC
<222> LOCATION: (506)..(506)
<223> OTHER INFORMATION: Q -> R (IN ISOFORMS WITHOUT EXON 13)
<220> FEATURE:
<221> NAME/KEY: VARSPLIC
<222> LOCATION: (507)..(535)
<223> OTHER INFORMATION: MISSING (IN ISOFORMS WITHOUT EXON 13)
<220> FEATURE:
<221> NAME/KEY: VARSPLIC
<222> LOCATION: (536)..(536)
<223> OTHER INFORMATION: N -> R (IN ISOFORMS WITHOUT EXON 14)
<220> FEATURE:
<221> NAME/KEY: VARSPLIC
<222> LOCATION: (537)..(604)
<223> OTHER INFORMATION: MISSING (IN ISOFORMS WITHOUT EXON 14)
<220> FEATURE:
<221> NAME/KEY: VARSPLIC
<222> LOCATION: (675)..(675)
<223> OTHER INFORMATION: R -> S (IN ISOFORMS WITHOUT EXON 19)
<220> FEATURE:
<221> NAME/KEY: VARSPLIC
<222> LOCATION: (676)..(742)
<223> OTHER INFORMATION: MISSING (IN ISOFORMS WITHOUT EXON 19)
<220> FEATURE:
<221> NAME/KEY: VARIANT
<222> LOCATION: (46)..(46)
<223> OTHER INFORMATION: R -> P (IN IN(A) ANTIGEN)

<400> SEQUENCE: 16

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160
```

-continued

```
Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Glu Asp Phe Ile
290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Arg Glu Asp Ser His Ser Thr Thr Gly Thr Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
450                 455                 460

His Gln Ala Gly Arg Arg Met Asp Met Asp Ser Ser His Ser Thr Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
```

-continued

```
                580                 585                 590
Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740
```

```
<210> SEQ ID NO 17
<211> LENGTH: 930
<212> TYPE: DNA
<213> ORGANISM: Homo sapiens
<220> FEATURE:
<221> NAME/KEY: Gene
<222> LOCATION: (1)..(930)
<223> OTHER INFORMATION: Tetraspan TM4SF (TSPAN-3), mRNA
<220> FEATURE:
<221> NAME/KEY: CDS
<222> LOCATION: (1)..(762)
<223> OTHER INFORMATION:
<300> PUBLICATION INFORMATION:
<301> AUTHORS: Todd, S.C., Doctor, V.S. and Levy, S.
<302> TITLE: Sequences and expression of six new members of the
       tetraspanin/TM4SF family
<303> JOURNAL: Biochim. Biophys. Acta
<304> VOLUME: 1399
<305> ISSUE: 1
<306> PAGES: 101-104
<307> DATE: 1998
<309> DATABASE ENTRY DATE:
<313> RELEVANT RESIDUES: (1)..(930)

<400> SEQUENCE: 17
```

```
atg ggc cag tgc ggc atc acc tcc tcc aag acc gtg ctg gtc ttt ctc        48
Met Gly Gln Cys Gly Ile Thr Ser Ser Lys Thr Val Leu Val Phe Leu
1               5                   10                  15 aac ctc atc ttc tgg ggg gca gct ggc att tta tgc tat gtg gga gcc        96
Asn Leu Ile Phe Trp Gly Ala Ala Gly Ile Leu Cys Tyr Val Gly Ala
                20                  25                  30 tat gtc ttc atc act tat gat gac tat gac cac ttc ttt gaa gat gtg       144
Tyr Val Phe Ile Thr Tyr Asp Asp Tyr Asp His Phe Phe Glu Asp Val
            35                  40                  45 tac acg ctc atc cct gct gta gtg atc ata gct gta gga gcc ctg ctt       192
Tyr Thr Leu Ile Pro Ala Val Val Ile Ile Ala Val Gly Ala Leu Leu
        50                  55                  60 ttc atc att ggg cta att ggc tgc tgt gcc aca atc cgg gaa agt cgc       240
Phe Ile Ile Gly Leu Ile Gly Cys Cys Ala Thr Ile Arg Glu Ser Arg
65                  70                  75                  80
```

-continued

```
tgt gga ctt gcc acg ttt gtc atc atc ctg ctc ttg gtt ttt gtc aca      288
Cys Gly Leu Ala Thr Phe Val Ile Ile Leu Leu Leu Val Phe Val Thr
             85                  90                  95 gaa gtt gtt gta gtg gtt ttg gga tat gtt tac aga gca aag gtg gaa      336
Glu Val Val Val Val Val Leu Gly Tyr Val Tyr Arg Ala Lys Val Glu
            100                 105                 110 aat gag gtt gat cgc agc att cag aaa gtg tat aag acc tac aat gga      384
Asn Glu Val Asp Arg Ser Ile Gln Lys Val Tyr Lys Thr Tyr Asn Gly
        115                 120                 125 acc aac cct gat gct gct agc cgg gct att gat tat gta cag aga cag      432
Thr Asn Pro Asp Ala Ala Ser Arg Ala Ile Asp Tyr Val Gln Arg Gln
    130                 135                 140 ctg cat tgt tgt gga att cac aac tac tca gac tgg gaa aat aca gat      480
Leu His Cys Cys Gly Ile His Asn Tyr Ser Asp Trp Glu Asn Thr Asp
145                 150                 155                 160 tgg ttc aaa gaa acc aaa aac cag agt gtc cct ctt agc tgc tgc aga      528
Trp Phe Lys Glu Thr Lys Asn Gln Ser Val Pro Leu Ser Cys Cys Arg
                165                 170                 175 gag act gcc agc aat tgt aat ggc agc ctg gcc cac cct tcc gac ctc      576
Glu Thr Ala Ser Asn Cys Asn Gly Ser Leu Ala His Pro Ser Asp Leu
            180                 185                 190 tat gct gag ggg tgt gag gct cta gtt gtg aag aag cta caa gaa atc      624
Tyr Ala Glu Gly Cys Glu Ala Leu Val Val Lys Lys Leu Gln Glu Ile
        195                 200                 205 atg atg cat gtg atc tgg gcc gca ctg gca ttt gca gct att cag ctg      672
Met Met His Val Ile Trp Ala Ala Leu Ala Phe Ala Ala Ile Gln Leu
    210                 215                 220 ctg ggc atg ctg tgt gct tgc atc gtg ttg tgc aga agg agt aga gat      720
Leu Gly Met Leu Cys Ala Cys Ile Val Leu Cys Arg Arg Ser Arg Asp
225                 230                 235                 240 cct gct tac gag ctc ctc atc act ggc gga acc tat gca tag             762
Pro Ala Tyr Glu Leu Leu Ile Thr Gly Gly Thr Tyr Ala
                245                 250 ttgacaactc ttgcctgagc tttttggtct tgttctgatt tggaaggtga attgagcagg    822
tctgctgctg ttggcctctg gagttcattt agttaaagca catgtacact ggtgttggac    882
agagcagctt ggcttttcat gtgcccaact acttactact actgcgat                 930
```

<210> SEQ ID NO 18
<211> LENGTH: 253
<212> TYPE: PRT
<213> ORGANISM: Homo sapiens
<220> FEATURE:
<221> NAME/KEY: DOMAIN
<222> LOCATION: (1)..(11)
<223> OTHER INFORMATION: Cytoplasmic (Potential)
<220> FEATURE:
<221> NAME/KEY: Gene
<222> LOCATION: (1)..(253)
<223> OTHER INFORMATION: Tetraspanin-3
<220> FEATURE:
<221> NAME/KEY: TRANSMEM
<222> LOCATION: (12)..(32)
<223> OTHER INFORMATION: Potential
<220> FEATURE:
<221> NAME/KEY: DOMAIN
<222> LOCATION: (33)..(50)
<223> OTHER INFORMATION: Extracellular (Potential)
<220> FEATURE:
<221> NAME/KEY: TRANSMEM
<222> LOCATION: (51)..(71)
<223> OTHER INFORMATION: Potential
<220> FEATURE:
<221> NAME/KEY: DOMAIN
<222> LOCATION: (72)..(85)
<223> OTHER INFORMATION: Cytoplasmic (potential)

```
<220> FEATURE:
<221> NAME/KEY: TRANSMEM
<222> LOCATION: (86)..(106)
<223> OTHER INFORMATION: Potential
<220> FEATURE:
<221> NAME/KEY: DOMAIN
<222> LOCATION: (107)..(212)
<223> OTHER INFORMATION: Extracellular (potential)
<220> FEATURE:
<221> NAME/KEY: TRANSMEM
<222> LOCATION: (213)..(233)
<223> OTHER INFORMATION: Potential
<220> FEATURE:
<221> NAME/KEY: DOMAIN
<222> LOCATION: (234)..(253)
<223> OTHER INFORMATION: Cytoplasmic (potential)
<220> FEATURE:
<221> NAME/KEY: CARBOHYD
<222> LOCATION: (127)..(127)
<223> OTHER INFORMATION: N-linked (GLCNAC...) (potential)
<220> FEATURE:
<221> NAME/KEY: CARBOHYD
<222> LOCATION: (152)..(152)
<223> OTHER INFORMATION: N-linked (GLCNAC...) (potential)
<220> FEATURE:
<221> NAME/KEY: CARBOHYD
<222> LOCATION: (167)..(167)
<223> OTHER INFORMATION: N-linked (GLCNAC...) (potential)
<220> FEATURE:
<221> NAME/KEY: CARBOHYD
<222> LOCATION: (183)..(183)
<223> OTHER INFORMATION: N-linked (GLCNAC...) (potential)

<400> SEQUENCE: 18

Met Gly Gln Cys Gly Ile Thr Ser Ser Lys Thr Val Leu Val Phe Leu
1               5                   10                  15

Asn Leu Ile Phe Trp Gly Ala Ala Gly Ile Leu Cys Tyr Val Gly Ala
            20                  25                  30

Tyr Val Phe Ile Thr Tyr Asp Asp Tyr Asp His Phe Phe Glu Asp Val
        35                  40                  45

Tyr Thr Leu Ile Pro Ala Val Val Ile Ala Val Gly Ala Leu Leu
    50                  55                  60

Phe Ile Ile Gly Leu Ile Gly Cys Cys Ala Thr Ile Arg Glu Ser Arg
65                  70                  75                  80

Cys Gly Leu Ala Thr Phe Val Ile Ile Leu Leu Leu Val Phe Val Thr
                85                  90                  95

Glu Val Val Val Val Leu Gly Tyr Val Tyr Arg Ala Lys Val Glu
            100                 105                 110

Asn Glu Val Asp Arg Ser Ile Gln Lys Val Tyr Lys Thr Tyr Asn Gly
            115                 120                 125

Thr Asn Pro Asp Ala Ala Ser Arg Ala Ile Asp Tyr Val Gln Arg Gln
        130                 135                 140

Leu His Cys Cys Gly Ile His Asn Tyr Ser Asp Trp Glu Asn Thr Asp
145                 150                 155                 160

Trp Phe Lys Glu Thr Lys Asn Gln Ser Val Pro Leu Ser Cys Cys Arg
                165                 170                 175

Glu Thr Ala Ser Asn Cys Asn Gly Ser Leu Ala His Pro Ser Asp Leu
            180                 185                 190

Tyr Ala Glu Gly Cys Glu Ala Leu Val Val Lys Lys Leu Gln Glu Ile
        195                 200                 205

Met Met His Val Ile Trp Ala Ala Leu Ala Phe Ala Ala Ile Gln Leu
    210                 215                 220

Leu Gly Met Leu Cys Ala Cys Ile Val Leu Cys Arg Arg Ser Arg Asp
225                 230                 235                 240
```

```
Pro Ala Tyr Glu Leu Leu Ile Thr Gly Gly Thr Tyr Ala
            245                 250

<210> SEQ ID NO 19
<211> LENGTH: 1317
<212> TYPE: DNA
<213> ORGANISM: Homo sapiens
<220> FEATURE:
<221> NAME/KEY: Gene
<222> LOCATION: (1)..(1317)
<223> OTHER INFORMATION: Vasoactive Intestinal Peptide Receptor-2
<220> FEATURE:
<221> NAME/KEY: CDS
<222> LOCATION: (1)..(1317)
<223> OTHER INFORMATION:
<300> PUBLICATION INFORMATION:
<301> AUTHORS: Svoboda, M., Tastenoy, M., Van Rampelbergh, J., Goossens,
      J.F., De Neef, P., Waelbroeck, M. and Robberecht, P.
<302> TITLE: Molecular cloning and functional characterization of a
      human VIP receptor from SUP-T1 lymphoblasts 205 (3), 1617-1624
      (1994)
<303> JOURNAL: Biochem. Biophys. Res. Commun.
<304> VOLUME: 205
<305> ISSUE: 3
<306> PAGES: 1617-1624
<307> DATE: 1994
<309> DATABASE ENTRY DATE:
<313> RELEVANT RESIDUES: (1)..(1317)

<400> SEQUENCE: 19 atg cgg acg ctg ctg cct ccc gcg ctg ctg acc tgc tgg ctg ctc gcc        48
Met Arg Thr Leu Leu Pro Pro Ala Leu Leu Thr Cys Trp Leu Leu Ala
1               5                  10                  15 ccc gtg aac agc att cac cca gaa tgc cga ttt cat ctg gaa ata cag        96
Pro Val Asn Ser Ile His Pro Glu Cys Arg Phe His Leu Glu Ile Gln
            20                  25                  30 gag gaa gaa aca aaa tgt aca gag ctt ctg agg tct caa aca gaa aaa       144
Glu Glu Glu Thr Lys Cys Thr Glu Leu Leu Arg Ser Gln Thr Glu Lys
        35                  40                  45 cac aaa gcc tgc agt ggc gtc tgg gac aac atc acg tgc tgg cgg cct       192
His Lys Ala Cys Ser Gly Val Trp Asp Asn Ile Thr Cys Trp Arg Pro
    50                  55                  60 gcc aat gtg gga gag acc gtc acg gtg ccc tgc cca aaa gtc ttc agc       240
Ala Asn Val Gly Glu Thr Val Thr Val Pro Cys Pro Lys Val Phe Ser
65                  70                  75                  80 aat ttt tac agc aaa gca gga aac ata agc aaa aac tgt acg agt gac       288
Asn Phe Tyr Ser Lys Ala Gly Asn Ile Ser Lys Asn Cys Thr Ser Asp
                85                  90                  95 gga tgg tca gag acg ttc cca gat ttc gtc gat gcc tgt ggc tac agc       336
Gly Trp Ser Glu Thr Phe Pro Asp Phe Val Asp Ala Cys Gly Tyr Ser
            100                 105                 110 gac ccg gag gat gag agc aag atc acg ttt tat att ctg gtg aag gcc       384
Asp Pro Glu Asp Glu Ser Lys Ile Thr Phe Tyr Ile Leu Val Lys Ala
        115                 120                 125 att tat acc ctg ggc tac agt gtc tct ctg atg tct ctt gca aca gga       432
Ile Tyr Thr Leu Gly Tyr Ser Val Ser Leu Met Ser Leu Ala Thr Gly
    130                 135                 140 agc ata att ctg tgc ctc ttc agg aag ctg cac tgc acc agg aat tac       480
Ser Ile Ile Leu Cys Leu Phe Arg Lys Leu His Cys Thr Arg Asn Tyr
145                 150                 155                 160 atc cac ctg aac ctg ttc ctg tcc ttc atc ctg aga gcc atc tca gtg       528
Ile His Leu Asn Leu Phe Leu Ser Phe Ile Leu Arg Ala Ile Ser Val
                165                 170                 175 ctg gtc aag gac gac gtt ctc tac tcc agc tct ggc acg ttg cac tgc       576
Leu Val Lys Asp Asp Val Leu Tyr Ser Ser Ser Gly Thr Leu His Cys
```

```
                 180                 185                 190
cct gac cag cca tcc tcc tgg gtg ggc tgc aag ctg agc ctg gtc ttc        624
Pro Asp Gln Pro Ser Ser Trp Val Gly Cys Lys Leu Ser Leu Val Phe
            195                 200                 205 ctg cag tac tgc atc atg gcc aac ttc ttc tgg ctg ctg gtg gag ggg        672
Leu Gln Tyr Cys Ile Met Ala Asn Phe Phe Trp Leu Leu Val Glu Gly
        210                 215                 220 ctc tac ctc cac acc ctc ctg gtg gcc atg ctc ccc cct aga agg tgc        720
Leu Tyr Leu His Thr Leu Leu Val Ala Met Leu Pro Pro Arg Arg Cys
225                 230                 235                 240 ttc ctg gcc tac ctc ctg atc gga tgg ggc ctc ccc acc gtc tgc atc        768
Phe Leu Ala Tyr Leu Leu Ile Gly Trp Gly Leu Pro Thr Val Cys Ile
                245                 250                 255 ggt gca tgg act gcg gcc agg ctc tac tta gaa gac acc ggt tgc tgg        816
Gly Ala Trp Thr Ala Ala Arg Leu Tyr Leu Glu Asp Thr Gly Cys Trp
            260                 265                 270 gat aca aac gac cac agt gtg ccc tgg tgg gtc ata cga ata ccg att        864
Asp Thr Asn Asp His Ser Val Pro Trp Trp Val Ile Arg Ile Pro Ile
        275                 280                 285 tta att tcc atc atc gtc aat ttt gtc ctt ttc att agt att ata cga        912
Leu Ile Ser Ile Ile Val Asn Phe Val Leu Phe Ile Ser Ile Ile Arg
290                 295                 300 att ttg ctg cag aag tta aca tcc cca gat gtc ggc ggc aac gac cag        960
Ile Leu Leu Gln Lys Leu Thr Ser Pro Asp Val Gly Gly Asn Asp Gln
305                 310                 315                 320 tct cag tac aag agg ctg gcc aag tcc acg ctc ctt atc ccg ctg            1008
Ser Gln Tyr Lys Arg Leu Ala Lys Ser Thr Leu Leu Leu Ile Pro Leu
                325                 330                 335 ttc ggc gtc cac tac atg gtg ttt gcc gtg ttt ccc atc agc atc tcc        1056
Phe Gly Val His Tyr Met Val Phe Ala Val Phe Pro Ile Ser Ile Ser
            340                 345                 350 tcc aaa tac cag ata ctg ttt gag ctg tgc ctc ggg tcg ttc cag ggc        1104
Ser Lys Tyr Gln Ile Leu Phe Glu Leu Cys Leu Gly Ser Phe Gln Gly
        355                 360                 365 ctg gtg gtg gcc gtc ctc tac tgt ttc ctg aac agt gag gtg cag tgc        1152
Leu Val Val Ala Val Leu Tyr Cys Phe Leu Asn Ser Glu Val Gln Cys
370                 375                 380 gag ctg aag cga aaa tgg cga agc cgg tgc ccg acc ccg tcc gcg agc        1200
Glu Leu Lys Arg Lys Trp Arg Ser Arg Cys Pro Thr Pro Ser Ala Ser
385                 390                 395                 400 cgg gat tac agg gtc tgc ggt tcc tcc ttc tcc cac aac ggc tcg gag        1248
Arg Asp Tyr Arg Val Cys Gly Ser Ser Phe Ser His Asn Gly Ser Glu
                405                 410                 415 ggc gcc ctg cag ttc cac cgc gcg tcc cga gcc cag tcc ttc ctg caa        1296
Gly Ala Leu Gln Phe His Arg Ala Ser Arg Ala Gln Ser Phe Leu Gln
            420                 425                 430 acg gag acc tcg gtc atc tag                                            1317
Thr Glu Thr Ser Val Ile
        435

<210> SEQ ID NO 20
<211> LENGTH: 438
<212> TYPE: PRT
<213> ORGANISM: Homo sapiens
<220> FEATURE:
<221> NAME/KEY: SIGNAL
<222> LOCATION: (1)..(23)
<223> OTHER INFORMATION: Potential
<220> FEATURE:
<221> NAME/KEY: GENE
<222> LOCATION: (1)..(438)
<223> OTHER INFORMATION: Vasoactive Intestinal Peptide Receptor 2
```

```
<220> FEATURE:
<221> NAME/KEY: CHAIN
<222> LOCATION: (24)..(438)
<223> OTHER INFORMATION: Vasoactive Intestinal Polypeptide Receptor 2
<220> FEATURE:
<221> NAME/KEY: DOMAIN
<222> LOCATION: (24)..(126)
<223> OTHER INFORMATION: 1 (Potential)
<220> FEATURE:
<221> NAME/KEY: TRANSMEM
<222> LOCATION: (127)..(151)
<223> OTHER INFORMATION: 1 (Potential)
<220> FEATURE:
<221> NAME/KEY: DOMAIN
<222> LOCATION: (152)..(158)
<223> OTHER INFORMATION: Cytoplasmic (potential)
<220> FEATURE:
<221> NAME/KEY: TRANSMEM
<222> LOCATION: (159)..(178)
<223> OTHER INFORMATION: 2 (Potential)
<220> FEATURE:
<221> NAME/KEY: DOMAIN
<222> LOCATION: (179)..(203)
<223> OTHER INFORMATION: Extracellular (Potential)
<220> FEATURE:
<221> NAME/KEY: TRANSMEM
<222> LOCATION: (204)..(227)
<223> OTHER INFORMATION: 3 (Potential)
<220> FEATURE:
<221> NAME/KEY: DOMAIN
<222> LOCATION: (228)..(240)
<223> OTHER INFORMATION: Cytoplasmic (Potential)
<220> FEATURE:
<221> NAME/KEY: TRANSMEM
<222> LOCATION: (241)..(262)
<223> OTHER INFORMATION: 4 (Potential)
<220> FEATURE:
<221> NAME/KEY: DOMAIN
<222> LOCATION: (263)..(279)
<223> OTHER INFORMATION: Extracellular (Potential)
<220> FEATURE:
<221> NAME/KEY: TRANSMEM
<222> LOCATION: (280)..(303)
<223> OTHER INFORMATION: 5 (Potential)
<220> FEATURE:
<221> NAME/KEY: DOMAIN
<222> LOCATION: (304)..(328)
<223> OTHER INFORMATION: Cytoplasmic (Potential)
<220> FEATURE:
<221> NAME/KEY: TRANSMEM
<222> LOCATION: (329)..(348)
<223> OTHER INFORMATION: 6 (Potential)
<220> FEATURE:
<221> NAME/KEY: DOMAIN
<222> LOCATION: (349)..(360)
<223> OTHER INFORMATION: Extracellular (Potential)
<220> FEATURE:
<221> NAME/KEY: TRANSMEM
<222> LOCATION: (361)..(380)
<223> OTHER INFORMATION: 7 (Potential)
<220> FEATURE:
<221> NAME/KEY: DOMAIN
<222> LOCATION: (381)..(438)
<223> OTHER INFORMATION: Cytoplasmic (potential)
<220> FEATURE:
<221> NAME/KEY: CARBOHYD
<222> LOCATION: (58)..(58)
<223> OTHER INFORMATION: N-linked (GLCNAC...) (Potential)
<220> FEATURE:
<221> NAME/KEY: CARBOHYD
<222> LOCATION: (88)..(88)
<223> OTHER INFORMATION: N-linked (GLCNAC...) (Potential)
<220> FEATURE:
<221> NAME/KEY: CARBOHYD
<222> LOCATION: (92)..(92)
<223> OTHER INFORMATION: N-linked (GLCNAC...) (Potential)

<400> SEQUENCE: 20
```

-continued

```
Met Arg Thr Leu Leu Pro Pro Ala Leu Leu Thr Cys Trp Leu Leu Ala
1               5                   10                  15

Pro Val Asn Ser Ile His Pro Glu Cys Arg Phe His Leu Glu Ile Gln
        20                  25                  30

Glu Glu Glu Thr Lys Cys Ala Glu Leu Leu Arg Ser Gln Thr Glu Lys
            35                  40                  45

His Lys Ala Cys Ser Gly Val Trp Asp Asn Ile Thr Cys Trp Arg Pro
50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
                85                  90                  95

Gly Trp Ser Glu Thr Phe Pro Asp Phe Val Asp Ala Cys Gly Tyr Ser
            100                 105                 110

Asp Pro Glu Asp Glu Ser Lys Ile Thr Phe Tyr Ile Leu Val Lys Ala
            115                 120                 125

Ile Tyr Thr Leu Gly Tyr Ser Val Ser Leu Met Ser Leu Ala Thr Gly
        130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
                165                 170                 175

Leu Val Lys Asp Asp Val Leu Tyr Ser Ser Gly Thr Leu His Cys
            180                 185                 190

Pro Asp Gln Pro Ser Ser Trp Val Gly Cys Lys Leu Ser Leu Val Phe
        195                 200                 205

Leu Gln Tyr Cys Ile Met Ala Asn Phe Phe Trp Leu Leu Val Glu Gly
    210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
                245                 250                 255

Gly Ala Trp Thr Ala Ala Arg Leu Tyr Leu Glu Asp Thr Gly Cys Trp
            260                 265                 270

Asp Thr Asn Asp His Ser Val Pro Trp Trp Val Ile Arg Ile Pro Ile
            275                 280                 285

Leu Ile Ser Ile Ile Val Asn Phe Val Leu Phe Ile Ser Ile Ile Arg
    290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Leu Ile Pro Leu
                325                 330                 335

Phe Gly Val His Tyr Met Val Phe Ala Val Phe Pro Ile Ser Ile Ser
            340                 345                 350

Ser Lys Tyr Gln Ile Leu Phe Glu Leu Cys Leu Gly Ser Phe Gln Gly
        355                 360                 365

Leu Val Val Ala Val Leu Tyr Cys Phe Leu Asn Ser Glu Val Gln Cys
    370                 375                 380

Glu Leu Lys Arg Lys Trp Arg Ser Arg Cys Pro Thr Pro Ser Ala Ser
385                 390                 395                 400

Arg Asp Tyr Arg Val Cys Gly Ser Ser Phe Ser Arg Asn Gly Ser Glu
                405                 410                 415

Gly Ala Leu Gln Phe His Arg Gly Ser Arg Ala Gln Ser Phe Leu Gln
```

```
                    420            425            430
Thr Glu Thr Ser Val Ile
           435

<210> SEQ ID NO 21
<211> LENGTH: 889
<212> TYPE: DNA
<213> ORGANISM: Homo sapiens
<220> FEATURE:
<221> NAME/KEY: Gene
<222> LOCATION: (1)..(889)
<223> OTHER INFORMATION: Pleiotrophin
<220> FEATURE:
<221> NAME/KEY: CDS
<222> LOCATION: (252)..(758)
<223> OTHER INFORMATION:
<300> PUBLICATION INFORMATION:
<301> AUTHORS: Li, Y.S., Milner, P.G., Chauhan, A.K., Watson, M.A.,
       Hoffman, R.M., Kodner, C.M., Milbrandt, J. and Deuel, T.F.
<302> TITLE: Cloning and expression of a developmentally regulated
       protein that induces mitogenic and neurite outgrowth activity
<303> JOURNAL: Science
<304> VOLUME: 250
<305> ISSUE: 4988
<306> PAGES: 1690-1694
<307> DATE: 1990
<309> DATABASE ENTRY DATE:
<313> RELEVANT RESIDUES: (1)..(889)

<400> SEQUENCE: 21
gtcaaaggca ggatcaggtt ccccgccttc cagtccaaaa atcccgccaa gagagcccca      60
gagcagagga aaatccaaag tggagagagg ggaagaaaga gaccagtgag tcatccgtcc     120
agaaggcggg gagagcagca gcggcccaag caggagctgc agcgagccgg gtacctggac     180
tcagcggtag caacctcgcc ccttgcaaca aaggcagact gagcgccaga gaggacgttt     240
ccaactcaaa a atg cag gct caa cag tac cag cag cag cgt cga aaa ttt      290
            Met Gln Ala Gln Gln Tyr Gln Gln Gln Arg Arg Lys Phe
             1               5                  10 gca gct gcc ttc ttg gca ttc att ttc ata ctg gca gct gtg gat act       338
Ala Ala Ala Phe Leu Ala Phe Ile Phe Ile Leu Ala Ala Val Asp Thr
     15                  20                  25 gct gaa gca ggg aag aaa gag aaa cca gaa aaa aaa gtg aag aag tct       386
Ala Glu Ala Gly Lys Lys Glu Lys Pro Glu Lys Lys Val Lys Lys Ser
 30              35                  40                  45 gac tgt gga gaa tgg cag tgg agt gtg tgt gtg ccc acc agt gga gac       434
Asp Cys Gly Glu Trp Gln Trp Ser Val Cys Val Pro Thr Ser Gly Asp
                 50                  55                  60 tgt ggg ctg ggc aca cgg gag ggc act cgg act gga gct gag tgc aag       482
Cys Gly Leu Gly Thr Arg Glu Gly Thr Arg Thr Gly Ala Glu Cys Lys
             65                  70                  75 caa acc atg aag acc cag aga tgt aag atc ccc tgc aac tgg aag aag       530
Gln Thr Met Lys Thr Gln Arg Cys Lys Ile Pro Cys Asn Trp Lys Lys
         80                  85                  90 caa ttt ggc gcg gag tgc aaa tac cag ttc cag gcc tgg gga gaa tgt       578
Gln Phe Gly Ala Glu Cys Lys Tyr Gln Phe Gln Ala Trp Gly Glu Cys
     95                 100                 105 gac ctg aac aca gcc ctg aag acc aga act gga agt ctg aag cga gcc       626
Asp Leu Asn Thr Ala Leu Lys Thr Arg Thr Gly Ser Leu Lys Arg Ala
110                 115                 120                 125 ctg cac aat gcc gaa tgc cag aag act gtc acc atc tcc aag ccc tgt       674
Leu His Asn Ala Glu Cys Gln Lys Thr Val Thr Ile Ser Lys Pro Cys
                130                 135                 140 ggc aaa ctg acc aag ccc aaa cct caa gca gaa tct aag aag aag aaa       722
Gly Lys Leu Thr Lys Pro Lys Pro Gln Ala Glu Ser Lys Lys Lys Lys
```

-continued

```
                145                 150                 155
aag gaa ggc aag aaa cag gag aag atg ctg gat taa aagatgtcac              768
Lys Glu Gly Lys Lys Gln Glu Lys Met Leu Asp
        160                 165 ctgtggaaca taaaaaggac atcagcaaac aggatcagtt aactattgca tttatatgta       828
ccgtaggctt tgtattcaaa aattatctat agctaagtac acaataagca aaaacaaaaa       888
g                                                                       889

<210> SEQ ID NO 22
<211> LENGTH: 168
<212> TYPE: PRT
<213> ORGANISM: Homo sapiens
<220> FEATURE:
<221> NAME/KEY: SIGNAL
<222> LOCATION: (1)..(32)
<223> OTHER INFORMATION:
<220> FEATURE:
<221> NAME/KEY: GENE
<222> LOCATION: (1)..(168)
<223> OTHER INFORMATION: Pleiotrophin
<220> FEATURE:
<221> NAME/KEY: CHAIN
<222> LOCATION: (33)..(168)
<223> OTHER INFORMATION: Pleiotrophin
<220> FEATURE:
<221> NAME/KEY: DISULFID
<222> LOCATION: (47)..(76)
<223> OTHER INFORMATION: By similarity.
<220> FEATURE:
<221> NAME/KEY: DISULFID
<222> LOCATION: (55)..(85)
<223> OTHER INFORMATION: By similarity.
<220> FEATURE:
<221> NAME/KEY: DISULFID
<222> LOCATION: (62)..(89)
<223> OTHER INFORMATION: By similarity.
<220> FEATURE:
<221> NAME/KEY: DISULFID
<222> LOCATION: (99)..(131)
<223> OTHER INFORMATION: By similarity.
<220> FEATURE:
<221> NAME/KEY: DISULFID
<222> LOCATION: (109)..(141)
<223> OTHER INFORMATION: By similarity.

<400> SEQUENCE: 22

Met Gln Ala Gln Gln Tyr Gln Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Lys Val Lys Lys Ser Asp Cys Gly
        35                  40                  45

Glu Trp Gln Trp Ser Val Cys Val Pro Thr Ser Gly Asp Cys Gly Leu
    50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140
```

```
Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 23
<211> LENGTH: 3143
<212> TYPE: DNA
<213> ORGANISM: Homo sapiens
<220> FEATURE:
<221> NAME/KEY: Gene
<222> LOCATION: (1)..(3143)
<223> OTHER INFORMATION: Osteopontin
<220> FEATURE:
<221> NAME/KEY: CDS
<222> LOCATION: (374)..(427)
<223> OTHER INFORMATION:
<220> FEATURE:
<221> NAME/KEY: CDS
<222> LOCATION: (537)..(575)
<223> OTHER INFORMATION:
<220> FEATURE:
<221> NAME/KEY: CDS
<222> LOCATION: (884)..(964)
<223> OTHER INFORMATION:
<220> FEATURE:
<221> NAME/KEY: CDS
<222> LOCATION: (1232)..(1273)
<223> OTHER INFORMATION:
<220> FEATURE:
<221> NAME/KEY: CDS
<222> LOCATION: (1597)..(1920)
<223> OTHER INFORMATION:
<220> FEATURE:
<221> NAME/KEY: CDS
<222> LOCATION: (2305)..(2709)
<223> OTHER INFORMATION:
<300> PUBLICATION INFORMATION:
<301> AUTHORS: Crosby, A.H., Edwards, S.J., Murray, J.C. and Dixon, M.J.
<302> TITLE: Genomic organization of the human osteopontin gene:
       exclusion of the locus from a causative role in the pathogenesis
       of dentinogenesis imperfecta type II
<303> JOURNAL: Genomics
<304> VOLUME: 27
<305> ISSUE: 1
<306> PAGES: 155-160
<307> DATE: 1995
<309> DATABASE ENTRY DATE:
<313> RELEVANT RESIDUES: (1)..(3143)

<400> SEQUENCE: 23
ggggaagtgt gggagcaggt gggctgggca gtggcagaaa cctgatgaca caatctcgcc      60
gcctccctgt gttggtggag gatgtctgca gcagcattta aattctggga gggcttggtt    120
gtcagcagca gcaggaggag gcagagacag catcgtcggg accagactcg tctcaggcca    180
gttgcagcct tctcagccaa acgccgacca aggtacagct tcagtttgct actgggttgt    240
gcattcagct gaatttcatg gggaagtcca aattctaagg aaaaaatgt ggtagtataa     300 aaaggtatca ctgttgtaac ctatgaagat gtcagctatt cctttgaaat attttgcagg    360
aaaactcact acc atg aga att gca gtg att tgc ttt tgc ctc cta ggc       409
             Met Arg Ile Ala Val Ile Cys Phe Cys Leu Leu Gly
                 1               5                   10 atc acc tgt gcc ata cca gtgagtacag ttgcatctta aagaaaattc             457
Ile Thr Cys Ala Ile Pro
                 15 ctgaaaataa ctgaattgtg tgcttccatg tgctaggagg acattcttgt aatctttctt    517 catcttttct gtttctaag gtt aaa cag gct gat tct gga agt tct gag gaa    569
                      Val Lys Gln Ala Asp Ser Gly Ser Ser Glu Glu
                            20                  25
```

```
aag cag gtaagcatct tttatgtttt tatatagtta aatcatttac tcaattatgg        625
Lys Gln
 30 cgagaggtgc aagaaacgta tttgctgcga tcaaatgagt tcatatttgt aaagcaattt     685 gaaagagtgc ctagcccaca gtaagtgcta cataagagtt tgttaaatga atctgcaaaa    745 aaaaaaaaaa ttacaaaaag gtacctaagg gtccgggtga ctatatgctt ccatcaagac    805 tagtgaagaa tggttgtttt ttccattcat ccctacattt cttttttaa taatgataaa     865 catgcaactt ttttgtag ctt tac aac aaa tac cca gat gct gtg gcc aca      916
                   Leu Tyr Asn Lys Tyr Pro Asp Ala Val Ala Thr
                                    35                   40 tgg cta aac cct gac cca tct cag aag cag aat ctc cta gcc cca cag      964
Trp Leu Asn Pro Asp Pro Ser Gln Lys Gln Asn Leu Leu Ala Pro Gln
         45                  50                  55 gtattttta acttctcata attaaactac agtgatgaaa gatagccaca ctcaggccat    1024
ttgggctgct cagatgaatc ctgccctgcc tgctggcaaa catgtgctta ggacattgac    1084
tgatctgcca tgttggcttc tctctgtgtt aagccatcca cagatgaggc tgaaaaataa    1144
aaactgcttt ggattaaaaa ggttaacttt tgaataaaaa agctaggcat gtgtgatgcg    1204
cactaacacg tgccattcct tcttcag aat gct gtg tcc tct gaa gaa acc aat    1258
                               Asn Ala Val Ser Ser Glu Glu Thr Asn
                                                60                  65 gac ttt aaa caa gag gtaagttctc attttcaatc agaggcccat catgccttga     1313
Asp Phe Lys Gln Glu
 70 agagatgaaa gaaggcattg cctggattct cttctgatga aatttcatta gcaagttttc    1373 cagctaattg gcagtctaaa acttgctcat aaataaaaca tgtatttact aaatatcaga    1433 aatactaggt ttcctcggat aacctaaaag ccatggtatg tactgtgaat gcaaagattc    1493 tgaaactaaa taaaagaaa gatagtaaaa gactaatgtg ctataaaggc taagggaaaa    1553 taaaaaccca tatattaatt ttcccggcca tcttaatttt cag acc ctt cca agt     1608
                                                   Thr Leu Pro Ser
                                                              75 aag tcc aac gaa agc cat gac cac atg gat gat atg gat gat gaa gat     1656
Lys Ser Asn Glu Ser His Asp His Met Asp Asp Met Asp Asp Glu Asp
         80                  85                  90 gat gat gac cat gtg gac agc cag gac tcc att gac tcg aac gac tct     1704
Asp Asp Asp His Val Asp Ser Gln Asp Ser Ile Asp Ser Asn Asp Ser
         95                 100                 105 gat gat gta gat gac act gat gat tct cac cag tct gat gag tct cac     1752
Asp Asp Val Asp Asp Thr Asp Asp Ser His Gln Ser Asp Glu Ser His
        110                 115                 120 cat tct gat gaa tct gat gaa ctg gtc act gat ttt ccc acg gac ctg     1800
His Ser Asp Glu Ser Asp Glu Leu Val Thr Asp Phe Pro Thr Asp Leu
125                 130                 135                 140 cca gca acc gaa gtt ttc act cca gtt gtc ccc aca gta gac aca tat     1848
Pro Ala Thr Glu Val Phe Thr Pro Val Val Pro Thr Val Asp Thr Tyr
                145                 150                 155 gat ggc cga ggt gat agt gtg gtt tat gga ctg agg tca aaa tct aag     1896
Asp Gly Arg Gly Asp Ser Val Val Tyr Gly Leu Arg Ser Lys Ser Lys
        160                 165                 170 aag ttt cgc aga cct gac atc cag gtaaatcctt taacagacac acctgatggt    1950
Lys Phe Arg Arg Pro Asp Ile Gln
        175                 180 tctgactagc gctcaagtct aggaaaccac agtttgcata ttcattcatt cattcatcca    2010
```

-continued

```
ttcattcatc cattcagcaa gaattcattc atattctact ttatgaccat tgaatacaaa     2070 tcttttctg cttggcggtt tttgtaagtc tacataattt ctctctagat ttgattctca      2130
aacacaattc tactttttga atcctggat caaagtaaca tgctagtatt atttcagcca      2190
gatttagaca attttagta taagatgacc taaaagctag agagtggaaa aggattacca     2250
tattcccatc cctagccgtt catataatta ttcttcattt gtgccgtgat tcag tac       2307
                                                            Tyr
```

| | |
|---|---|
| cct gat gct aca gac gag gac atc acc tca cac atg gaa agc gag gag<br>Pro Asp Ala Thr Asp Glu Asp Ile Thr Ser His Met Glu Ser Glu Glu<br>          185                  190                  195 | 2355 |
| ttg aat ggt gca tac aag gcc atc ccc gtt gcc cag gac ctg aac gcg<br>Leu Asn Gly Ala Tyr Lys Ala Ile Pro Val Ala Gln Asp Leu Asn Ala<br>    200                  205                  210 | 2403 |
| cct tct gat tgg gac agc cgt ggg aag gac agt tat gaa acg agt cag<br>Pro Ser Asp Trp Asp Ser Arg Gly Lys Asp Ser Tyr Glu Thr Ser Gln<br>       215                  220                  225 | 2451 |
| ctg gat gac cag agt gct gaa acc cac agc cac aag cag tcc aga tta<br>Leu Asp Asp Gln Ser Ala Glu Thr His Ser His Lys Gln Ser Arg Leu<br>230                  235                  240                  245 | 2499 |
| tat aag cgg aaa gcc aat gat gag agc aat gag cat tcc gat gtg att<br>Tyr Lys Arg Lys Ala Asn Asp Glu Ser Asn Glu His Ser Asp Val Ile<br>                250                  255                  260 | 2547 |
| gat agt cag gaa ctt tcc aaa gtc agc cgt gaa ttc cac agc cat gaa<br>Asp Ser Gln Glu Leu Ser Lys Val Ser Arg Glu Phe His Ser His Glu<br>       265                  270                  275 | 2595 |
| ttt cac agc cat gaa gat atg ctg gtt gta gac ccc aaa agt aag gaa<br>Phe His Ser His Glu Asp Met Leu Val Val Asp Pro Lys Ser Lys Glu<br>    280                  285                  290 | 2643 |
| gaa gat aaa cac ctg aaa ttt cgt att tct cat gaa tta gat agt gca<br>Glu Asp Lys His Leu Lys Phe Arg Ile Ser His Glu Leu Asp Ser Ala<br>       295                  300                  305 | 2691 |
| tct tct gag gtc aat taa aaggagaaaa aatacaattt ctcactttgc<br>Ser Ser Glu Val Asn<br>310 | 2739 |

```
atttagtcaa aagaaaaaat gctttatagc aaaatgaaag agaacatgaa atgcttcttt     2799
ctcagtttat tggttgaatg tgtatctatt tgagtctgga aataactaat gtgtttgata     2859
attagtttag tttgtggctt catggaaact ccctgtaaac aaaagcttca gggttatgtc     2919
tatgttcatt ctatagaaga aatgcaaact atcactgtat tttaatattt gttattctct     2979
catgaataga aatttatgta gaagcaaaca aaatactttt acccacttaa aaagagaata    3039
taacatttta tgtcactata atctttttgtt ttttaagtta gtgtatattt tgttgtgatt    3099
atcttttgtg gtgtgaataa atcttttatc ttgaatgtaa taag                      3143
```

```
<210> SEQ ID NO 24
<211> LENGTH: 314
<212> TYPE: PRT
<213> ORGANISM: Homo sapiens
<220> FEATURE:
<221> NAME/KEY: SIGNAL
<222> LOCATION: (1)..(16)
<223> OTHER INFORMATION: Potential
<220> FEATURE:
<221> NAME/KEY: Gene
<222> LOCATION: (1)..(314)
<223> OTHER INFORMATION: Osteopontin
<220> FEATURE:
<221> NAME/KEY: CHAIN
<222> LOCATION: (17)..(314)
<223> OTHER INFORMATION: Osteopontin
<220> FEATURE:
```

-continued

```
<221> NAME/KEY: SITE
<222> LOCATION: (159)..(161)
<223> OTHER INFORMATION: Cell attachment site
<220> FEATURE:
<221> NAME/KEY: CARBOHYD
<222> LOCATION: (79)..(79)
<223> OTHER INFORMATION: N-linked (GLCNAC...) (Potential)
<220> FEATURE:
<221> NAME/KEY: CARBOHYD
<222> LOCATION: (106)..(106)
<223> OTHER INFORMATION: N-linked (GLCNAC...) (Potential)
<220> FEATURE:
<221> NAME/KEY: VARSPLIC
<222> LOCATION: (31)..(57)
<223> OTHER INFORMATION: Missing (In Isoform C)
<220> FEATURE:
<221> NAME/KEY: VARSPLIC
<222> LOCATION: (58)..(71)
<223> OTHER INFORMATION: Missing (In Isoform B)

<400> SEQUENCE: 24

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300
```

Glu Leu Asp Ser Ala Ser Ser Glu Val Asn
305                 310

<210> SEQ ID NO 25
<211> LENGTH: 259
<212> TYPE: PRT
<213> ORGANISM: Homo sapiens
<220> FEATURE:
<221> NAME/KEY: Gene
<222> LOCATION: (1)..(259)
<223> OTHER INFORMATION: Carbonic Anhydrase domain of human carbonic
      anhydrase III

<400> SEQUENCE: 25

Ala Lys Glu Trp Gly Tyr Ala Ser His Asn Gly Pro Asp His Trp His
1               5                   10                  15

Glu Leu Phe Pro Asn Ala Lys Gly Glu Asn Gln Ser Pro Ile Glu Leu
            20                  25                  30

His Thr Lys Asp Ile Arg His Asp Pro Ser Leu Gln Pro Trp Ser Val
        35                  40                  45

Ser Tyr Asp Gly Gly Ser Ala Lys Thr Ile Leu Asn Asn Gly Lys Thr
50                  55                  60

Cys Arg Val Val Phe Asp Asp Thr Tyr Asp Arg Ser Met Leu Arg Gly
65                  70                  75                  80

Gly Pro Leu Pro Gly Pro Tyr Arg Leu Arg Gln Phe His Leu His Trp
                85                  90                  95

Gly Ser Ser Asp Asp His Gly Ser Glu His Thr Val Asp Gly Val Lys
            100                 105                 110

Tyr Ala Ala Glu Leu His Leu Val His Trp Asn Pro Lys Tyr Asn Thr
        115                 120                 125

Phe Lys Glu Ala Leu Lys Gln Arg Asp Gly Ile Ala Val Ile Gly Ile
130                 135                 140

Phe Leu Lys Ile Gly His Glu Asn Gly Glu Phe Gln Ile Phe Leu Asp
145                 150                 155                 160

Ala Leu Asp Lys Ile Lys Thr Lys Gly Lys Glu Ala Pro Phe Thr Lys
                165                 170                 175

Phe Asp Pro Ser Cys Leu Phe Pro Ala Cys Arg Asp Tyr Trp Thr Tyr
            180                 185                 190

Gln Gly Ser Phe Thr Thr Pro Pro Cys Glu Glu Cys Ile Val Trp Leu
        195                 200                 205

Leu Leu Lys Glu Pro Met Thr Val Ser Ser Asp Gln Met Ala Lys Leu
210                 215                 220

Arg Ser Leu Leu Ser Ser Ala Glu Asn Glu Pro Pro Val Pro Leu Val
225                 230                 235                 240

Ser Asn Trp Arg Pro Pro Gln Pro Ile Asn Asn Arg Val Val Arg Ala
                245                 250                 255

Ser Phe Lys

<210> SEQ ID NO 26
<211> LENGTH: 260
<212> TYPE: PRT
<213> ORGANISM: Homo sapiens
<220> FEATURE:
<221> NAME/KEY: Gene
<222> LOCATION: (1)..(260)
<223> OTHER INFORMATION: Carbonic anhydrase domain of human carbonic
      anhydrase I

<400> SEQUENCE: 26

```
Ala Ser Pro Asp Trp Gly Tyr Asp Asp Lys Asn Gly Pro Glu Gln Trp
1               5                   10                  15

Ser Lys Leu Tyr Pro Ile Ala Asn Gly Asn Asn Gln Ser Pro Val Asp
            20                  25                  30

Ile Lys Thr Ser Glu Thr Lys His Asp Thr Ser Leu Lys Pro Ile Ser
        35                  40                  45

Val Ser Tyr Asn Pro Ala Thr Ala Lys Glu Ile Ile Asn Val Gly His
    50                  55                  60

Ser Phe His Val Asn Phe Glu Asp Asn Asp Asn Arg Ser Val Leu Lys
65                  70                  75                  80

Gly Gly Pro Phe Ser Asp Ser Tyr Arg Leu Phe Gln Phe His Phe His
                85                  90                  95

Trp Gly Ser Thr Asn Glu His Gly Ser Glu His Thr Val Asp Gly Val
            100                 105                 110

Lys Tyr Ser Ala Glu Leu His Val Ala His Trp Asn Ser Ala Lys Tyr
        115                 120                 125

Ser Ser Leu Ala Glu Ala Ala Ser Lys Ala Asp Gly Leu Ala Val Ile
    130                 135                 140

Gly Val Leu Met Lys Val Gly Glu Ala Asn Pro Lys Leu Gln Lys Val
145                 150                 155                 160

Leu Asp Ala Leu Gln Ala Ile Lys Thr Lys Gly Lys Arg Ala Pro Phe
                165                 170                 175

Thr Asn Phe Asp Pro Ser Thr Leu Leu Pro Ser Ser Leu Asp Phe Trp
            180                 185                 190

Thr Tyr Pro Gly Ser Leu Thr His Pro Pro Leu Tyr Glu Ser Val Thr
        195                 200                 205

Trp Ile Ile Cys Lys Glu Ser Ile Ser Val Ser Ser Glu Gln Leu Ala
    210                 215                 220

Gln Phe Arg Ser Leu Leu Ser Asn Val Glu Gly Asp Asn Ala Val Pro
225                 230                 235                 240

Met Gln His Asn Asn Arg Pro Thr Gln Pro Leu Lys Gly Arg Thr Val
                245                 250                 255

Arg Ala Ser Phe
            260

<210> SEQ ID NO 27
<211> LENGTH: 337
<212> TYPE: PRT
<213> ORGANISM: Homo sapiens
<220> FEATURE:
<221> NAME/KEY: Gene
<222> LOCATION: (1)..(337)
<223> OTHER INFORMATION: Carbonic anhydrase domain of human carbonic
      anhydrase VIX

<400> SEQUENCE: 27

Met Leu Phe Ser Ala Leu Leu Leu Glu Val Ile Trp Ile Leu Ala Ala
1               5                   10                  15

Asp Gly Gly Gln His Trp Thr Tyr Glu Gly Pro His Gly Gln Asp His
            20                  25                  30

Trp Pro Ala Ser Tyr Pro Glu Cys Gly Asn Asn Ala Gln Ser Pro Ile
        35                  40                  45

Asp Ile Gln Thr Asp Ser Val Thr Phe Asp Pro Asp Leu Pro Ala Leu
    50                  55                  60

Gln Pro His Gly Tyr Asp Gln Pro Gly Thr Glu Pro Leu Asp Leu His
65                  70                  75                  80
```

```
Asn Asn Gly His Thr Val Gln Leu Ser Leu Pro Ser Thr Leu Tyr Leu
                85                  90                  95
Gly Gly Leu Pro Arg Lys Tyr Val Ala Ala Gln Leu His Leu His Trp
            100                 105                 110
Gly Gln Lys Gly Ser Pro Gly Gly Ser Glu His Gln Ile Asn Ser Glu
        115                 120                 125
Ala Thr Phe Ala Glu Leu His Ile Val His Tyr Asp Ser Asp Ser Tyr
    130                 135                 140
Asp Ser Leu Ser Glu Ala Ala Glu Arg Pro Gln Gly Leu Ala Val Leu
145                 150                 155                 160
Gly Ile Leu Ile Glu Val Gly Glu Thr Lys Asn Ile Ala Tyr Glu His
                165                 170                 175
Ile Leu Ser His Leu His Glu Val Arg His Lys Asp Gln Lys Thr Ser
            180                 185                 190
Val Pro Pro Phe Asn Leu Arg Glu Leu Leu Pro Lys Gln Leu Gly Gln
        195                 200                 205
Tyr Phe Arg Tyr Asn Gly Ser Leu Thr Thr Pro Pro Cys Tyr Gln Ser
    210                 215                 220
Val Leu Trp Thr Val Phe Tyr Arg Arg Ser Gln Ile Ser Met Glu Gln
225                 230                 235                 240
Leu Glu Lys Leu Gln Gly Thr Leu Phe Ser Thr Glu Glu Pro Ser
                245                 250                 255
Lys Leu Leu Val Gln Asn Tyr Arg Ala Leu Gln Pro Leu Asn Gln Arg
            260                 265                 270
Met Val Phe Ala Ser Phe Ile Gln Ala Gly Ser Ser Tyr Thr Thr Gly
        275                 280                 285
Glu Met Leu Ser Leu Gly Val Gly Ile Leu Val Gly Cys Leu Cys Leu
    290                 295                 300
Leu Leu Ala Val Tyr Phe Ile Ala Arg Lys Ile Arg Lys Lys Arg Leu
305                 310                 315                 320
Glu Asn Arg Lys Ser Val Val Phe Thr Ser Ala Gln Ala Thr Thr Glu
                325                 330                 335
Ala
```

<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
cagcagttgg atggaagagg ac                                           22

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
cactgagatt ctggcactat tc                                           22

<210> SEQ ID NO 30
<211> LENGTH: 21
<212> TYPE: DNA
<213> ORGANISM: Artificial sequence -continued

```
<220> FEATURE:
<223> OTHER INFORMATION: Primer

<400> SEQUENCE: 30
aacaattcca gggtctcact c                                              21

<210> SEQ ID NO 31
<211> LENGTH: 21
<212> TYPE: DNA
<213> ORGANISM: Artificial sequence
<220> FEATURE:
<223> OTHER INFORMATION: Primer

<400> SEQUENCE: 31
ttgactggct caggagtata g                                              21

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
ctgataatga gggctcccaa c                                              21

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
ctctgcactt cctggtaaaa ctct                                           24

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
cagcagttgg atggaagagg ac                                             22

<210> SEQ ID NO 35
<211> LENGTH: 24
<212> TYPE: DNA
<213> ORGANISM: Artificial sequence
<220> FEATURE:
<223> OTHER INFORMATION: Primer

<400> SEQUENCE: 35
ctctgcactt cctggtaaaa ctct                                           24
```